United States Patent
Wu et al.

(10) Patent No.: US 10,844,051 B2
(45) Date of Patent: Nov. 24, 2020

(54) SUBSTITUTED OXAZOLES FOR THE TREATMENT OF CANCER

(71) Applicant: THE ROYAL INSTITUTION FOR THE ADCANCEMENT OF LEARNING/McGILL UNIVERSITY, Montreal (CA)

(72) Inventors: Jian Hui Wu, Saint-Laurent (CA); Xiaohong Tian, Urumqi (CN); Qianhui Yi, Westmount (CA)

(73) Assignee: THE ROYAL INSTITUTION FOR THE ADVANCEMENT OF LEARNING/MCGILL UNIVERSITY

( * ) Notice: Subject to any disclaimer, the term of this patent is extended or adjusted under 35 U.S.C. 154(b) by 0 days.

(21) Appl. No.: 15/746,230

(22) PCT Filed: Jul. 22, 2016

(86) PCT No.: PCT/CA2016/050866
§ 371 (c)(1),
(2) Date: Jan. 19, 2018

(87) PCT Pub. No.: WO2017/011920
PCT Pub. Date: Jan. 26, 2017

(65) Prior Publication Data
US 2018/0208586 A1 Jul. 26, 2018

Related U.S. Application Data

(60) Provisional application No. 62/195,485, filed on Jul. 22, 2015.

(51) Int. Cl.

| | |
|---|---|
| A61K 31/421 | (2006.01) |
| C07D 263/32 | (2006.01) |
| C07D 413/04 | (2006.01) |
| C07D 401/14 | (2006.01) |
| C07D 405/14 | (2006.01) |
| C07D 413/14 | (2006.01) |
| C07D 413/06 | (2006.01) |
| C07D 211/16 | (2006.01) |
| C07D 211/42 | (2006.01) |
| C07D 211/52 | (2006.01) |
| C07D 295/192 | (2006.01) |
| C07D 233/64 | (2006.01) |
| C07D 307/68 | (2006.01) |
| C07D 211/32 | (2006.01) |
| C07D 211/44 | (2006.01) |
| C07D 405/12 | (2006.01) |
| C07D 405/04 | (2006.01) |
| A61P 35/00 | (2006.01) |
| A61K 31/4178 | (2006.01) |

(Continued)

(52) U.S. Cl.
CPC ........ *C07D 413/04* (2013.01); *A61K 31/4178* (2013.01); *A61K 31/421* (2013.01); *A61K 31/422* (2013.01); *A61K 31/451* (2013.01); *A61K 31/454* (2013.01); *A61K 31/495* (2013.01); *A61K 31/496* (2013.01); *A61K 31/5377* (2013.01); *A61K 45/06* (2013.01); *A61P 35/00* (2018.01); *C07D 211/16* (2013.01); *C07D 211/32* (2013.01); *C07D 211/42* (2013.01); *C07D 211/44* (2013.01); *C07D 211/52* (2013.01); *C07D 233/64* (2013.01); *C07D 263/32* (2013.01); *C07D 295/192* (2013.01); *C07D 307/68* (2013.01); *C07D 401/06* (2013.01); *C07D 401/14* (2013.01); *C07D 403/06* (2013.01); *C07D 403/12* (2013.01); *C07D 405/04* (2013.01); *C07D 405/12* (2013.01); *C07D 405/14* (2013.01); *C07D 413/06* (2013.01); *C07D 413/12* (2013.01); *C07D 413/14* (2013.01)

(58) Field of Classification Search
CPC ........................... A61K 31/421; C07D 263/32
USPC ........................................... 514/374; 548/235
See application file for complete search history.

(56) References Cited

U.S. PATENT DOCUMENTS

| | | | |
|---|---|---|---|
| 5,262,540 A | 11/1993 | Meanwell | |
| 2005/0080113 A1 | 4/2005 | Ohkawa et al. | |
| 2013/0158003 A1* | 6/2013 | Campbell | C07D 401/06 514/210.21 |

FOREIGN PATENT DOCUMENTS

| | | |
|---|---|---|
| CA | 2496203 | 3/2004 |
| WO | 9636617 | 11/1996 |

(Continued)

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Li, et al. Chemical Communications, 50(33), 2014, 4328-4330.*
Ang J.E., Olmos D., de Bono J.S. CYP17 blockade by abiraterone: Further evidence for frequent continued hormone-dependence in castration-resistant prostate cancer. Br. J. Cancer 2009, 100(5), 671-675.

(Continued)

*Primary Examiner* — Douglas M Willis
(74) *Attorney, Agent, or Firm* — Lavery, De Billy, LLP

(57) ABSTRACT

There are provided compounds, their preparation and their use in the treatment of medical conditions including cancers and immune disorders.

(Continued)

-continued

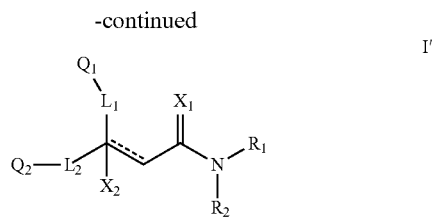

12 Claims, 36 Drawing Sheets

(51) Int. Cl.
| | |
|---|---|
| A61K 31/422 | (2006.01) |
| A61K 31/451 | (2006.01) |
| A61K 31/454 | (2006.01) |
| A61K 31/495 | (2006.01) |
| A61K 31/496 | (2006.01) |
| A61K 31/5377 | (2006.01) |
| A61K 45/06 | (2006.01) |
| C07D 401/06 | (2006.01) |
| C07D 403/06 | (2006.01) |
| C07D 403/12 | (2006.01) |
| C07D 413/12 | (2006.01) |

(56) References Cited

FOREIGN PATENT DOCUMENTS

| WO | 2004016086 | 2/2004 |
|---|---|---|
| WO | 2005047266 | 5/2005 |
| WO | 2006014325 | 2/2006 |
| WO | 2008006795 | 1/2008 |
| WO | 2013132380 | 9/2013 |

OTHER PUBLICATIONS

Attard G., Clark J., Ambroisine L. et al. Duplication of the fusion of TMPRSS2 to ERG sequences identifies fatal human prostate cancer. Oncogene 2008, 27(3), 253-263.
Attard G., Cooper C.S., de Bono J.S. Steroid hormone receptors in prostate cancer: a hard habit to break? Cancer Cell 2009, 16(6), 458-462.
Attard G., Reid A.H.M., Olmos D., de Bono J.S. Antitumor activity with CYP17 blockade indicates that castration-resistant prostate cancer frequently remains hormone driven. Cancer Res. 2009, 69(12), 4937-4940.
Balk S.P. Androgen receptor as a target in androgen-independent prostate cancer. Urology 2002, 60(3A), 132-138.
Braun M., Goltz D., Shaikhibrahim Z. et al. ERG protein expression and genomic rearrangement status in primary and metastatic prostate cancer—A comparative study of two monoclonal antibodies. Prostate Cancer and Prostatic Diseases 2012, 15(2), 165-169.
Bresnick, E. H.; Katsumura, K. R.; Lee, H. Y.; Johnson, K. D.; Perkins, A. S. Master regulatory GATA transcription factors: mechanistic principles and emerging links to hematologic malignancies. Nucleic Acids Res. 2012, 40, 5819-5831.
Culig Z., Klocker H., Bartsch G., Hobisch A. Androgen receptors in prostate cancer. Endocr. Relat. Cancer 2002, 9(3), 155-170.
Demichelis F., Fall K., Perner S. et al. TMPRSS2:ERG gene fusion associated with lethal prostate cancer in a watchful waiting cohort. Oncogene 2007, 26(31), 4596-4599.
Fitzgerald L.M., Agalliu I., Johnson K. et al. Association of TMPRSS2-ERG gene fusion with clinical characteristics and outcomes: results from a population-based study of prostate cancer. BMC Cancer 2008, 8, 230.
Furusato B., Tan S.H., Young D. et al. ERG oncoprotein expression in prostate cancer: clonal progression of ERG-positive tumor cells and potential for ERG-based stratification. Prostate Cancer Prostatic Dis. 2010, 13(3), 228-237.
Gao X., Li L.Y., Zhou F.J. et al. ERG rearrangement for predicting subsequent cancer diagnosis in high-grade prostatic intraepithelial neoplasia and lymph node metastasis. Clin. Cancer Res. 2012, 18(15), 4163-4172.
Gysin, S.; Salt, M.; Young, A.; McCormick, F. Therapeutic strategies for targeting ras proteins. Genes Cancer 2011, 2, 359-372.
Katsumura, K. R.; Yang, C. X.; Boyer, M. E.; Li, L. J.; Bresnick, E. H. Molecular basis of crosstalk between oncogenic Ras and the master regulator of hematopoiesis GATA-2. EMBO Rep. 2014, 15, 938-947.
Kumar, M. S.; Hancock, D. C.; Molina-Arcas, M.; Steckel, M.; East, P.; Diefenbacher, M.; Armenteros-Monterroso, E.; Lassailly, F.; Matthews, N.; Nye, E.; Stamp, G.; Behrens, A.; Downward, J. The GATA2 transcriptional network is requisite for RAS oncogene-driven non-small cell lung cancer. Cell 2012, 149, 642-655.
Kunderfranco P., Mello-Grand M., Cangemi R. et al. ETS transcription factors control transcription of EZH2 and epigenetic silencing of the tumor suppressor gene Nkx3.1 in prostate cancer. PLoS ONE 2010, 5(5).
Leshem O., Madar S., Kogan-Sakin I. et al. TMPRSS2/ERG promotes epithelial to mesenchymal transition through the ZEB1/ZEB2 axis in a prostate cancer model. PLoS ONE 2011, 6(7).
Mallucci, L.; Wells, V. The end of KRAS, and other, cancers? A new way forward. Drug Discov. Today 2014, 19, 383-387.
Masuda, A.; Hashimoto, K.; Yokoi, T.; Doi, T.; Kodama, T.; Kume, H.; Ohno, K.; Matsuguchi, T. Essential role of GATA transcriptional factors in the activation of mast cells. J. Immunol. 2007, 178, 360-368.
Mehra R., Tomlins S.A., Shen R. et al. Comprehensive assessment of TMPRSS2 and ETS family gene aberrations in clinically localized prostate cancer. Mod. Pathol. 2007, 20(5), 538-544.
Mehra R., Tomlins S.A., Yu J.J. et al. Characterization of TMPRSS2-ETS gene aberrations in androgen-independent metastatic prostate cancer. Cancer Res. 2008, 68(10), 3584-3590.
Mohamed A.A., Tan S.H., Sun C. et al. ERG oncogene modulates prostaglandin signaling in prostate cancer cells. Cancer Biology and; Therapy 2011, 11(4), 410-417.
Munugalavadla, V.; Dore, L. C.; Tan, B. L.; Hong, L.; Vishnu, M.; Weiss, M. J.; Kapur, R. Repression of c-kit and its downstream substrates by GATA-1 inhibits cell proliferation during erythroid maturation. Mol. Cell Biol. 2005, 25, 6747-6759.
Oikawa T. ETS transcription factors: possible targets for cancer therapy. Cancer Sci. 2004, 95(8), 626-633.
Perner S., Svensson M.A., Hossain R.R. et al. ERG rearrangement metastasis patterns in locally advanced prostate cancer. Urology 2010, 75(4), 762-767.
Petrylak D.P., Tangen C.M., Hussain M.H. et al. Docetaxel and estramustine compared with mitoxantrone and prednisone for advanced refractory prostate cancer. N. Engl. J. Med. 2004, 351(15), 1513-1520.
Riely, G. J.; Marks, J.; Pao, W. KRAS mutations in non-small cell lung cancer. Proc. Am. Thorac. Soc. 2009, 6, 201-205.
Rosen P., Sesterhenn I.A., Brassell S.A., McLeod D.G., Srivastava S., Dobi A. Clinical potential of the ERG oncoprotein in prostate cancer. Nature Reviews Urology 2012, 9(3), 131-137.
Rubin M.A., Maher C.A., Chinnaiyan A.M. Common gene rearrangements in prostate cancer. J. Clin. Oncol. 2011, 29(27), 3659-3668.
Rylski, M.; Welch, J. J.; Chen, Y. Y.; Letting, D. L.; Diehl, J. A.; Chodosh, L. A.; Blobel, G. A.; Weiss, M. J. GATA-1-mediated proliferation arrest during erythroid maturation. Mol. Cell Biol. 2003, 23, 5031-5042.
Scher H.I., Beer T.M., Higano C.S. et al. Antitumour activity of MDV3100 in castration-resistant prostate cancer: a phase 1-2 study. Lancet 2010, 375(9724), 1437-1446.
Scher H.I., Beer T.M., Higano CS et al. Phase I/II study of MDV3100 in patients (pts) with progressive castration-resistant prostate cancer (CRPC). J. Clin. Oncol. (Meeting Abstracts) 2008, 26(15_suppl), 5006.

(56) References Cited

OTHER PUBLICATIONS

Scholl, C.; Frohling, S.; Dunn, I. F.; Schinzel, A. C.; Barbie, D. A.; Kim, S. Y.; Silver, S. J.; Tamayo, P.; Wadlow, R. C.; Ramaswamy, S.; Dohner, K.; Bullinger, L.; Sandy, P.; Boehm, J. S.; Root, D. E.; Jacks, T.; Hahn, W. C.; Gilliland, D. G. Synthetic Lethal Interaction between Oncogenic KRAS Dependency and STK33 Suppression in Human Cancer Cells. Cell 2009, 137, 821-834.

Shen H.C., Balk S.P. Development of Androgen Receptor Antagonists with Promising Activity in Castration-Resistant Prostate Cancer. Cancer Cell 2009, 15(6), 461-463.

Shen, S.; Mao, C. Q.; Yang, X. Z.; Du, X. J.; Liu, Y.; Zhu, Y. H.; Wang, J. Cationic lipid-assisted polymeric nanoparticle mediated GATA2 siRNA delivery for synthetic lethal therapy of KRAS mutant non-small-cell lung carcinoma. Mol. Pharm. 2014, 11, 2612-2622.

Singh, A.; Greninger, P.; Rhodes, D.; Koopman, L.; Violette, S.; Bardeesy, N.; Settleman, J. A Gene Expression Signature Associated with "K-Ras Addiction" Reveals Regulators of EMT and Tumor Cell Survival. Cancer Cell 2009, 15, 489-500.

Sreenath T.L., Dobi A., Petrovics G., Srivastava S. Oncogenic activation of ERG: A predominant mechanism in prostate cancer. J. Carcinog. 2011, 10, 37.

St.John J., Powell K., Katie Conley-LaComb M., Chinni S.R. TMPRSS2-ERG fusion gene expression in prostate tumor cells and its clinical and biological significance in prostate cancer progression. Journal of Cancer Science and Therapy 2012, 4(4), 94-101.

Steckel, M.; Molina-Arcas, M.; Weigelt, B.; Marani, M.; Warne, P. H.; Kuznetsov, H.; Kelly, G.; Saunders, B.; Howell, M.; Downward, J.; Hancock, D. C. Determination of synthetic lethal interactions in KRAS oncogene-dependent cancer cells reveals novel therapeutic targeting strategies. Cell Res. 2012, 22, 1227-1245.

Sun C., Dobi A., Mohamed A. et al. TMPRSS2-ERG fusion, a common genomic alteration in prostate cancer activates C-MYC and abrogates prostate epithelial differentiation. Oncogene 2008, 27(40), 5348-5353.

Tannock I.F., de Wit R., Berry W.R. et al. Docetaxel plus prednisone or mitoxantrone plus prednisone for advanced prostate cancer. N. Engl. J. Med. 2004, 351(15), 1502-1512.

Taplin M.E., Ho S.M. The endocrinology of prostate cancer. J. Clin. Endocrinol. Metab. 2001, 86(8), 3467-3477.

Tomlins S.A., Bjartell A., Chinnaiyan A.M. et al. ETS Gene Fusions in Prostate Cancer: From Discovery to Daily Clinical Practice. Eur. Urol. 2009, 56(2), 275-286.

Tomlins S.A., Laxman B., Varambally S. et al. Role of the TMPRSS2-ERG gene fusion in prostate cancer. Neoplasia 2008, 10(2), 177-188.

Tomlins S.A., Rhodes D.R., Perner S. et al. Recurrent Fusion of TMPRSS2 and ETS Transcription Factor Genes in Prostate Cancer. Science 2005, 310(5748), 644-648.

Tran C., Ouk S., Clegg N.J. et al. Development of a Second-Generation Antiandrogen for Treatment of Advanced Prostate Cancer. Science 2009, 324(5928), 787-790.

Wang J., Cai Y., Shao L.J. et al. Activation of NF-{kappa}B by TMPRSS2/ERG Fusion Isoforms through Toll-Like Receptor-4. Cancer Res. 2011, 71(4), 1325-1333.

Wang J., Cai Y., Yu W., Ren C., Spencer D.M., Ittmann M. Pleiotropic biological activities of alternatively spliced TMPRSS2/ERG fusion gene transcripts. Cancer Res. 2008, 68(20), 8516-8524.

Whyte, D. B.; Kirschmeier, P.; Hockenberry, T. N.; Nunez-Oliva, I.; James, L.; Catino, J. J.; Bishop, W. R.; Pai, J. K. K- and N-Ras are geranylgeranylated in cells treated with farnesyl protein transferase inhibitors. J. Biol. Chem. 1997, 272, 14459-14464.

Zheng, R.; Blobel, G. A. GATA Transcription Factors and Cancer. Genes Cancer 2010, 1, 1178-1188.

Adjei, Alex A. K-ras as a Target for Lung Cancer Therapy. Journal of Thoracic Oncology 2008, 3(6), Supplement 2.

Baena E., Shao Z., Linn D.E. et al. ETV1 directs androgen metabolism and confers aggressive prostate cancer in targeted mice and patients. Genes Dev. 2013, 27(6), 683-698.

Collins MA, Bednar F, Zhang Y et al. Oncogenic Kras is required for both the initiation and maintenance of pancreatic cancer in mice. J. Clin. Invest. 2012, 122(2), 639-653.

Flajollet S., Tian T.V., Flourens A. et al. Abnormal expression of the ERG transcription factor in prostate cancer cells activates osteopontin. Molecular Cancer Research 2011, 9(7), 914-924.

Garrido-Laguna I, Hidalgo M. Pancreatic cancer: from state-of-the-art treatments to promising novel therapies. Nat. Rev. Clin. Oncol. 2015, 12(6), 319-334.

Gu, Xiao-Hui et al. Synthesis and Biological Activities of Bis (3-indolyl) thiazoles, Analogues of Marine Bis (indole) alkaloid Nortopsentins. Biorganic and; Medicinal Chemistry Letters 1999, 9, 569-572.

He B., Lanz R.B., Fiskus W. et al. GATA2 facilitates steroid receptor coactivator recruitment to the androgen receptor complex. Proc. Natl. Acad. Sci. USA 2014, 111(51), 18261-18266.

International Search Report and Written Opinion, PCT/CA2016/050866, dated Oct. 6, 2016.

Iwamoto, K.-I., Kimura, H., Oike, M., Sato. M. Org. Biomol. Chem. 2008, 6, 912-915.

James, A. David. et al. Conjugated indole-imidazole derivatives displaying cytotoxicity against multidrug resistant cancer cell lines. Biorganic and; Medicinal Chemistry Letters 2006, 16, 5164-5168.

Lewis, Leland R. Purine Nucleosides. II. The Preparation of 6-Substituted 9-(Tetrhydro-2-furyl)purines and 6-Substittued 9-(Tetrahydro-2-thienyl)purines as Models of Purine Deoxynucleosides. J. Org. Chem. 1961, 26(10), 3837-3842.

Lim SM, Westover KD, Ficarro SB et al. Therapeutic targeting of oncogenic K-Ras by a covalent catalytic site inhibitor. Angew Chem. Int. Ed. Engl. 2014, 53(1), 199-204.

Lito P, Solomon M, Li LS, Hansen R, Rosen N. Allele-specific inhibitors inactivate mutant KRAS G12C by a trapping mechanism. Science 2016, 351(6273), 604-608.

Martin, Arnold R. et al. Heterocyclic Ring-Closure reactions. I. A Novel Oxazole Synthesis from S,S'-Dialkyl or-Diaryl Dithiooxaldiimidates and Aromatic Aldehydes. 1966, 31(11), 3612-3615.

Meanwell, N. A. et al. J. Med. Chem. 1993, 36, 3884-3903.

Meanwell, N. A.; Rosenfeld, M. J.; Trehan, A. K. Wright, J. J. K.; Brassard, C. L.; Buchanan, J.; Federici, M. E.; Fleming, J. S.; Gamberdella, M.; Zavoico, G. B.; Seiler, S. M. J.Med. Chem. 1992, 35, 3483-3497.

Mizumoto Y, Kyo S, Kiyono T et al. Activation of NF-kappaB is a novel target of KRAS-induced endometrial carcinogenesis. Clin. Cancer Res. 2011, 17(6), 1341-1350.

Nelson W.G., De Marzo A.M., Yegnasubramanian S. Epigenetic alterations in human prostate cancers. Endocrinol. 2009, 150(9), 3991-4002.

Ostrem JM, Peters U, Sos ML, Wells JA, Shokat KM. K-Ras(G12C) inhibitors allosterically control GTP affinity and effector interactions. Nature 2013, 503(7477), 548-551.

Pews-Davtyan, Anahit et al. Efficient and simple zinc-mediated synthesis of 3-amidoindoles. Org. Biomol. Chem. 2011, 9, 6331.

Pylayeva-Gupta Y, Grabocka E, Bar-Sagi D. RAS oncogenes: weaving a tumorigenic web. Nat. Rev. Cancer 2011, 11(11), 761-774.

Rahim S., Beauchamp E.M., Kong Y., Brown M.L., Toretsky J.A., Aoeren A. YK-4-279 inhibits ERG and ETV1 mediated prostate cancer cell invasion. PLoS ONE 2011, 6(4).

Raju, Gollapalli Naga. Synthesis, Characterization and Biological Activity of some 1,3,4-oxadiazole derivatives with benzoxazole moiety. Journal of Drug Discovery and Therapeutics Jun. 2015, 3929), 8-15.

Ran L., Sirota I., Cao Z. et al. Combined inhibition of MAP kinase and KIT signaling synergistically destabilizes ETV1 and suppresses GIST tumor growth. Cancer Discov. 2015, 5(3), 304-315.

Roy, Sudipta et al. Synthesis of Novel Oxazolyl-indoles. Synthesis 2006, 23, 3948-3954.

Ryan DP, Hong TS, Bardeesy N. Pancreatic adenocarcinoma. N. Engl. J. Med. 2014, 371(22), 2140-2141.

Salman, Asmaa S et al. Synthesis, Reactions and Antimicrobial Activity of Some New 3-Substituted Indole Derivatives. International Journal of Organic Chemistry, Jun. 2015, 5, 81-99.

(56) References Cited

OTHER PUBLICATIONS

Sebastien De Bono J., Sandhu S., Allard G. Beyond Hormone Therapy for Prostate Cancer with PARP inhibitors. Cancer Cell 2011, 19(5), 573-574.

Szucova, Lucie et al. Synthesis, characterization and biological activity of ring-substituted 6-benzylamino-9-tetrahydroyran-2-yl and 9-tetrahydrofuran-2-ylpurine derivatives. Biorganic and; Medicinal Chemistry 2009, 17, 1938-1947.

Tan, Jiajing et al. Suzuki-Miyaura Cross-Coupling Reactions of Unprotected Haloimidazoles. J. Org. Chem. 2014, 79, 8871-8876.

Timpe, H-J et al. 2,4,5-Triphenyloxazol—New Preparative Pathway and Properties in Photoinduced Electron Transfer Reactions. J.prakt. Chem. 1992, 334, 410-416.

Travnicek, Zdenec et al. N-(2-Methoxybenzyl)-9-(oxolan-2-yl)-9H-purin-6-amine. Acta Crystallographica Section E, 2013, E69, 0588.

Vaillard, Victoria A. et al. Synthesis of 6-substituted 2-Pyrrolyl and Indolyl Benzoxazoles by Intramoleculare O-arylation in Photostimulated Reactions. J. Org. Chem. 2012, 77, 1507-1519.

Verniest, Guido et al. Gold- and Silver-Mediated Cycloisomerizations of N-Propargylamides. Organic Letters 2008, 109190 4379-4382.

Woo S.R., Fuertes M.B., Corrales L. et al. STING-dependent cytosolic DNA sensing mediates innate immune recognition of immunogenic tumors. Immunity 2014, 41(5), 830-842.

Xie L., Gazin C., Park S.M. et al. A synthetic interaction screen identifies factors selectively required for proliferation and TERT transcription in p53-deficient human cancer cells. PLoS Genet. 2012, 8(12), e1003151.

Xie, Cen et al. Metabolism and bioactivation of famitinib, a novel inhibitor of receptor tyrosine kinase, in cancer patients. British Journal of Pharmacology 2013, 168, 1687-1706.

Yu J., Yu J., Mani R.S. et al. An Integrated Network of Androgen Receptor, Polycomb, and TMPRSS2-ERG Gene Fusions in Prostate Cancer Progression. Cancer Cell 2010, 17(5), 443-454.

Zhu, Gui-Dong et al. Discovery and SAR of oxindole-pyridine-based protein kinase B/ Akt inhibitors for treating cancers. Biorganic and; Medicinal Chemistry Letters 2006, 16, 3424-3429.

Extended European Search Report in corresponding EP Application No. 16826974.4 dated May 28, 2019.

* cited by examiner

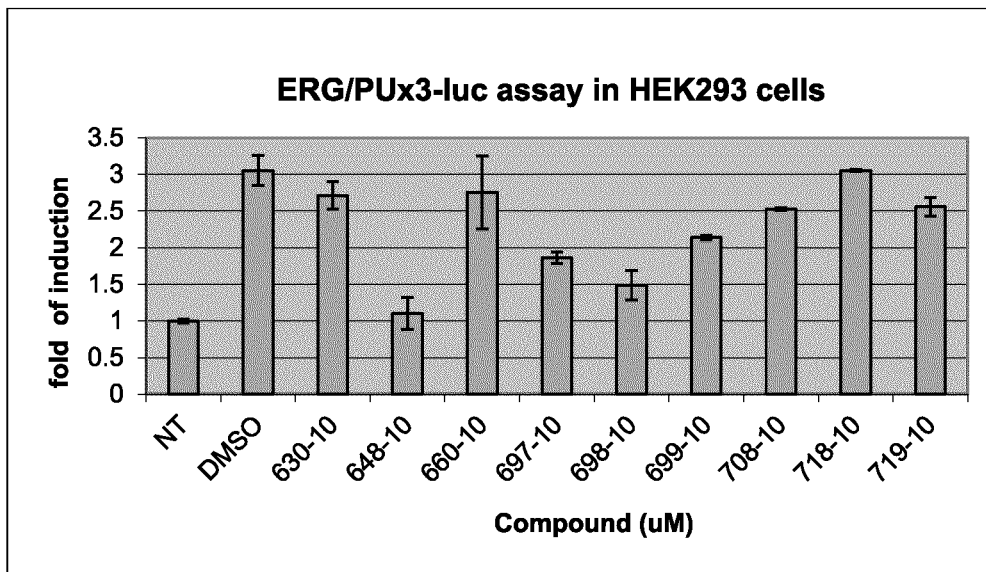
Figure 1.1a)
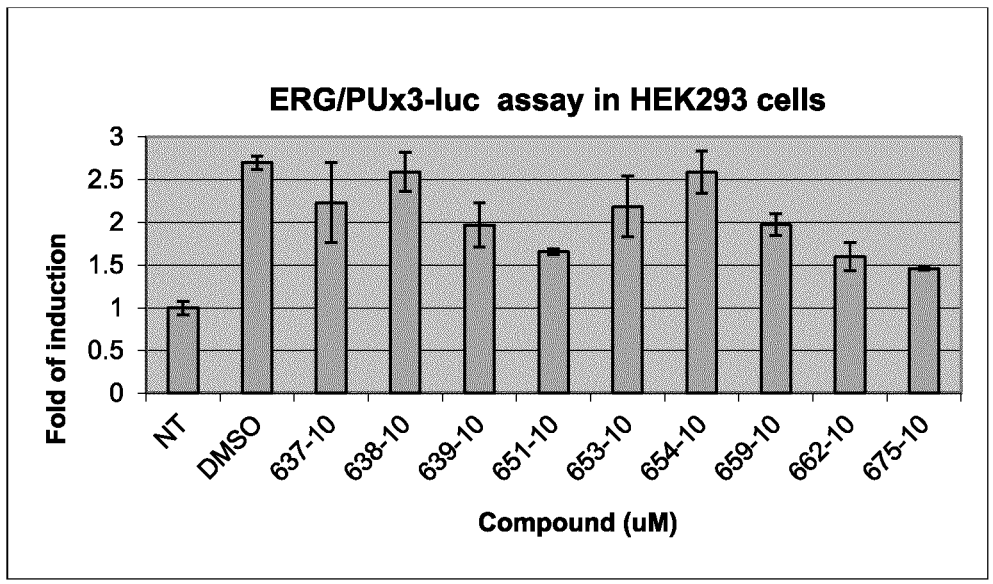
Figure 1.1b)

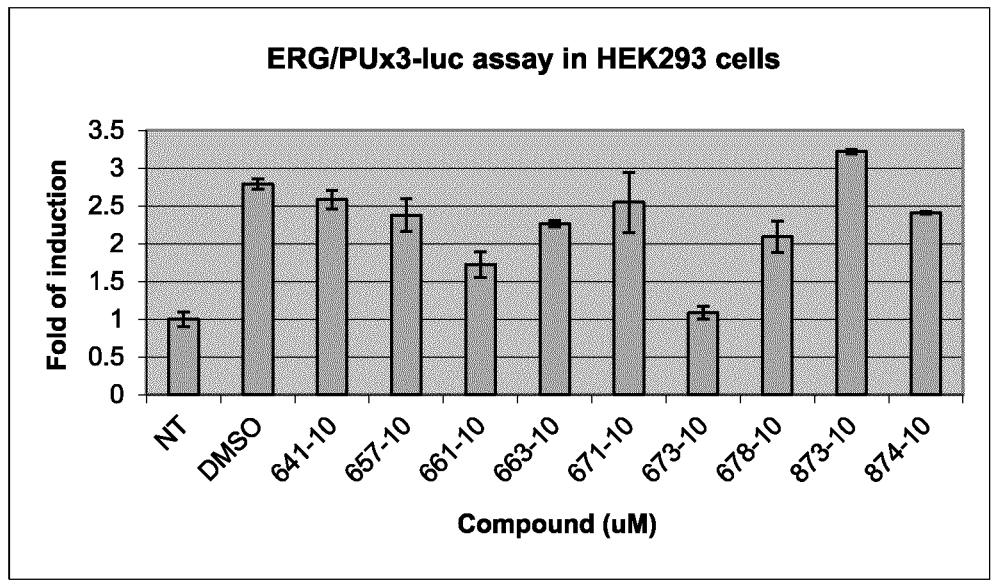
Figure 1.1c)
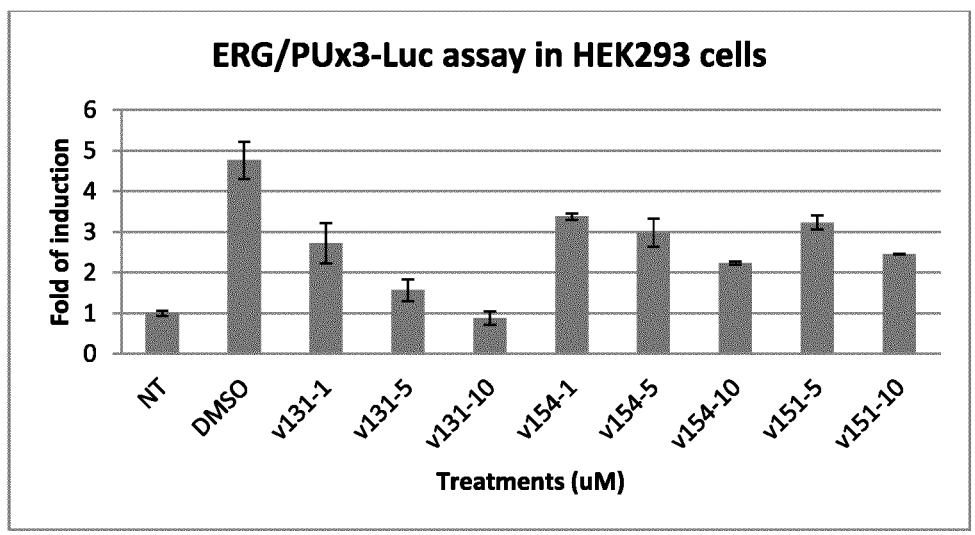
Figure 1.1d)

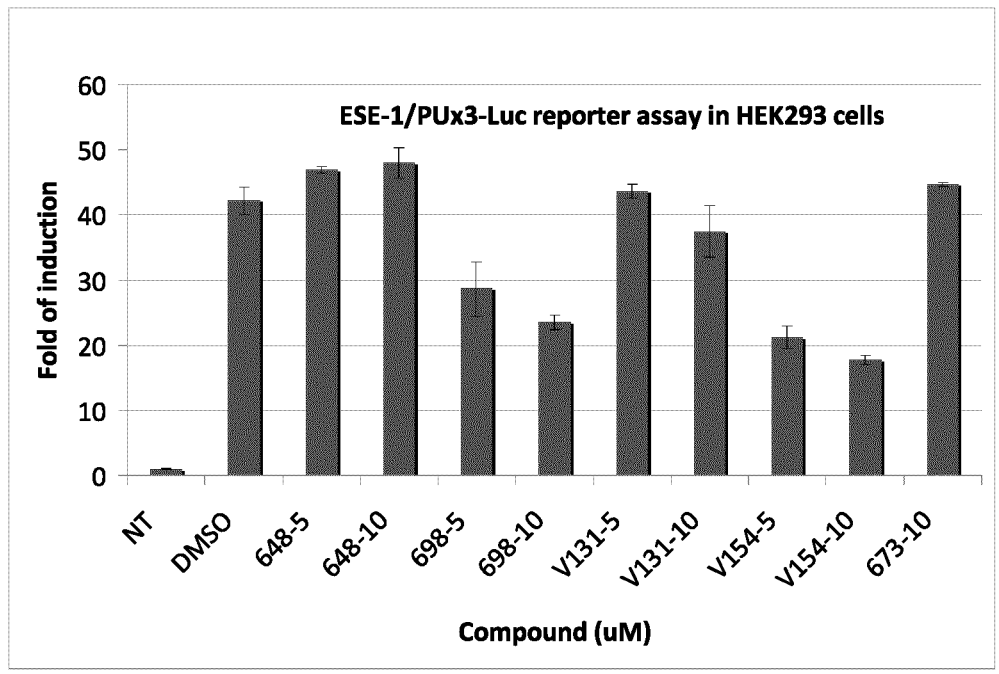
Figure 1.2
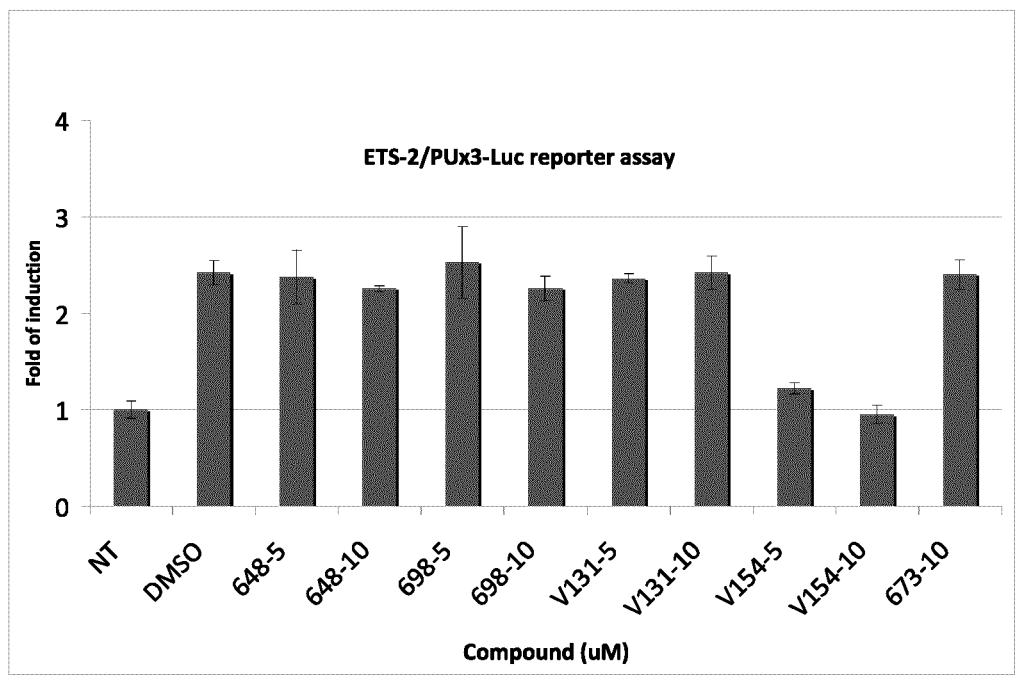
Figure 1.3

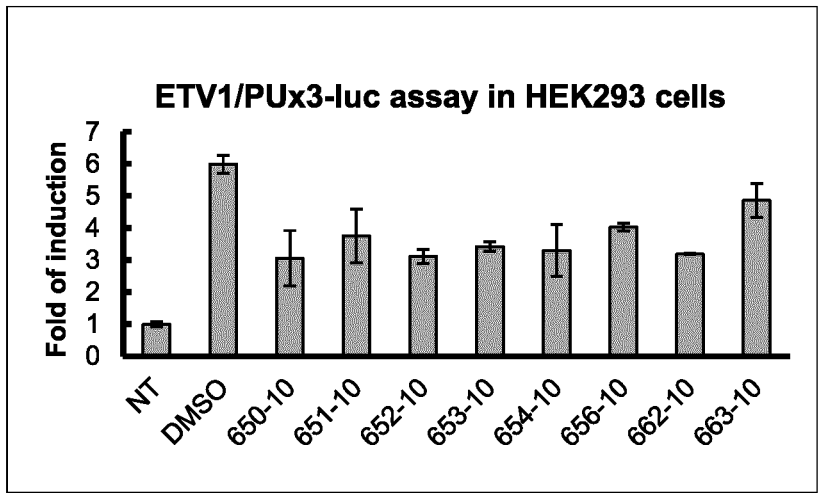
Figure 1.4a)
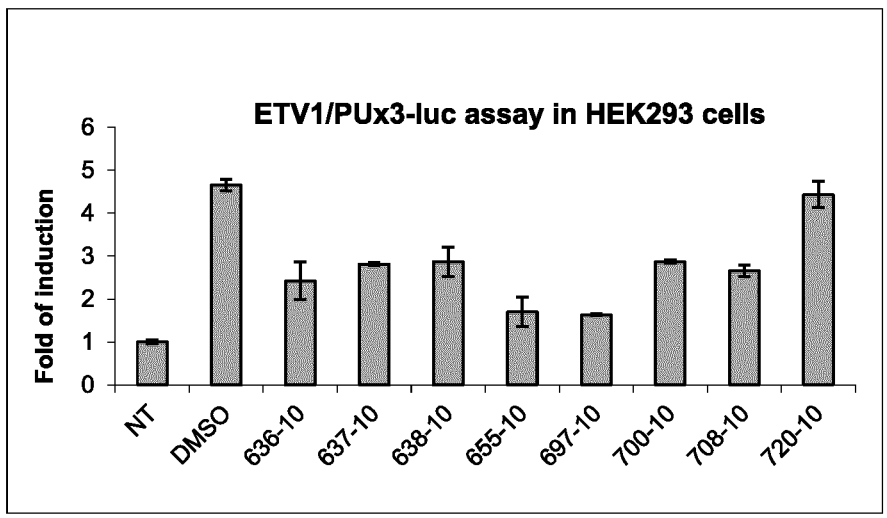
Figure 1.4b)

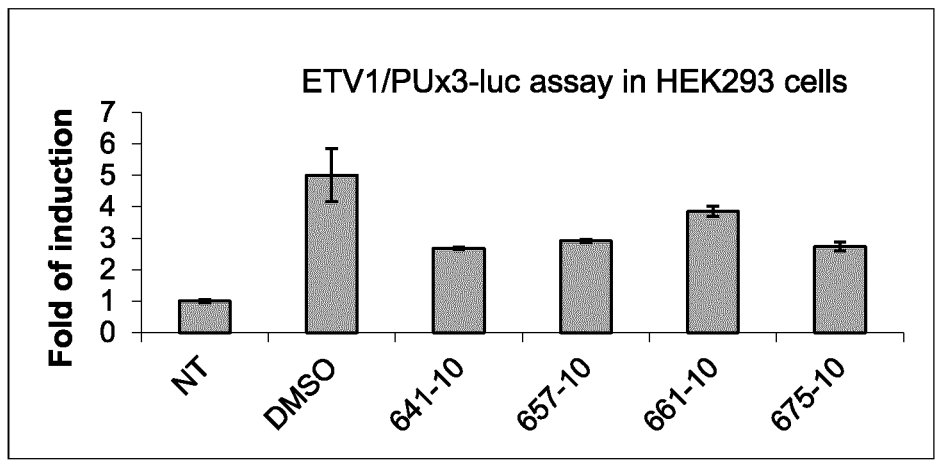
Figure 1.4c)
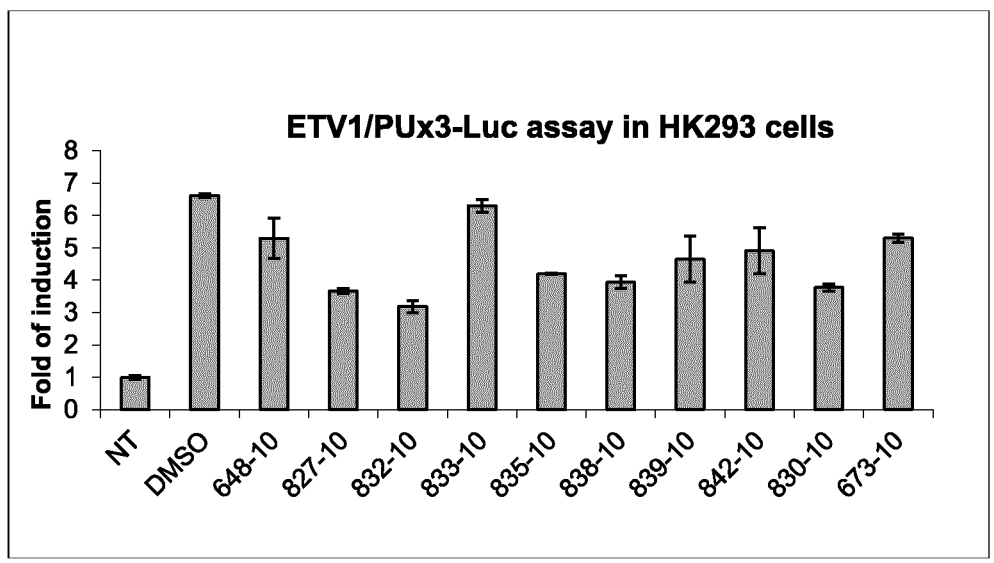
Figure 1.4d)

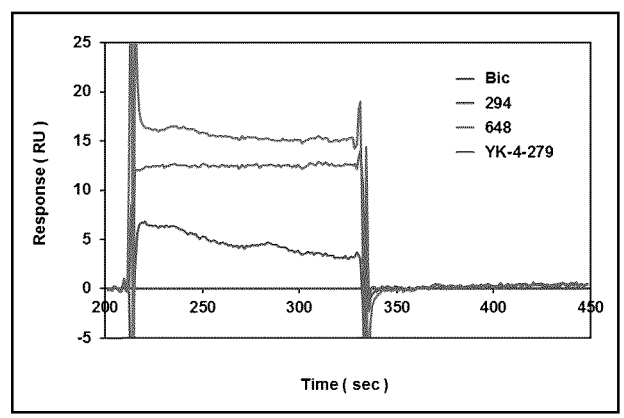
Figure 1.5a)
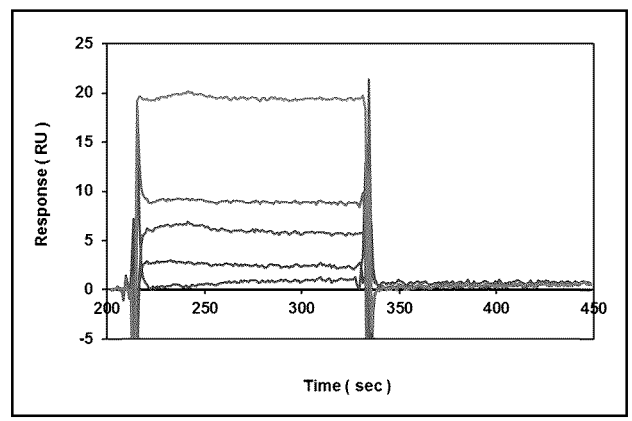
Figure 1.5b)
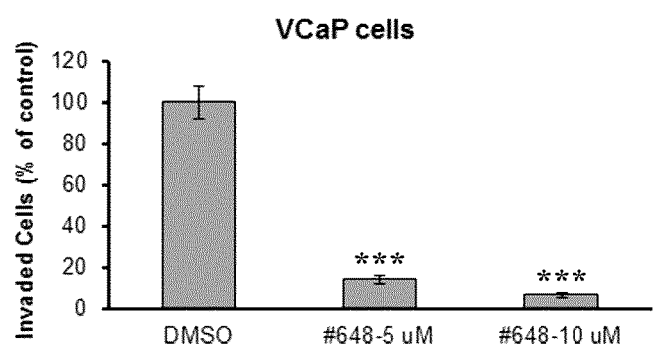
Figure 1.6

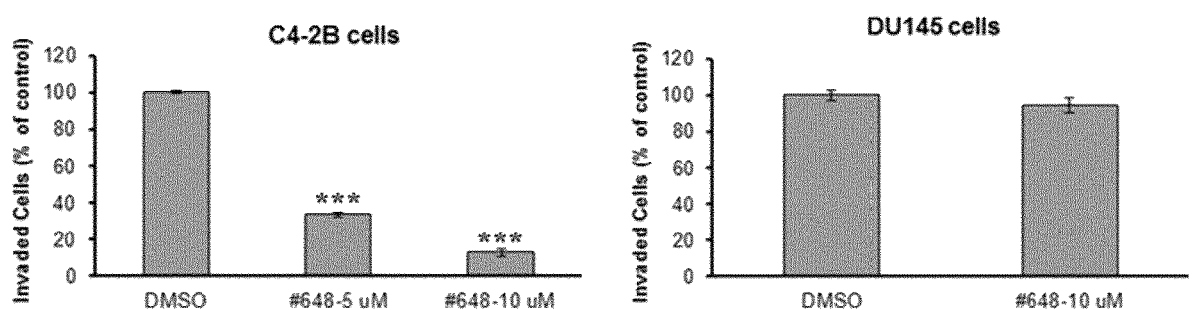
Figure 1.7
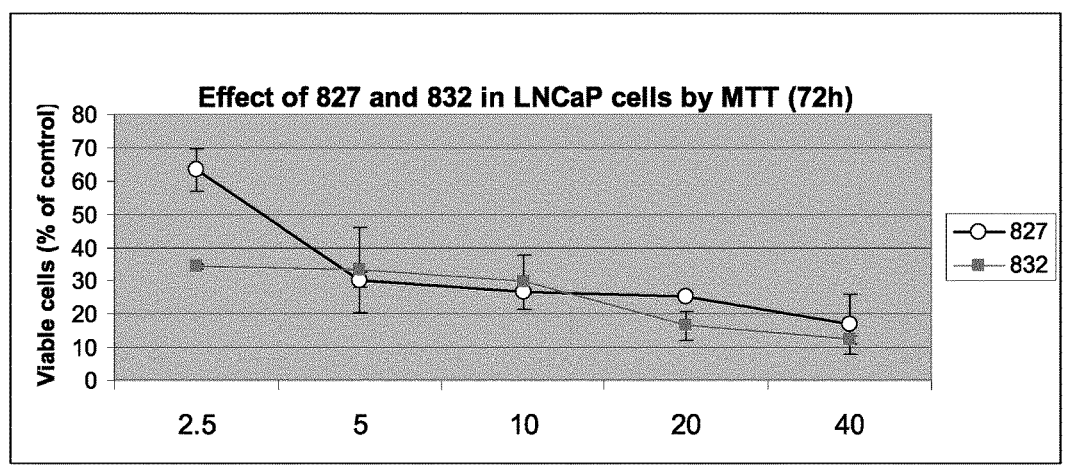
Figure 1.8

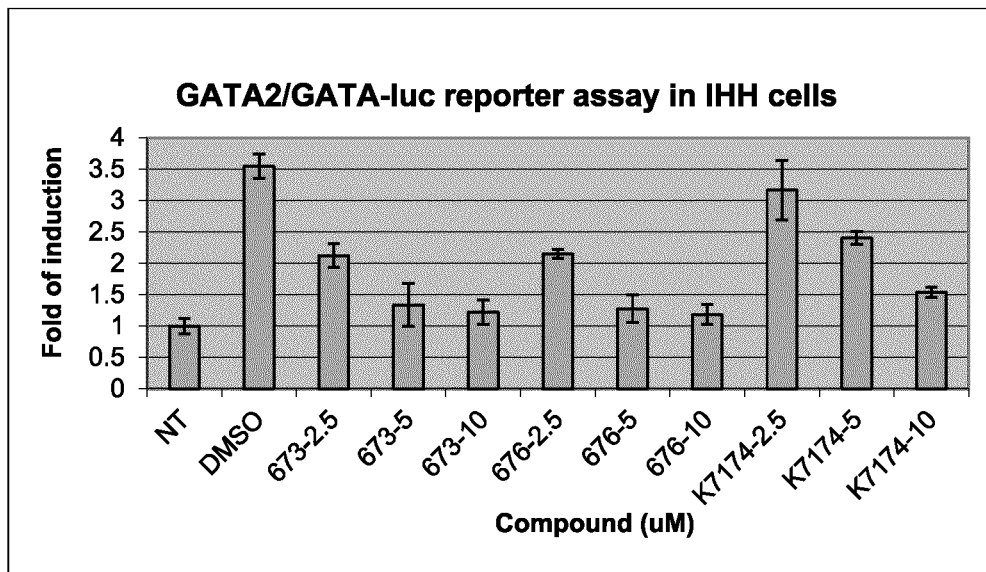
Figure 2.1a)
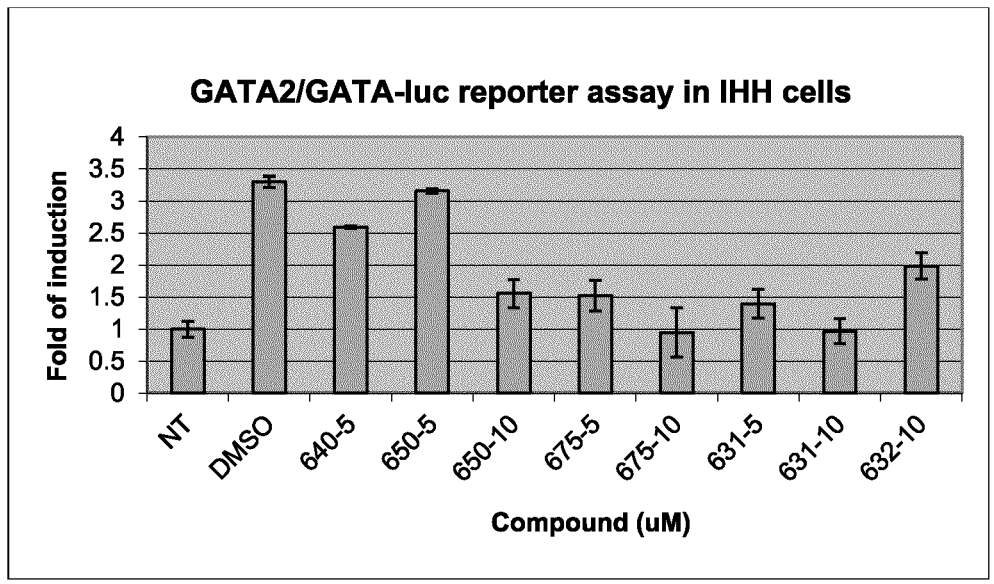
Figure 2.1b)

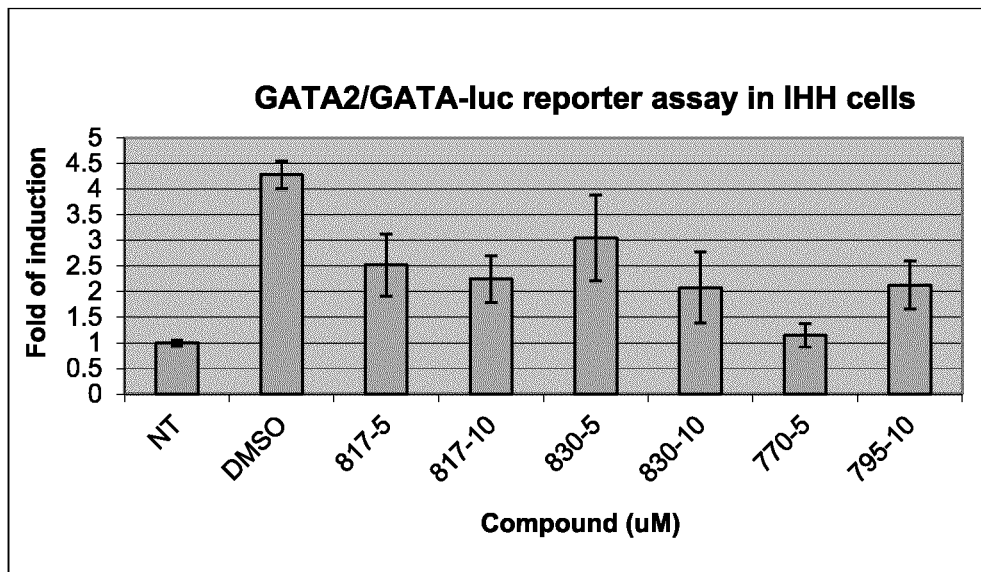
Figure 2.2a)
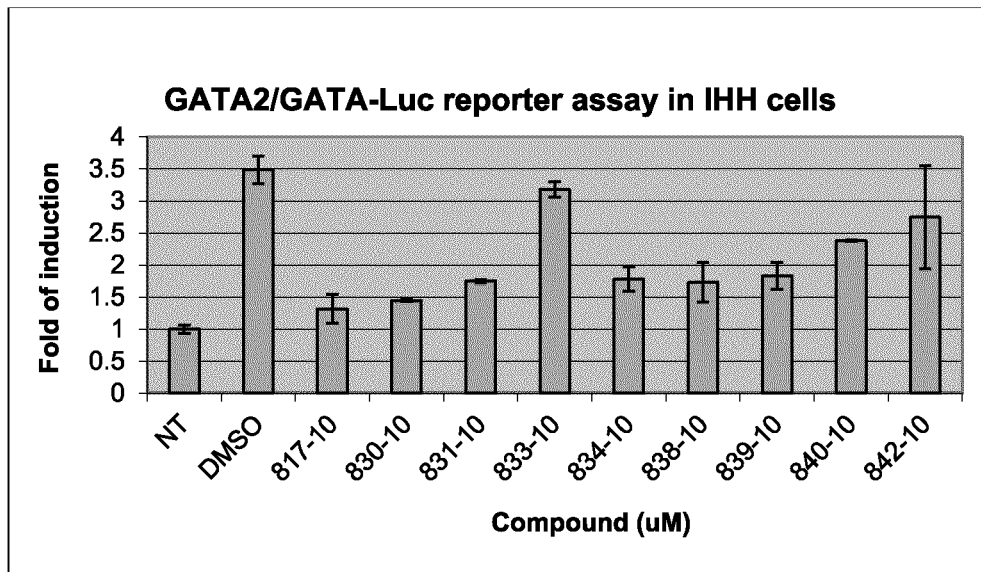
Figure 2.2b)

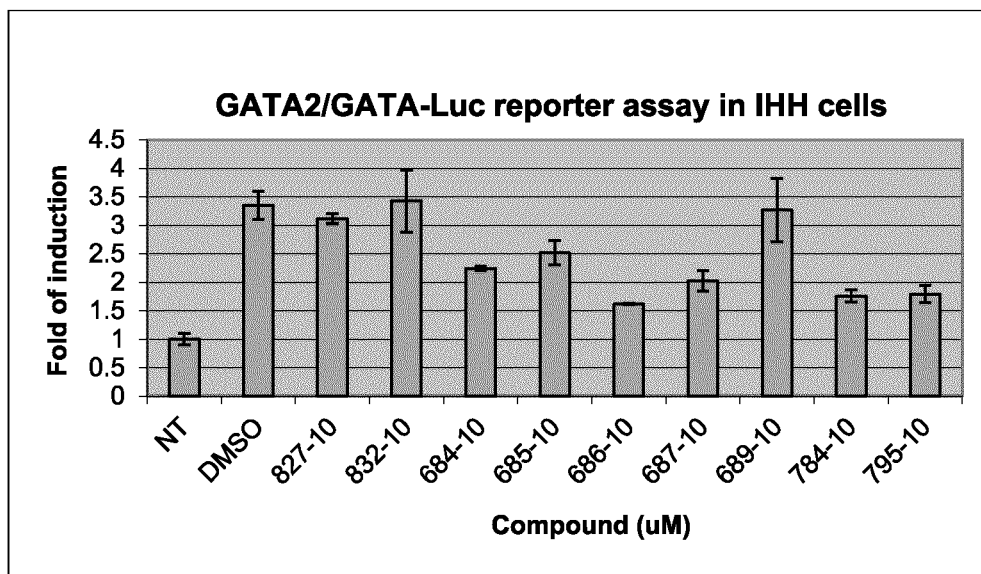
Figure 2.2c)
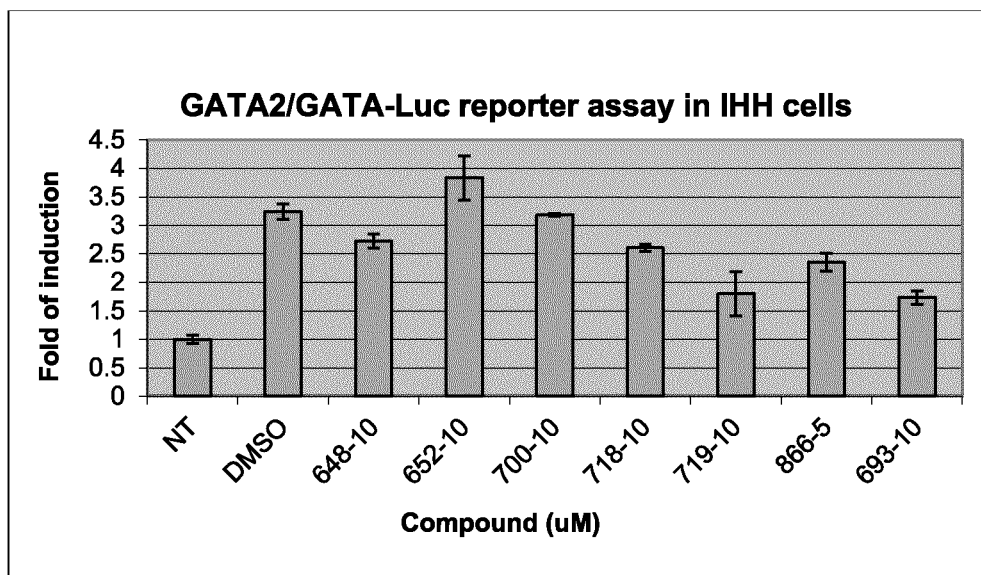
Figure 2.2d)

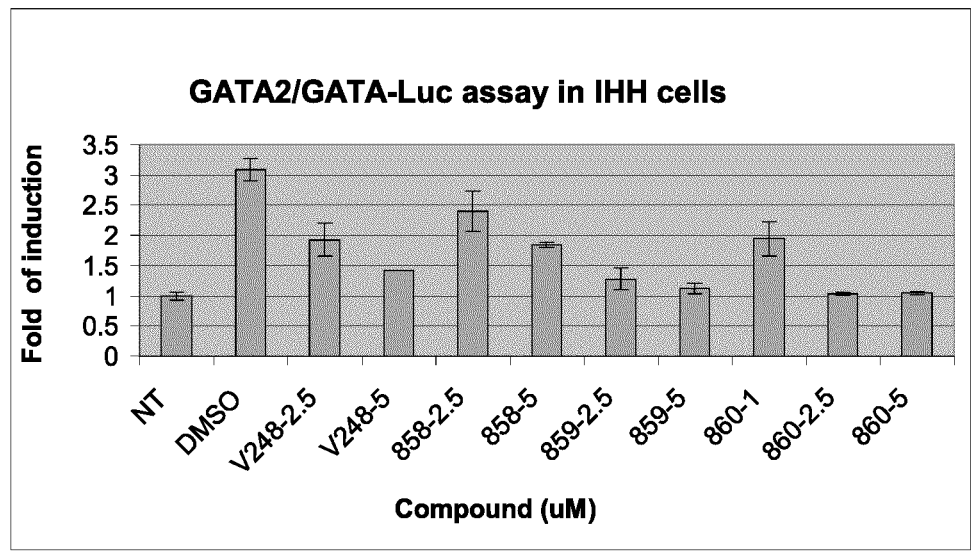
Figure 2.2e)
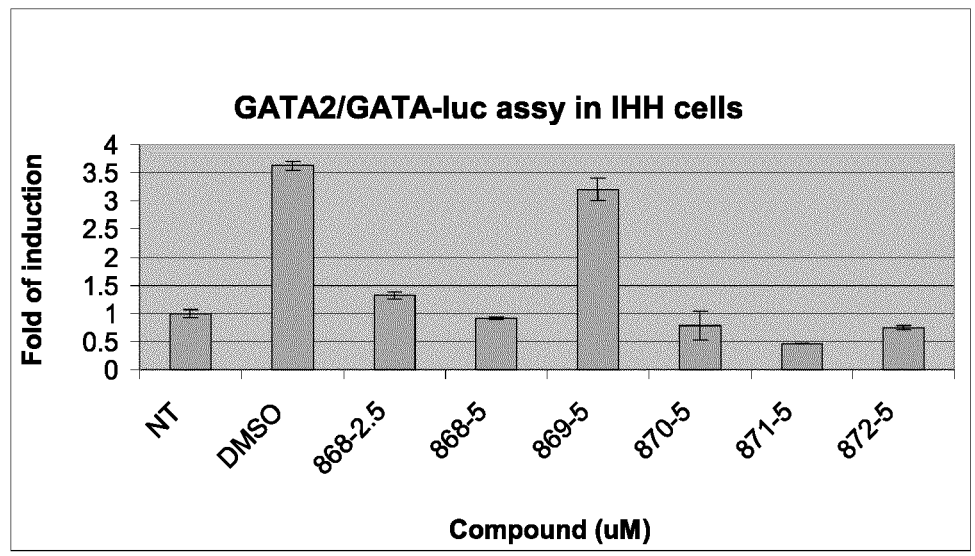
Figure 2.2f)

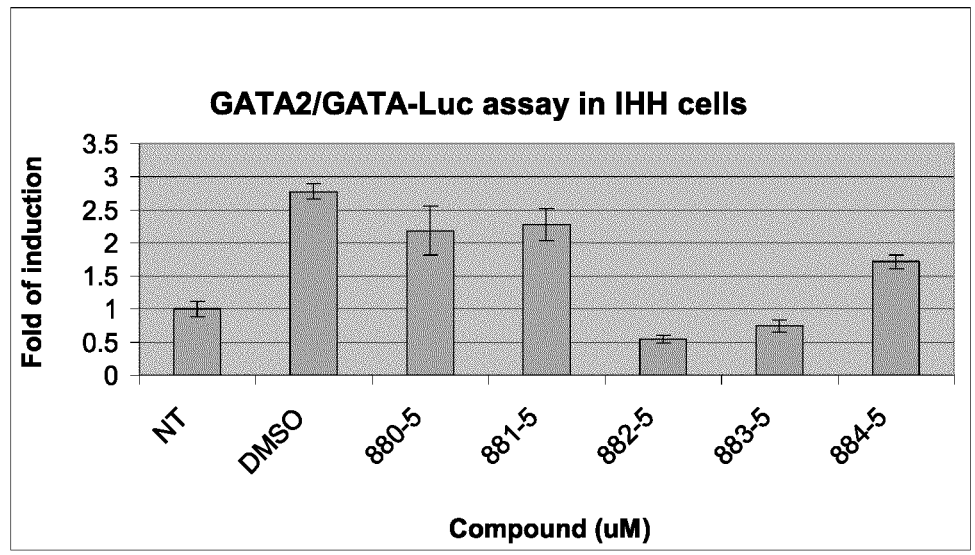
Figure 2.2g)
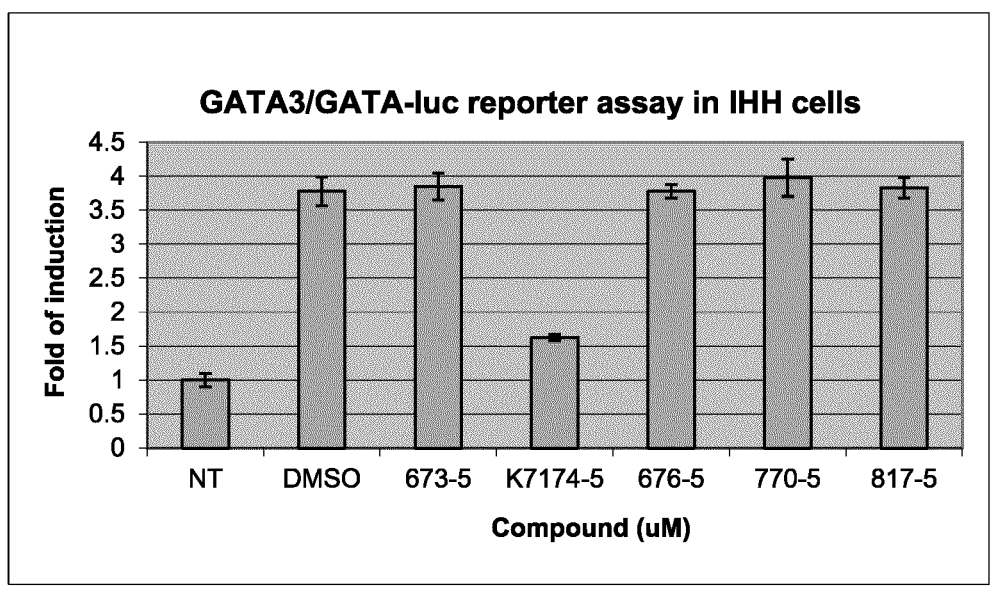
Figure 2.3a)

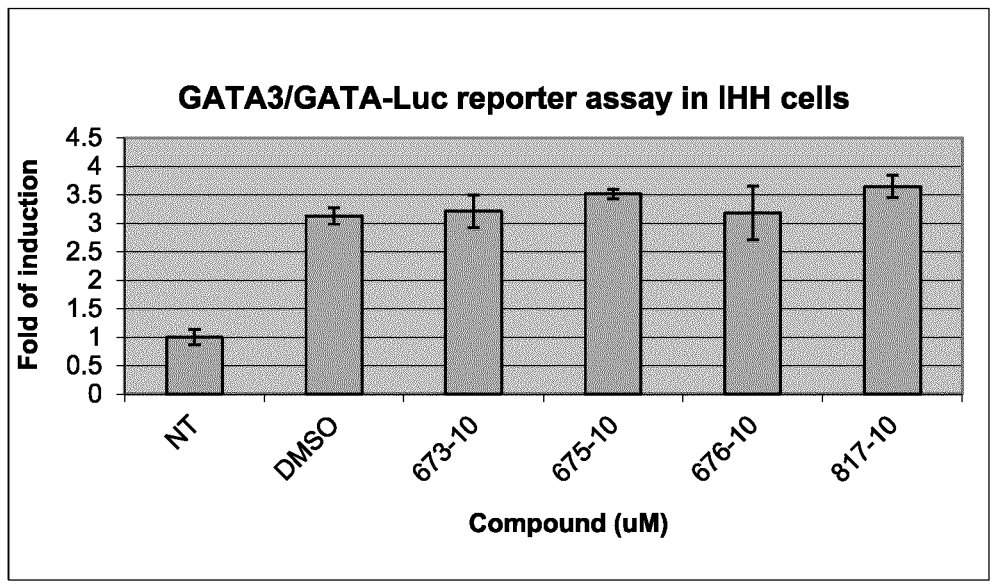
Figure 2.3b)
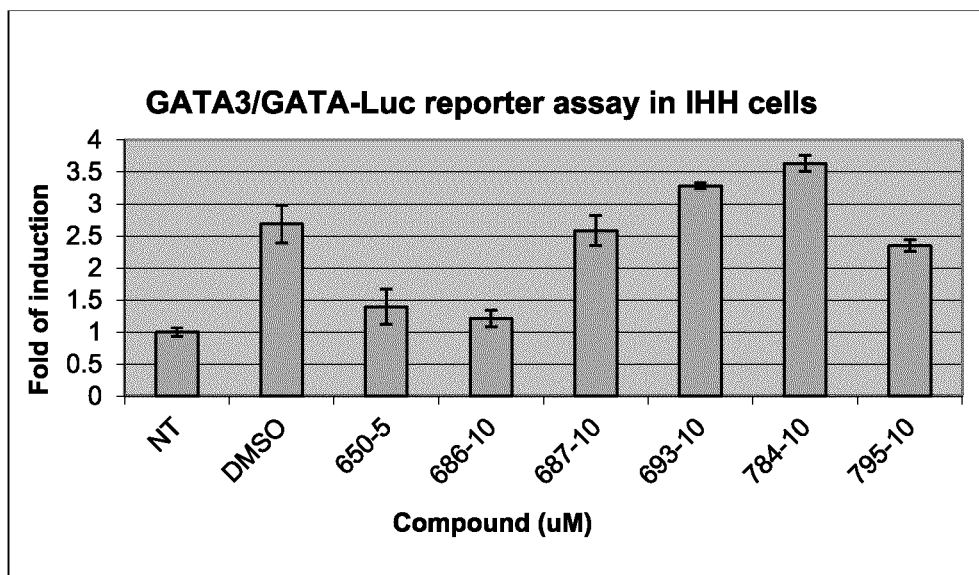
Figure 2.3c)

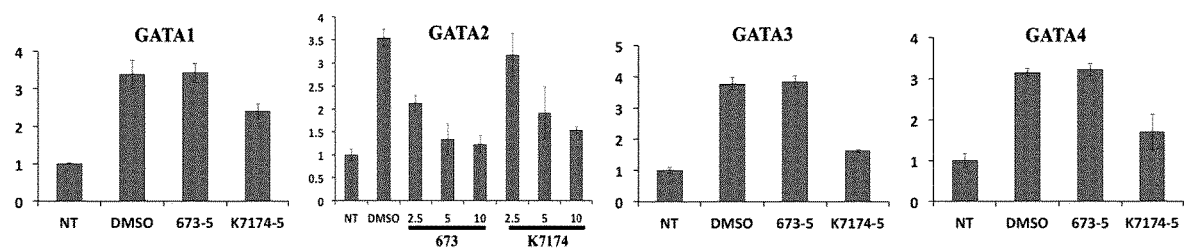
Figure 2.4
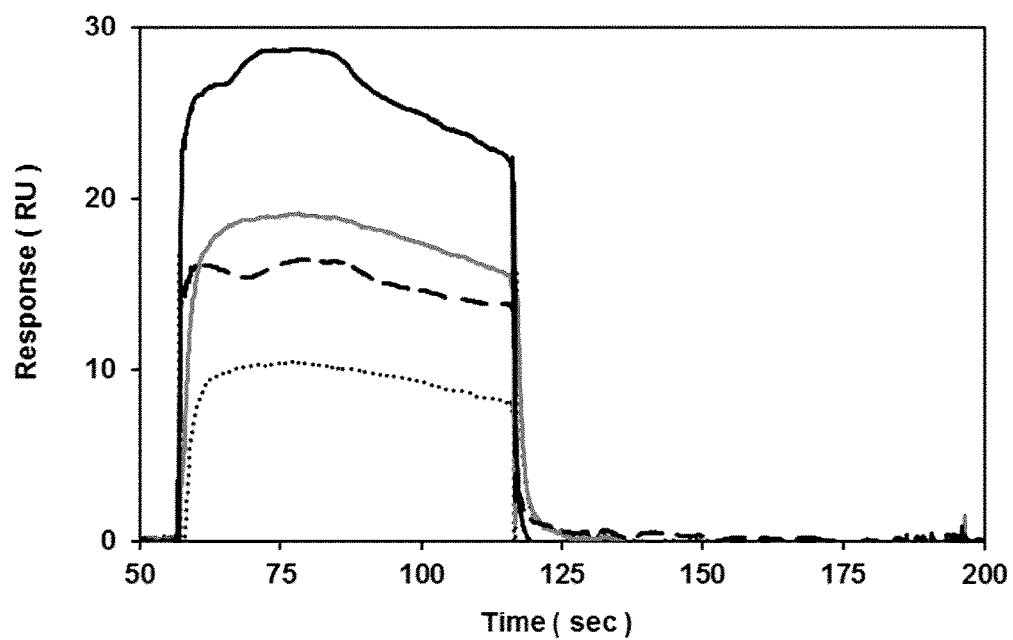
Figure 2.5a)

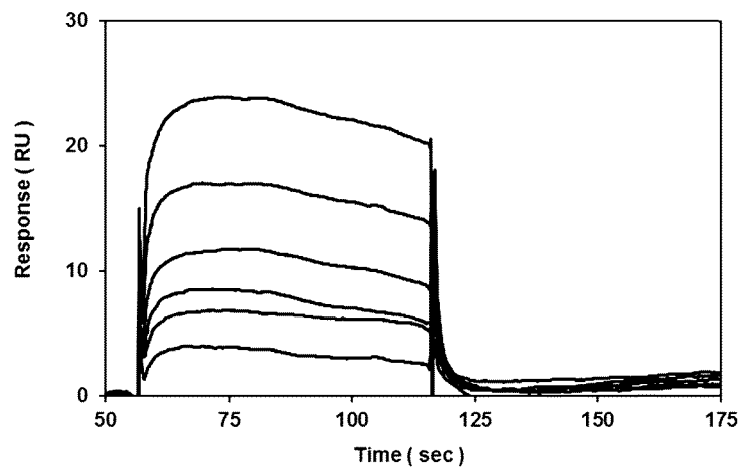
Figure 2.5b)
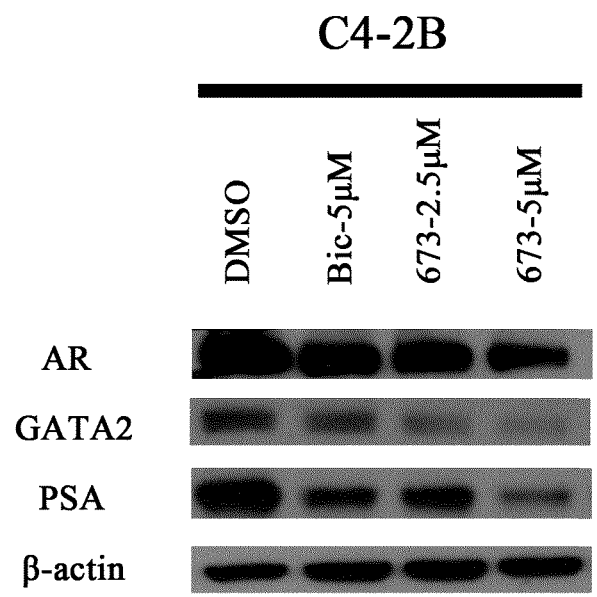
Figure 2.6

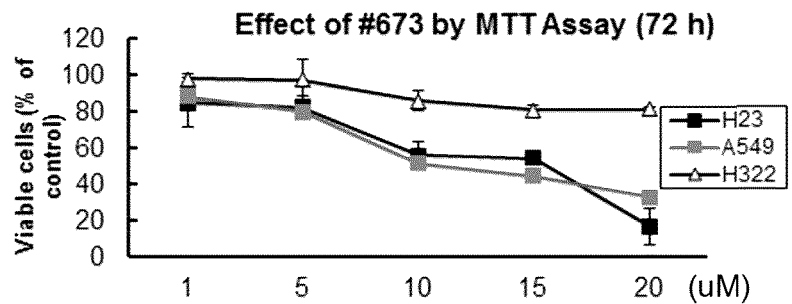
Figure 2.7
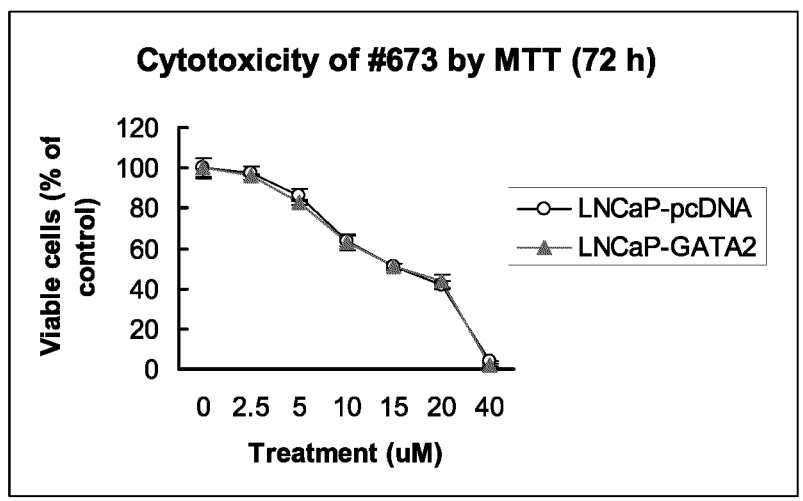
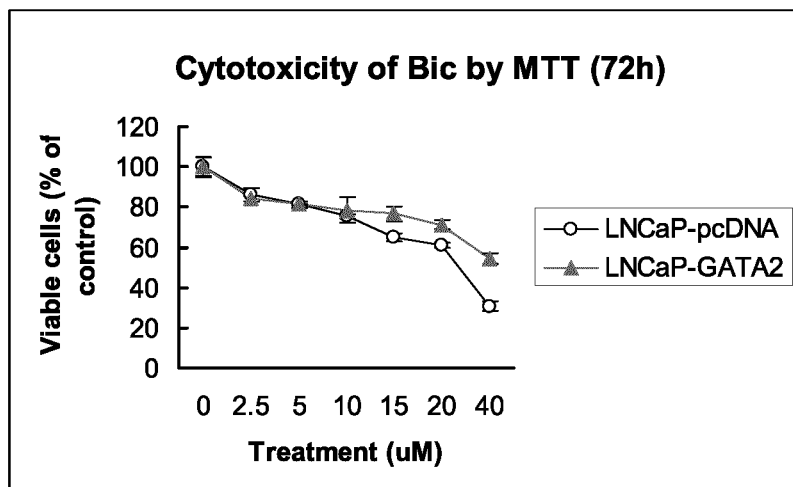
Figure 2.8

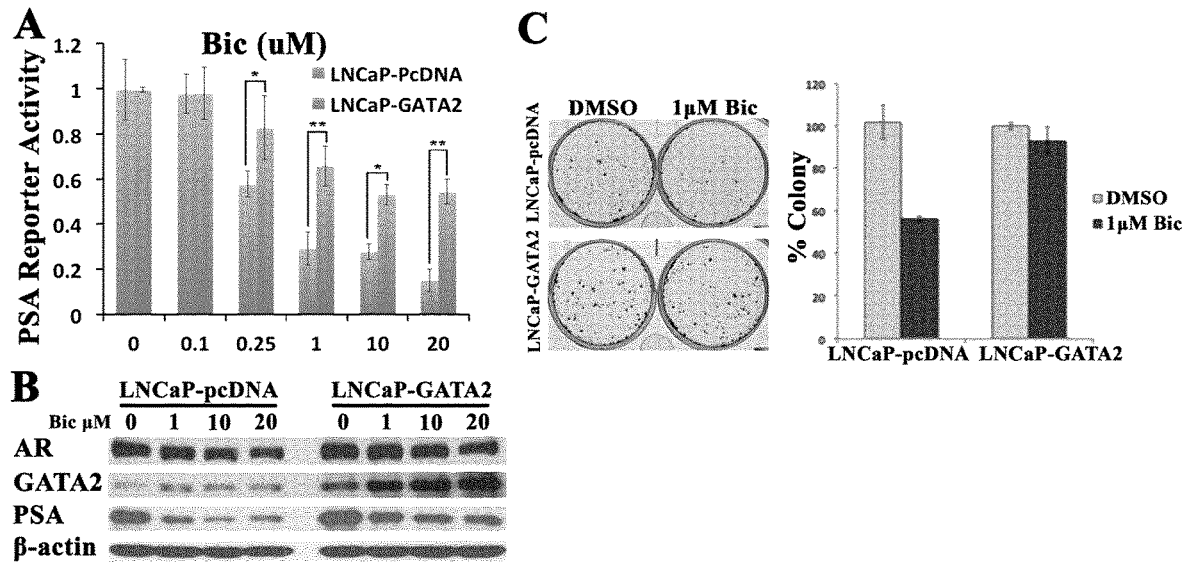
Figure 2.9
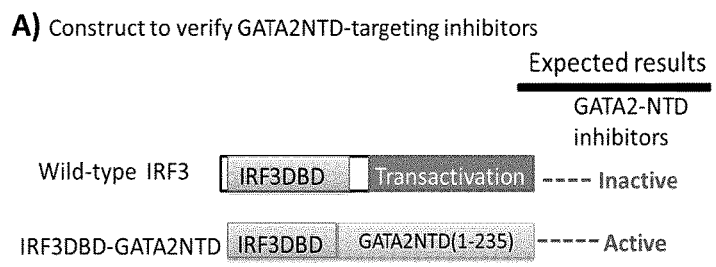
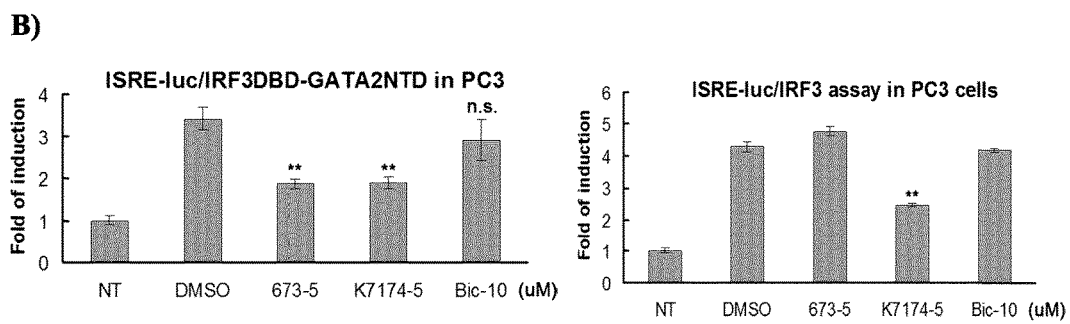
Figure 2.10

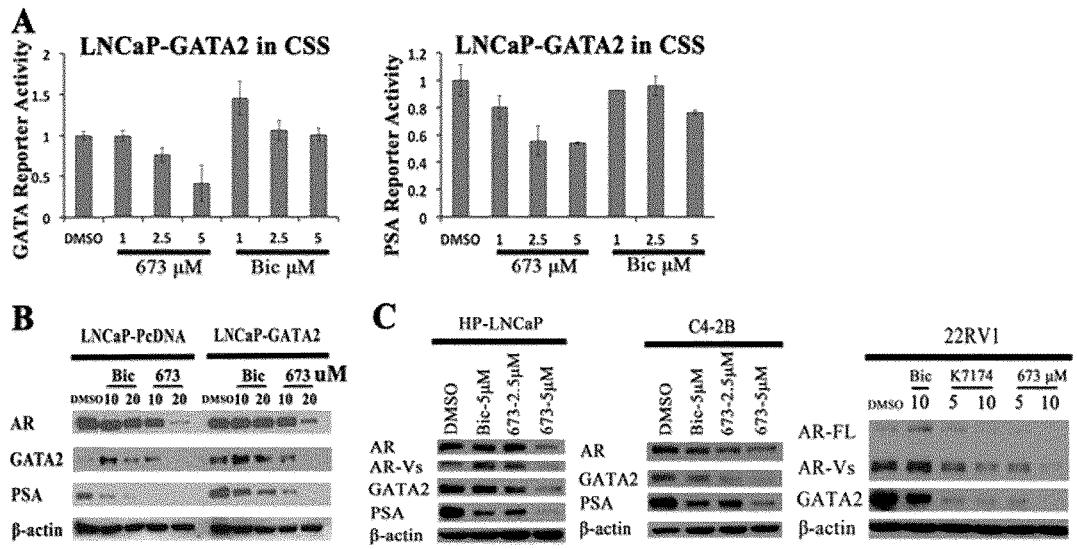
Figure 2.11
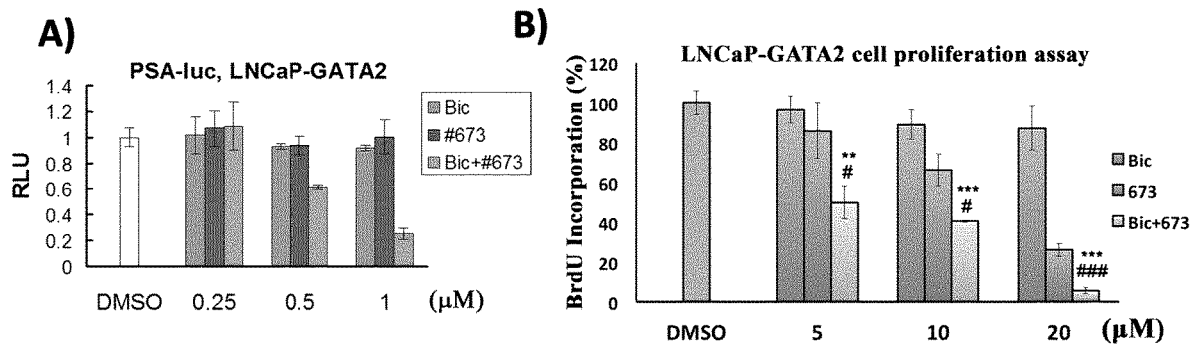
Figure 2.12

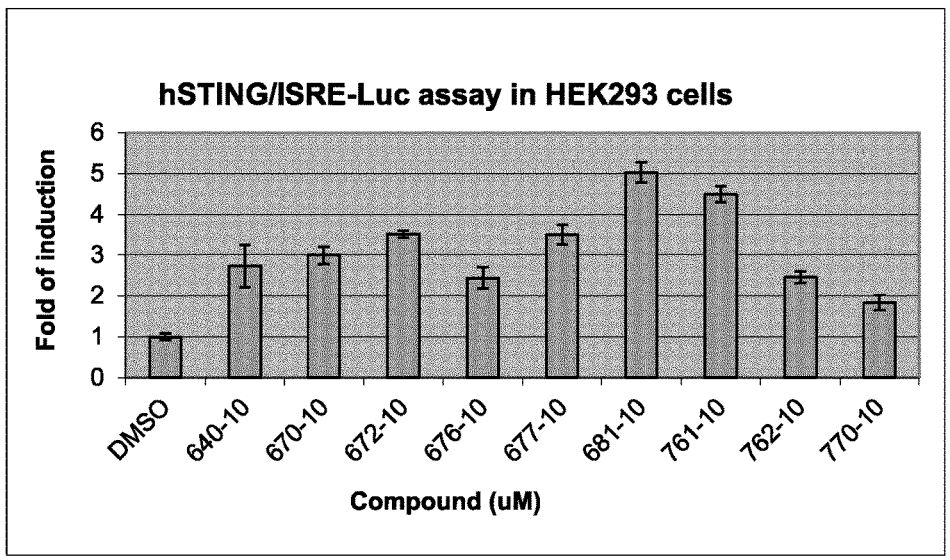
Figure 3.1a)
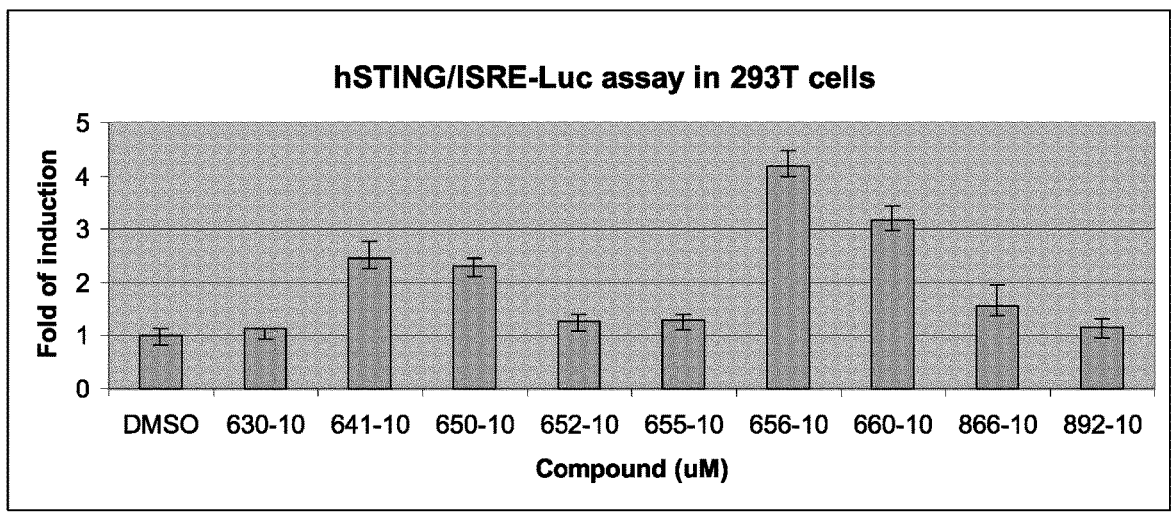
Figure 3.1b)

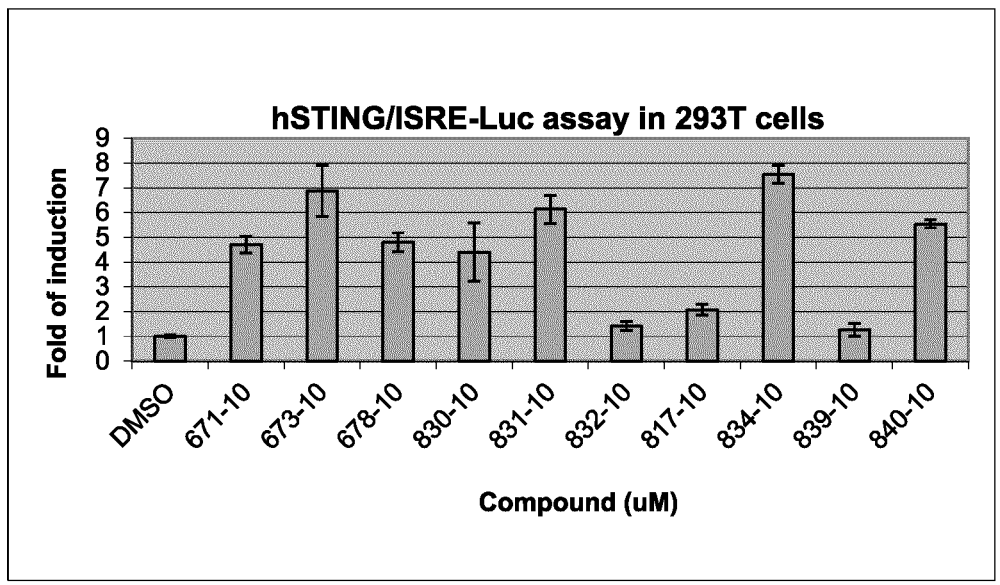
Figure 3.1c)
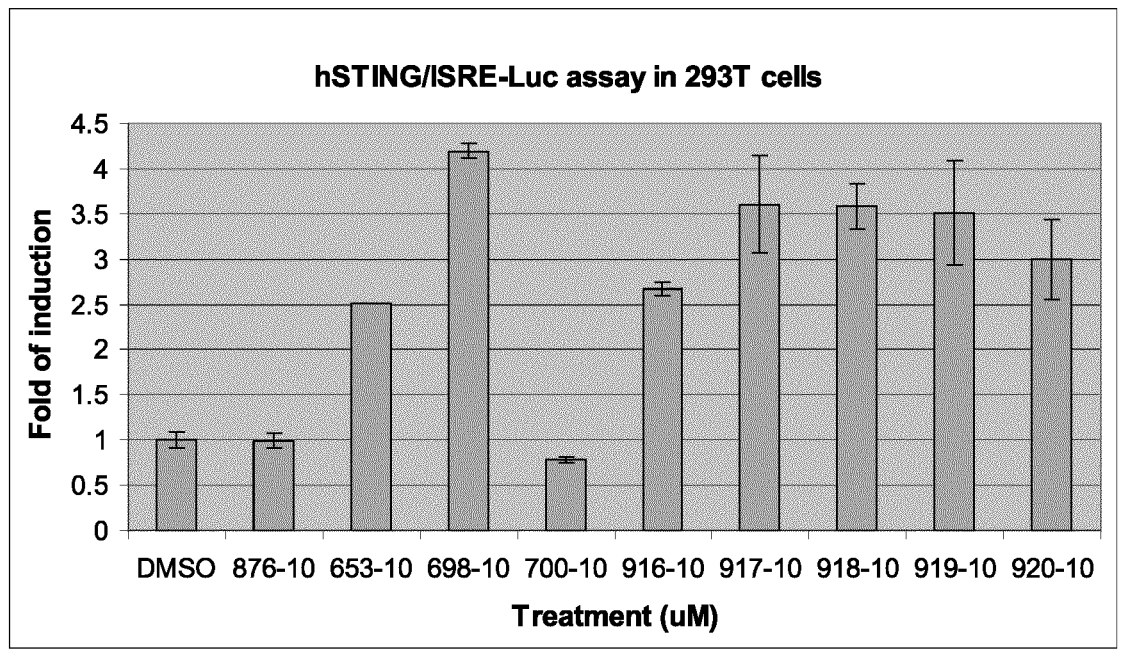
Figure 3.1d)

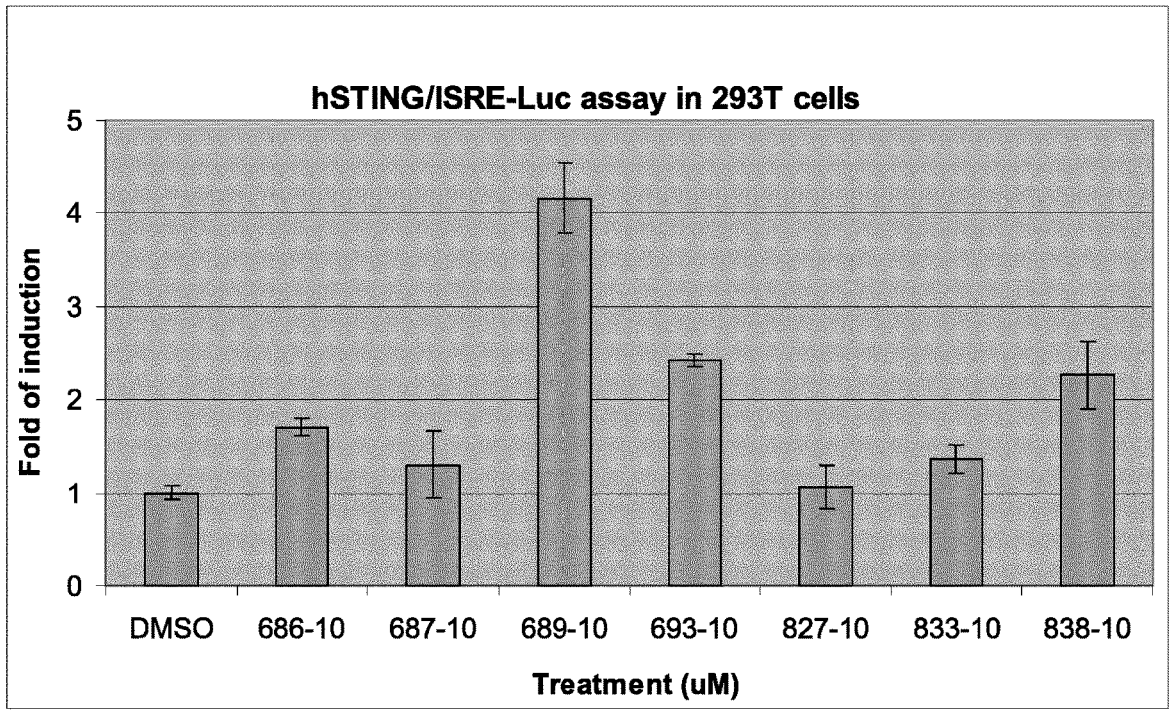
Figure 3.1e)
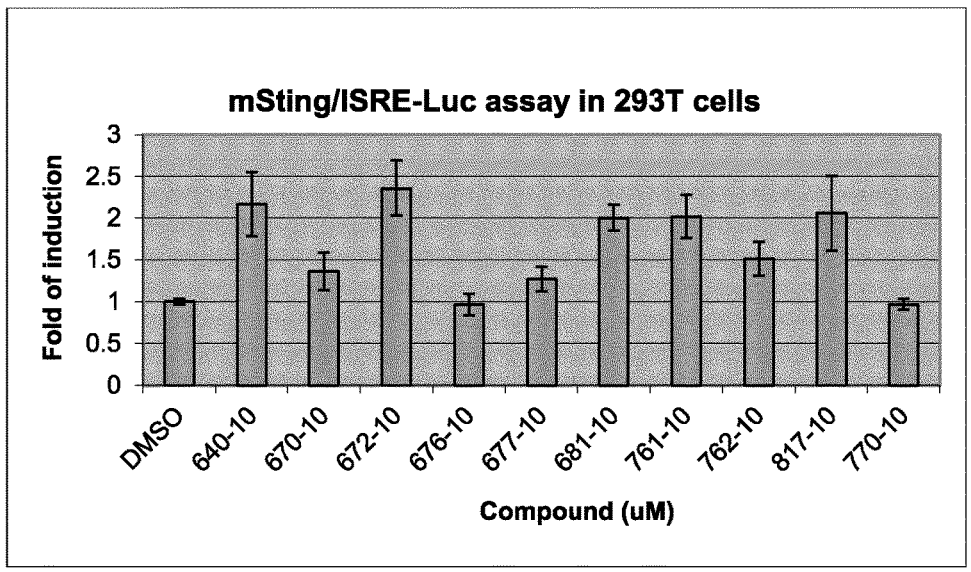
Figure 3.2

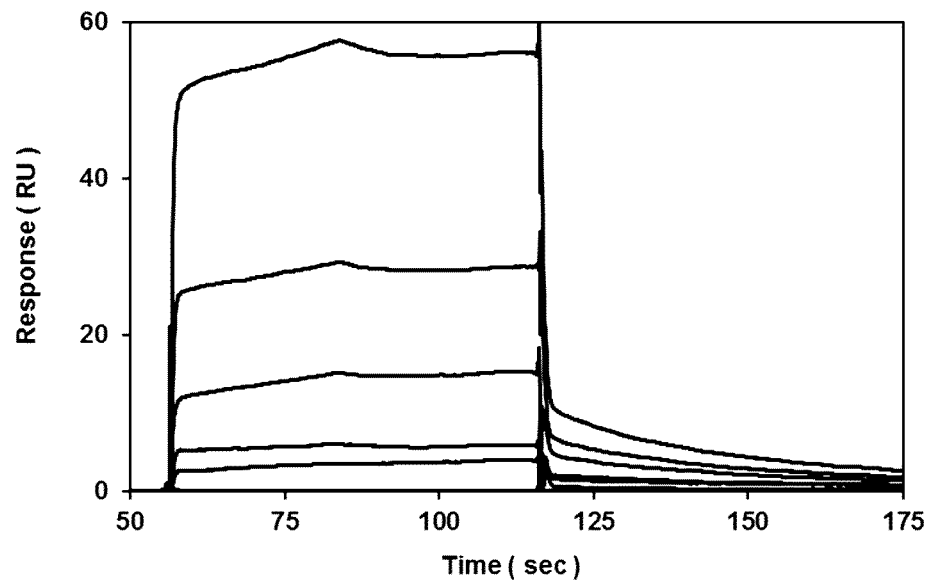
Figure 3.3
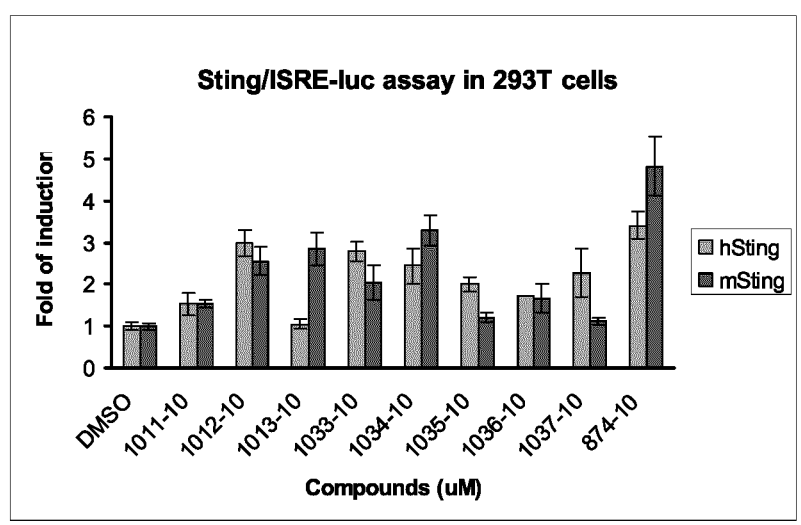
Figure 3.4a)

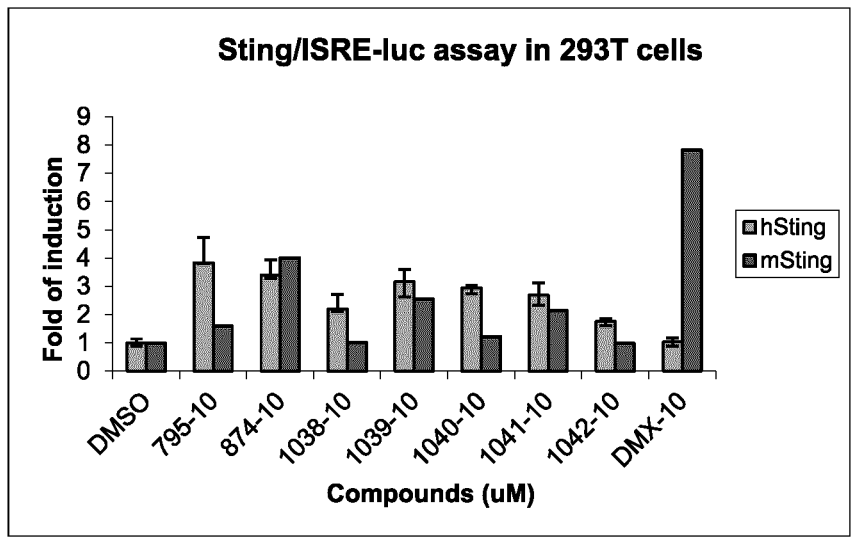
Figure 3.4b)
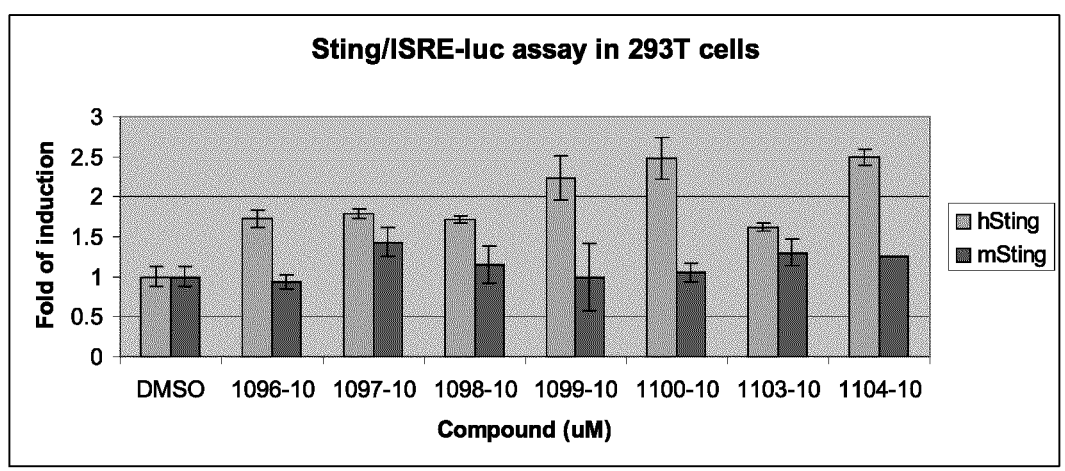
Figure 3.4c)

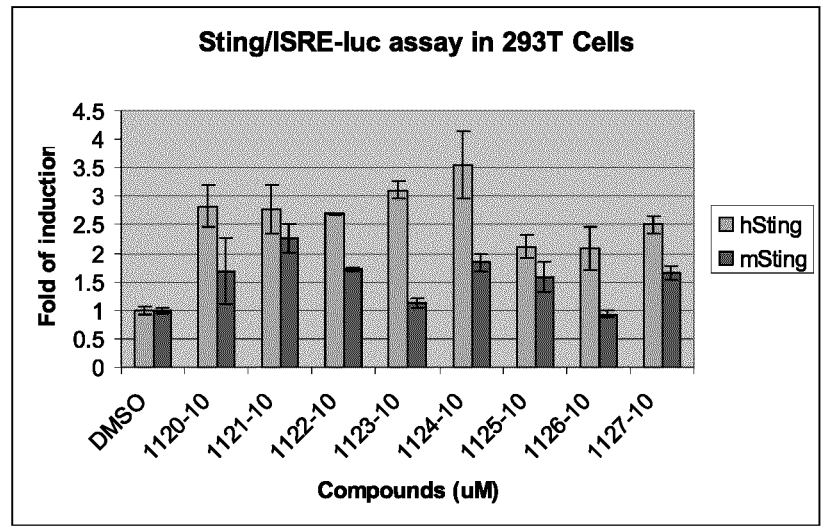
Figure 3.4d)
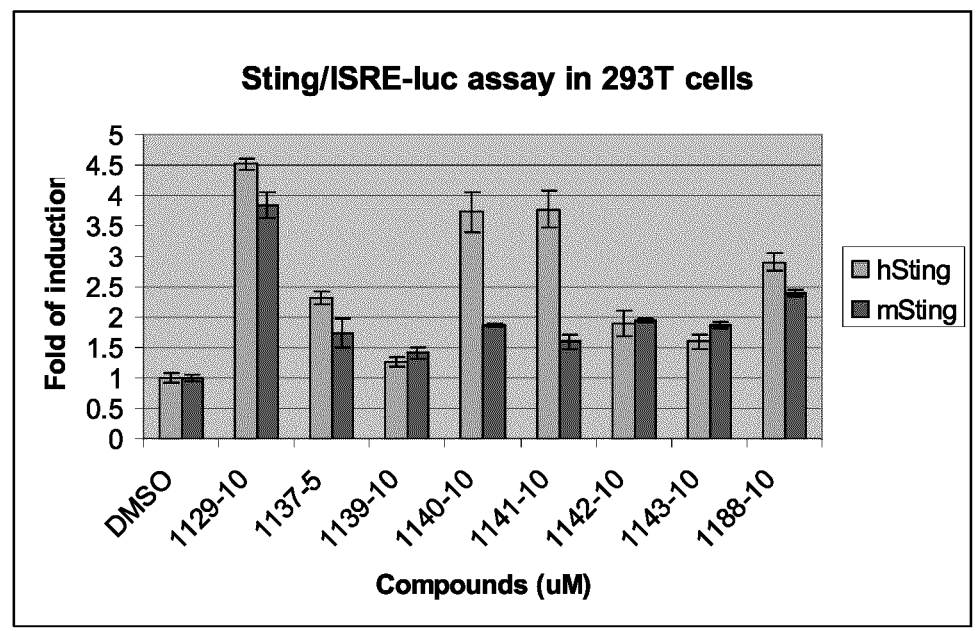
Figure 3.4e)

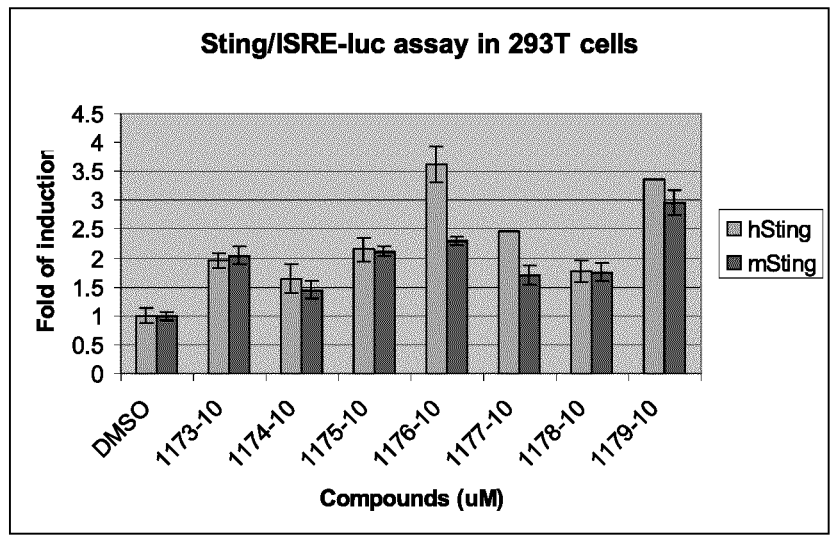
Figure 3.4f)
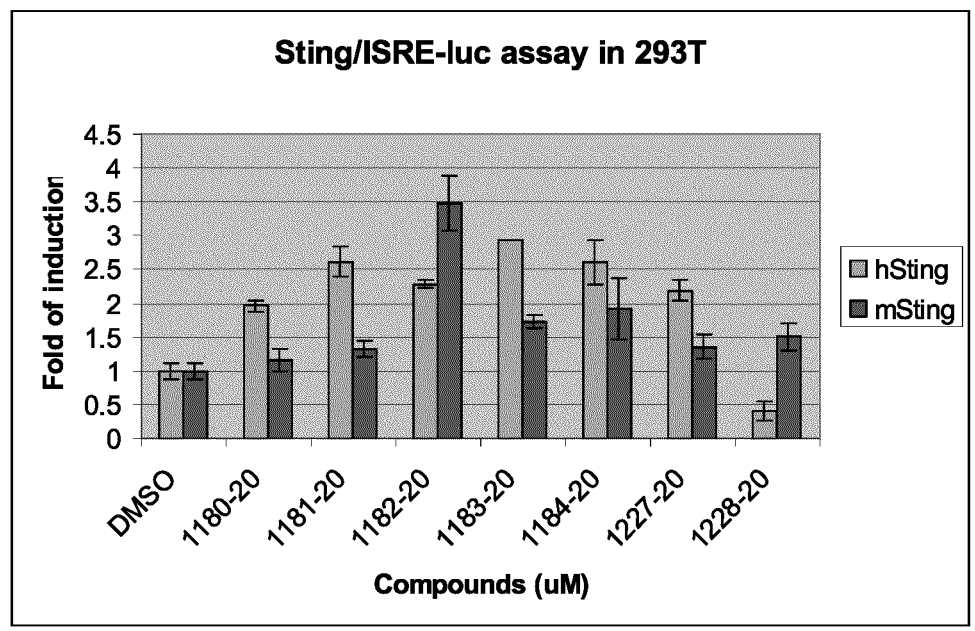
Figure 3.4g)

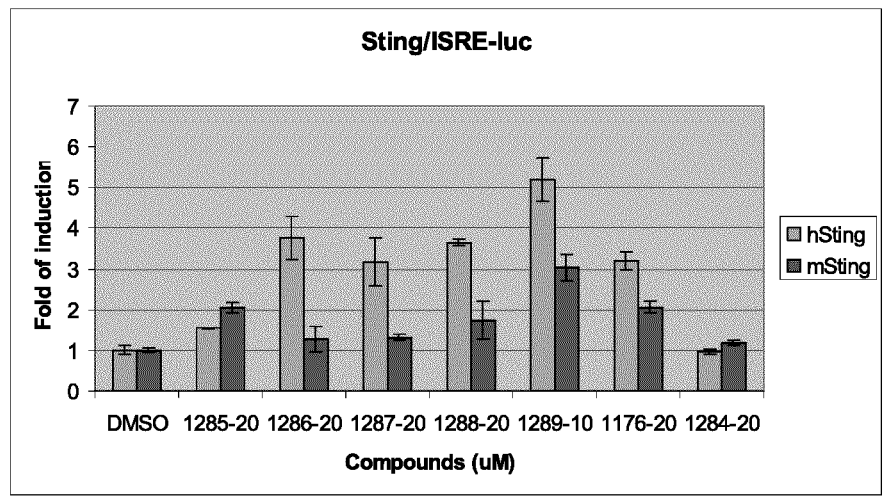
Figure 3.4h)
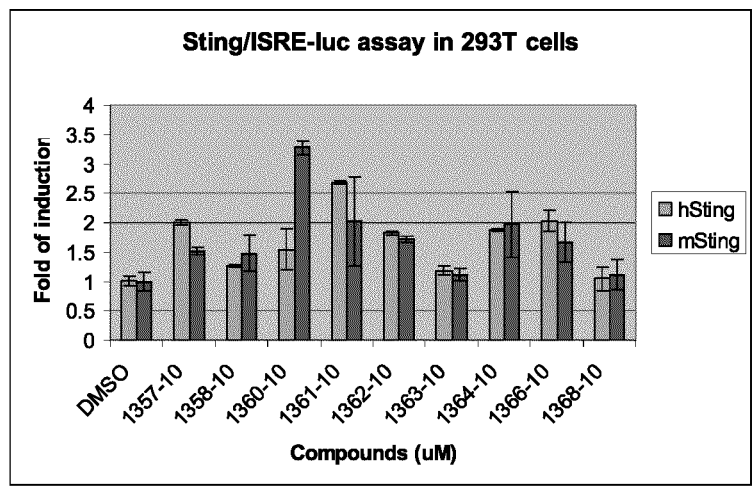
Figure 3.4i)

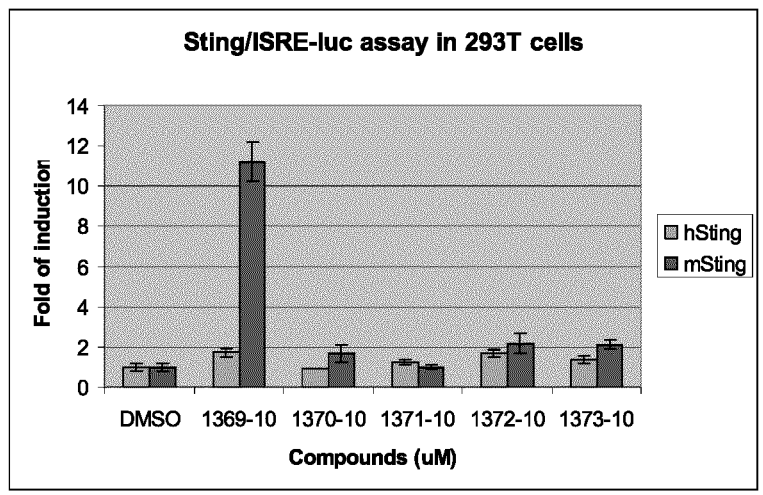
Figure 3.4j)
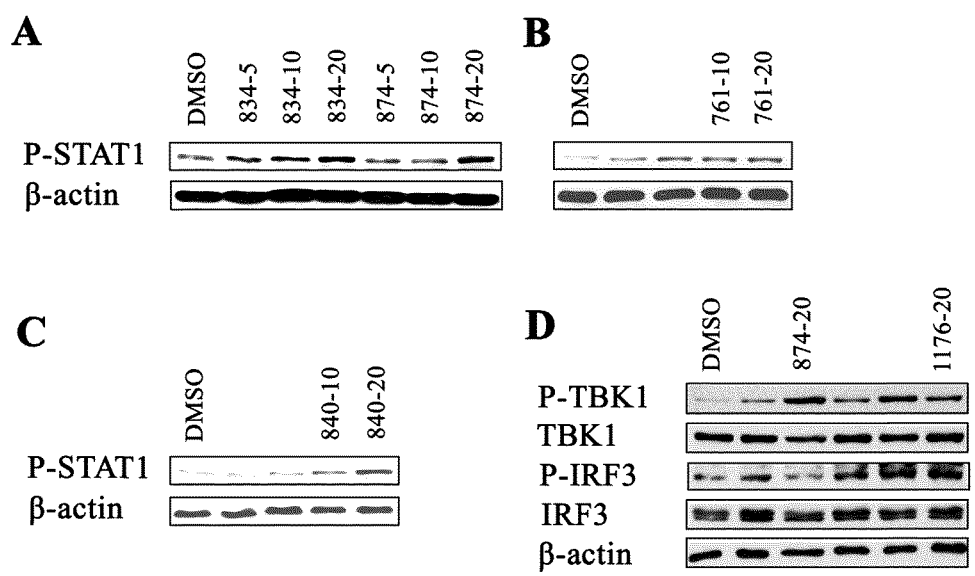
Figure 3.5

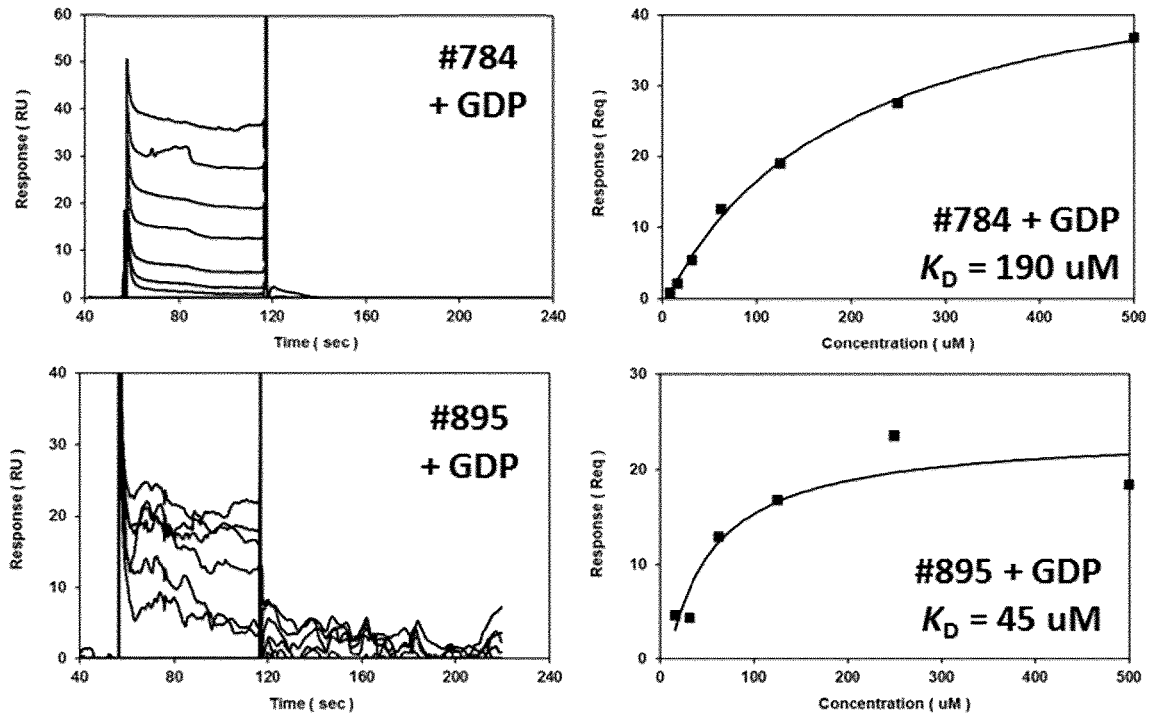
Figure 4.1
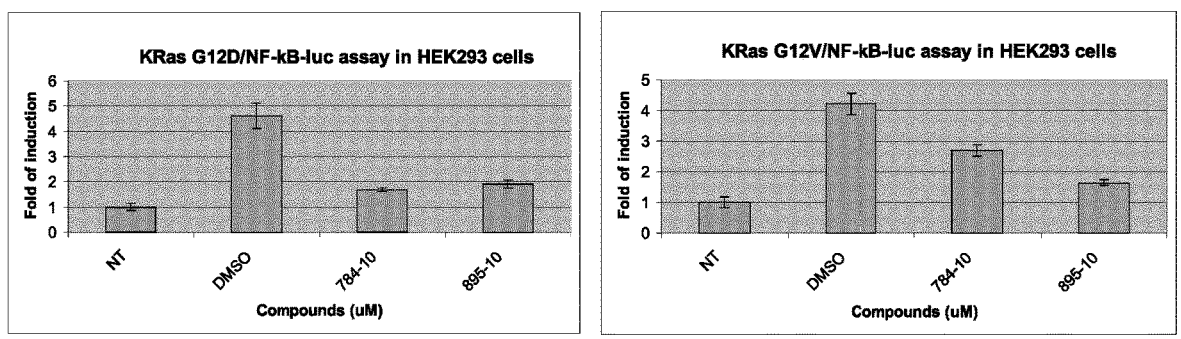

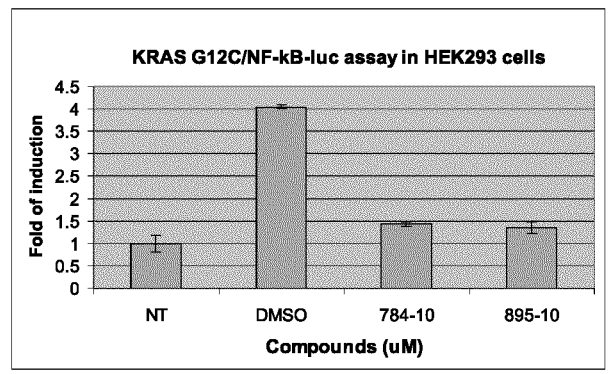
Figure 4.2a)
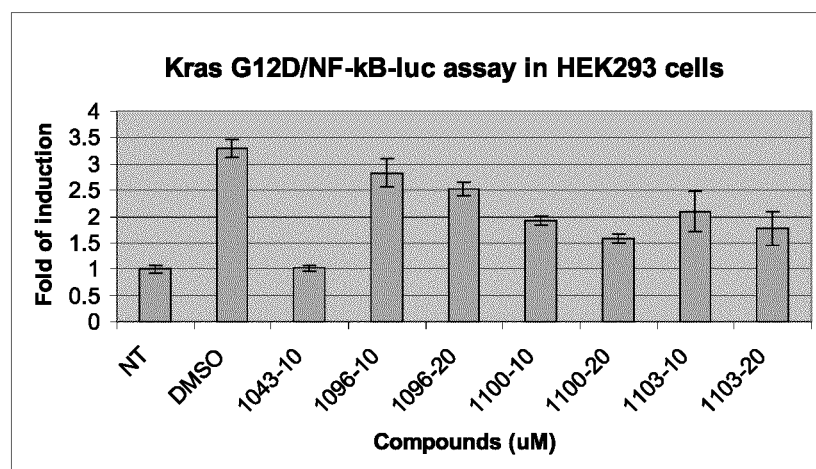
Figure 4.2b)

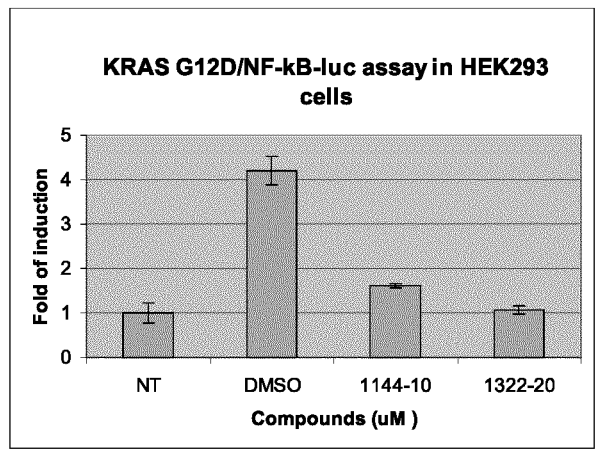
Figure 4.2c)
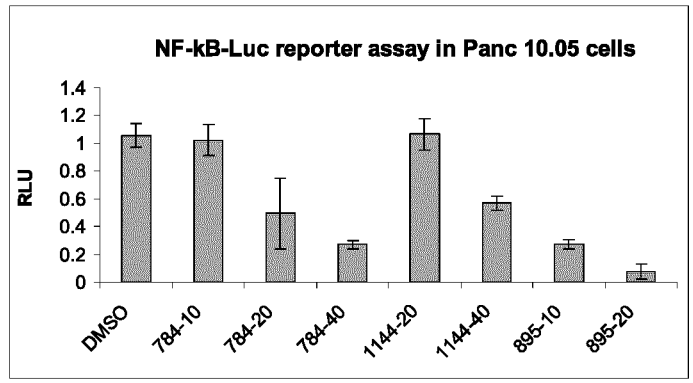
Figure 4.3a)
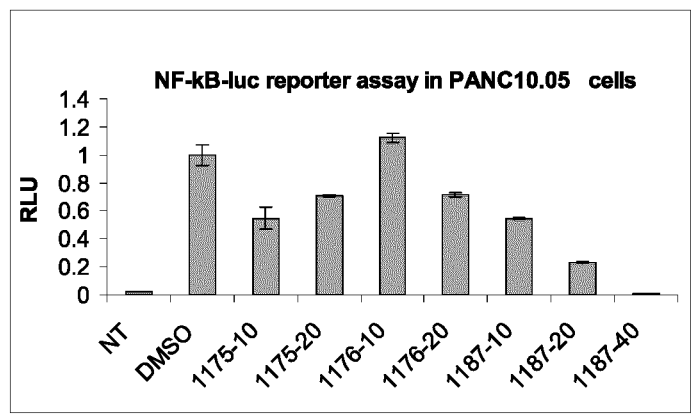
Figure 4.3b)

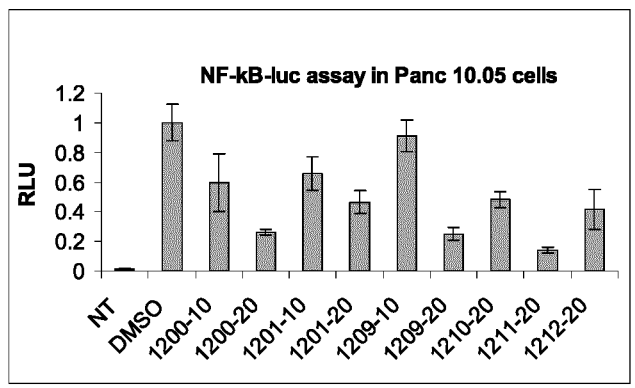
Figure 4.3c)
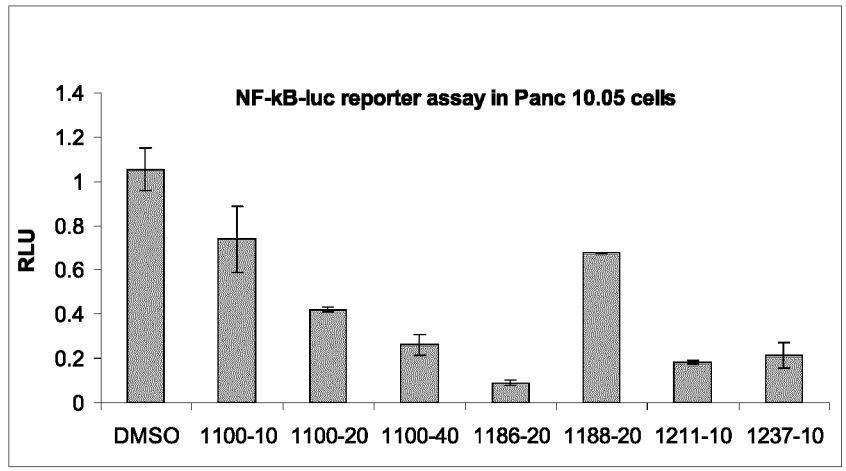
Figure 4.3d)
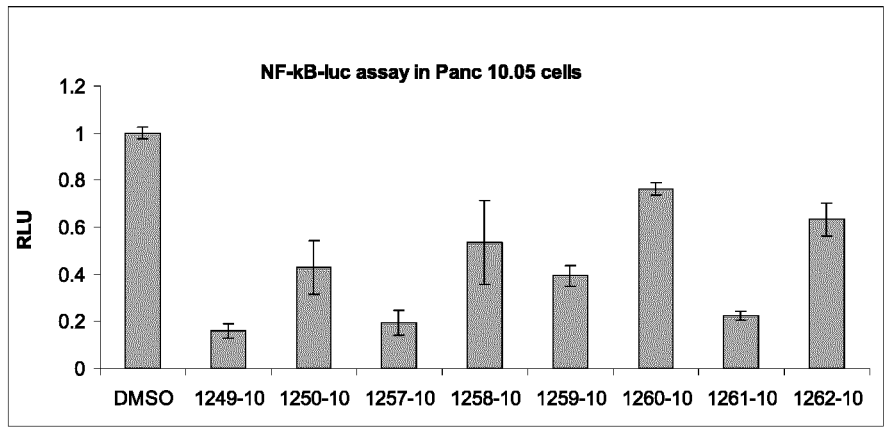
Figure 4.3e)

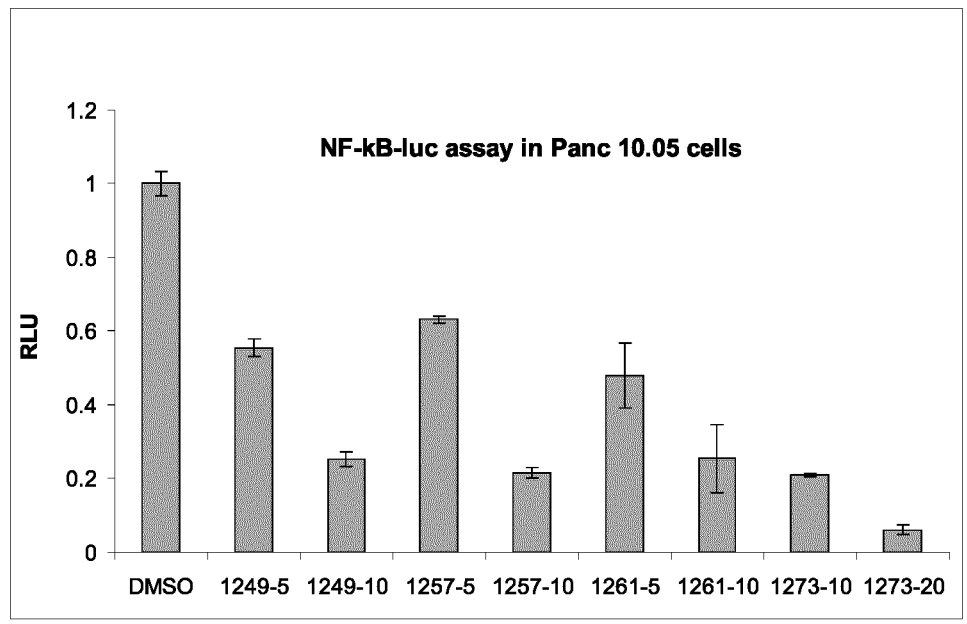
Figure 4.3f)
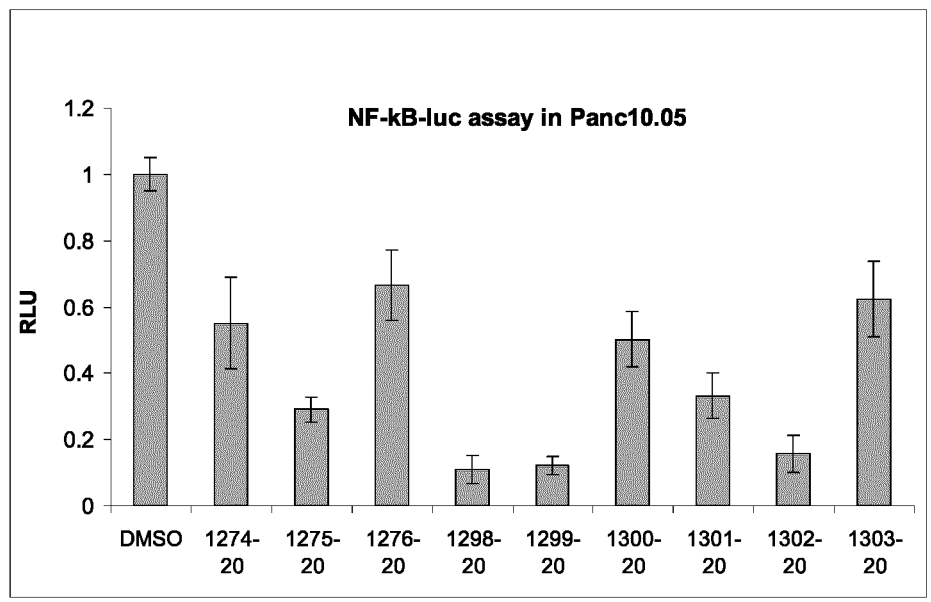
Figure 4.3g)

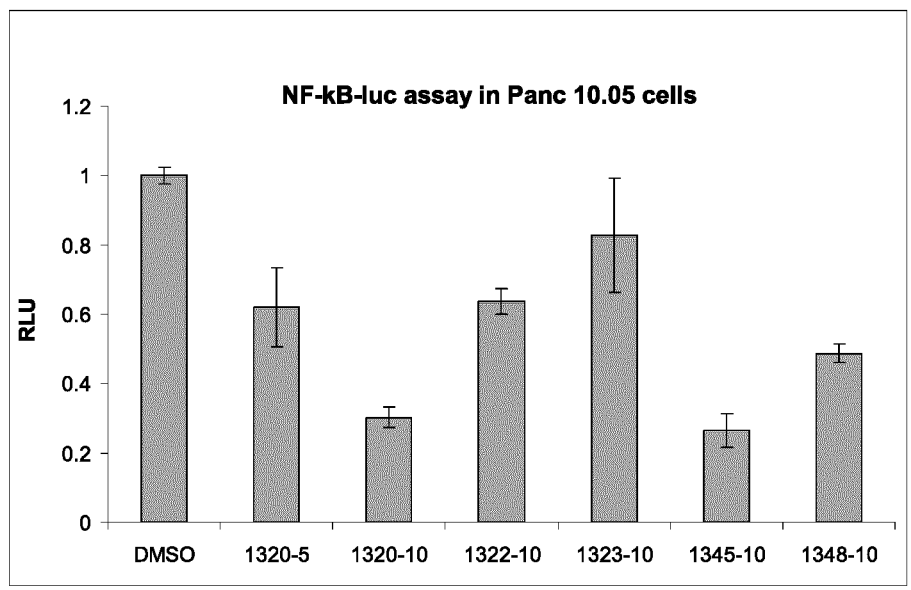
Figure 4.3h)
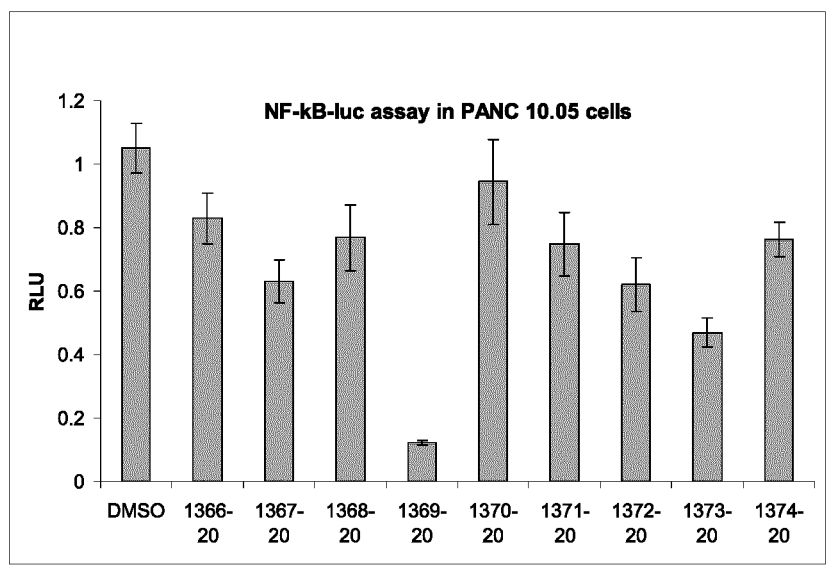
Figure 4.3i)

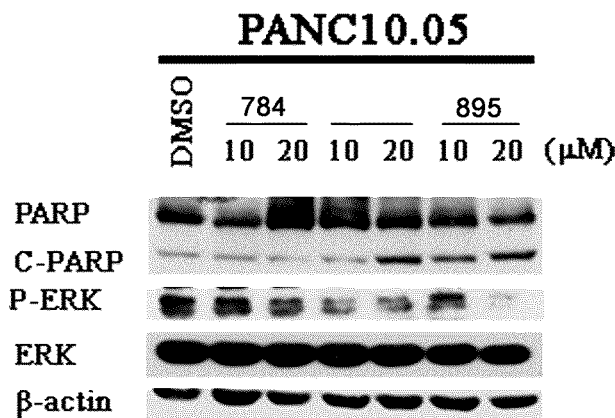
Figure 4.4a)
PANC 10.05 cells
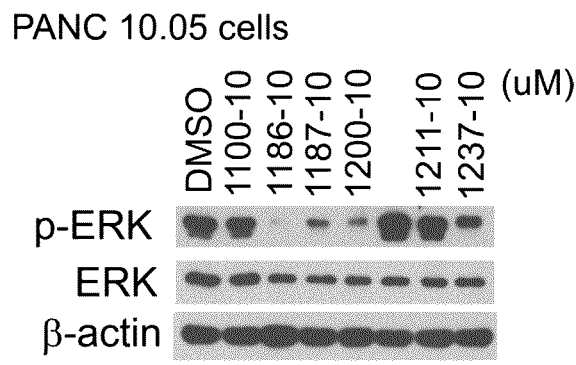
Figure 4.4b)
HCT-116 cells
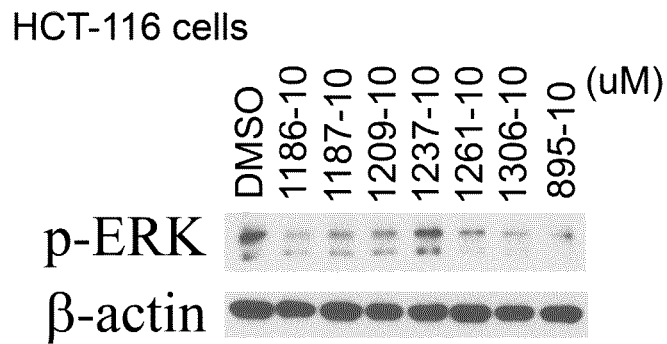
Figure 4.4c)

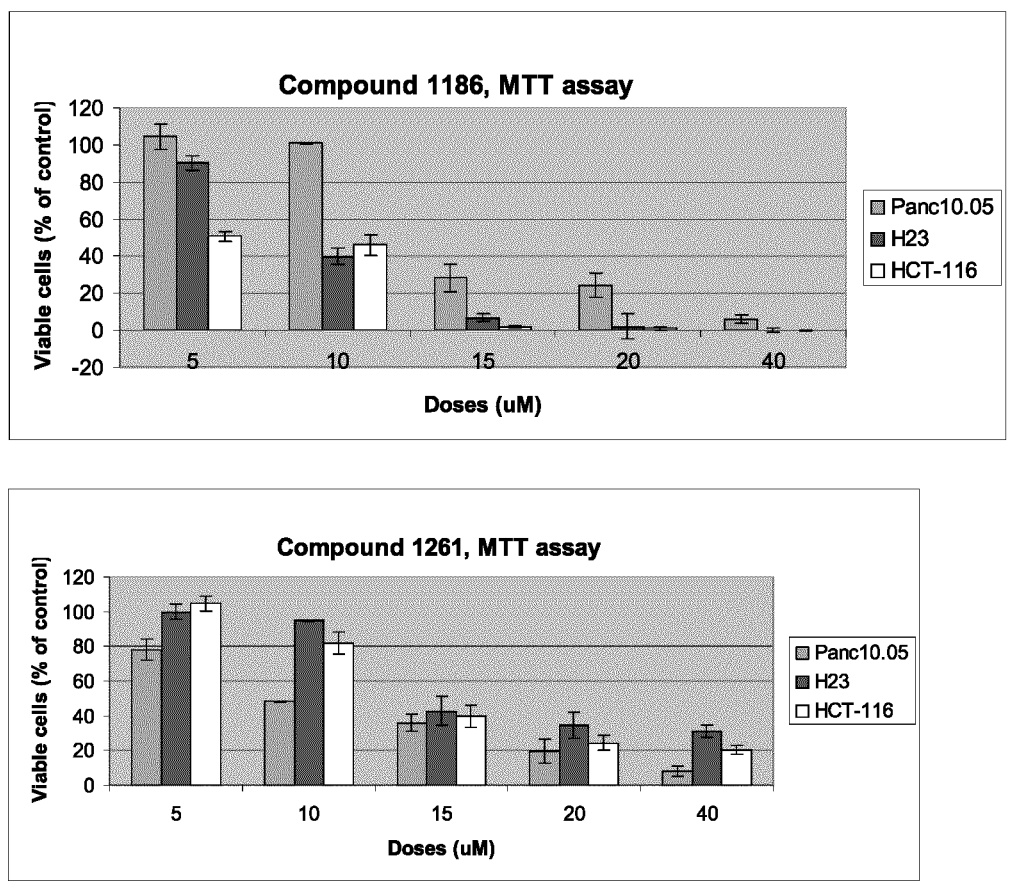
Figure 4.5

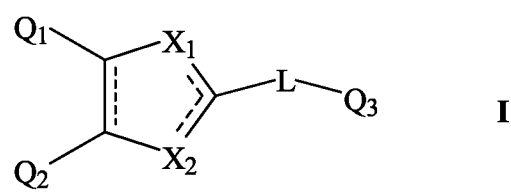
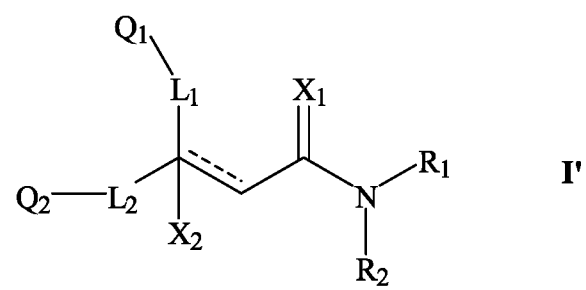
Figure 5

SUBSTITUTED OXAZOLES FOR THE TREATMENT OF CANCER

CROSS-REFERENCE TO RELATED APPLICATIONS

This application is a is a National Entry Application of PCT application no PCT/CA2016/050866 filed on Jul. 22, 2016 and published in English under PCT Article 21(2), under number WO 2017/011920 A1 which itself claims benefit of U.S. provisional application Ser. No. U.S. 62/195,485, filed on Jul. 22, 2015. All documents above are incorporated herein in their entirety by reference.

FIELD OF THE INVENTION

The invention relates generally to compounds, their preparation and their use in the treatment of medical conditions such as cancers and other medical conditions including immune disorders.

BACKGROUND OF THE INVENTION

Lung cancer is one of the leading causes of cancer-related death worldwide. Recent studies indicate that non-small cell lung cancer (NSCLC) patients with KRAS mutation fail to benefit from adjuvant chemotherapy and do not respond to EGFR inhibitors. Up until today, no approved therapy exists for patients with KRAS mutations, which comprise at least 25% of patients with lung cancer.[1] Current efforts to develop inhibitors of KRAS have fallen short of expectation so far, for example: 1) farnesyl protein transferase inhibitors were developed to alter RAS membrane localization, but they failed in the treatment of RAS-dependent cancers because of a compensatory prenylation of RAS;[2] 2) efforts to inhibit KRAS protein synthesis by oligonucleotides have been hindered by drug delivery issues;[3] 3) efforts to inhibit downstream effectors of KRAS have been on for decades, but it turned out that Ras inhibitors can activate ERK via feedback loop and MEK inhibitors can activate AKT.[4] Several kinases were shown to be synthetic lethal with KRAS mutant NSCLC.[5,6]

Recently, GATA2 transcriptional factor was found to be essential for the viability of KRAS mutant NSCLC cells, but not for the wild-type KRAS cells.[7,8] Critically, whole-body deletion of GATA2 after KRAS-mutant tumors had already formed was well tolerated by the host and led to dramatic tumor regression in mice.[7] In another study, Shen et al. demonstrated that nanoparticle mediated GATA2 siRNA delivery significantly inhibited tumor growth in the KRAS mutant A549 xenograft, but was harmless to KRAS wild-type H226 model.[9] Katsumura et al. further showed that GATA2 network can be activated by RAS via p38, conferring a selective advantage to RAS-transforming cells.[10] These studies indicated that GATA2 is an attractive target for therapeutic exploitation for KRAS-mutant NSCLC. Accordingly, there is a need to develop chemical inhibitors of GATA2.

However, it is not trivial to identify selective inhibitors of GATA2. Firstly, transcriptional factors are traditionally considered difficult to be inhibited by small molecules and because of this, they are thought to be 'undruggable'. Secondly, it is important for chemical inhibitors to achieve selectivity towards GATA2 and avoid any interference with other members of GATA family. For example, GATA1 contributes to the silencing of genes associated with cellular proliferation such as Kit and Myc11,[12] whereas GATA3 might function similarly to tumor suppressor.[13] The structures of GATA family members share highly conservative zinc finger domains. Fortunately, outside the zinc finger domains such as the N-terminus, there is relatively little conservation between distinct members of the GATA family[13,14] and we believe this could provide a structural basis for achieving selectivity toward GATA2. It appears that to date, there is only one GATA inhibitor, K7174, with an IC50 of approximately 15 µM in reporter assay.[15] Selectivity of K7174 among the six GATA members does not appear to be known.

On a related front, currently, advanced prostate cancer is treated by suppressing androgen receptor (AR) signaling.[16,17] Since AR could be activated via multiple mechanisms, inhibition of one or two of these mechanisms could be initially effective, but drug resistance can rapidly develop due to kick-in of other mechanisms, resulting in lethal castration-resistant prostate cancer (CRPC).[18] Current treatment modalities for patients with established CRPC are limited to docetaxel-based chemotherapy. The median survival time for CRPC patients is <2 years.[19,20] MDV3100 (Xtandi) and abiraterone acetate were recently approved by FDA for treating CRPC patients. MDV3100 is a novel antiandrogen that acts as a full antagonist even under elevated level of the AR. Abiraterone acetate is an oral 17α-hydroxylase inhibitor that blocks steroid biosynthesis in the adrenal gland and possibly within the tumor.[21] Clinical data from recent phase I/II and III clinical trials of both abiraterone acetate and MDV3100 have reported a high level of antitumor activity in CRPC patients.[22-24] However, reports from clinical trials to date also suggest that resistance to abiraterone acetate and MDV3100 commonly develops within 1-3 years in CRPC patients.[25-27] The therapeutic effects of all of the currently available AR-targeting agents are short-lived. The AR-GATA2 feedback loop likely plays a role in the emergence of resistance to castration and to the use of antiandrogens. Therefore, use of a GATA2 inhibitor, alone or in combination with an antiandrogen may lead to a long-lasting inhibition of the AR signaling in cancers such as prostate cancer and thus constitutes an effective therapy.

According, there is a need to develop chemical compounds that inhibit GATA2. More specifically, there is a need to develop chemical compounds that selectively inhibit GATA2. Moreover, there is a need to develop chemical compounds that selectively inhibit GATA2 and that are selectively toxic to the KRAS mutant NSCL and/or effective against CRPC cells.

On another related front, protein products of tumor specific chromosomal translocations provide unique targets for antitumor therapies. Fusions between the androgen-regulated TMPRSS2 and ETS transcription factors were discovered in prostate cancer.[28] The most common fusion, TMPRSS2-ERG, is present in approximately 50% of localized prostate cancers and metastatic prostate cancer.[29,30] ERG is a member of ETS family transcriptional factors, which are critical for the regulation of expression of cell cycle-, apoptosis-, angiogenesis- and metastasis-related genes.[31] As it is the TMPRSS2 promoter that is fused with ERG, the protein product of TMPRSS2-ERG is ERG protein.[32] As TMPRSS2 is an AR target, TMPRSS2-ERG fusion results in regulation of ERG protein expression by AR via the TMPRSS2 promoter.[33] Accumulated studies in patients, mouse and cellular models of prostate cancer have indicated that aberrant ERG expression as a result of TMPRSS2-ERG fusion plays a critical role in prostate cancer initiation and progression, suggesting that it is a driver of prostate cancer.[33]

In patients, TMPRSS2-ERG status has been linked to poor outcomes and prostate cancer specific death.[34-36] Fusion positive prostate cancers have been associated with high grade tumors,[37] and are more prone to metastasis.[38-40] Investigations of TMPRSS2-ERG fusion status as a prognosis marker reported mixed results, but the majority of findings indicate that the presence of TMPRSS2-ERG fusion gene expression in prostate cancer patients is associated with poor clinical prognosis,[34-36] and this has been extensively reviewed.[33] In mice, shRNA[41] or siRNA[42] knockdown of ERG inhibited xenograft growth of prostate cancer VCaP cells, which endogenously harbor TMPRSS-ERG fusion. Normal prostate epithelial cells do not express ERG. Expression of ERG oncoprotein due to TMPRSS2-ERG fusion are only found in prostate cancer cells and about 20% of high grade prostatic intraepithelial neoplasia (PIN) intermingled with prostate cancer cells,[43-45] underlying the specificity of ERG for prostate cancer. At the molecular level, ERG was found to directly regulate a series of targets that are critical for prostate cancer progression:[46] 1) ERG promotes epithelial to mesenchymal transition (EMT) in immortalized prostate epithelial cells through the ZEB1/ZEB2 axis;[47] 2) ERG promotes invasiveness and migration of prostate cancer cells by upregulating expression of EZH2, CXCR4, ADAM19, PLAU, PLAT, PLA1A, Osteopontin, MMP1, MMP3 and MMP9;[46,48-50] 3) ERG regulates prostate inflammation via HPGD, NF-κB and TLR4;[51,52] 4) ERG regulates prostate cancer cells' epigenetic reprogramming through EZH2, HAT and HDACs;[50,53] 5) ERG inhibits a number of prostate differentiation genes such as SLC45A3/Prostein, and abrogates the prostate epithelial differentiation program;[32,42] and 6) ERG upregulates c-Myc oncogene and down-regulates tumor suppressor NKX3.1 expression in prostate cancer cells.[42,50]

It is thus desirable to identify chemical inhibitors of ERG. However, ERG has no obvious functional sites to be inhibited. It has been considered difficult to identify chemical inhibitors of a transcriptional factor such as ERG.[39] Full-length ERG contains one pointed (PNT) domain (residues 120-206) and one ETS DNA-binding domain (DBD) (residues 318-398). To date, only one compound, YK-4-279, was shown to inhibit ERG.[55]

On yet another related front, ETV1 is an oncogenic ETS transcriptional factor. Recent studies showed that ETV1 directs androgen metabolism and confers aggressive prostate cancer.[56] The oncogenic KIT kinase signaling in gastrointestinal stromal tumors (GIST) is potentiated by a positive feedback circuit that involves ETV1. Targeting ETV1 can disrupt this feedback circuit and represents a promising new therapeutic approach for the treatment of GISTs.[57] Importantly, an RNA interference (RNAi)-based synthetic interaction screen revealed that ETV1 is preferentially required for proliferation of diverse p53-deficient human cancer cells.[58]

Accordingly, there is also a need to develop chemical compounds that are inhibitors of oncogenic ETS proteins including ERG and ETV1.

On yet another related front, immunotherapy has emerged as a viable therapeutic option for patients with prostate cancer. Sipuleucel-T is a therapeutic cancer vaccine designed to target tumor associated antigen PAP and was approved for the treatment of minimally symptomatic metastatic prostate cancer in 2010. This provided proof of the important principle that manipulation of the immune response can affect the survival of patients with prostate cancer. Recent studies have identified the host STING (stimulator of interferon genes) pathway as a critical mechanism of innate immune sensing of cancer, that drives type I interferons (IFNs) production and promotes aggressive antitumor responses.[59] Thus, STING agonists could be candidates for testing as stimulants for anticancer immune activity. STING could be a drug target for medical conditions with immune disorders, such as cancers. Also, recent studies indicate that elevated level of STING signaling plays a critical role in various autoimmune diseases and that STING agonists induce an aggressive antiviral immune response against a series of viruses.

Accordingly, there is a need to develop chemical compounds that are STING agonists as immunotherapy for cancer. Such cancer includes prostate cancer lung cancer, melanoma as well as other types of cancer. STING agonists could also be developed as antivirus agents. There is also a need to develop chemical compounds that are STING antagonists as novel therapeutics for other medical conditions with immune disorders such as autoimmune diseases.

On yet another related front, pancreatic ductal adenocarcinoma (PDAC) is the fourth among cancer-related death in the USA.[62] The overall 5-year survival rate is <5% over the past 3 decades despite the important advances in the understanding of the molecular biology of pancreatic cancer and the tremendous efforts in the development of therapeutic strategies.[63] Oncogenic KRAS is mutationally activated in >90% PDAC. In PDAC, activated mutations of KRAS are found predominantly at codon G12 (98%) of all KRAS mutations in PDAC and the predominant substitution is G12D (51%), followed by G12V (30%). Recent findings in mouse models have shown that oncogenic KRAS mutants are sufficient for pancreatic cancer initiation, progression and maintenance.[64,65] KRAS mutants are also critical drivers of colorectal cancer, lung cancer, endometrium cancer, ovarian cancer and other cancers.

Recently, small molecule inhibitors were discovered that covalently bind to the Cys at residue 12 in KRAS mutant (KRAS G12C), which is the most common KRAS mutation in non-small-cell lung cancer (NSCLC).[66] For the first time, the study suggests that it is possible to target the KRAS G12C mutant with a small molecule. By using the same strategy, another group also discovered a mutant-specific inhibitor ARS-853 that is covalently binding to KRAS G12C.[67] In addition, a GDP mimetic compound SML-10-70-1 was shown to covalently bind to KRAS G12C.[68] However, all of these G12C mutant inhibitors are inactive against the KRAS G12D or KRAS G12V mutants.

Accordingly, there is a need to develop chemical compounds that inhibit various KRAS mutants including G12D, G12C, G12V G13D, etc.

SUMMARY OF THE INVENTION

The inventors have designed and prepared novel chemical compounds. The compounds according to the invention may be used in the treatment of medical conditions involving GATA2; ERG, ETV1 or other immune disorders; STING and/or KRAS mutants. Such medical conditions may, for example, be various types of cancer or medical conditions with immune disorders.

In an aspect, compounds according to the invention are GATA2 inhibitors. As such they may be used in the treatment of: KRAS mutant cancers, for example, KRAS mutant NSCLC and KRAS mutant colon cancer; prostate cancer, both AR positive prostate cancer and AR negative prostate cancer; leukemia; breast cancer including triple negative breast cancer and melanoma.

In another aspect, compounds according to the invention are ERG inhibitors. As such, they may be used in the treatment of: prostate cancer including TMPRSS2-ERG positive prostate cancer; leukemia.

In yet another aspect compounds according to the invention are ETV1 inhibitors. As such, they may be used in the treatment of: p53-negative or p-53 defective human cancers; prostate cancer including TMPRSS2-ETV1 positive cancer; gastrointestinal stromal tumors (GIST).

In yet another aspect, compounds of the invention are STING agonists. As such, they may be used as immunotherapy for cancer patients or as stimulants in patients undergoing cancer treatment.

In yet another aspect, compounds of the invention are direct inhibitors of various KRAS mutants including but not limited to G12D, G12C, G12V and G13D. As such, they may be used in the treatment of pancreatic cancer, lung cancer, colorectal cancer and other KRAS mutant-driven cancers.

The invention thus provides the following according to aspects thereof:

(1) A compound of general formula I below, or a pharmaceutically acceptable salt thereof, or a solvate or hydrate thereof

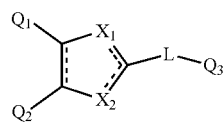

I wherein:
$Q_1$, $Q_2$ and $Q_3$ are each independently present or absent, and are each independently selected from alkyl, cycloalkyl, alkene, alkyne, aryl and alkylaryl, a 5 to 12-member single or bicyclo ring, or $Q_1$ and $Q_2$ together form a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, $NH_2$, a halogen atom, a halogeno alkyl, a halogeno alkoxy, a halogeno thioalkoxy, CN, $NO_2$, $S(=O)_2$ and $Se(=O)_2$;

$X_1$ and $X_2$ are each independently selected from O, S, $S(=O)_2$ $Se(=O)_2$, C, N and NR wherein R is selected from H, $S(=O)_2R^1$, $S(=O)_2NR^1R^2$, $COR^1$, $Se(=O)_2R^1$, alkyl, cycloalkyl, alkene, alkyne, aryl, alkylaryl, a 5 to 8-member ring comprising one or more heteroatom which are the same or different; optionally, the ring comprises one or more heteroatom which are the same or different, also optionally, the ring is substituted with substituents selected from alkyl, alkene, alkyne, aryl, acyl, $CF_3$, $CH_2CF_3$, OH, $OCH_3$, $OC_2H_5$, $OCF_3$, SH, $SCH_3$, $NH_2$, a halogen atom, CN, $CH_2CN$, $(CH_2)_nCN$ (n=1-15), $NO_2$, $S(=O)_2$, $S(=O)_2R^1$, $Se(=O)_2$ and $Se(=O)_2R^1$; wherein $R^1$ and $R^2$ are each independently selected from alkyl, cycloalkyl and aryl;

L is present or absent and is a group comprising one or more of $(CH_2)$, (CH), O, S, and C=X and C—X wherein X is O, S, Se, N or $NR_1R_2$ wherein $R_1$ and $R_2$ are each independently selected from H, alkyl, cycloalkyl, alkene, alkyne, aryl, alkylaryl, a 5 to 8-member ring comprising one or more heteroatom which are the same or different; optionally, the ring comprises one or more heteroatom which are the same or different, also optionally, the ring is substituted with a substituent selected from alkyl, OH, SH, $NH_2$, a halogen atom, CN, $NO_2$ and $SO_2$; and

- - - - denotes a chemical bond that is present or absent, and wherein the heteroatom is selected from O, N, S and Se.

(2) A compound according to (1) having the general formula II below

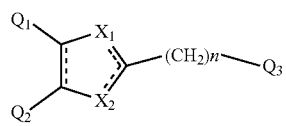

II wherein:
n is an integer from 0 to 12.

(3) A compound according to (1) having the general formula III below

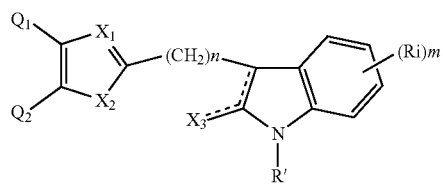

III wherein:
n is an integer from 0 to 12;
$X_3$ is as defined in (1) for $X_1$ and $X_2$ and is independent thereof;
R' and each Ri are each independently selected from H, alkyl, cycloalkyl, alkoxy, thioalkoxy, OH, SH, $NH_2$, a halogen atom, a halogeno alkyl, a halogeno alkoxy, a halogeno thioalkoxy, CN, CN, $CH_2CN$, $(CH_2)_nCN$, $NO_2$, $S(=O)_2$, $S(=O)_2R^1$, wherein $R^1$ is as defined in (1); and m is an integer from 0 to 4.

(4) A compound according to (1) having the general formula IVA or IVB below

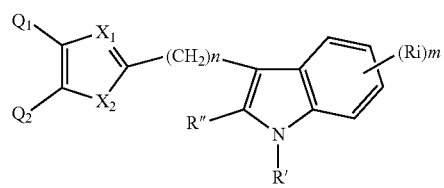

IVA

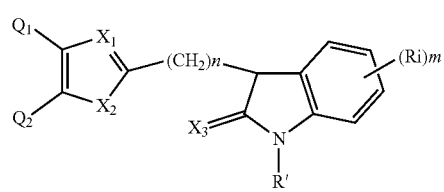

IVB wherein:
n is an integer from 0 to 12;
$X_3$ is as defined in (1) for $X_1$ and $X_2$ and is independent thereof;
R', R" and each Ri are each independently selected from H, alkyl, cycloalkyl, alkoxy, CN, $CH_2CN$, $(CH_2)_nCN$, a halogeno thioalkoxy, CN, NO$_2$, S(=O)$_2$, S(=O)$_2$R$^1$, wherein R$^1$ is as defined in (1); and m is an integer from 0 to 4.

(5) A compound according to (1) having the general formula VA, VB or VC below

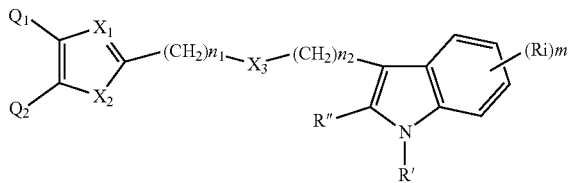

VA

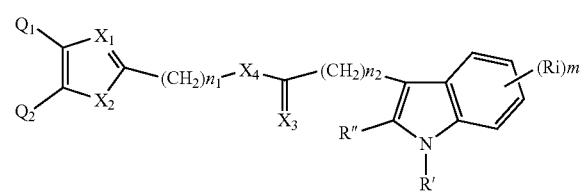

VB

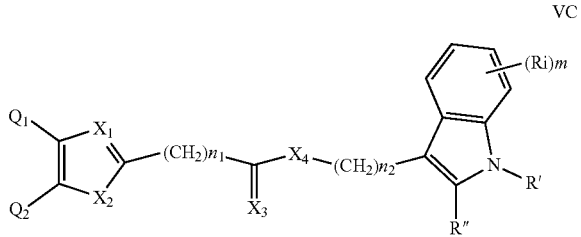

VC wherein:
n1 and n2 are each independently an integer from 0 to 6;
X$_3$ and X$_4$ are each independently as defined in (1) for X$_1$ and X$_2$ and are independent thereof;
R', R" and each Ri are each independently selected from H, alkyl, cycloalkyl, alkoxy, thioalkoxy, OH, SH, NH$_2$, a halogen atom, a halogeno alkyl, a halogeno alkoxy, a halogeno thioalkoxy, CN, CN, CH$_2$CN, (CH$_2$)$_n$CN, NO$_2$, S(=O)$_2$, S(=O)$_2$R$^1$, wherein R$^1$ is as defined in (1); and
m is an integer from 0 to 4.

(6) A compound according to (1) having the general formula VI below

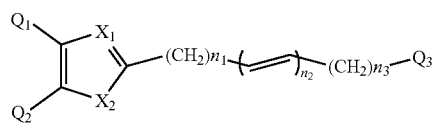

VI wherein:
n1, n2 and n3 are each independently an integer from 0 to 6.

(7) A compound according to (1) having the general formula VII

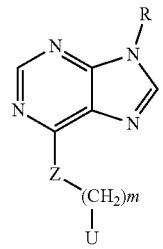

VII wherein:
U is as defined in (1) for Q$_1$, Q$_2$ or Q$_3$;
Z is a heteroatom selected from O, N, S and Se;
R is selected from H, alkyl, cycloalkyl, alkoxy, thioalkoxy, OH, SH, NH$_2$, a halogen atom, a halogeno alkyl, a halogeno alkoxy, a halogeno thioalkoxy, CH$_2$CN, (CH$_2$)$_n$CN, CN, NO$_2$, S(=O)$_2$, S(=O)$_2$R$^1$, wherein R$^1$ is as defined in (1); and
m is an integer from 0 to 6.

(8) A compound according to (1) or (7) having the general formula VIII below

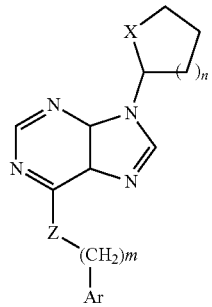

VIII wherein:
Ar is a mono or bicyclic carbocyclic ring system or a multiple ring system wherein the rings are fused together, optionally, the ring comprises one or more heteroatom which are the same or different, also optionally, the ring is substituted with substituents selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, wherein R$^1$ is as defined in (1);
X is as defined in (1) for X$_1$ or X$_2$;
n is an integer from 0 to 6; and
m is an integer from 0 to 12.

(9) A compound according to (1) having the general formula "Class Ia'", "Class Ib'", "Class Ic'" or "Class Id'" below

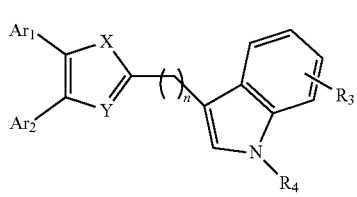

Class Ia'

-continued

Class Ib'

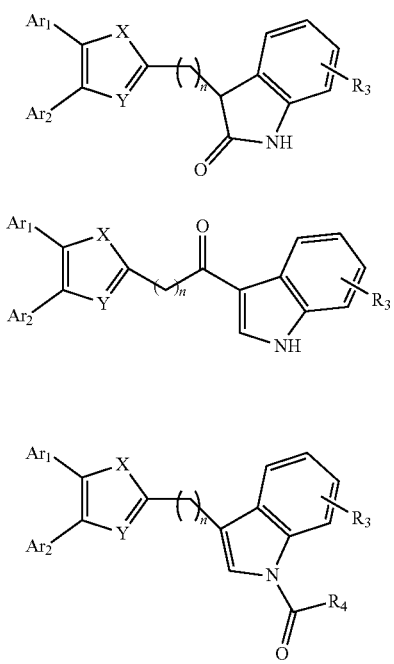

Class Ic'

Class Id' wherein:
Ar$_1$ and Ar$_2$ are each independently a mono or bicyclic carbocyclic ring system or a multiple ring system wherein the rings are fused together, optionally, the ring comprises one or more heteroatom which are the same or different, also optionally, the ring is substituted with substituents selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, wherein R$^1$ is as defined in (1);

X and Y are each independently as defined in (1) for X$_1$ or X$_2$;

R$_3$ and R$_4$ are each independently selected from H, alkyl, cycloalkyl, alkoxy, thioalkoxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, where R$^1$ is as defined in (1); and n is an integer from 0 to 12.

(10) A compound according to (9) having the general formula "Class Ia", "Class Ib", "Class Ic" or "Class Id" below Class Ia

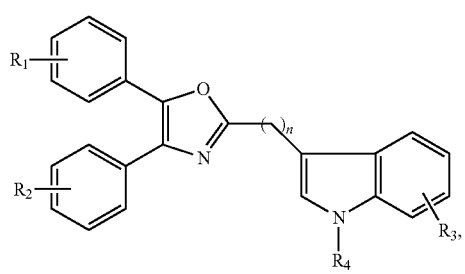

-continued

Class Ib

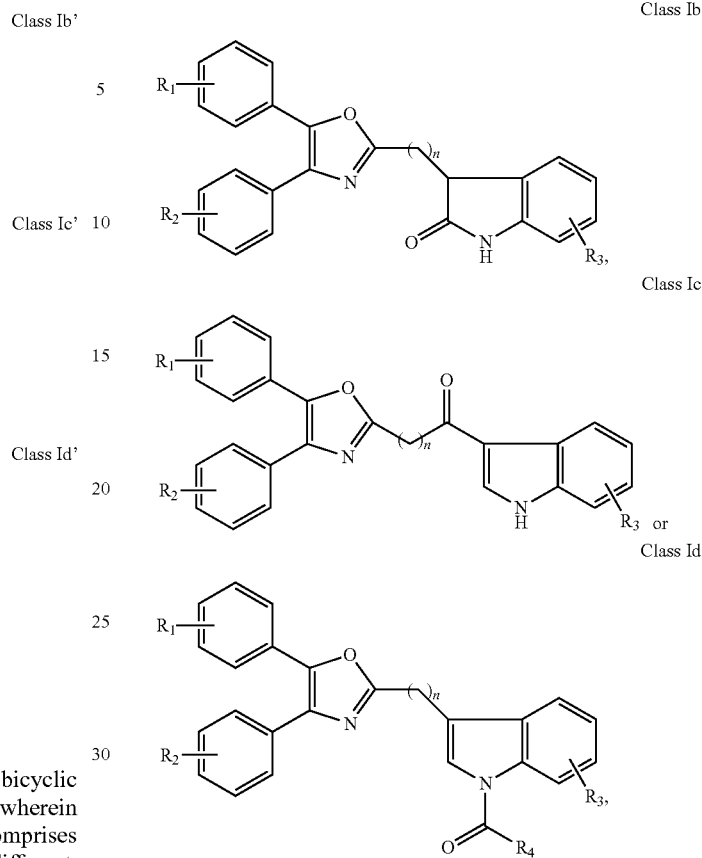

Class Ic

Class Id wherein:
R$_1$ and R$_2$ are each independently as defined in (9) for R$_3$ and R$_4$.

(11) A compound according to (10), wherein: R$_1$ to R$_4$ are each independently selected from H, OH, SH, halogen atom, alkoxy, halogeno alkyl; and n is an integer from 0 to 6.

(12) A compound according to (1) having the general formula "Class II" below

Class II

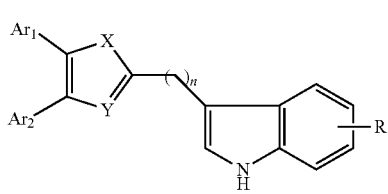

wherein:
Ar$_1$ and Ar$_2$ are each independently a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, where R$^1$ is as defined in (1);

X and Y are each independently as defined in (1) for $X_1$ and $X_2$;

R is selected from H, alkyl, cycloalkyl, alkoxy, thioalkoxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is as defined in (1); and n is an integer from 0 to 12.

(13) A compound according to (12) having the general formula "Class IIa" below

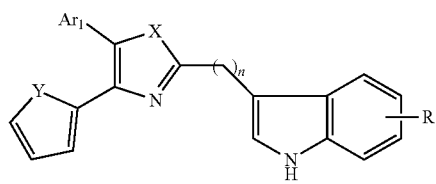

Class IIa wherein:

Ar is as defined in (12) for $Ar_1$ and $Ar_2$; and

Y is as defined in (12) for X and Y.

(14) A compound according to (13), wherein: Ar is a mono carbocyclic ring optionally comprising O or S, and optionally substituted with OH, SH, halogen atom, alkoxy, halogeno alkyl; X and Y are each independently selected from O, S and NH; R is selected from H and alkyl; and n in an integer from 0 to 6.

(15) A compound according to (1) having the general formula "Class III" below

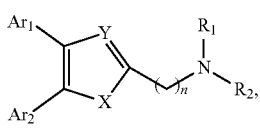

Class III wherein:

$Ar_1$ and $Ar_2$ are each independently selected from a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thio-alkylaryloxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is as defined in (1);

X and Y are each independently as defined in (1) for $X_1$ and $X_2$;

$R_1$ and $R_2$ are each independently selected from H, alkyl, cycloalkyl, alkene, alkyne, aryl and alkylaryl, a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thio-alkylaryloxy, OH, SH, $NH_2$, a halogen atom, a halogeno alkyl, a halogeno alkoxy, a halogeno thioalkoxy, $CH_2CN$, $(CH_2)_nCN$, CN, $NO_2$, $S(=O)_2$, $S(=O)_2R^1$, where $R^1$ is as defined in (1); optionally $R_1$ and $R_2$ together form a ring which is as defined above for $R_1$ and $R_2$; and n is an integer form 0 to 12.

(16) A compound according to (15) having the general formula "Class IIIa" below

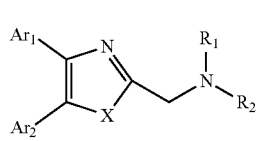

Class IIIa wherein:

X is as defined in (15) for X and Y.

(17) A compound according to (15) or (16), wherein: $Ar_1$ and $Ar_2$ are each independently a mono carbocyclic ring optionally comprising O or S, and optionally substituted with OH, SH, halogen atom, alkoxy, halogeno alkyl; and X is selected from O, S and NH.

(18) A compound according to (1) having the general formula "Class IIIa1", "Class IIIa2" or "Class IIIa3" below

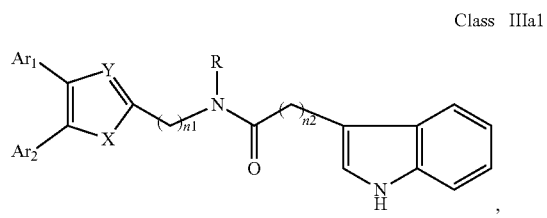

Class IIIa1

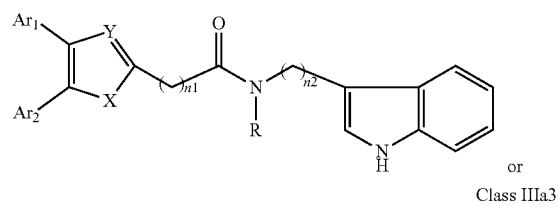

Class IIIa2 or

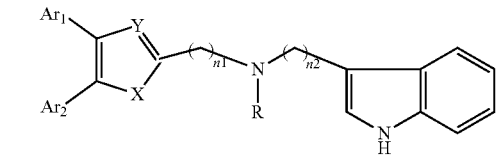

Class IIIa3 wherein:

$Ar_1$ and $Ar_2$ are each independently selected from a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thio-alkylaryloxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is as defined in (1);

X and Y are each independently as defined in (1) for $X_1$ and $X_2$;

R is selected from H, alkyl, cycloalkyl, alkoxy, thioalkoxy, OH, SH, $NH_2$, a halogen atom, a halogeno alkyl, a halogeno alkoxy, a halogeno thioalkoxy, $CH_2CN$, $(CH_2)_nCN$, CN, $NO_2$, $S(=O)_2$, $S(=O)_2R^1$, where $R^1$ is as defined in (1); and n1 and n2 are each independently an integer from 0 to 12.

(19) A compound according to (19) having the general formula "Class IIIa1'", "Class IIIa2'" or "Class IIIa3'" below

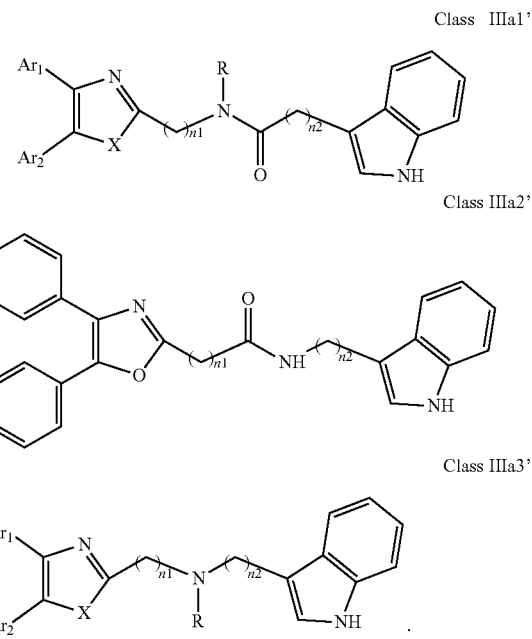

Class IIIa1'

Class IIIa2'

Class IIIa3'

(20) A compound according to (19), wherein $Ar_1$ and $Ar_2$ are each independently a mono carbocyclic ring optionally comprising O or S, and optionally substituted with OH, SH, halogen atom, alkoxy, halogeno alkyl; and X is selected from O, S and NH.

(21) A compound according to (1) having the general formula "Class IIIb1", "Class IIIb2" or "Class IIIb3" below

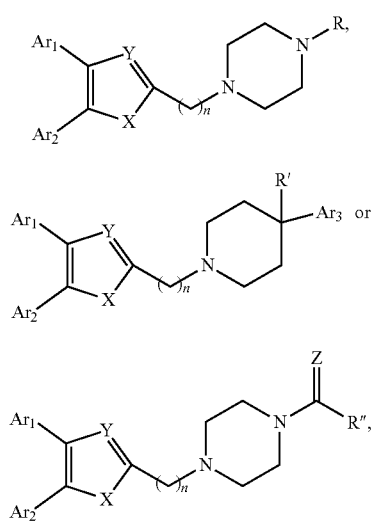

Class IIIb1

Class IIIb2

Class IIIb3 wherein:
$Ar_1$ to $Ar_3$ are each independently selected from a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is as defined in (1);
X and Y are each independently as defined in (1) for $X_1$ and $X_2$;
Z is selected from O, S, N and C;
R and R' are each independently selected from H, alkyl, cycloalkyl, alkoxy, thioalkoxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is as defined in (1); and
R" is selected from H, alkyl, cycloalkyl, alkene, alkyne, aryl and alkylaryl, a 5 to 12-member single or bicyclo ring, or $Q_1$ and $Q_2$ together form a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, $NH_2$, a halogen atom, a halogeno alkyl, a halogeno alkoxy, a halogeno thioalkoxy, CN, $NO_2$, $S(=O)_2$, $S(=O)_2R^1$, where $R^1$ is as defined in (1).

(22) A compound according to (21) having the general formula "Class IIIb1'", "Class IIIb2'" or "Class IIIb3'" below

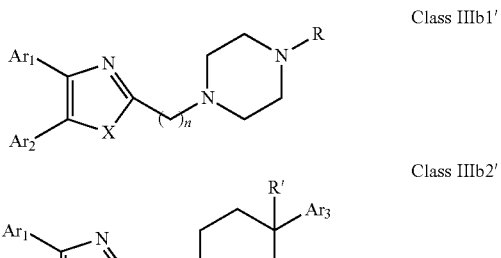

Class IIIb1'

Class IIIb2'

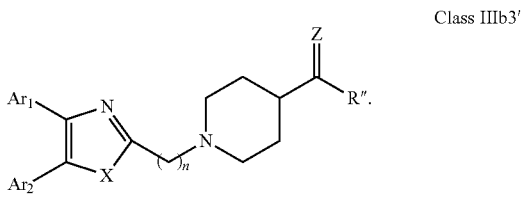

Class IIIb3'

(23) A compound according to (22), wherein $Ar_1$ and $Ar_2$ are each independently a mono carbocyclic ring optionally comprising O or S, and optionally substituted with OH, SH, halogen atom, alkoxy, halogeno alkyl; X is selected from O, S and NH; and Y is selected from O and S.

(24) A compound according to (1) having the general formula "Class IV" below

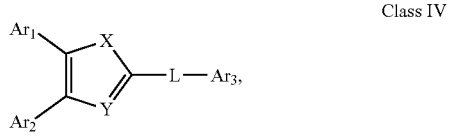

Class IV wherein:
Ar$_1$ to Ar$_3$ are each independently selected from a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, where R$^1$ is as defined in (1); and
X and Y are each independently as defined in (1) for X$_1$ and X$_2$.

(25) A compound according to (24) having the general formula "Class IVa" below

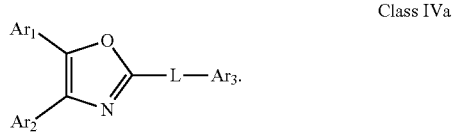

Class IVa

(26) A compound according to (25), wherein Ar$_1$ to Ar$_3$ are each independently a mono carbocyclic ring optionally comprising O or S, and optionally substituted with OH, SH, halogen atom, alkoxy, halogeno alkyl; and L comprises one or more of (CH$_2$) and (CH) or a combination thereof.

(27) A compound according to (1), which is selected from the group of compounds depicted in the Table 2 herein below.

(28) A compound according to (10) or (27), which is compound 935, 698, 641, 673, 924, 697, 866, 857, or 720.

(29) A compound according to (1), which is selected from the group of compounds depicted in the Table 3 herein below.

(30) A compound according to (13) or (29), which is 919, 817, 839 or 834.

(31) A compound according to (1), which is selected from the group of compounds depicted in the Table 4 herein below.

(32) A compound according to (19) or (31), which is 784, 855, 874, 1186, 1187, 1188, 1372 or 1396.

(33) A compound according to (22) or (31), which is 1076, 1227, 1371, 1127, 1124, 1077, 1229, 1176, 1177, 1125, 1289, 1368 or 1401.

(34) A compound according to (1), which is selected from the group of compounds depicted in the Table 5 herein below.

(35) A compound according to (25) or (34), which is 689, 926, 1012 or 1013.

(36) A compound of general formula I' below, or a pharmaceutically acceptable salt thereof, or a solvate or hydrate thereof.

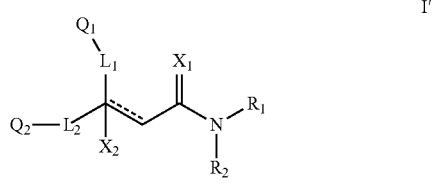

I' wherein:
Q$_1$ and Q$_2$ are each independently selected from alkyl, cycloalkyl, alkene, alkyne, aryl and alkylaryl, a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, NO$_2$, S(=O)$_2$, S(=O)$_2$R$^1$, wherein R$^1$ and R$^2$ are each independently selected from alkyl, cycloalkyl and aryl;
X$_1$ is selected from O, S and NR wherein R is selected from H, alkyl and cycloalkyl;
X$_2$ selected from OR, SR and NR wherein R is selected from H, alkyl and cycloalkyl; a halogen atom;
L1 and L2 are each independently present or absent and are each a group comprising one or more of (CH$_2$), (CH=CH) or a combination thereof;
R$_1$ and R$_2$ are each independently selected from alkyl, cycloalkyl, alkene, alkyne, aryl and alkylaryl, a 5 to 12-member single or bicyclo ring; optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, NH$_2$, a halogen atom, a halogeno alkyl, a halogeno alkoxy, a halogeno thioalkoxy, CN, CH$_2$CN, (CH$_2$)$_n$CN, NO$_2$, S(=O)$_2$, S(=O)$_2$R$^1$, where R$^1$ is as defined in (1); and
- - - - denotes a chemical bond that is present or absent, and wherein the heteroatom is selected from O, N, S and Se.

(37) A compound according to (36) having the general formula IIA' or IIB' below

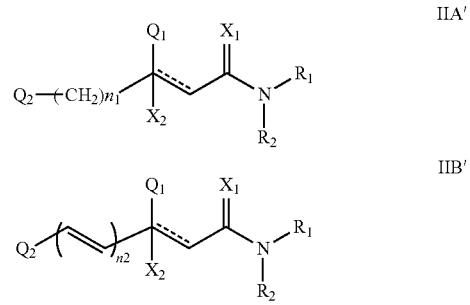

wherein:
n1 is an integer from 1 to 6; and
n2 is an integer from 1 to 3.

(38) A compound according to (37) having the general formula IIIA', IIIB', IIIC' or IIID' below

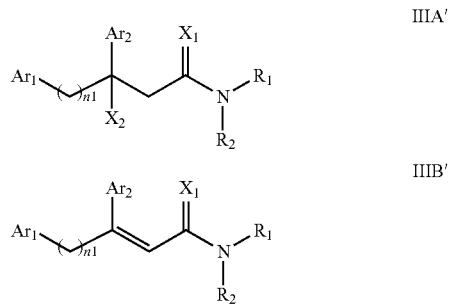

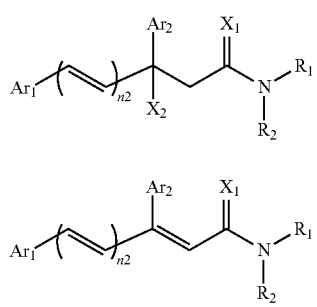

IIIC'

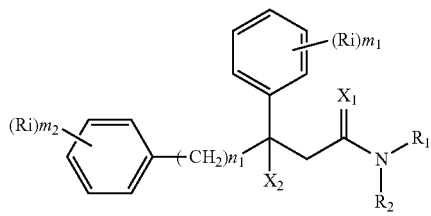

IIID' wherein:

Ar₁ and Ar₂ are each independently selected from a mono or bicyclic carbocyclic ring system or a multiple ring system wherein the rings are fused together, optionally, the ring comprises one or more heteroatom which are the same or different, also optionally, the ring is substituted with a substituent selected from alkyl, cycloalkyl alkoxy, alkoxy, thioalkoxy, aryl, aryloxy, thioaryloxy, alkyaryloxy, thioalkylaryloxy, OH, SH, $NH_2$, a halogen atom, a halogeno alkyl, a halogeno alkoxy, a halogeno thioalkoxy, $CF_3$, CN, $NO_2$, $S(=O)_2$, $S(=O)_2R^1$, where $R^1$ is as defined in (1); and n1 and n2 are each independently an integer from 0 to 5.

(39) A compound according to (38) having the general formula IIIA", IIIB", IIIC" or IIID" below

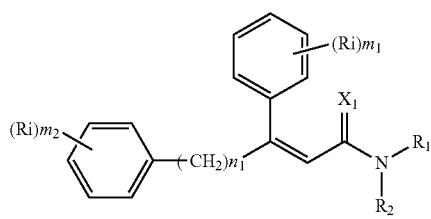

IIIA"

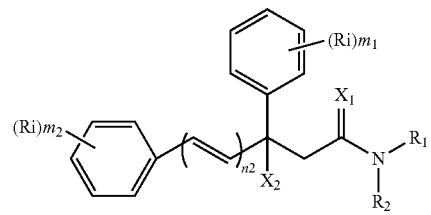

IIIB"

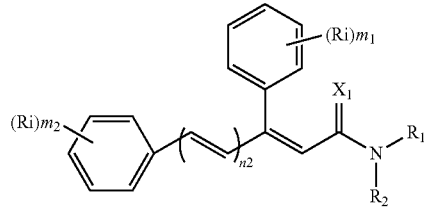

IIIC"

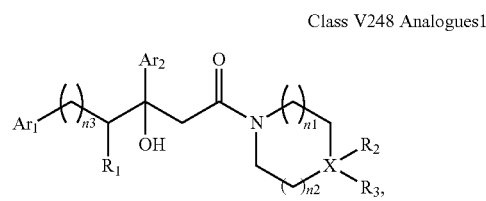

IIID"

wherein:

each Ri is as defined in (36) for $R_1$ and $R_2$; and m1 and m2 are each independently an integer from 0 to 5.

(40) A compound according to (38) having the general formula "V248 Analogues1", "V248 Analogues2" or "V248 Analogues3" below Class V248 Analogues1

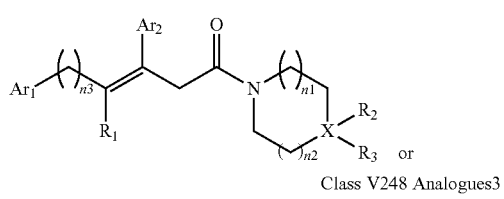

Class V248 Analogues2

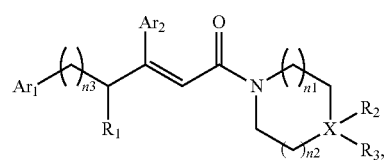

or

Class V248 Analogues3

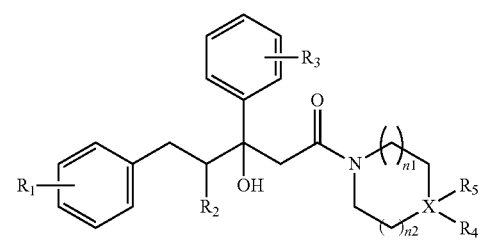

wherein:

$R_3$ is as defined in (30) for $R_1$ and $R_2$;

X is selected from C and N; and n1, n2 and n3 are each independently an integer from 0 to 12.

(41) A compound according to (40) having the general formula "V248 Analogues1a", "V248 Analogues2a" or "V248 Analogues3a" below Class V248 Analogues1a -continued Class V248 Analogues2a

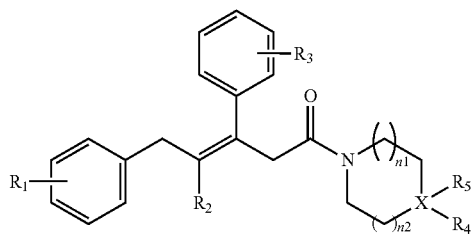

Class V248 Analogues3a

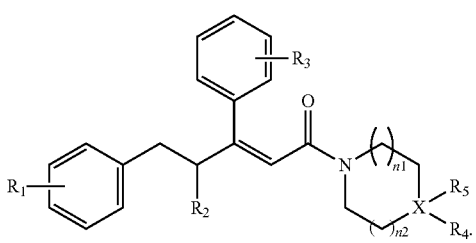

(42) A compound according to (40) or (41), wherein X is selected from N, O and C; and n1 and n2 are each independently an integer from 0 to 6.

(43) A compound according to (36), which is selected from the group of compounds depicted in Table 7 herein below.

(44) A compound according to (40) or (43), which is 895, 1306, 1302, 1322, 1236, 1237, 1259, 872, 881, 880 or 1407.

(45) A pharmaceutical composition comprising a compound as defined in any one of (1) to (36), and a pharmaceutically acceptable carrier.

(46) A compound according to any one of (1) to (44), which targets GATA transcription factors, preferably GATA2 transcription factor.

(47) A compound according to any one of (1) to (44), which targets ETS transcriptional factors, preferably ERG and ETV1.

(48) A compound according to any one of (1) to (44), which is agonist or antagonist of stimulator of interferon genes (STING) including human STING and mouse STING.

(49) A compound according to any one of (1) to (44), which is an inhibitor of a KRAS mutant, preferably G12D, G12C, G12V and G13D.

(50) A method of treating a medical condition that may or may not involve GATA2; ERG, ETV1 or other ETS transcriptional factors; STING; or a KRAS mutant, comprising administering to a subject a therapeutically effective amount of a compound as defined in any one of (1) to (44), or a compound which is compound V151, V154, V131 or V248 or an analogue thereof, or a therapeutically effective amount of a pharmaceutical composition as defined in (45)

V151

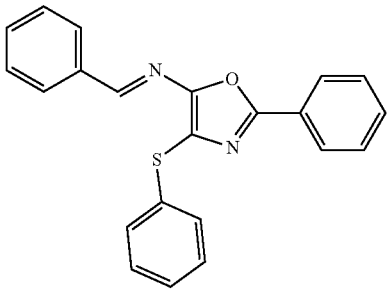

V154

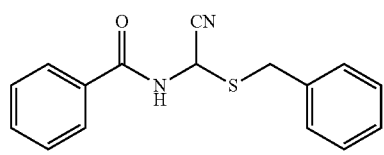

V131

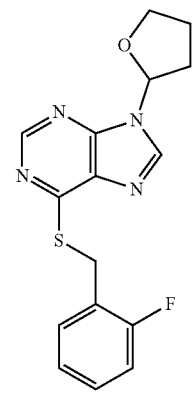

V248

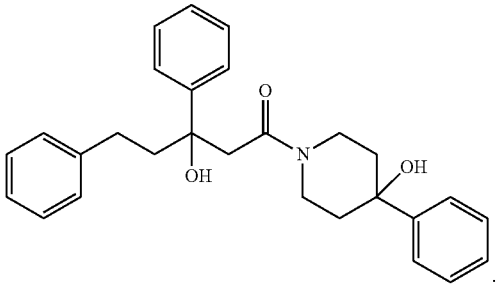

(51) A method of treating a medical condition that may or may not involve GATA2; ERG, ETV1 or other ETS transcriptional factors; STING; or a KRAS mutant, comprising administering to a subject a therapeutically effective amount of a compound as defined in any one of (1) to (44), or a compound which is compound V151, V154, V131 or V248 or an analogue thereof, or a therapeutically effective amount of a pharmaceutical composition as defined in (45), together with an antiandrogen.

(52) A method of treating a medical condition that may or may not involve GATA2; ERG, ETV1 or other ETS transcriptional factors; STING or a KRAS mutant, comprising administering to a subject a therapeutically effective amount of a compound as defined in any one of (1) to (44), or a compound which is compound V151, V154, V131 or V248 or an analogue thereof, or a therapeutically effective amount of a pharmaceutical composition as defined in (45), wherein the compound acts as inhibitor of GATA2 and/or ERG and/or ETV1, and/or other ETS transcriptional factors, and/or wherein the compound acts as STING agonist or antagonist.

(53) A method according to any one of (50) to (52), wherein the medical condition is selected from: KRAS mutant-driven cancers, for example, KRAS mutant NSCLC, KRAS mutant pancreatic cancer, KRAS mutant colorectal cancer and KRAS mutant endometrium cancer; prostate cancer, both AR positive prostate cancer and AR negative prostate cancer; leukemia; melanoma; ovarian cancer; and breast cancer including triple negative breast cancer.

(54) A method according to any one of (50) to (52), wherein the medical condition is selected from: prostate cancer including TMPRSS2-ERG positive or TMPRSS2-ETV1 positive prostate cancer; pancreatic cancer; lung cancer; non small cell lung cancer (NSCLC); colorectal cancer; ovarian cancer; melanoma and leukemia.

(55) A method according to any one of (50) to (52), wherein the medical condition is selected from: p53-negative or p-53-defective human cancers; prostate cancer including TMPRSS2-ETV1 positive cancer; pancreatic cancer; lung cancer; and gastrointestinal stromal tumors (GIST).

(56) A method according to any one of (50) to (52), wherein the treatment is immunotherapy, and the medical condition is a medical condition with immune disorder such as cancer, including prostate cancer, pancreatic cancer, lung cancer, NSCLC, melanoma, leukemia, etc, or the medical condition is a medical condition that involves viruses.

(57) A method according to any one of (50) to (52), wherein the medical condition is cancer or an autoimmune disease or other immune diseases.

(58) A method according to any one of (50) to (57), further comprising treating the subject with a second cancer therapy.

(59) A method according to any one of (50) to (58), wherein the compound is administered orally, intravenously, intra-arterially, subcutaneously, topically or intramuscularly.

(60) A method according to any one of (50) to (59), wherein the cancer is primary or multi-drug resistant, metastatic and/or recurrent.

(61) A method according to any one of (50) to (60), wherein the method comprises inhibiting cancer growth, killing cancer cells, reducing tumor burden, reducing tumor size, improving the subject's quality of life and/or prolonging the subject's length of life.

(62) A method according to any one of (50) to (61), wherein the subject is human.

(63) A method according to any one of (50) to (61), wherein the subject is a non-human animal.

(64) A method according to any one of (50) to (52), wherein the compound inhibits GATA, preferably GATA2, and is selected from compounds 673, 676, 650, 675, 631, 632, 817, 830, 770, 795, 831, 834, 838, 839, 840, 684, 685, 686, 687, 784, 795, 719, 866, 693, V248, 858, 859, 860, 868, 869, 870, 871, 872, 880, 881, 882, 883 and 884.

(65) A method according to any one of (50) to (52), wherein the compound inhibits ERG, and is selected from compounds: 648, 697, 698, 699, 639, 651, 659, 662, 675, 661, 673, 678, V131, V154 and V151.

(66) A method according to any one of (50) to (52), wherein the compound inhibits ETV1, and is selected from compounds: 650, 651, 652, 653, 654, 656, 662, 636, 637, 638, 655, 697, 700, 708, 641, 657, 661, 675, 648, 827, 832, 838 and 830.

(67) A method according to (50), wherein the compound activates STING, and is selected from compounds: 640, 670, 672, 676, 677, 681, 761, 762, 770, 641, 650, 656, 660, 671, 673, 678, 830, 831, 817, 834, 840, 653, 698, 916, 917, 918, 919, 920, 689, 693, 838, 1176, 1289 or 1401.

(68) A method according to (50), wherein the compound inhibits a KRAS mutant, and is selected from compounds: 784, 895, 1043, 1100, 1103, 1144, 1322, 1175, 1176, 1187, 1200, 1201, 1209, 1210, 1211, 1212, 1186, 1188, 1237, 1249, 1250, 1257, 1258, 1259, 1261, 1262, 1273, 1274, 1275, 1276, 1298, 1300, 1301, 1302, 1303, 1320, 1322, 1345, 1367, 1368, 1369, 1371, 1372 and 1373.

(69) Use of a compound as defined in any one of (1) to (44), or a compound which is compound V151, V154, V131 or V248 or an analogue thereof, or a pharmaceutical composition as defined in (45), for treating in a subject, a medical condition that may or may not involve GATA2; ERG, ETV1 or other ETS transcriptional factors; STING; or a KRAS mutant.

(70) Use of a compound as defined in any one of (1) to (44), or a compound which is compound V151, V154, V131 or V248 or an analogue thereof, in the manufacture of a medicament for treating a medical condition that may or may not involve GATA2; ERG, ETV1 or other ETS transcriptional factors; STING; or a KRAS mutant.

(71) A compound as defined in any one of (1) to (44), or a compound which is compound V151, V154, V131 or V248 or an analogue thereof, for use in the treatment of a medical condition that may or may not involve GATA2; ERG, ETV1 or other ETS transcriptional factors; STING; or a KRAS mutant.

(72) A pharmaceutical composition as defined in (45), for use in the treatment of a medical condition that may or may not involve GATA2; ERG, ETV1 or other ETS transcriptional factors; STING; or a KRAS mutant.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1.1a) ERG-dependent reporter assay in HEK293 cells indicated that compounds 648, 697, 698 and 699 (in Table 2 below) are ERG inhibitors. HEK293 cells were transiently transfected with empty vector (for the NT) or ERG-expressing plasmid as well as pRL-TK (internal control) and PUx3-Luc reporter. Cells were then exposed to DMSO vehicle or compounds at designated doses for 48 hours. Experiments were done in triplicate.

FIG. 1.1b) ERG-dependent reporter assay in HEK293 cells indicated that compounds 639, 651, 659, 662 and 675 (in Table 2 below) are ERG inhibitors. Experiments were done as described above in FIG. 1.1a).

FIG. 1.1c) ERG-dependent reporter assay in HEK293 cells indicated that compounds 661, 673 and 678 (in Table 2 below) are ERG inhibitors. Experiments were done as described above in FIG. 1.1a).

FIG. 1.1d) ERG-dependent reporter assay in HEK293 cells indicated that compounds V131, V154 and V151 (in Table 6 below) are ERG inhibitors. Experiments were done as described above in FIG. 1.1a).

FIG. 1.2 ESE-1 dependent reporter assay in HEK293 cells indicated that compounds 698, V131 and V154 are ESE-1 inhibitors. Experiments were done as described above in FIG. 1.1a) except that ERG plasmid was replaced by ESE-1 plasmid.

FIG. 1.3 ETS-2 dependent reporter assay in HEK293 cells indicated that compound V154 is an ETS-2 inhibitor. Experiments were done as described above in FIG. 1.1a) except that ERG plasmid was replaced by ETS-2 plasmid.

FIG. 1.4a) ETV1-dependent reporter assay in HEK293 cells indicated that compounds 650, 651, 652, 653, 654, 656 and 662 (in Table 2 below) are ETV1 inhibitors. Experiments were done as described above in FIG. 1.1a) except that ERG plasmid was replaced by ETV1 plasmid.

FIG. 1.4b) ETV1-dependent reporter assay in HEK293 cells indicated that compounds 636, 637, 638, 655, 697, 700 and 708 (in Table 2 below) are ETV1 inhibitors. Experiments were done as described above in FIG. 1.1a) except that ERG plasmid was replaced by ETV1 plasmid.

FIG. 1.4c) ETV1-dependent reporter assay in HEK293 cells indicated that compounds 641, 657, 661 and 675 are ETV1 inhibitors. Experiments were done as described above in FIG. 1.1a) except that ERG plasmid was replaced by ETV1 plasmid.

FIG. 1.4d) ETV1-dependent reporter assay in HEK293 cells indicated that compounds 648, 827, 832, 838 and 830 (in Table 3 below) are ETV1 inhibitors. Experiments were done as described above in FIG. 1.1a) except that ERG plasmid was replaced by ETV1 plasmid.

FIG. 1.5a) Surface Plasmon Resonance (SPR) analysis indicated that compound 648 (in Table 2 below) has direct binding with human ERG protein. Steady-state kinetics of compound 648, YK-4-279 (positive control) and bicalutamide (Bic) (negative control) over amine-coupled ERG surfaces with 50 μM injection (25 μL/min×120 sec association+120 sec dissociation). High-density ERG (6000 RU) and reference surface (no ERG) were amine-coupled to CM5 sensors using BIACORE 3000 instrumentation. YK-4-279 is a known ERG inhibitor. Bic is an antagonist of the androgen receptor.

FIG. 1.5b) Preliminary SPR data to characterize binding affinity of compound 648. Rapid on/off kinetics for compound 648 when titrated over amine-coupled ERG surfaces at 0, 10, 20, 30, 40, and 50 μM (25 μL/min×120 sec association+120 sec dissociation). After DMSO solvent correction, fitting of the data to a "steady-state affinity" model predicts low micromolar $K_D$ values for compound 648.

FIG. 1.6 Compounds 648, 698 and 891 at 10 μM inhibit expression of EZH2, c-Myc and ERG in VCaP cells. VCaP cells were exposed to DMSO vehicle control, 648, 698 and 891 at 10 μM for 72 hours in DMEM medium plus 10% FBS or phenol red-free DMEM medium plus 10% charcoal-stripped FBS (CS-FBS).

FIG. 1.7 Compound 648 potently inhibits invasion of VCaP and C4-2B cells, but not the DU145 cells. Invasion assay was performed using (8.0 μm pore size) BD Matrigel Invasion chambers in 24-well plate (Catalog: 354480, BD Biosc.). 750 μL medium (with 20% FBS) was added into lower chamber of each well (DMEM for VCaP, RPMI 1640 for C4-2B and DU145). Next, 5×10$^5$ VCaP or 5×10$^5$ C4-2B or 1×10$^4$ DU145 cells in 500 μL medium (with 0.5% FBS) were seeded into the upper chamber of each well. DMSO vehicle or compounds in DMSO solution were added into upper chamber to reach the designated doses. After 48 hours incubation, the invasive cells attached to the lower surface of the membrane insert were fixed in 10% formalin at room temperature for 30 minutes and stained with 0.05% crystal violet. The number of invasive cells was then counted under a microscope. Invasion experiments were performed in duplicate. ***$p<0.0001$ when compared with vehicle control.

FIG. 1.8 Cytotoxicity of compounds 827 and 832 in the ETV1-postive LNCaP cells as evaluated by MTT assay (72 hours).

FIG. 2.1a) GATA2-dependent reporter assay in IHH cells indicated that compounds 673 and 676 are GATA2 inhibitors. K7174 is a known GATA2 inhibitor. The IHH cells were transiently transfected with empty vector (for the NT) or human GATA2-expressing plasmid as well as pRL-TK (internal control) and GATA-Luc reporter plasmids. Cells were exposed to DMSO vehicle or compounds for 48 h. Experiments were in triplicate.

FIG. 2.1b) GATA2-dependent reporter assay in IHH cells indicated that compounds 650, 675, 631 and 632 are GATA2 inhibitors. Experiments were done as described above in FIG. 2.1a).

FIG. 2.2a) GATA2-dependent reporter assay in IHH cells indicated that compounds 817, 830, 770 and 795 are GATA2 inhibitors. Experiments were done as described above in FIG. 2.1a).

FIG. 2.2b) GATA2-dependent reporter assay in IHH cells indicated that compounds 817, 830, 831, 834, 838, 839 and 840 are GATA2 inhibitors. Experiments were done as described above in FIG. 2.1a).

FIG. 2.2c) GATA2-dependent reporter assay in IHH cells indicated that compounds 684, 685, 686, 687, 784 and 795 are GATA2 inhibitors. Experiments were done as described above in FIG. 2.1a).

FIG. 2.2d) GATA2-dependent reporter assay in IHH cells indicated that compounds 719, 866 and 693 are GATA2 inhibitors. Experiments were done as described above in FIG. 2.1a).

FIG. 2.2e) GATA2-dependent reporter assay in IHH cells indicated that V248, 858, 859 and 860 are GATA2 inhibitors. Experiments were done as described in FIG. 2.1a).

FIG. 2.2f) GATA2-dependent reporter assay in IHH cells indicated that 868, 869, 870, 871 and 872 are GATA2 inhibitors. Experiments were done as described in FIG. 2.1a).

FIG. 2.2g) GATA2-dependent reporter assay in IHH cells indicated that 880, 881, 882, 883 and 884 are GATA2 inhibitors. Experiments were done as described in FIG. 2.1a).

FIG. 2.3a) GATA3-dependent reporter assay in IHH cells indicated that compounds 673, 676, 770 and 817 at 5 μM are inactive against GATA3, indicating these compounds are selective toward GATA2 (see FIG. 2.2). In contrast, K7174 is active against GATA3. The IHH cells were transiently transfected with empty vector (for the NT) or human GATA3-expressing plasmid as well as pRL-TK (internal control) and GATA-Luc reporter plasmids. Cells were exposed to DMSO vehicle or compounds for 48 hours. Experiments were done in triplicate.

FIG. 2.3b) GATA3-dependent reporter assay in IHH cells indicated that compounds 673, 675, 676 and 817 at 10 μM are inactive against GATA3. Experiments were done as described above in FIG. 2.3a).

FIG. 2.3c) GATA3-dependent reporter assay in IHH cells indicated that compounds 687, 693, 784 and 795 at 10 μM are inactive against GATA3, whereas compounds 650 and 686 are active against GATA3. Experiments were done as described in FIG. 2.3a).

FIG. 2.4 Compound 673 selectively inhibits GATA2 among GATA family members. In contrast, K7174 is not selective. GATA1-, GATA2-, GATA3- and GATA4-dependent reporter assays were done in IHH cells which were exposed to DMSO vehicle, compound 673 or K7174 (μM) in CSS medium for 48 hours.

FIG. 2.5a) Specific binding of compounds (50 µM each in PBST running buffer containing 5% DMSO) to amine-coupled GATA2 (9,000 RU) at 25 µL/min (reference-subtracted data with DMSO solvent correction), as assessed by Surface Plasmon Resonance (SPR) analysis: solid black line, compound 817; solid grey line, compound 673; dashed black line, V248; dotted grey line, compound 670; flat baseline, bicalutamide (BIC) (0 RU=negative control).

FIG. 2.5b) Specific and dose-dependent binding of compound 673 to amine-coupled GATA2 (9,000 RU) at 25 µL/min (reference-subtracted data with DMSO solvent correction) (0-50 µM, 2-fold dilution series in PBST running buffer containing 5% DMSO), as assessed by SPR analysis.

FIG. 2.6a Western blot analysis revealed that compound 673 suppresses the androgen receptor (AR) signaling in C4-2B prostate cancer cells. Compound 673 also inhibits GATA2 expression in C4-2B cells.

FIG. 2.7 Compound 673 is cytotoxic in KRAS-mutant NSCLC cells (A549 and H23), but is not toxic the KRAS wild-type NSCLC cells (H322). Cells were exposed to vehicle or compounds (µM) for 72 hours. Viable cells were evaluated by MTT assays.

FIG. 2.8 Compound 673 is equally cytotoxic to LNCaP cells stably transfected with empty vector pcDNA3.1 (LNCaP-pcDNA) and LNCaP cells stably transfected with GATA2-expressing plasmid (LNCaP-GATA2) (upper figure). In contrast, antiandrogen bicalutamide (BIC) is less active in LNCaP-GATA2 cells when compared with its activity in LNCaP-pcDNA cells. Cells were exposed to DMSO vehicle or compounds for 72 hours. Vial cells were evaluated by MTT assays. Experiments were done in triplicate.

FIG. 2.9 GATA2 overexpression confers resistance to antiandrogen in prostate cancer cells. (A) PSA-luc reporter assay and (B) Western Blot analysis revealed the attenuated inhibition effect of Bic (Bicalutamide) in LNCaP-GATA2 cells in FBS medium; (C) Colony formation assay and quantification of LNCaP-pcDNA and LNCaP-GATA2 cells exposed to 1 µM BIC in FBS medium for 28 days indicated that GATA2 expression confers resistance to BIC. *p<0.05, **p<0.001.

FIG. 2.10 (A) Plasmid construct for expressing fusion protein IRF3DBD-GATA2NTD, in which GATA2 NTD is fused to the DBD of IRF3; (B) ISRE-luc reporter assay in PC3 cells showed that compound 673 at 5 µM is active against fusion protein IRF3DBD-GATA2NTD, but inactive against wild-type IRF3. This indicates that 673 is targeting the GATA2 NTD. **p<0.005 when compared with DMSO vehicle.

FIG. 2.11 By breaking AR-GATA2 feedback loop, compound 673 suppresses the AR signaling in CRPC cells. (A) GATA-luc or PSA-luc reporter assay in LNCaP-GATA2 cells following 72 hours treatment with BIC or 673 in CSS medium; (B and C) WB analysis indicated that, in contrast to Bic, 673 is effective in suppressing AR signaling in LNCaP-GATA2 cells in FBS medium (B) and in CRPC cells, including HP-LNCaP, C4-2B and 22Rv1, in CSS medium (C). Cells were exposed to DMSO vehicle, BIC, 673 or K7174 at designated doses (µM) for 72 hours.

FIG. 2.12 Synergistic effect of compound 673 with bicalutamide (BIC) in PSA-luc reporter assay (A) and BrdU cell proliferation assay (B) in LNCaP-GATA2 cells in regular medium (RPM11640 plus 10% FBS). (A) PSA-luc reporter assay in LNCaP-GATA2 cells, which were exposed to DMSO vehicle, BIC, 673, or equi-molar combination of Bic and 673 for 72 hours in FBS medium. RLU, relative luciferase unit; (B) BrdU Cell Proliferation Assay (Assay Kit #6813, Cell Signaling Tech.). LNCaP-GATA2 cells were exposed to DMSO vehicle, Bic, 673 or equi-molar combination of Bic and 673 for 48 hours. In the last 8 hours, 10 µM BrdU was added to the plate. p<0.001, *p<0.001 when compared with BIC at the same doses; #p<0.05, ##p<0.001 when compared with 673 at the same doses.

FIG. 3.1a) Compounds 640, 670, 672, 676, 677, 681, 761, 762 and 770 activate human STING (hSTING) in ISRE-luc reporter assay in 293T cells. ISRE-luc (reporter), pRL-TK (internal control) and hSTING-expressing plasmids were transiently transfected into 293T cells. Cells were exposed to DMSO vehicle control or compounds for 24 hours. Experiments were done in triplicate.

FIG. 3.1b) Compounds 641, 650, 656 and 660 activate hSTING in ISRE-luc reporter assay in 293T cells. Experiments were done as described above in FIG. 3.1a).

FIG. 3.1c) Compounds 671, 673, 678, 830, 831, 817, 834 and 840 activate hSTING in ISRE-luc reporter assay in 293T cells. Experiments were done as described above in FIG. 3.1a).

FIG. 3.1d) Compounds 653, 698, 916, 917, 918, 919 and 920 activate hSTING in ISRE-luc reporter assay in 293T cells. Experiments were done as described above in FIG. 3.1a).

FIG. 3.1e) Compounds 689, 693 and 838 activate hSTING in ISRE-luc reporter assay in 293T cells. Experiments were done as described above in FIG. 3.1a).

FIG. 3.2 Compounds 640, 672, 681, 761 and 817 activate mouse STING (mSTING) in ISRE-luc reporter assay in 293T cells. ISRE-luc (reporter), pRL-TK (internal control) and mSTING-expressing plasmids were transiently transfected into 293T cells. Cells were exposed to DMSO vehicle control or compounds for 24 hours. Experiments were done in triplicate.

FIG. 3.3 Specific, dose-dependent binding of compound 817 (0-50 µM, 2-fold dilution series in PBST running buffer containing 5% DMSO) to amine-coupled human STING (8,700 RU) at 25 µL/min (reference-subtracted data with DMSO solvent correction), as assessed by SPR analysis.

FIG. 3.4a) Compounds 1011, 1012, 1013, 1033, 1035, 1036, 1037 and 874 at 10 µM activate hSTING and/or mSting in ISRE-luc reporter assay in 293T cells. ISRE-luc (reporter), pRL-TK (internal control) and hSTING- or mSTING-expressing plasmids were transiently transfected into 293T cells. Cells were exposed to DMSO vehicle control or compounds for 24 hours. Experiments were done in triplicate.

FIG. 3.4b) Compounds 795, 874, 1038, 1039, 1040, 1041 and 1042 activate hSTING and/or mSTING in ISRE-luc reporter assay in 293T cells. Experiments were done as described in FIG. 3.4a). DMXAA (DMX) is a known agonist of mSTING and was included as a control.

FIG. 3.4c) Compounds 1096, 1097, 1098, 1099, 1100, 1103 and 1104 activate hSTING and/or mSTING in ISRE-luc reporter assay in 293T cells. Experiments were done as described in FIG. 3.4a).

FIG. 3.4d) Compounds 1120, 1121, 1122, 1123, 1124, 1125, 1126 and 1127 activate hSTING and/or mSTING in ISRE-luc reporter assay in 293T cells. Experiments were done as described in FIG. 3.4a).

FIG. 3.4e) Compounds 1129, 1137, 1139, 1140, 1141, 1142, 1143 and 1188 activate hSTING and/or mSTING in ISRE-luc reporter assay in 293T cells. Experiments were done as described in FIG. 3.4a).

FIG. 3.4f) Compounds 1173, 1174, 1175, 1176, 1177, 1178 and 1179 at 10 µM activate hSTING and/or mSTING in ISRE-luc reporter assay in 293T cells. Experiments were done as described in FIG. 3.4a).

FIG. 3.4g) Compounds 1180, 1181, 1182, 1183, 1184, 1227 and 1228 at 20 μM activate hSTING and/or mSTING in ISRE-luc reporter assay in 293T cells. Experiments were done as described in FIG. 3.4a).

FIG. 3.4h) Compounds 1285, 1286, 1287, 1288, 1289 and 1176 activate hSTING and/or mSTING in ISRE-luc reporter assay in 293T cells. Experiments were done as described in FIG. 3.4a).

FIG. 3.4i) Compounds 1357, 1360, 1361, 1364 and 1366 activate hSTING and/or mSTING in ISRE-luc reporter assay in 293T cells. Experiments were done as described in FIG. 3.4a).

FIG. 3.4j) Compounds 1369, 1370, 1372 and 1373 activate hSTING and/or mSTING in ISRE-luc reporter assay in 293T cells. Experiments were done as described in FIG. 3.4a).

FIG. 3.5 Compounds 834, 874, 761, 840 and 1176 activate interferon signaling pathway in THP-1 cells. THP1 cells were treated for 16 hours with the indicated concentration (μM) of compounds or DMSO vehicle control. Whole-cell extracts were prepared and subjected to Western blot analysis with the antibodies as indicated.

FIG. 4.1 SPR analysis. Left panels, SPR sensorgrams for compounds 784 and 895 binding to 3500 RU amine-coupled KRAS (G12D mutant) at 25 μL/min in PBS-T containing 1 μM GDP. Right panels, corresponding non-linear regression analyses of steady-state binding responses versus concentration to determine apparent equilibrium dissociation constants ($K_D$).

FIG. 4.2a) KRAS mutant-dependent NF-kB-luc reporter assays in HEK293 cells. Compounds 784 and 895 at 10 μM potently inhibit KRAS 12D, 12V and 12C-dependent NF-kB-luc reporter assay. NF-kB-luc reporter, pRL-TK internal control and KRAS 12D or 12V or 12C mutant-expressing plasmids were transiently transfected into HEK293 cells. NT cells were transfected with NF-kK-luc, pRL-TK and empty vector. Cells were exposed to DMSO vehicle or compounds at designated dose for 24 hours. Experiments were done in triplicate.

FIG. 4.2b) Compounds 1043, 1100 and 1103 potently inhibit KRAS 12D-dependent NF-kB-luc reporter assay in HEK293 cells. Experiments were done as described in FIG. 4.2a).

FIG. 4.2c) Compounds 1144 and 1322 potently inhibit KRAS 12D-dependent NF-kB-luc reporter assay in HEK293 cells. Experiments were done as described in FIG. 4.2a).

FIG. 4.3a) Compounds 784, 895 and 1144 potently inhibit NF-kB-luc reporter assay in Panc 10.05 cells. NF-kB-luc reporter and pRL-TK internal control were transiently transfected into Panc 10.05 cells. Cells were exposed to DMSO vehicle or compounds at designated dose for 24 hours. Experiments were done in triplicate. RLU, relative luciferase unit.

FIG. 4.3b) Compounds 1175, 1176 and 1187 potently inhibit NF-kB-luc reporter assay in Panc 10.05 cells. Experiments were done as described in FIG. 4.3a).

FIG. 4.3c) Compounds 1200, 1201, 1209, 1210, 1211 and 1212 potently inhibit NF-kB-luc reporter assay in Panc 10.05 cells. Experiments were done as described in FIG. 4.3a).

FIG. 4.3d) Compounds 1100, 1186, 1188, 1211 and 1237 potently inhibit NF-kB-luc reporter assay in Panc 10.05 cells. Experiments were done as described in FIG. 4.3a).

FIG. 4.3e) Compounds 1249, 1250, 1257, 1258, 1259, 1261 and 1262 potently inhibit NF-kB-luc reporter assay in Panc 10.05 cells. Experiments were done as described in FIG. 4.3a).

FIG. 4.3f) Compounds 1249, 1257, 1261 and 1273 potently inhibit NF-kB-luc reporter assay in Panc 10.05 cells. Experiments were done as described in FIG. 4.3a).

FIG. 4.3g) Compounds 1274, 1275, 1276, 1298, 1300, 1301, 1302 and 1303 at 20 μM potently inhibit NF-kB-luc reporter assay in Panc 10.05 cells. Experiments were done as described in FIG. 4.3a).

FIG. 4.3h) Compounds 1320, 1322, 1345 and 1348 potently inhibit NF-kB-luc reporter assay in Panc 10.05 cells. Experiments were done as described in FIG. 4.3a).

FIG. 4.3i) Compounds 1367, 1368, 1369, 1371, 1372, 1373 and 1374 at 20 μM inhibit NF-kB-luc reporter assay in Panc 10.05 cells. Experiments were done as described in FIG. 4.3a).

FIG. 4.4a) Western blot analysis indicated that compounds 784 and 895 dose-dependently suppressed phosphorylation of ERK and induced apoptosis in Panc 10.05 cells. C-PARP, cleaved PARP. Panc10.05 cells were exposed to DMSO vehicle or compounds at designated doses for 24 hours.

FIG. 4.4b) Western blot analysis indicated that compounds 1100, 1186, 1187, 1200 and 1237 at 10 μM potently suppressed phosphorylation of ERK in Panc 10.05 cells. Panc10.05 cells were exposed to DMSO vehicle or compounds at designated doses for 24 hours.

FIG. 4.4c) Western blot analysis indicated that compounds 1186, 1187, 1209, 1237, 1306 and 895 at 10 μM potently suppressed phosphorylation of ERK in HCT-116 cells. HCT-116 cells were exposed to DMSO vehicle or compounds at designated doses for 24 hours.

FIG. 4.5) MTT analysis indicated that compounds 1186 and 1261 dose-dependently inhibit proliferation of Panc10.05 pancreatic cancer cells, H23 non-small lung cancer cells and HCT-116 colorectal cancer cells. Panc 10.05, H23 and HCT-116 cells express endogenous KRAS 12D, 12C and 13D mutants, respectively. Cells were exposed to DMSO vehicle or compounds at designated doses for 72 hours. Experiments were done in triplicate.

FIG. 5 General formulae of compounds according to embodiments of the invention.

DESCRIPTION OF ILLUSTRATIVE EMBODIMENTS

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments, and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

As used herein, the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used herein, the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein, term "alkyl" or "alk" represents a monovalent group derived from a straight or branched chain saturated hydrocarbon comprising, unless otherwise specified, from 1 to 15 carbon atoms and is exemplified by methyl, ethyl, n- and iso-propyl, n-, sec-, iso- and tert-butyl, neopentyl and the like and may be optionally substituted with one, two, three or, in the case of alkyl groups comprising two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) $C(O)NR^CR^D$, where each of $R^C$ and $R^D$ is independently selected from the group consisting of (a) hydrogen, (b) alkyl, (c) aryl and (d) arylalkyl, where the alkylene group comprises one to six carbon atoms; (28) $S(O)R^E$, where $R^E$ is selected from the group consisting of (a) alkyl, (b) aryl, (c) arylalkyl, where the alkylene group comprises one to six carbon atoms, and (d) hydroxyl; (29) $S(O)_2R^E$, where $R^E$ is selected from the group consisting of (a) alkyl, (b) aryl, (c) arylalkyl, where the alkylene group comprises one to six carbon atoms, and (d) hydroxyl; (30) $S(O)_2NR^FR^G$, where each of $R^F$ and $R^G$ is independently selected from the group consisting of (a) hydrogen, (b) alkyl, (c) aryl and (d) arylalkyl, where the alkylene group comprises one to six carbon atoms; and (31) $—NR^HR^I$, where each of $R^H$ and $R^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The terms "alkoxy" or "alkyloxy" as used interchangeably herein, represent an alkyl group attached to the parent molecular group through an oxygen atom.

The term "alkylthio" or "thioalkoxy" as used interchangeably herein, represents an alkyl group attached to the parent molecular group through a sulfur atom.

The term "alkylene" as used herein, represents a saturated divalent hydrocarbon group derived from a straight or branched chain saturated hydrocarbon by the removal of two hydrogen atoms, and is exemplified by methylene, ethylene, isopropylene and the like.

The term "alkenyl" as used herein, represents monovalent straight or branched chain groups of, unless otherwise specified, from 2 to 15 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) $OC(O)R^A$, where $R^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) $C(O)R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) $CO_2R^B$, where $R^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) C(O)NR$^C$R$^D$, where each of R$^C$ and R$^D$ is independently selected from the group consisting of (a) hydrogen, (b) alkyl, (c) aryl and (d) arylalkyl, where the alkylene group comprises one to six carbon atoms; (28) S(O)R$^E$, where R$^E$ is selected from the group consisting of (a) alkyl, (b) aryl, (c) arylalkyl, where the alkylene group comprises one to six carbon atoms, and (d) hydroxyl; (29) S(O)$_2$R$^E$, where R$^E$ is selected from the group consisting of (a) alkyl, (b) aryl, (c) arylalkyl, where the alkylene group comprises one to six carbon atoms, and (d) hydroxyl; (30) S(O)$_2$NR$^F$R$^G$, where each of R$^F$ and R$^G$ is independently selected from the group consisting of (a) hydrogen, (b) alkyl, (c) aryl and (d) arylalkyl, where the alkylene group comprises one to six carbon atoms; and (31) —NR$^H$R$^I$, where each of R$^H$ and R$^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "alkynyl" as used herein, represents monovalent straight or branched chain groups of from two to six carbon atoms comprising a carbon-carbon triple bond and is exemplified by ethynyl, 1-propynyl, and the like and may be optionally substituted with one, two, three or four substituents independently selected from the group consisting of: (1) alkoxy of one to six carbon atoms; (2) alkylsulfinyl of one to six carbon atoms; (3) alkylsulfonyl of one to six carbon atoms; (4) alkynyl of two to six carbon atoms; (5) amino; (6) aryl; (7) arylalkoxy, where the alkylene group comprises one to six carbon atoms; (8) azido; (9) cycloalkyl of three to eight carbon atoms; (10) halo; (11) heterocyclyl; (12) (heterocycle)oxy; (13) (heterocycle)oyl; (14) hydroxyl; (15) hydroxyalkyl of one to six carbon atoms; (16) N-protected amino; (17) nitro; (18) oxo or thiooxo; (19) perfluoroalkyl of 1 to 4 carbon atoms; (20) perfluoroalkoxyl of 1 to 4 carbon atoms; (21) spiroalkyl of three to eight carbon atoms; (22) thioalkoxy of one to six carbon atoms; (23) thiol; (24) OC(O)R$^A$, where R$^A$ is selected from the group consisting of (a) substituted or unsubstituted $C_{1-6}$ alkyl, (b) substituted or unsubstituted $C_6$ or $C_{10}$ aryl, (c) substituted or unsubstituted $C_{7-16}$ arylalkyl, where the alkylene group comprises one to six carbon atoms, (d) substituted or unsubstituted $C_{1-9}$ heterocyclyl, and (e) substituted or unsubstituted $C_{2-15}$ heterocyclylalkyl, where the alkylene group comprises one to six carbon atoms; (25) C(O)R$^B$, where R$^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (26) CO$_2$R$^B$, where R$^B$ is selected from the group consisting of (a) hydrogen, (b) substituted or unsubstituted $C_{1-6}$ alkyl, (c) substituted or unsubstituted $C_6$ or $C_{10}$ aryl, (d) substituted or unsubstituted $C_{7-16}$ arylalkyl, where the alkylene group comprises one to six carbon atoms, (e) substituted or unsubstituted $C_{1-9}$ heterocyclyl, and (f) substituted or unsubstituted $C_{2-15}$ heterocyclylalkyl, where the alkylene group comprises one to six carbon atoms; (27) C(O)NR$^C$R$^D$, where each of R$^C$ and R$^D$ is independently selected from the group consisting of (a) hydrogen, (b) alkyl, (c) aryl and (d) arylalkyl, where the alkylene group comprises one to six carbon atoms; (28) S(O)R$^E$, where R$^E$ is selected from the group consisting of (a) alkyl, (b) aryl, (c) arylalkyl, where the alkylene group comprises one to six carbon atoms, and (d) hydroxyl; (29) S(O)$_2$R$^E$, where R$^E$ is selected from the group consisting of (a) alkyl, (b) aryl, (c) arylalkyl, where the alkylene group comprises one to six carbon atoms, and (d) hydroxyl; (30) S(O)$_2$NR$^F$R$^G$, where each of R$^F$ and R$^G$ is independently selected from the group consisting of (a) hydrogen, (b) alkyl, (c) aryl and (d) arylalkyl, where the alkylene group comprises one to six carbon atoms; and (31) —NR$^H$R$^I$, where each of R$^H$ and R$^I$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, (i) alkcycloalkyl, where the cycloalkyl group comprises three to eight carbon atoms, and the alkylene group comprises one to ten carbon atoms, (j) alkanoyl of one to six carbon atoms, (k) aryloyl of 6 to 10 carbon atoms, (l) alkylsulfonyl of one to six carbon atoms, and (m) arylsulfonyl of 6 to 10 carbons atoms, with the proviso that no two groups are bound to the nitrogen atom through a carbonyl group or a sulfonyl group.

The term "aryl" as used herein, represents mono- and/or bicyclic carbocyclic ring systems and/or multiple rings fused together and is exemplified by phenyl, naphthyl, 1,2-dihydronaphthyl, 1,2,3,4-tetrahydronaphthyl, fluorenyl, indanyl, indenyl and the like and may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups are independently comprised of one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) (CH$_2$)$_q$CO$_2$R$^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where $R^B$ and $R^C$ are independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms, and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

As used herein, the term "alkylaryl" represents an aryl group attached to the parent molecular group through an alkyl group.

The term "cycloalkyl" as used herein, represents a monovalent saturated or unsaturated non-aromatic cyclic hydrocarbon group of three to eight carbon atoms, unless otherwise specified, and is exemplified by cyclopropyl, cyclobutyl, cyclopentyl, cyclohexyl, cycloheptyl, bicyclo[2.2.1]heptyl and the like. The cycloalkyl groups of the present disclosure can be optionally substituted with: (1) alkanoyl of one to six carbon atoms; (2) alkyl of one to six carbon atoms; (3) alkoxy of one to six carbon atoms; (4) alkoxyalkyl, where the alkyl and alkylene groups independently comprise from one to six carbon atoms; (5) alkylsulfinyl of one to six carbon atoms; (6) alkylsulfinylalkyl, where the alkyl and alkylene groups independently comprise from one to six carbon atoms; (7) alkylsulfonyl of one to six carbon atoms; (8) alkylsulfonylalkyl, where the alkyl and alkylene groups independently comprise from one to six carbon atoms; (9) aryl; (10) arylalkyl, where the alkyl group comprises one to six carbon atoms; (11) amino; (12) aminoalkyl of one to six carbon atoms; (13) aryl; (14) arylalkyl, where the alkylene group comprises one to six carbon atoms; (15) aryloyl; (16) azido; (17) azidoalkyl of one to six carbon atoms; (18) carboxaldehyde; (19) (carboxaldehyde)alkyl, where the alkylene group comprises one to six carbon atoms; (20) cycloalkyl of three to eight carbon atoms; (21) alkcycloalkyl, where the cycloalkyl group comprises three to eight carbon atoms and the alkylene group comprises one to ten carbon atoms; (22) halo; (23) haloalkyl of one to six carbon atoms; (24) heterocyclyl; (25) (heterocyclyl)oxy; (26) (heterocyclyl)oyl; (27) hydroxy; (28) hydroxyalkyl of one to six carbon atoms; (29) nitro; (30) nitroalkyl of one to six carbon atoms; (31) N-protected amino; (32) N-protected aminoalkyl, where the alkylene group comprises one to six carbon atoms; (33) oxo; (34) thioalkoxy of one to six carbon atoms; (35) thioalkoxyalkyl, where the alkyl and alkylene groups independently comprise from one to six carbon atoms; (36) $(CH_2)_qCO_2R^A$, where q is an integer ranging from zero to four and $R^A$ is selected from the group consisting of (a) alkyl, (b) aryl, and (c) arylalkyl, where the alkylene group comprises one to six carbon atoms; (37) $(CH_2)_qC(O)NR^BR^C$, where each of $R^B$ and $R^C$ is independently selected from the group consisting of (a) hydrogen, (b) alkyl, (c) aryl, and (d) arylalkyl, where the alkylene group comprises one to six carbon atoms; (38) $(CH_2)_qS(O)_2R^D$, where $R^D$ is selected from the group consisting of (a) alkyl, (b) aryl, and (c) arylalkyl, where the alkylene group comprises one to six carbon atoms; (39) $(CH_2)_qS(O)_2NR^ER^F$, where each of $R^E$ and $R^F$ is independently, selected from the group consisting of (a) hydrogen, (b) alkyl, (c) aryl, and (d) arylalkyl, where the alkylene group comprises one to six carbon atoms; (40) $(CH_2)_qNR^GR^H$, where each of $R^G$ and $R^H$ is independently selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) arylalkyl, where the alkylene group comprises one to six carbon atoms; (h) cycloalkyl of three to eight carbon atoms and (i) alkcycloalkyl, where the cycloalkyl group comprises three to eight carbon atoms, and the alkylene group comprises one to ten carbon atoms, with the proviso that no two groups are bound to the nitrogen atom through a carbonyl group or a sulfonyl group; (41) oxo; (42) thiol; (43) perfluoroalkyl; (44) perfluoroalkoxy; (45) aryloxy; (46) cycloalkoxy; (47) cycloalkylalkoxy; and (48) arylalkoxy.

The term "halogen" or "halo" as used interchangeably herein, represents F, Cl, Br and I.

The term "heteroatom" as used herein, is understood as being oxygen, sulfur or nitrogen.

The term "carbonyl" as used herein, represents a C(O) group, which can also be represented as C=O.

The terms "acyl" or "alkanoyl" as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups comprise from 2 to 10 carbons.

The term "analogue" as used herein, is understood as being a substance similar in structure to another compound but differing in some slight structural detail.

The term "salt(s)" as used herein, is understood as being acidic and/or basic salts formed with inorganic and/or organic acids or bases. Zwitterions (internal or inner salts) are understood as being included within the term "salt(s)" as used herein, as are quaternary ammonium salts such as alkylammonium salts. Nontoxic, pharmaceutically acceptable salts are preferred, although other salts may be useful, as for example in isolation or purification steps. Examples of acid addition salts include but are not limited to acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, phosphoric, 2-hydroxyethanesulfonate, lactate, maleate, mandelate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate. Examples of base addition salts include but are not limited to alkali metal salts and alkaline earth metal salts. Non limiting examples of alkali metal salts include lithium, sodium and potassium salts. Non-limiting examples of alkaline earth metal salts include magnesium and calcium salts.

The term "immune disorder" as used herein, is understood as a dysfunction of the immune system. The disorder may be characterized in several ways. For example by dysfunctional component(s) of the immune system, or by whether the immune system is overactive or underactive, or by whether the immune function is weakened or impaired or evaded, or by whether immune tolerance is dysfunctional, or by whether the condition is congenital or acquired.

The term "autoimmune disease" as used herein, is understood as a disease which arises from abnormal immune response of the body against some of its own substances or tissues as though they were foreign substances or tissues.

The inventors have designed and prepared novel chemical compounds. The compounds according to the invention may be used in the treatment of medical conditions involving GATA2; ERG, ETV1 or other immune disorders; STING and/or KRAS mutants. Such medical conditions may, for example, be various types of cancer or medical conditions with immune disorders.

In an aspect, compounds according to the invention are GATA2 inhibitors. As such they may be used in the treatment of: KRAS mutant cancers, for example, KRAS mutant NSCLC and KRAS mutant colon cancer; prostate cancer, both AR positive prostate cancer and AR negative prostate cancer; leukemia; breast cancer including triple negative breast cancer and melanoma.

In another aspect, compounds according to the invention are ERG inhibitors. As such, they may be used in the treatment of: prostate cancer including TMPRSS2-ERG positive prostate cancer; leukemia.

In yet another aspect compounds according to the invention are ETV1 inhibitors. As such, they may be used in the treatment of: p53-negative or p-53 defective human cancers; prostate cancer including TMPRSS2-ETV1 positive cancer; gastrointestinal stromal tumors (GIST).

In yet another aspect, compounds of the invention are STING agonists. As such, they may be used as immunotherapy for cancer patients or as stimulants in patients undergoing cancer treatment.

In yet another aspect, compounds of the invention are direct inhibitors of various KRAS mutants including but not limited to G12D, G12C, G12V and G13D. As such, they may be used in the treatment of pancreatic cancer, lung cancer, colorectal cancer and other KRAS mutant-driven cancers.

The present invention is illustrated in further details by the following non-limiting examples.

Chemistry

Compounds according to embodiments of the invention have a general formula I or formula I' illustrated in FIG. 5.

Example 1—Preparation of Certain Intermediate Compounds Used the Preparation of Compounds According to the Invention Scheme 1 below outlines the chemical synthesis of certain compounds that are intermediates in the various chemical syntheses of the compounds according to the invention. In particular, Scheme 1 outlines the chemical synthesis of Intermediates 4-25 shown in Table 1 below.

Scheme 1 - Preparation of Intermediates 4-25.

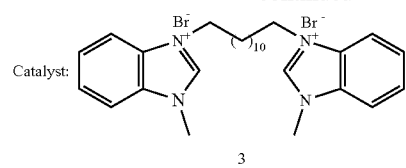

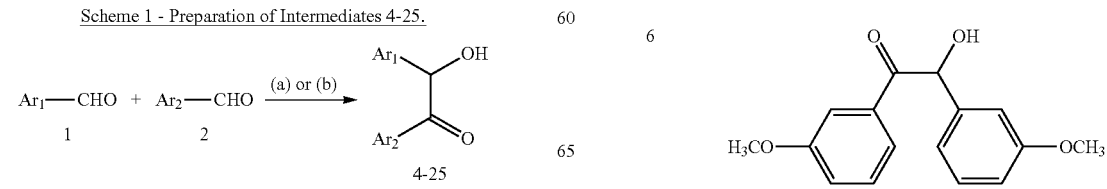

(a) Catalyst 3 (10%), DBU (20%), $H_2O$, r.t; (b) NaCN, EtOH, $H_2O$, reflux, 4 h.

Preparation of Intermediates 4-25.

Preparation of the catalyst compound 3: It was prepared according to the literature procedures with modification.[60] A mixture of N-methylbenzimidazole (6.6 g, 50 mmol) and 1,12-dibromododecane (8.4 g, 25 mmol) in acetonitrile (100 mL) was refluxed for 24 hours. After cooling, the white precipitate 3 was collected by filtration, which was pure enough without further purification. Yield: 81.3%.

General procedure for the preparation of Intermediates 4-25:

Method (a): Intermediates 4-25 were synthesized according to the literature procedures with modifications as illustrated in Scheme 1.[60] Aryl aldehydes 1 (5 mmol) and 2 (5 mmol) was added to 10 mL water. Then catalyst 3 (10 mol %) and DBU (20 mol %) were added. The reaction mixture was stirred at room temperature vigorously for 3-6 hours. Dichloromethane was added. The combined organic phase was washed with brine, dried over $Na_2SO_4$ and concentrated under reduced pressure to give the crude residue, which was purified by column chromatography to give the desired Intermediates 4-11, 13-21 and 23-25.

Method (b): A mixture of NaCN (490 mg, 10 mmol, 1 equiv) in water (2 mL) was added to aryl aldehyde 1 (1362 mg, 10 mmol, 1 equiv) in ethanol (10 mL) at room temperature. The reaction mixture was heated to reflux for 4 hours and then quenched with water (20 mL) at ambient temperature. The resulting mixture was extracted with $CH_2Cl_2$ (20 mL×3). The combined organic layers were dried over $Na_2SO_4$, filtered and concentrated under reduced pressure. The crude residue was purified by column chromatography to give the desired Intermediates 12 and 22.

TABLE 1

Structures of Intermediates 4-25.

| ID | Structure |
|---|---|
| 4 | 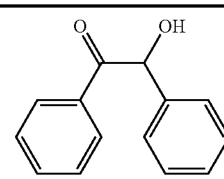 |
| 5 | 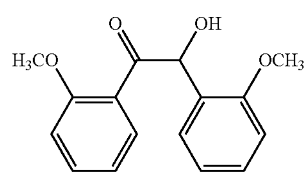 [SMILES: COc1ccccc1C(=O)C(O)c1ccccc1OC] |
| 6 | 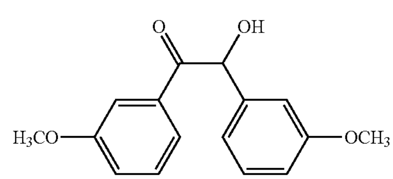 [SMILES: COc1cccc(C(=O)C(O)c2cccc(OC)c2)c1] |

TABLE 1-continued

Structures of Intermediates 4-25.

| ID | Structure |
|----|-----------|
| 7 | 1-(4-methoxyphenyl)-2-hydroxy-2-(4-methoxyphenyl)ethanone |
| 8 | 1-(2-trifluoromethylphenyl)-2-hydroxy-2-(2-trifluoromethylphenyl)ethanone |
| 9 | 1-(3-trifluoromethylphenyl)-2-hydroxy-2-(3-trifluoromethylphenyl)ethanone |
| 10 | 1-(4-trifluoromethylphenyl)-2-hydroxy-2-(4-trifluoromethylphenyl)ethanone |
| 11 | 1-(2-fluorophenyl)-2-hydroxy-2-(2-fluorophenyl)ethanone |
| 12 | 1-(3-fluorophenyl)-2-hydroxy-2-(3-fluorophenyl)ethanone |
| 13 | 1-(4-fluorophenyl)-2-hydroxy-2-(4-fluorophenyl)ethanone |
| 14 | 1-(2-chlorophenyl)-2-hydroxy-2-(2-chlorophenyl)ethanone |
| 15 | 1-(3-chlorophenyl)-2-hydroxy-2-(3-chlorophenyl)ethanone |
| 16 | 1-(4-chlorophenyl)-2-hydroxy-2-(4-chlorophenyl)ethanone |
| 17 | 1-(2-methylphenyl)-2-hydroxy-2-(2-methylphenyl)ethanone |
| 18 | 1-(3-methylphenyl)-2-hydroxy-2-(3-methylphenyl)ethanone |
| 19 | 1-(4-methylphenyl)-2-hydroxy-2-(4-methylphenyl)ethanone |
| 20 | 1-(2-methoxyphenyl)-2-hydroxy-2-phenylethanone |
| 21 | 1-(2-methoxyphenyl)-2-hydroxy-2-(2-methoxyphenyl)ethanone |

TABLE 1-continued

Structures of Intermediates 4-25.

| ID | Structure |
|---|---|
| 22 | (3-fluorophenyl)-hydroxy-furan-2-yl ketone |
| 23 | (3-methoxyphenyl)-hydroxy-pyrrol-2-yl ketone |
| 24 | (3-methoxyphenyl)-hydroxy-furan-2-yl ketone |
| 25 | furan-2-yl-hydroxy-furan-2-yl ketone |

Characterization of Intermediates 6-25:

6: Colorless crystal. Yield: 68%. $^1$H NMR (500 MHz, CDCl$_3$) δ 7.50-7.44 (m, 2H), 7.29 (t, J=8.0 Hz, 1H), 7.24 (t, J=8.0 Hz, 1H), 7.08-7.05 (m, 1H), 6.97-6.90 (m, 1H), 6.86-6.84 (m, 1H), 6.83-6.79 (m, 1H), 5.89 (d, J=5.9 Hz, 1H), 4.51 (d, J=6.1 Hz, 1H), 3.80 (s, 3H), 3.76 (s, 3H).

7: White solid. Yield: 71%. $^1$H NMR (500 MHz, CDCl$_3$) δ 7.95-7.86 (m, 2H), 7.26-7.24 (m, 2H), 6.92-6.80 (m, 4H), 5.85 (d, J=6.0 Hz, 1H), 4.57 (dd, J=6.0, 1.0 Hz, 1H), 3.82 (s, 3H), 3.76 (s, 3H).

8: White solid. Yield: 67%. $^1$H NMR (500 MHz, CDCl$_3$) δ 7.71-7.70 (m, 1H), 7.63-7.56 (m, 2H), 7.55-7.48 (m, 2H), 7.44 (t, J=7.7 Hz, 1H), 7.40-7.38 (m, 1H), 6.93 (d, J=7.8 Hz, 1H), 6.11 (d, J=5.0 Hz, 1H), 4.41 (d, J=5.0, 1H).

9: White solid. Yield: 65%. $^1$H NMR (500 MHz, CDCl$_3$) δ 8.39 (s, 1H), 8.30 (s, 2H), 8.19 (d, J=7.8 Hz, 2H), 7.97-7.93 (m, 2H), 7.90-7.88 (m, 1H), 7.70 (t, J=7.8 Hz, 2H), 7.65 (t, J=7.8 Hz, 1H).

10: White solid. Yield: 60%. $^1$H NMR (500 MHz, CDCl$_3$) δ 7.93 (ddd, J=8.2, 5.2, 2.5 Hz, 2H), 7.30 (ddd, J=8.2, 5.2, 2.5 Hz, 2H), 7.15-7.06 (m, 2H), 7.06-6.98 (m, 2H), 5.89 (d, J=5.8 Hz, 1H), 4.50 (d, J=5.8 Hz, 1H).

11: White solid. Yield: 72%. $^1$H NMR (500 MHz, CDCl$_3$) δ 7.89-7.81 (m, 2H), 7.49-7.43 (m, 1H), 7.22-7.11 (m, 3H), 7.08-6.91 (m, 3H), 6.06-6.04 (m, 1H), 4.47-4.40 (m, 1H).

12: White solid, yield: 68.4%. $^1$H NMR (500 MHz, CDCl$_3$) δ 7.70-7.60 (m, 1H), 7.58-7.55 (m, 1H), 7.37 (td, J=8.0, 5.5 Hz, 1H), 7.28 (td, J=8.0, 5.5 Hz, 1H), 7.25-7.16 (m, 1H), 7.09 (d, J=7.7 Hz, 1H), 7.04-6.91 (m, 2H), 5.87 (d, J=6.0 Hz, 1H), 4.43 (d, J=6.1 Hz, 1H).

13: White solid, yield: 77.4%. $^1$H NMR (500 MHz, CDCl$_3$) δ 8.16 (d, J=8.2 Hz, 1H), 7.97 (d, J=8.1 Hz, 2H), 7.70-7.66 (m, 2H), 7.58 (d, J=8.1 Hz, 2H), 7.43 (d, J=8.1 Hz, 2H), 5.99 (s, 1H).

19: White solid. Yield: 83%. $^1$H NMR (500 MHz, CDCl$_3$) δ 7.79 (d, J=8.3 Hz, 2H), 7.21-7.13 (m, 4H), 7.09 (d, J=7.9 Hz, 2H), 5.86 (d, J=6.0 Hz, 1H), 4.51 (d, J=6.0 Hz, 1H), 2.32 (s, 3H), 2.26 (s, 3H).

20: White solid. Yield: 42%. $^1$H NMR (500 MHz, CDCl$_3$) δ 7.95 (d, J=7.2 Hz, 2H), 7.53-7.50 (m, 1H), 7.39 (t, J=7.8 Hz, 2H), 7.33-7.25 (m, 1H), 7.20 (d, J=7.6 Hz, 1H), 6.94-6.89 (m, 2H), 6.28 (s, 1H), 3.88 (s, 3H).

21: White solid. Yield: 77%. $^1$H NMR (500 MHz, CDCl$_3$) δ 7.70-7.65 (m, 1H), 7.38-7.34 (m, 1H), 7.21-7.17 (m, 1H), 7.17-7.13 (m, 1H), 6.94-6.90 (m, 1H), 6.85-6.82 (m, 1H), 6.78-6.74 (m, 2H), 6.10 (d, J=5.7 Hz, 1H), 4.46 (d, J=5.7 Hz, 1H), 3.73 (s, 3H), 3.71 (s, 3H).

22: White solid, yield: 32%. $^1$H NMR (500 MHz, cdcl$_3$) δ 7.61-7.59 (m, 1H), 7.34-7.29 (m, 1H), 7.27-7.23 (m, 2H), 7.21 (d, J=7.7 Hz, 1H), 7.15-7.10 (m, 1H), 7.03-6.95 (m, 1H), 6.56-6.51 (m, 1H), 5.76 (s, 1H).

23: White solid, yield: 77.4%. $^1$H NMR (500 MHz, CDCl$_3$) δ 9.39 (br, 1H), 7.23 (t, J=7.9 Hz, 1H), 7.02-6.99 (m, 1H), 6.96 (d, J=7.6 Hz, 1H), 6.90-6.88 (m, 1H), 6.82-6.78 (m, 2H), 6.20-6.18 (m, 1H), 5.60 (d, J=5.9 Hz, 1H), 4.41 (t, J=5.9 Hz, 1H), 3.75 (s, 3H).

24: White solid, yield: 54%. $^1$H NMR (500 MHz, CDCl$_3$) δ 7.58-7.57 (m, 1H), 7.30-7.25 (m, 1H), 7.22-7.21 (m, 1H), 7.02-6.97 (m, 1H), 6.93-6.92 (m, 1H), 6.85-6.82 (m, 1H), 6.51-6.47 (m, 1H), 5.72 (s, 1H), 4.33 (br, 1H), 3.78 (s, 3H).

25: White solid, yield: 55%. $^1$H NMR (500 MHz, CDCl$_3$) δ 7.59 (d, J=4.8 Hz, 1H), 7.40-7.30 (m, 1H), 7.24-7.21 (m, 2H), 6.51 (s, 1H), 6.43-6.36 (m, 1H), 6.33 (s, 1H), 5.77 (d, J=5.4 Hz, 1H).

Example 2—Preparation of Compounds of Class Ia, Class Ib, Class Ic and Class Id

Schemes 2-6 below outline the chemical synthesis of compounds identified as "Class Ia". These compounds are shown in Table 2 below.

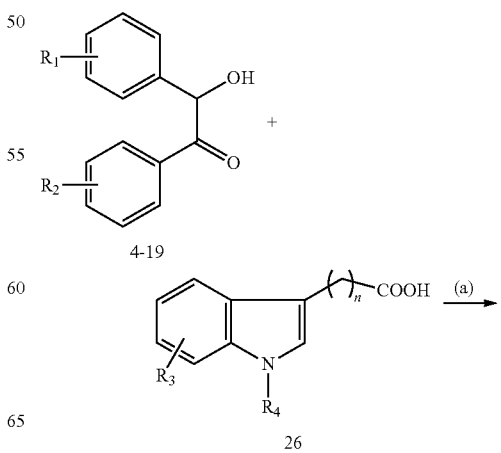

Scheme 2 - Preparation of compounds of Class Ia.

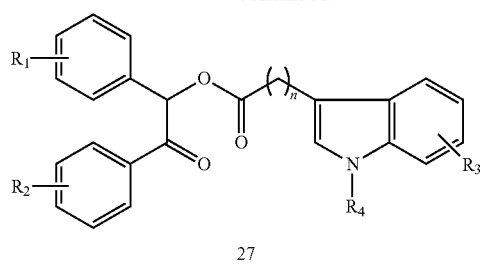

27

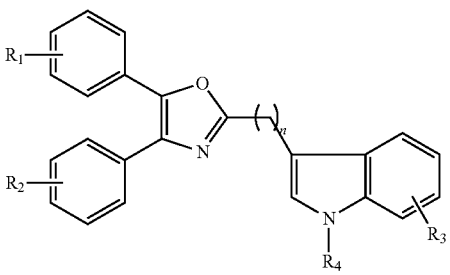

Class Ia (a) DCC, DMAP, CH$_2$Cl$_2$, rt; (b) CH$_3$COONH$_4$, acetic acid, reflux, 2 h.

Compounds of Class Ia may be prepared by typical methods as illustrated in Scheme 2. The appropriate benzoin 4-19 is condensed with substituted indole acid 26, the intermediate ester 27 is obtained, which is then followed by the reaction with ammonium acetate in acetic acid under reflux for 2 hours to generate the desired products, compounds of Class Ia: 708, 630-632, 636-641, 649-663, 670-673, 677-679, 681, 696, 761, 762.

Scheme 3 - Preparation of compounds of Class Ib.

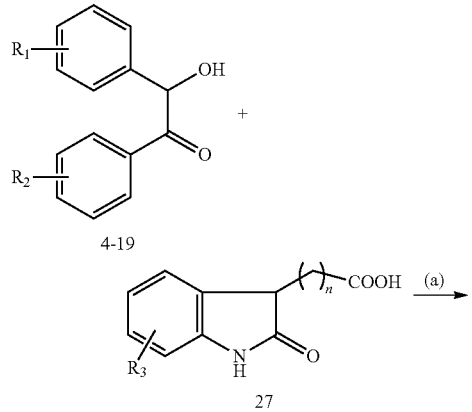

4-19

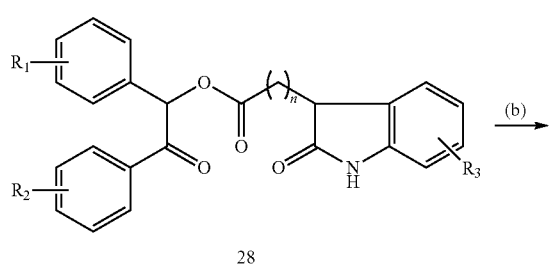

28

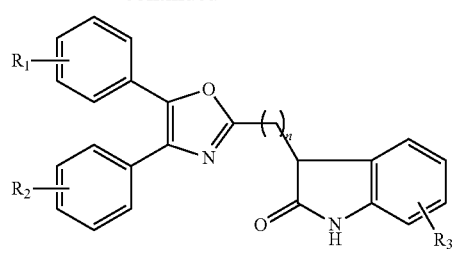

Class Ib (a) DCC, DMAP, CH$_2$Cl$_2$, rt; (b) CH$_3$COONH$_4$, acetic acid, reflux, 2 h.

Scheme 4 - Preparation of compounds of Class Ic.

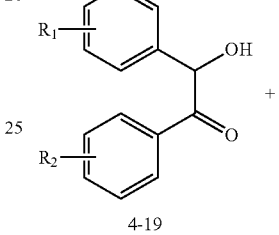

4-19

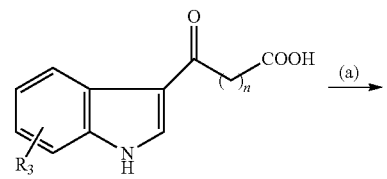

29

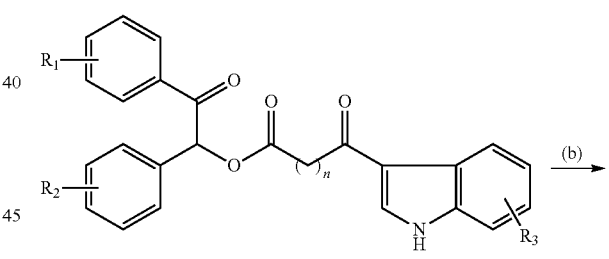

30

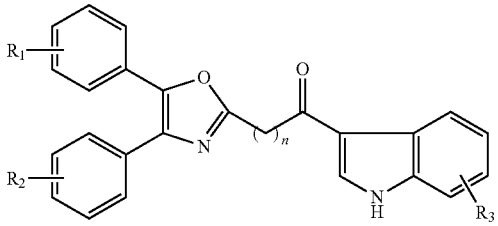

Class Ic (a) DCC, DMAP, CH$_2$Cl$_2$; (b) CH$_3$COONH$_4$, acetic acid, reflux, 2 h.

Similarly, compounds of Class Ib and Ic may be prepared by the same method used for the preparation of the compounds of Class Ia as illustrated in Scheme 3 and Scheme 4. Compounds 700, 770, 866 and 857 were obtained.

Scheme 5 - Preparation of compounds of Class Id.

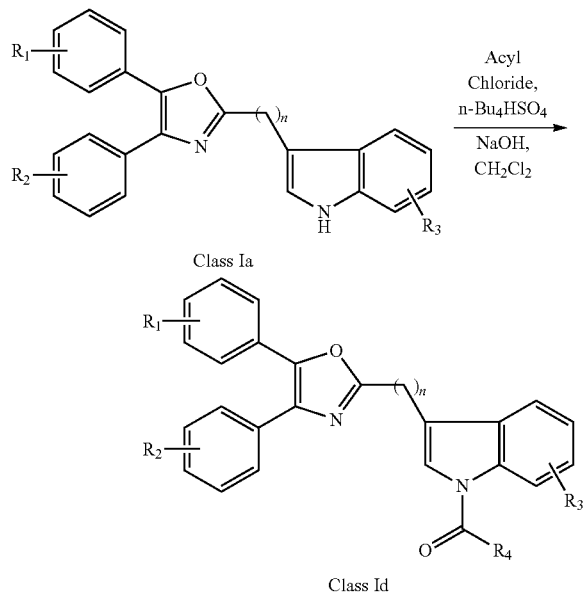

Scheme 6 - Preparation of other compounds of Class Ia.

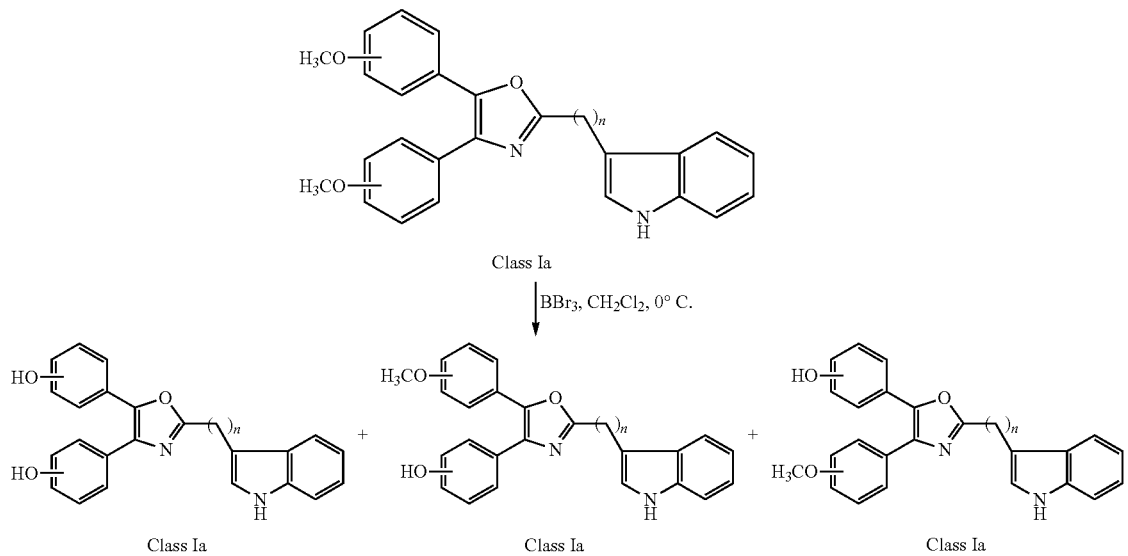

Several of the compounds of Class Ia prepared according to Scheme 2 were subject to additional transformations as indicated in Scheme 5 and Scheme 6. As illustrated in Scheme 5, by acylation of compounds of Class Ia, compounds of Class Id, for example compound 720, were obtained. Through demethylation of appropriate compounds of Class Ia with BBr$_3$ as illustrated in Scheme 6, demethylated products, compounds of Class Ia: 648, 698, 675, 676, 697, 699, 718, 719, 891, 924, 925, 931, 936 were obtained.

General Procedure for the Preparation of Intermediate Compound 27 as Illustrated in Scheme 2, Intermediate 28 as Illustrated in Scheme 3, and Intermediate 30 as Illustrated in Scheme 4.

To a vacuum flame-dried flask was added 4-19 (1 mmol), acid 26 (or 29) (1.1 mmol), dicyclohexylcarbodiimide (0.206 g, 1 mmol), 4-dimethylaminopyridine (12.2 mg, 0.1 mmol), dichloromethane (10 mL) under nitrogen atmosphere. The reaction mixture was stirred for 2 hours at room temperature. Then ethyl acetate was added and the reaction mixture was filtered. The filtrate was then washed with 5% HCl, saturated NaHCO$_3$, brine and dried with Na$_2$SO$_4$. After filtration, the solvent was concentrated in vacuum. This crude residue was then purified by flash chromatography to give Intermediate 27 (28 or 30).

General Procedure for the Preparation of Compounds of Classes Ia-Ic as Illustrated in Schemes 2-4.

A mixture of 27 (28 or 30) (0.5 mmol), ammonium acetate (2.5 mmol) in glacial acetic acid (5 mL) was refluxed for 2 hours. After cooling, water was added to the reaction mixture. After extracting with ethyl acetate, the combined organic phase was washed with saturated NaHCO$_3$, brine, dried with Na$_2$SO$_4$, filtered, and concentrated in vacuum. The crude residue was then purified by flash chromatography to give the desired products, compounds of Classes Ia-Ic: 708, 630-632, 636-641, 649-663, 670-673, 677-679, 681, 696, 761, 762, 892, 916, 917, 932.

General Procedure for the Preparation of Compounds of Class Id as Illustrated in Scheme 5.

To a mixture of compounds of Class Ia (1 mmol), n-Bu$_4$NHSO$_4$ (7 g, 0.018 mmol) and powered NaOH (0.99 g, 25 mmol) in CH$_2$Cl$_2$ (10 mL), acetyl chloride (0.11 mL, 1.5 mmol) in CH$_2$Cl$_2$ (6 mL) was added dropwise to the vigorously stirring solution. After 2 hours at room temperature, TLC showed complete consumption of the 708. After removal of the solvent, the crude residue was purified by flash chromatography on silica gel to give compound 720 (0.332 g, 85%).

General Procedure for the Preparation of Demethylated Compounds of Class Ia as Illustrated in Scheme 6.

To a mixture of an appropriate compound of Class Ia (1 mmol) in dry dichloromethane (10 mL) at 0° C. under N$_2$, BBr$_3$ (1M in dichloromethane, 3.5 mL, 3.5 mmol) was added dropwise. The resulting mixture was allowed to warm to room temperature and stirred for 4 hours. Then ice water (50 mL) was added to quench the reaction and extracted with CH$_2$Cl$_2$ (3×15 mL). The combined organic phase was washed with water, brine and dried over magnesium sulfate. After removal of the solvent, the crude residue was purified by column chromatography to give the desired products, compounds of Class Ia: 648, 698, 675, 676, 697, 699, 718, 719, 891, 924, 925, 931, 936.

TABLE 2

Structures of compounds of Classes Ia-Id.

| ID | Structure |
| --- | --- |
| 679 | |
| 649 | |
| 658 | |
| 935 | |
| 648 | |
| 698 | 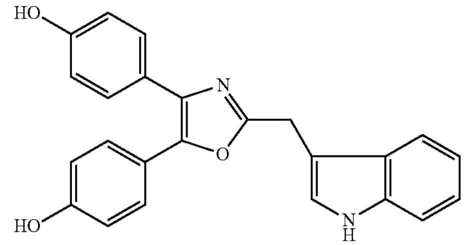 [SMILES: Oc1ccc(-c2nc(Cc3c[nH]c4ccccc34)oc2-c2ccc(O)cc2)cc1] |
| 630 | 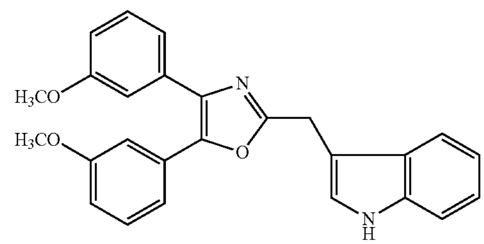 |
| 660 | 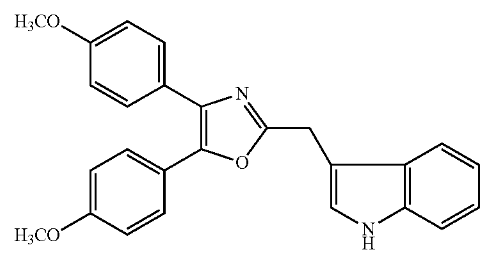 [SMILES: COc1ccc(-c2nc(Cc3c[nH]c4ccccc34)oc2-c2ccc(OC)cc2)cc1] |
| 719 | 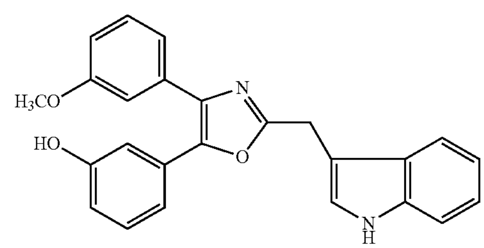 |
| 718 | 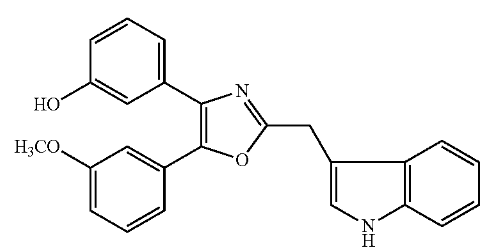 [SMILES: COc1cccc(-c2oc(Cc3c[nH]c4ccccc34)nc2-c2cccc(O)c2)c1] |
| 699 | 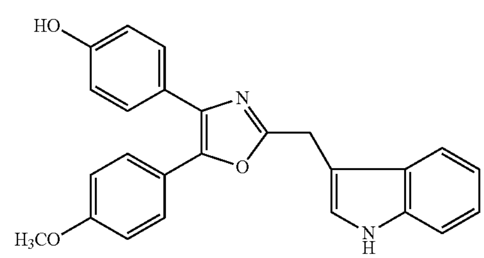 |

TABLE 2-continued

Structures of compounds of Classes Ia-Id.

| ID | Structure |
|---|---|
| 697 | (4-methoxyphenyl and 4-hydroxyphenyl substituted oxazole linked via CH2 to indole) |
| 891 | (bis(2-hydroxyphenyl) substituted oxazole linked via CH2 to indole) |
| 892 | (bis(2-methoxyphenyl) substituted oxazole linked via CH2 to indole) |
| 708 | (4,5-diphenyl oxazole linked via CH2 to indole) |
| 700 | (4,5-diphenyl oxazole linked to oxindole) |
| 636 | (4,5-diphenyl oxazole linked via CH2 to 5-fluoroindole) |
| 637 | (4,5-diphenyl oxazole linked via CH2 to 2-methylindole) |
| 638 | (4,5-diphenyl oxazole linked via CH2 to N-methylindole) |
| 639 | (4,5-diphenyl oxazole linked via CH2 to 2-methyl-5-methoxyindole) |
| 720 | (4,5-diphenyl oxazole linked via CH2 to N-acetylindole) |
| 655 | (bis(2-fluorophenyl) substituted oxazole linked via CH2 to indole) |
| 650 | (bis(3-fluorophenyl) substituted oxazole linked via CH2 to indole) |

TABLE 2-continued
Structures of compounds of Classes Ia-Id.
| ID | Structure |
|---|---|
| 652 | 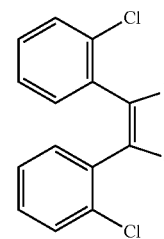 |
| 651 | 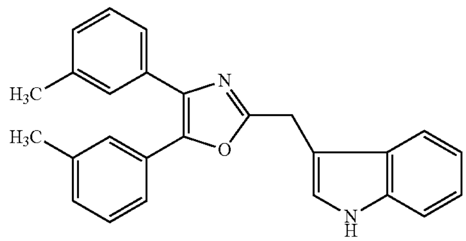 [SMILES: Cc1cccc(-c2nc(Cc3c[nH]c4ccccc34)oc2-c2cccc(C)c2)c1] |
| 654 | 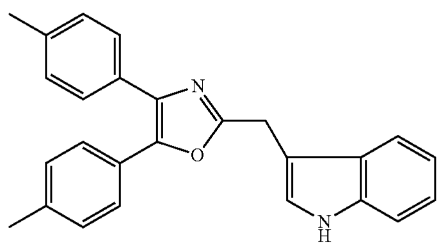 [SMILES: Cc1ccc(-c2nc(Cc3c[nH]c4ccccc34)oc2-c2ccc(C)cc2)cc1] |
| 659 | 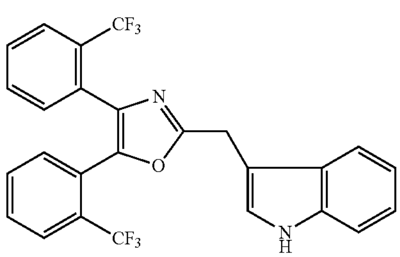 |
| 656 | 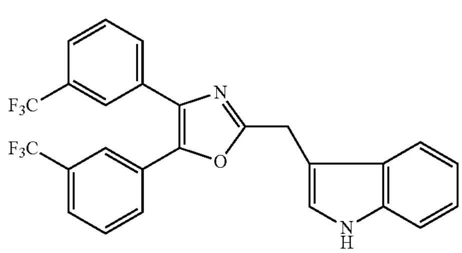 [SMILES: FC(F)(F)c1cccc(-c2nc(Cc3c[nH]c4ccccc34)oc2-c2cccc(C(F)(F)F)c2)c1] |
| 653 | 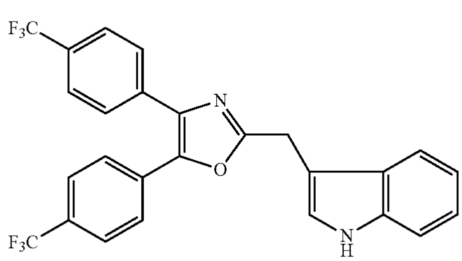 [SMILES: FC(F)(F)c1ccc(-c2nc(Cc3c[nH]c4ccccc34)oc2-c2ccc(C(F)(F)F)cc2)cc1] |
TABLE 2-continued
Structures of compounds of Classes Ia-Id.
| ID | Structure |
|---|---|
| 662 | 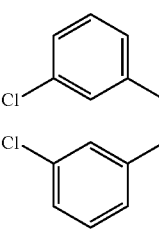 |
| 663 | 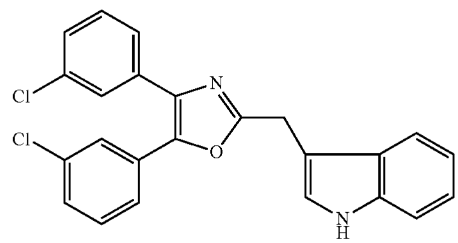 [SMILES: Clc1cccc(-c2nc(Cc3c[nH]c4ccccc34)oc2-c2cccc(Cl)c2)c1] |
| 661 | 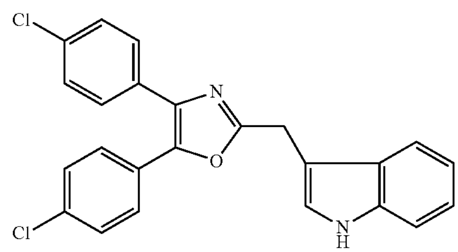 [SMILES: Clc1ccc(-c2nc(Cc3c[nH]c4ccccc34)oc2-c2ccc(Cl)cc2)cc1] |
| 696 | 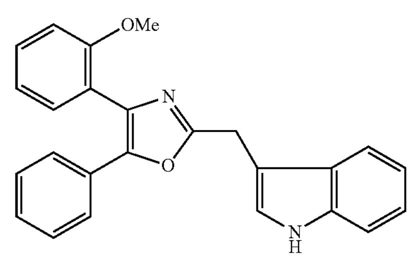 [SMILES: COc1ccccc1-c1nc(Cc2c[nH]c3ccccc23)oc1-c1ccccc1] |
| 631 | 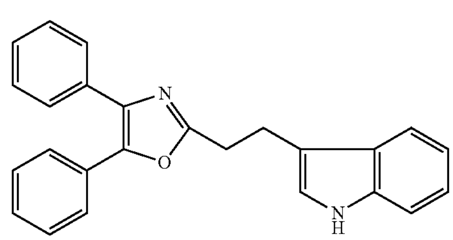 |
| 657 | 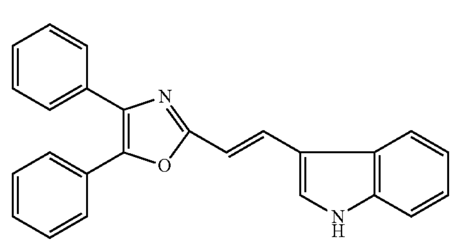 [SMILES: C(=C\c1c[nH]c2ccccc12)/c1nc(-c2ccccc2)c(-c2ccccc2)o1] |

TABLE 2-continued

Structures of compounds of Classes Ia-Id.

| ID | Structure |
|---|---|
| 641 | 3,3'-dimethoxyphenyl oxazole with ethyl-indole |
| 917 | 2,2'-dimethoxyphenyl oxazole with ethyl-indole |
| 932 | 4,4'-dimethoxyphenyl oxazole with ethyl-indole |
| 933 | 3,3'-bis(trifluoromethyl)phenyl oxazole with ethyl-indole |
| 931 | 2,2'-dihydroxyphenyl oxazole with ethyl-indole |
| 936 | 4,4'-dihydroxyphenyl oxazole with ethyl-indole |
| 675 | 3,3'-dihydroxyphenyl oxazole with ethyl-indole |
| 918 | 4,4'-bis(trifluoromethyl)phenyl oxazole with ethyl-indole |
| 920 | 2,2'-bis(trifluoromethyl)phenyl oxazole with ethyl-indole |
| 761 | 3,3'-difluorophenyl oxazole with ethyl-indole |
| 866 | 3,3'-difluorophenyl oxazole with ethyl-oxindole |
| 924 | 2-hydroxyphenyl / 2-methoxyphenyl oxazole with ethyl-indole |

TABLE 2-continued

Structures of compounds of Classes Ia-Id.

| ID | Structure |
|---|---|
| 673 | 4-(3-fluorophenyl)-5-(3-fluorophenyl)-2-(3-(1H-indol-3-yl)propyl)oxazole |
| 678 | 4-(2-fluorophenyl)-5-(2-fluorophenyl)-2-(3-(1H-indol-3-yl)propyl)oxazole |
| 671 | 4,5-bis(4-fluorophenyl)-2-(3-(1H-indol-3-yl)propyl)oxazole |
| 770 | 3-(3-(4,5-bis(3-fluorophenyl)oxazol-2-yl)propyl)indolin-2-one |
| 762 | 4,5-bis(3-chlorophenyl)-2-(3-(1H-indol-3-yl)propyl)oxazole |
| 632 | 2-(3-(1H-indol-3-yl)propyl)-4,5-diphenyloxazole |
| 640 | 2-(3-(1H-indol-3-yl)propyl)-4,5-bis(3-methoxyphenyl)oxazole |
| 670 | 2-(3-(1H-indol-3-yl)propyl)-4,5-bis(4-methoxyphenyl)oxazole |
| 916 | 2-(3-(1H-indol-3-yl)propyl)-4,5-bis(2-methoxyphenyl)oxazole |
| 676 | 3,3'-(2-(3-(1H-indol-3-yl)propyl)oxazole-4,5-diyl)diphenol |
| 677 | 2-(3-(1H-indol-3-yl)propyl)-4,5-bis(2-(trifluoromethyl)phenyl)oxazole |
| 681 | 2-(3-(1H-indol-3-yl)propyl)-4,5-bis(3-(trifluoromethyl)phenyl)oxazole |

TABLE 2-continued

Structures of compounds of Classes Ia-Id.

| ID | Structure |
|---|---|
| 672 | 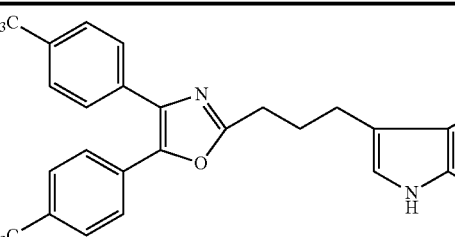 |
| 925 | 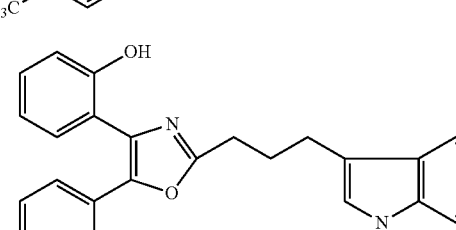 |
| 857 | 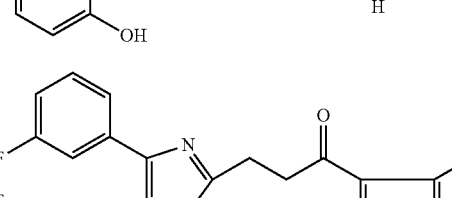 |

Characterization of Compounds of Classes Ia-Id:

679: White solid, yield: 43.2%. $^1$H NMR (500 MHz, acetone-d$_6$) δ 8.50 (s, 1H), 8.44-8.35 (m, 1H), 7.96 (d, J=2.8 Hz, 1H), 7.79-7.73 (m, 2H), 7.73-7.66 (m, 2H), 7.48-7.25 (m, 9H).

649: White solid, yield: 53.4%. $^1$H NMR (500 MHz, CDCl$_3$) δ 8.44-8.37 (m, 1H), 7.86 (s, 1H), 7.81-7.76 (m, 2H), 7.73-7.69 (m, 2H), 7.45-7.29 (m, 9H), 3.89 (s, 3H).

658: White solid, yield: 44.6%. $^1$H NMR (500 MHz, CDCl$_3$) δ 9.67 (d, J=2.2 Hz, 1H), 8.88 (d, J=1.9 Hz, 1H), 8.22-8.15 (m, 1H), 7.98-7.91 (m, 1H), 7.84-7.70 (m, 5H), 7.64-7.61 (m, 1H), 7.49-7.35 (m, 6H).

935: White solid, yield: 47.5%. $^1$H NMR (500 MHz, CDCl$_3$) δ 8.77 (br, 1H), 8.16-8.09 (m, 1H), 7.82 (s, 2H), 7.72 (d, J=2.7 Hz, 1H), 7.69 (d, J=7.5 Hz, 2H), 7.55 (d, J=7.8 Hz, 2H), 7.44 (t, J=7.8 Hz, 2H), 7.41-7.39 (m, 1H), 7.29-7.26 (m, 2H).

648: White solid, yield: 92.5%. $^1$H NMR (500 MHz, acetone-d$_6$) δ 10.16 (br, 1H), 8.50 (s, 1H), 8.36 (s, 1H), 7.72 (d, J=7.8 Hz, 1H), 7.39 (d, J=7.8 Hz, 2H), 7.20 (dd, J=15.7, 7.8 Hz, 2H), 7.17-7.15 (m, 1H), 7.15-7.08 (m, 2H), 7.08-6.99 (m, 3H), 6.87-6.75 (m, 2H), 4.31 (s, 2H). MS (ESI) m/z Found: 383.1 [M+H]$^+$, Calcd: 383.4.

698: White solid, yield: 55%. $^1$H NMR (500 MHz, acetone-d$_6$) δ 10.14 (br, 1H), 8.68 (s, 1H), 8.49 (s, 1H), 7.73 (d, J=7.9 Hz, 1H), 7.53-7.46 (m, 2H), 7.44-7.35 (m, 4H), 7.18-7.08 (m, 1H), 7.06-7.03 (m, 1H), 6.92-6.81 (m, 4H), 4.30 (s, 2H).

630: White solid, yield: 89.3%. $^1$H NMR (500 MHz, CDCl$_3$) δ 8.30 (br, 1H), 7.79 (d, J=7.7 Hz, 1H), 7.34 (d, J=8.0 Hz, 1H), 7.30-7.12 (m, 8H), 7.09 (s, 1H), 6.92-6.81 (m, 2H), 4.39 (s, 2H), 3.76 (s, 3H), 3.72 (s, 3H).

660: White solid, yield: 76%. $^1$H NMR (500 MHz, CDCl$_3$) δ 8.09 (br, 1H), 7.76 (d, J=7.8 Hz, 1H), 7.55-7.49 (m, 2H), 7.46-7.40 (m, 2H), 7.34 (d, J=7.2 Hz, 1H), 7.22-7.16 (m, 2H), 7.16-7.11 (m, 1H), 6.89-6.78 (m, 4H), 4.29 (s, 2H), 3.80 (s, 3H), 3.78 (s, 3H).

719: White solid, yield: 17%. $^1$H NMR (500 MHz, acetone-d$_6$) δ 10.17 (s, 1H), 8.52 (s, 1H), 7.74-7.73 (m, 1H), 7.42-7.38 (m, 2H), 7.32-7.26 (m, 1H), 7.25-7.20 (m, 3H), 7.12-7.10 (m, 1H), 7.08-7.03 (m, 3H), 6.92-6.88 (m, 1H), 6.84-6.82 (m, 1H), 4.33 (s, 2H), 3.75 (s, 3H).

718: White solid, yield: 13%. $^1$H NMR (500 MHz, acetone-d$_6$) δ 10.17 (s, 1H), 8.38 (s, 1H), 7.75 (d, J=8.0 Hz, 1H), 7.41-7.40 (m, 2H), 7.30 (t, J=8.0 Hz, 1H), 7.21 (t, J=8.0 Hz, 1H), 7.19-7.17 (m, 1H), 7.16-7.10 (m, 4H), 7.07-7.04 (m, 1H), 6.92-6.90 (m, 1H), 6.84-6.80 (m, 1H), 4.33 (d, J=0.8 Hz, 2H), 3.73 (s, 3H).

699: Yellow syrup, yield: 17%. $^1$H NMR (500 MHz, acetone-d$_6$) δ 10.14 (br, 1H), 7.72 (d, J=7.9 Hz, 1H), 7.58-7.52 (m, 2H), 7.42-7.32 (m, 4H), 7.11-7.08 (m, 1H), 7.06-6.99 (m, 1H), 6.97-6.89 (m, 2H), 6.89-6.80 (m, 2H), 4.29 (s, 2H), 3.81 (s, 3H).

697: White solid, yield: 14%. $^1$H NMR (500 MHz, acetone-d$_6$) δ 10.14 (br, 1H), 8.52 (s, 1H), 7.73 (d, J=7.9 Hz, 1H), 7.50-7.43 (m, 4H), 7.39-7.36 (m, 2H), 7.13-7.08 (m, 1H), 7.06-7.02 (m, 1H), 6.96-6.90 (m, 2H), 6.88-6.81 (m, 2H), 4.29 (s, 2H), 3.80 (s, 3H).

891: Colorless crystal, yield: 57%. $^1$H NMR (500 MHz, acetone-d$_6$) δ 11.15 (s, 1H), 10.20 (br, 1H), 8.69 (s, 1H), 7.76-7.65 (m, 1H), 7.42-7.40 (m, 2H), 7.39-7.36 (m, 2H), 7.16-7.07 (m, 3H), 7.07-7.02 (m, 2H), 7.02-6.96 (m, 1H), 6.86-6.81 (m, 1H), 6.61-6.58 (m, 1H), 4.43 (d, J=0.8 Hz, 2H).

892: White solid, yield: 69%. $^1$H NMR (500 MHz, CDCl$_3$) δ 8.12 (s, 1H), 7.81 (d, J=7.2 Hz, 1H), 7.56 (dd, J=7.6, 1.8 Hz, 1H), 7.37 (dd, J=7.6, 1.8 Hz, 1H), 7.36-7.33 (m, 1H), 7.29-7.24 (m, 2H), 7.24-7.21 (m, 1H), 7.17-7.12 (m, 1H), 6.97-6.94 (td, J=7.5, 1.0 Hz, 1H), 6.91 (td, J=7.5, 1.0 Hz, 1H), 6.82-6.79 (m, 2H), 4.35 (s, 2H), 3.37 (s, 6H).

708: White solid, yield: 87.6%. $^1$H NMR (500 MHz, CDCl$_3$), δ 8.32 (d, J=21.5 Hz, 1H), 7.77 (d, J=7.6 Hz, 1H), 7.66-7.60 (m, 2H), 7.53-7.50 (m, 2H), 7.39-7.25 (m, 7H), 7.22-7.09 (m, 3H), 4.43 (s, 1H), 4.39 (s, 1H). MS (ESI) m/z Found: 351.1 [M+H]$^+$, Calcd: 351.4.

700: White solid, yield: 65%. $^1$H NMR (500 MHz, acetone-d$_6$) δ 9.51 (br, 1H), 7.66-7.59 (m, 2H), 7.56-7.53 (m, 2H), 7.45-7.31 (m, 5H), 7.24 (d, J=7.6 Hz, 1H), 7.19 (t, J=7.7 Hz, 1H), 6.95-6.91. (m, 2H), 4.01 (dd, J=8.2, 5.0 Hz, 1H), 3.61 (dd, J=16.0, 5.0 Hz, 1H), 3.29 (dd, J=16.0, 8.2 Hz, 1H), 2.80 (d, J=17.0 Hz, 3H). MS (ESI) m/z Found: 367.1 [M+H]$^+$, Calcd: 367.4.

636: White solid, yield 82.5%. C$_{24}$H$_{17}$FN$_2$O, $^1$H NMR (500 MHz, CDCl$_3$) δ 8.15 (s, 1H), 7.68-7.62 (m, 2H), 7.60-7.52 (m, 2H), 7.44 (dd, J=9.6, 2.4 Hz, 1H), 7.40-7.27 (m, 8H), 6.96 (td, J=9.0, 2.5 Hz, 1H), 4.30 (s, 2H).

637: White solid, yield: 79.5%. C$_{25}$H$_{20}$N$_2$O, $^1$H NMR (500 MHz, CDCl$_3$) δ 7.87 (br, 1H), 7.72-7.70 (m, 1H), 7.65-7.60 (m, 2H), 7.53-7.47 (m, 2H), 7.39-7.27 (m, 6H), 7.16-7.09 (m, 2H), 4.27 (s, 2H), 2.52 (s, 3H).

638: Colorless syrup, yield: 68.5%. $^1$H NMR (500 MHz, CDCl$_3$) δ 7.78 (d, J=7.9 Hz, 1H), 7.65-7.63 (m, 2H), 7.56-7.51 (m, 2H), 7.38-7.22 (m, 8H), 7.18-7.13 (m, 1H), 7.10 (s, 1H), 4.33 (s, 2H), 3.76 (s, 3H).

639: White solid, yield: 62.1%. $^1$H NMR (500 MHz, CDCl$_3$) δ 7.77 (s, 1H), 7.65-7.59 (m, 2H), 7.54-7.49 (m, 2H), 7.40-7.27 (m, 6H), 7.17 (t, J=5.7 Hz, 2H), 6.78 (dd, J=8.7, 2.5 Hz, 1H), 4.23 (s, 2H), 3.85 (s, 3H), 2.50 (s, 3H).

720: White solid, yield: 65%. $^1$H NMR (500 MHz, CDCl$_3$) δ 8.46 (d, J=7.6 Hz, 1H), 7.73-7.72 (m, 1H), 7.69-7.64 (m, 2H), 7.60-7.57 (m, 1H), 7.56-7.52 (m, 2H), 7.43-7.31 (m, 8H), 4.36 (s, 2H), 2.64 (s, 3H).

655: White solid, yield: 77.3%. $^1$H NMR (500 MHz, CDCl$_3$) δ 8.11 (br, 1H), 7.76 (d, J=8.0 Hz, 1H), 7.67 (td, J=7.6, 1.8 Hz, 1H), 7.43 (td, J=7.6, 1.8 Hz, 1H), 7.36-7.33 (m, 1H), 7.31-7.26 (m, 2H), 7.23-7.14 (m, 4H), 7.13-7.09 (m, 1H), 7.05-6.98 (m, 2H), 4.36 (s, 2H).

650: White solid, yield: 76.5%. $^1$H NMR (500 MHz, CDCl$_3$) δ 8.08 (br, 1H), 7.78-7.72 (m, 1H), 7.40-7.25 (m, 5H), 7.23-7.19 (m, 2H), 7.17-7.14 (m, 1H), 7.04-6.94 (m, 2H), 4.32 (s, 2H).

652: White solid, yield: 83.5%. $^1$H NMR (500 MHz, CDCl$_3$) δ 8.08 (br, 1H), 7.75 (d, J=8.0 Hz, 1H), 7.72 (d, J=8.0 Hz, 2H), 7.62-7.59 (m, 4H), 7.57 (d, J=8.6 Hz, 2H), 7.39-7.35 (m, 1H), 7.24 (d, J=2.3 Hz, 1H), 7.21-7.19 (m, 1H), 7.17-7.14 (m, 1H), 4.35 (s, 2H).

651: White solid, yield: 88.6%. $^1$H NMR (500 MHz, CDCl$_3$) δ 8.06 (br, 1H), 7.76 (d, J=7.6, 1H), 7.49 (s, 1H), 7.41-7.33 (m, 3H), 7.33-7.28 (m, 1H), 7.22-7.12 (m, 5H), 7.12-7.03 (m, 2H), 4.32 (s, 2H), 2.32 (s, 3H), 2.28 (s, 3H).

654: White solid, yield: 83.2%. $^1$H NMR (500 MHz, CDCl$_3$) δ 8.06 (br, 1H), 7.77-7.75 (m, 1H), 7.52-7.47 (m, 2H), 7.43-7.38 (m, 2H), 7.36-7.30 (m, 1H), 7.22-7.16 (m, 2H), 7.16-7.07 (m, 5H), 4.30 (s, 2H), 2.33 (s, 3H), 2.32 (s, 3H).

659: White solid, yield: 63%. $^1$H NMR (500 MHz, CDCl$_3$) δ 8.02 (br, 1H), 7.85-7.80 (m, 1H), 7.68 (d, J=7.9 Hz, 1H), 7.62 (d, J=7.9 Hz, 1H), 7.60-7.57 (m, 1H), 7.55 (t, J=7.6 Hz, 1H), 7.50-7.42 (m, 4H), 7.31 (d, J=8.1 Hz, 1H), 7.18-7.15 (m, 1H), 7.1-7.12 (m, 2H), 7.09-7.15 (m, 1H), 3.95-3.79 (m, 2H).

656: Yellow syrup, yield: 66.9%. $^1$H NMR (500 MHz, CDCl$_3$) δ 8.10 (br, 1H), 7.90 (s, 1H), 7.77 (d, J=8.1 Hz, 3H), 7.64 (d, J=7.8 Hz, 1H), 7.58 (d, J=8.1 Hz, 1H), 7.54 (d, J=7.8 Hz, 1H), 7.46 (t, J=7.8 Hz, 1H), 7.43 (t, J=7.8 Hz, 1H), 7.36 (d, J=8.1 Hz, 1H), 7.24 (d, J=2.3 Hz, 1H), 7.23-7.13 (m, 2H), 4.35 (s, 2H).

653: White solid, yield: 82.6%. $^1$H NMR (500 MHz, CDCl$_3$) δ 8.09 (br, 1H), 7.75 (d, J=8.2 Hz, 1H), 7.61-7.52 (m, 2H), 7.50-7.41 (m, 2H), 7.38-7.32 (m, 1H), 7.23-7.18 (m, 2H), 7.16-7.13 (m, 1H), 7.08-6.93 (m, 4H), 4.31 (s, 2H).

662: Yellow solid, yield: 79%. $^1$H NMR (500 MHz, CDCl$_3$) δ 8.08 (br, 1H), 7.77-7.72 (m, 1H), 7.64-7.63 (m, 1H), 7.52-7.50 (m, 1H), 7.46-7.42 (m, 1H), 7.39-7.32 (m, 2H), 7.31-7.23 (m, 4H), 7.23-7.18 (m, 2H), 7.17-7.14 (m, 1H), 4.32 (s, 2H).

663: White solid, yield: 82%. $^1$H NMR (500 MHz, CDCl$_3$) δ 8.08 (br, 1H), 7.74 (d, J=8.0 Hz, 1H), 7.40-7.36 (m, 1H), 7.36-7.32 (m, 2H), 7.27-7.23 (m, 3H), 7.23-7.17 (m, 4H), 7.17-7.11 (m, 2H), 4.37 (s, 2H).

661: White solid, yield: 76%. $^1$H NMR (500 MHz, CDCl$_3$) δ 8.07 (br, 1H), 7.74 (d, J=7.8 Hz, 1H), 7.54-7.49 (m, 2H), 7.44-7.38 (m, 2H), 7.35 (d, J=8.1 Hz, 1H), 7.33-7.25 (m, 4H), 7.22-7.18 (m, 2H), 7.14-7.12 (m, 1H), 4.31 (s, 2H).

696: White solid, yield: 65%. $^1$H NMR (500 MHz, cdcl$_3$) δ 8.31 (br, 1H), 7.78 (d, J=7.8 Hz, 1H), 7.57-7.56 (m, 2H), 7.45-7.34 (m, 3H), 7.33-7.23 (m, 4H), 7.20 (t, J=7.5 Hz, 1H), 7.15 (t, J=7.5 Hz, 1H), 7.02-6.96 (m, 1H), 6.94 (d, J=8.3 Hz, 1H), 4.51-4.47 (m, 2H), 3.54 (s, 3H).

631: White solid, yield: 82.7%. $^1$H NMR (500 MHz, CDCl$_3$) δ 8.09 (br, 1H), 7.66-7.58 (m, 3H), 7.51-7.49 (m, 2H), 7.40-7.28 (m, 7H), 7.19-7.14 (m, 1H), 7.11-7.18 (m, 2H), 3.44-3.24 (m, 4H).

657: Yellow solid, yield: 55.2%. $^1$H NMR (500 MHz, CDCl$_3$) δ 8.44 (s, 1H), 8.05-8.00 (m, 1H), 7.83 (d, J=16.4 Hz, 1H), 7.75-7.65 (m, 4H), 7.52-7.26 (m, 10H), 7.05 (d, J=16.4 Hz, 1H).

641: White solid, yield: 86.3%. $^1$H NMR (500 MHz, CDCl$_3$) δ 8.00 (br, 1H), 7.65-7.59 (m, 1H), 7.36-7.31 (m, 1H), 7.28-7.02 (m, 9H), 6.87-6.82 (m, 2H), 3.76 (s, 3H), 3.72 (s, 3H), 3.37-3.28 (m, 2H), 3.28-3.18 (m, 2H).

917: Colorless syrup, yield: 67%. $^1$H NMR (500 MHz, CDCl$_3$) δ 8.01 (br, 1H), 7.65 (d, J=6.8 Hz, 1H), 7.5-7.55 (m, 1H), 7.40-7.34 (m, 2H), 7.33-7.24 (m, 2H), 7.23-7.16 (m, 1H), 7.16-7.07 (m, 2H), 6.99-6.93 (m, 2H), 6.85-6.81 (m, 2H), 3.42 (s, 3H), 3.40 (s, 3H), 3.36-3.32 (m, 2H), 3.29-3.23 (m, 2H).

932: White solid, yield: 83.1%. $^1$H NMR (500 MHz, CDCl$_3$) δ 8.04 (br, 1H), 7.64 (d, J=7.9 Hz, 1H), 7.59-7.53 (m, 2H), 7.48-7.44 (m, 2H), 7.35 (d, J=8.1 Hz, 1H), 7.22-7.16 (m, 1H), 7.15-7.09 (m, 1H), 7.05-7.04 (m, 1H), 6.92-6.85 (m, 4H), 3.83 (s, 3H), 3.82 (s, 3H), 3.34-3.31 (m, 2H), 3.25-3.19 (m, 2H).

933: White solid, yield: 77.6%. $^1$H NMR (500 MHz, CDCl$_3$) δ 8.00 (br, 1H), 7.92 (s, 1H), 7.79 (d, J=7.7 Hz, 1H), 7.75 (s, 1H), 7.67-7.57 (m, 4H), 7.52-7.45 (m, 2H), 7.40-7.36 (m, 1H), 7.23-7.18 (m, 1H), 7.15-7.10 (m, 1H), 7.09-9.08 (m, 1H), 3.40-3.32 (m, 2H), 3.30-3.26 (m, 2H).

931: White solid, yield: 77.6%. $^1$H NMR (500 MHz, Acetone-d$_6$) δ 11.00 (s, 1H), 8.01 (br, 1H), 7.61-7.56 (m, 1H), 7.41-7.33 (m, 3H), 7.24-7.17 (m, 2H), 7.16-7.10 (m, 2H), 7.07 (d, J=2.4 Hz, 1H), 7.00 (dddd, J=6.2, 3.8, 3.0, 1.2 Hz, 3H), 6.72-6.99 (m, 1H), 3.38-3.32 (m, 2H), 3.31-3.26 (m, 2H).

936: White solid, yield: 83.6%. $^1$H NMR (500 MHz, Acetone-d$_6$) δ 9.99 (br, 1H), 8.66 (br, 1H), 8.47 (br, 1H), 7.64-7.57 (m, 1H), 7.51-7.45 (m, 2H), 7.42-7.34 (m, 3H), 7.25-7.19 (m, 1H), 7.11-7.08 (m, 1H), 7.06-6.98 (m, 1H), 6.92-6.81 (m, 4H), 3.33-3.26 (m, 2H), 3.20-3.13 (m, 2H).

675: Yellow syrup, yield: 85%. $^1$H NMR (500 MHz, acetone-d$_6$) δ 10.00 (br, 1H), 8.53 (s, 1H), 8.39 (s, 1H), 7.62 (d, J=7.9 Hz, 1H), 7.38 (d, J=8.1 Hz, 1H), 7.26-7.17 (m, 4H), 7.16-6.99 (m, 5H), 6.86-6.81 (m, 2H), 3.33-3.30 (m, 2H), 3.23-3.20 (m, 2H).

918: White solid, yield: 73%. $^1$H NMR (500 MHz, CDCl$_3$) δ 8.00 (br, 1H), 7.62 (d, J=7.9 Hz, 1H), 7.61-7.56 (m, 2H), 7.50-7.44 (m, 2H), 7.36 (d, J=8.1 Hz, 1H), 7.22-7.18 (m, 1H), 7.14-7.10 (m, 1H), 7.10-7.01 (m, 5H), 3.35-3.31 (m, 2H), 3.26-3.21 (m, 2H).

920: White solid, yield: 81%. $^1$H NMR (500 MHz, CDCl$_3$) δ 7.93 (br, 1H), 7.90 (d, J=7.6 Hz, 1H), 7.71 (d, J=7.9 Hz, 1H), 7.65 (t, J=8.7 Hz, 2H), 7.61-7.51 (m, 4H), 7.33 (d, J=8.1 Hz, 1H), 7.20-7.15 (m, 1H), 7.13 (s, 1H), 7.12-7.05 (m, 1H), 6.97 (d, J=2.3 Hz, 1H), 3.16-3.06 (m, 2H), 2.91-2.81 (m, 2H).

761: White solid, yield: 84.6%. $^1$H NMR (500 MHz, CDCl$_3$) δ 8.03 (br, 1H), 7.6-7.57 (m, 1H), 7.44-7.24 (m, 6H), 7.19-7.16 (m, 2H), 7.12-6.98 (m, 4H), 3.35-3.24 (m, 4H).

866: White solid. Yield: 74%. $^1$H NMR (500 MHz, CDCl$_3$) δ 7.66 (s, 1H), 7.38-7.27 (m, 5H), 7.26-7.15 (m, 3H), 7.06-6.97 (m, 3H), 6.85 (d, J=7.8 Hz, 1H), 3.66 (t, J=6.1 Hz, 1H), 3.07-2.93 (m, 2H), 2.63-2.49 (m, 2H).

924: White solid, yield: 73%. $^1$H NMR (500 MHz, CDCl$_3$) δ 11.26 (s, 1H), 7.98 (br, 1H), 7.65-7.59 (m, 1H), 7.46-7.44 (m, 1H), 7.42-7.33 (m, 2H), 7.22-7.19 (m, 1H), 7.15-7.13 (m, 2H), 7.07-6.96 (m, 5H), 6.63-6.60 (m, 1H), 3.68 (s, 3H), 3.36-3.32 (m, 2H), 3.32-3.21 (m, 2H).

673: White solid, yield: 76%. $^1$H NMR (500 MHz, CDCl$_3$) δ 7.94 (br, 1H), 7.65-7.58 (m, 1H), 7.40-7.35 (m, 1H), 7.35-7.27 (m, 5H), 7.22-7.20 (m, 1H), 7.19-7.14 (m, 1H), 7.10-7.07 (m, 1H), 7.04-6.97 (m, 3H), 2.92-2.88 (m, 4H), 2.29-2.14 (m, 2H). MS (ESI) m/z Found: 415.2 [M+H]⁺, Calcd: 414.5.

678: Yellow syrup, yield: 77%. ¹H NMR (500 MHz, CDCl₃) δ 7.95 (br, 1H), 7.69-7.63 (m, 1H), 7.61 (d, J=7.9 Hz, 1H), 7.44-7.41 (m, 1H), 7.34-7.25 (m, 3H), 7.19-7.04 (m, 5H), 7.04-6.97 (m, 2H), 2.95-2.90 (m, 4H), 2.30-2.24 (m, 2H).

671: White solid, yield: 74%. ¹H NMR (500 MHz, CDCl₃) δ 7.94 (br, 1H), 7.71 (d, J=8.1 Hz, 2H), 7.66-7.57 (m, 8H), 7.35-7.30 (m, 1H), 7.18-7.15 (m, 1H), 7.10-7.07 (m, 1H), 7.01 (d, J=2.2 Hz, 1H), 2.93-2.90 (m, 4H), 2.30-2.24 (m, 2H).

770: White solid, yield: 71%. ¹H NMR (500 MHz, CDCl₃) δ 7.66 (s, 1H), 7.44-7.38 (m, 1H), 7.38-7.28 (m, 4H), 7.25 (s, 1H), 7.22-7.16 (m, 2H), 7.05-7.00 (m, 3H), 6.84 (d, J=7.7 Hz, 1H), 3.52-3.50 (m, 1H), 2.99-2.89 (m, 2H), 2.13-2.08 (m, 2H), 2.02-1.82 (m, 2H).

762: Yellow syrup, yield: 81%. ¹H NMR (500 MHz, CDCl₃) δ 7.92 (br, 1H), 7.59-7.50 (m, 2H), 7.43 (d, J=7.0 Hz, 1H), 7.35 (s, 1H), 7.31-7.16 (m, 7H), 7.08-7.00 (m, 2H), 2.95-2.85 (m, 2H), 2.34-2.24 (m, 2H).

632: White solid, yield: 83.2%. ¹H NMR (500 MHz, CDCl₃), δ 7.99 (br, 1H), 7.64-7.56 (m, 3H), 7.43-7.27 (m, 8H), 7.22 (s, 1H), 7.15-6.99 (m, 3H), 3.14 (d, J=6.7 Hz, 2H), 2.96 (t, J=6.9 Hz, 2H), 2.40-2.36 (m, 2H).

640: White solid, yield: 81.2%. ¹H NMR (500 MHz, CDCl₃) δ 8.00 (s, 1H), 7.64 (d, J=8 Hz, 1H), 7.35 (d, J=8 Hz, 1H), 7.32-7.26 (m, 1H), 7.25-7.15 (m, 5H), 7.15-7.07 (m, 2H), 7.042-7.039 (m, 1H), 6.88-6.84 (m, 2H), 3.78 (s, 3H), 3.74 (s, 3H), 2.93 (t, J=7.3 Hz, 4H), 2.28 (p, J=7.5 Hz, 2H). MS (ESI) m/z Found: 439.2 [M+H]⁺, Calcd: 439.5.

670: White solid, yield: 33%. ¹H NMR (500 MHz, CDCl₃) δ 7.98 (br, 1H), 7.64-7.58 (m, 1H), 7.57-7.50 (m, 2H), 7.48-7.42 (m, 2H), 7.33-7.31 (m, 1H), 7.20-7.13 (m, 1H), 7.13-7.05 (m, 1H), 7.01-7.79 (m, 1H), 6.91-6.81 (m, 4H), 3.80 (s, 6H), 2.91-2.86 (m, 4H), 2.27-2.21 (m, 2H). MS (ESI) m/z Found: 439.2 [M+H]⁺, Calcd: 439.5.

916: White solid, yield: 67%. ¹H NMR (500 MHz, CDCl₃) δ 7.94 (br, 1H), 7.64 (d, J=7.9 Hz, 1H), 7.56 (dd, J=7.6, 1.8 Hz, 1H), 7.39 (dd, J=7.6, 1.8 Hz, 1H), 7.35 (d, J=8.1 Hz, 1H), 7.31-7.24 (m, 2H), 7.21-7.16 (m, 1H), 7.12-7.09 (m, 1H), 7.05 (d, J=2.2 Hz, 1H), 6.98-6.93 (m, 2H), 6.84 (d, J=8.4 Hz, 1H), 6.81 (d, J=8.4 Hz, 1H), 3.42 (s, 3H), 3.39 (s, 3H), 2.94 (t, J=7.6 Hz, 4H), 2.32-2.24 (m, 2H).

676: Yellow syrup, yield: 88%. ¹H NMR (500 MHz, acetone-d₆) δ 9.99 (br, 1H), 8.53 (s, 1H), 8.38 (s, 1H), 7.63 (d, J=7.9 Hz, 1H), 7.38 (d, J=8.1 Hz, 1H), 7.25-7.19 (m, 4H), 7.15 (d, J=7.7 Hz, 1H), 7.11-7.06 (m, 3H), 7.05-6.97 (m, 1H), 6.91-6.77 (m, 2H), 2.94 (t, J=7.5 Hz, 2H), 2.90 (t, J=7.5 Hz, 2H), 2.24 (p, J=7.5 Hz, 2H).

677: Yellow syrup, yield: 77%. ¹H NMR (500 MHz, CDCl₃) δ 7.92-7.91 (m, 2H), 7.72 (d, J=7.9 Hz, 1H), 7.65-7.50 (m, 5H), 7.45 (t, J=7.6 Hz, 1H), 7.32 (d, J=8.1 Hz, 1H), 7.18-7.13 (m, 1H), 7.10 (s, 1H), 7.10-7.04 (m, 1H), 6.95 (d, J=2.2 Hz, 1H), 2.78 (t, J=7.3 Hz, 2H), 2.58-2.38 (m, 2H), 2.09-1.97 (m, 2H).

681: Colorless syrup, yield: 84%. ¹H NMR (500 MHz, CDCl₃) δ 7.92 (br, 1H), 7.89 (s, 1H), 7.80-7.74 (m, 2H), 7.67-7.54 (m, 4H), 7.49-7.41 (m, 2H), 7.32 (d, J=8.1 Hz, 1H), 7.19-7.13 (m, 1H), 7.11-7.05 (m, 1H), 7.02 (d, J=2.2 Hz, 1H), 2.94-2.91 (m, 4H), 2.31-2.25 (p, J=7.4 Hz, 2H). HRMS (ESI) m/z Found: 515.15723 [M+H]⁺, Calcd: 515.1526[M+M]⁺.

672: Colorless crystal, yield: 86%. ¹H NMR (500 MHz, CDCl₃) δ 7.95 (br, 1H), 7.60 (d, J=7.9 Hz, 1H), 7.58-7.52 (m, 2H), 7.50-7.42 (m, 2H), 7.33-7.32 (m, 1H), 7.19-7.14 (m, 1H), 7.13-7.06 (m, 1H), 7.06-6.98 (m, 5H), 2.92-2.87 (m, 4H), 2.28-2.22 (m, 2H).

925: White solid, yield: 73%. ¹H NMR (500 MHz, CDCl₃) δ 11.05 (s, 2H), 7.97 (br 1H), 7.62-7.60 (m, 1H), 7.44-7.32 (m, 3H), 7.21-7.16 (m, 2H), 7.14-7.09 (m, 2H), 7.06-6.97 (m, 4H), 6.71-6.68 (m, 1H), 2.99-2.85 (m, 4H), 2.32-2.26 (m, 2H).

Example 3—Preparation of Compounds of Class II

Scheme 7 below outlines the chemical synthesis of compounds identified as compounds of "Class II". These compounds are shown in Table 3 below.

Scheme 7 - Preparation of compounds of Class II.

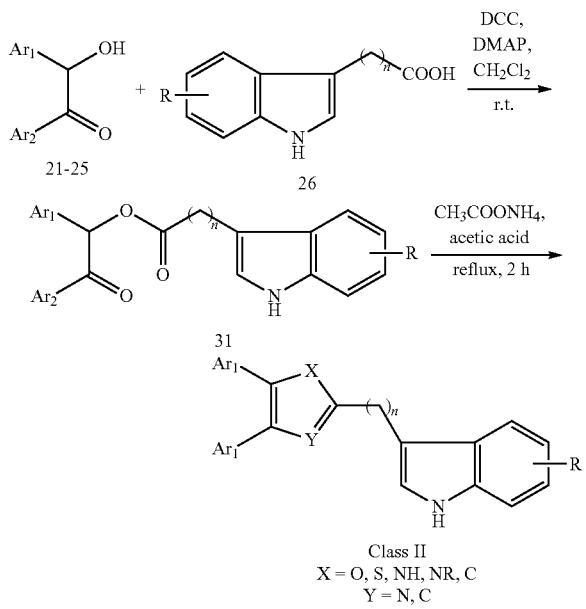

Compounds of Class II may be prepared by typical methods as illustrated in Scheme 7. The appropriate benzoin 21-25 is condensed with substituted indole acid 26, the intermediate ester 31 is obtained, which is then followed by the reaction with ammonium acetate in acetic acid under reflux for 2 hours to generate the desired products, compounds of Class II: 817, 827, 831-834, 838-840, 842, 919, 927, 934.

General Procedure for the Preparation of an Intermediate 31.

To a vacuum flame-dried flask was added a compound 21-25 (1 mmol), acid 26 (1.1 mmol), dicyclohexylcarbodiimide (0.206 g, 1 mmol), 4-dimethylaminopyridine (12.2 mg, 0.1 mmol), dichloromethane (10 mL) under nitrogen atmosphere. The reaction mixture was stirred for 2 hours at room temperature. Then ethyl acetate was added and the reaction mixture was filtered. The filtrate was then washed with 5% HCl, saturated NaHCO₃, brine and dried with Na₂SO₄. After filtration, the solvent was concentrated in vacuum. This crude residue was then purified by flash chromatography to give an intermediate 31.

General Procedure for the Preparation of Compounds of Class II.

A mixture of a compound 31 (0.5 mmol), ammonium acetate (2.5 mmol) in glacial acetic acid (5 mL) was refluxed for 2 hours. After cooling, water was added to the reaction mixture. After extracting with ethyl acetate, the combined organic phase was washed with saturated NaHCO$_3$, brine, dried with Na$_2$SO$_4$, filtered, and concentrated in vacuum. The crude residue was then purified by flash chromatography to give the desired product.

TABLE 3

Structures of compounds of Class II.

| ID | Structure |
|---|---|
| 827 | 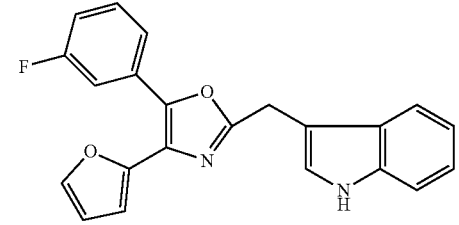 |
| 832 | 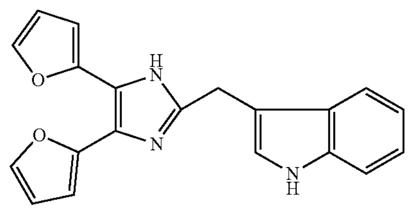 [SMILES: c1coc(-c2nc(Cc3c[nH]c4ccccc34)[nH]c2-c2ccco2)c1] |
| 919 | 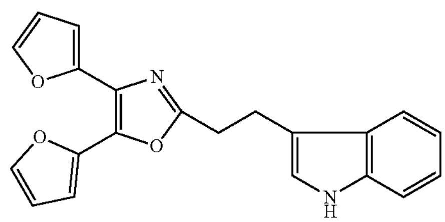 [SMILES: c1coc(-c2nc(CCc3c[nH]c4ccccc34)oc2-c2ccco2)c1] |
| 934 | 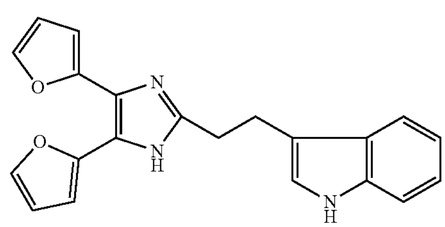 [SMILES: c1coc(-c2nc(CCc3c[nH]c4ccccc34)[nH]c2-c2ccco2)c1] |
| 831 | 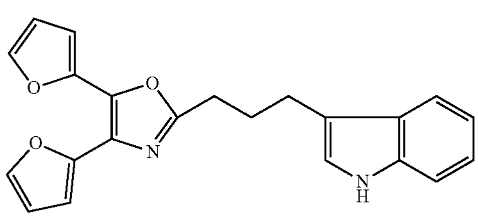 [SMILES: c1coc(-c2nc(CCCc3c[nH]c4ccccc34)oc2-c2ccco2)c1] |
| 817 | 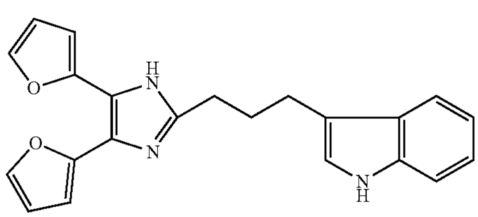 [SMILES: c1coc(-c2nc(CCCc3c[nH]c4ccccc34)[nH]c2-c2ccco2)c1] |

TABLE 3-continued

Structures of compounds of Class II.

| ID | Structure |
|---|---|
| 838 | 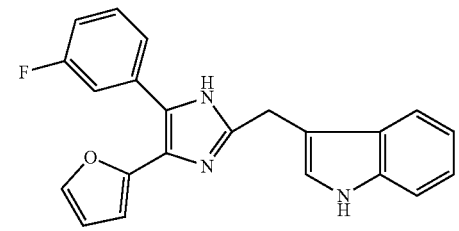 |
| 839 | 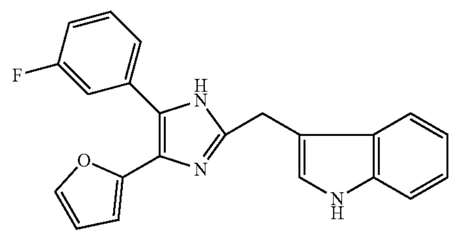 [SMILES: Fc1cccc(-c2[nH]c(Cc3c[nH]c4ccccc34)nc2-c2ccco2)c1] |
| 834 | 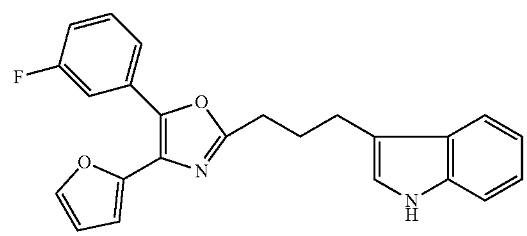 [SMILES: Fc1cccc(-c2oc(CCCc3c[nH]c4ccccc34)nc2-c2ccco2)c1] |
| 842 | 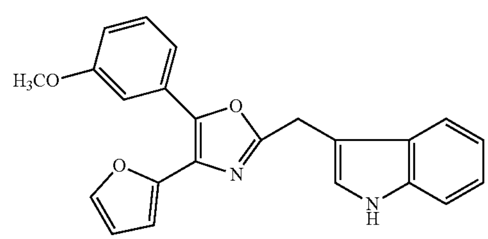 [SMILES: COc1cccc(-c2oc(Cc3c[nH]c4ccccc34)nc2-c2ccco2)c1] |
| 840 | 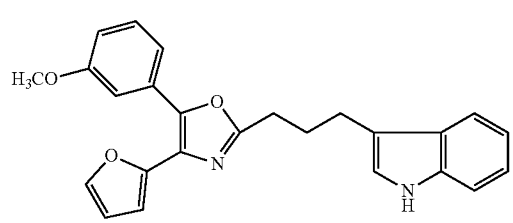 [SMILES: COc1cccc(-c2oc(CCCc3c[nH]c4ccccc34)nc2-c2ccco2)c1] |
| 833 | 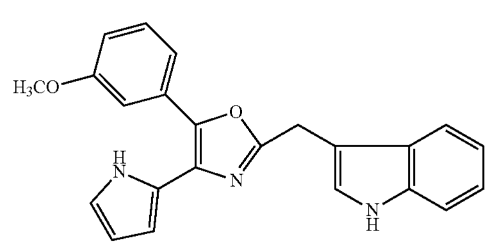 [SMILES: COc1cccc(-c2oc(Cc3c[nH]c4ccccc34)nc2-c2ccc[nH]2)c1] |

TABLE 3-continued

Structures of compounds of Class II.

| ID | Structure |
|---|---|
| 830 | (structure: oxazole with 3-methoxyphenyl, pyrrole, and indolylmethyl substituents) |
| 927 | (structure: oxazole with 3-fluorophenyl, furan, and indolylethyl substituents) |

Characterization of Compounds of Class II:

827: White solid. Yield: 36%. $^1$H NMR (500 MHz, CDCl$_3$) δ 10.19 (br, 1H), 7.70-7.67 (m, 2H), 7.41-7.39 (m, 2H), 7.13-7.10 (m, 1H), 7.04-7.02 (m, 2H), 6.90-6.89 (m, 1H), 6.62-6.58 (m, 2H), 4.33 (s, 2H).

832: White solid. Yield: 32%. $^1$H NMR (500 MHz, CDCl$_3$) δ 8.90 (br, 1H), 8.22 (br, 1H), 7.56 (d, J=8.0 Hz, 1H), 7.42 (d, J=8.2 Hz, 1H), 7.24 (d, J=8.0 Hz, 1H), 7.19 (s, 1H), 7.13 (t, J=7.5 Hz, 1H), 6.87 (br, 2H), 6.47 (br, 2H), 4.33 (s, 2H).

919: colorless syrup, yield: 47%. $^1$H NMR (500 MHz, CDCl$_3$) δ 8.02 (br, 1H), 7.65 (d, J=7.9 Hz, 1H), 7.55-7.53 (m, 2H), 7.38-7.30 (m, 1H), 7.19-7.17 (m, 1H), 7.14-7.12 (m, 1H), 7.03 (d, J=2.3 Hz, 1H), 6.98-6.89 (m, 2H), 6.54-6.50 (m, 2H), 3.36-3.30 (m, 2H), 3.28-3.20 (m, 2H).

934: Colorless syrup, yield: 23.4%. $^1$H NMR (500 MHz, CDCl$_3$) δ 8.03 (br, 1H), 7.62 (t, J=8.3 Hz, 1H), 7.43-7.41 (m, 2H), 7.39-7.38 (m, 1H), 7.25-7.19 (m, 1H), 7.17-7.10 (m, 1H), 6.99-6.98 (m, 1H), 6.86-6.85 (m, 2H), 6.48-6.47 (m, 2H), 3.27-3.23 (m, 2H), 3.23-3.18 (m, 2H).

831: White solid. Yield: 55%. $^1$H NMR (500 MHz, CDCl$_3$) δ 7.94 (br, 1H), 7.62-7.58 (m, 1H), 7.52-7.50 (m, 2H), 7.33-7.31 (m, 1H), 7.18-7.13 (m, 1H), 7.10-7.07 (m, 1H), 7.01 (d, J=2.3 Hz, 1H), 6.92 (dd, J=3.4, 0.7 Hz, 1H), 6.90 (dd, J=3.4, 0.7 Hz, 1H), 6.51 (dd, J=3.4, 1.8 Hz, 1H), 6.49 (dd, J=3.4, 1.8 Hz, 1H), 2.90-2.84 (m, 4H), 2.28-2.19 (m, 2H). HRMS (ESI) m/z. Found: 359.1407 [M+H]$^+$, Calcd: 359.1390.

817: White solid. Yield: 10%. $^1$H NMR (500 MHz, CDCl$_3$) δ 9.05 (br, 1H), 7.99 (s, 1H), 7.57 (d, J=7.5 Hz, 1H), 7.41 (s, 2H), 7.32 (d, J=7.5 Hz, 1H), 7.16 (t, J=7.2 Hz, 1H), 7.08 (d, J=7.2 Hz, 1H), 6.97 (s, 1H), 6.90-6.70 (m, 2H), 6.46 (s, 2H), 2.86-2.78 (dt, J=26.2, 7.0 Hz, 4H), 2.23-2.09 (m, 2H). HRMS (ESI) m/z. Found: 358.1555 [M+H]$^+$, Calcd: 358.1550.

838: White solid. Yield: 48%. $^1$H NMR (500 MHz, CDCl$_3$) δ 8.11 (s, 1H), 7.79-7.73 (m, 1H), 7.57 (ddd, J=7.8, 1.5, 1.0 Hz, 1H), 7.54-7.50 (m, 1H), 7.49 (dt, J=1.8, 1.1 Hz, 1H), 7.40-7.37 (m, 1H), 7.37-7.32 (m, 1H), 7.25-7.20 (m, 2H), 7.17 (ddd, J=8.0, 7.1, 1.1 Hz, 1H), 7.02 (tdd, J=8.4, 2.6, 0.9 Hz, 1H), 6.84-6.80 (m, 1H), 6.51 (td, J=3.5, 1.4 Hz, 1H), 4.34 (d, J=0.9 Hz, 2H).

839: Yellow syrup. Yield: 25%. $^1$H NMR (500 MHz, CDCl$_3$) δ 8.17 (s, 1H), 7.58 (d, J=7.9 Hz, 1H), 7.42 (d, J=8.2 Hz, 1H), 7.35 (br, 2H), 7.25-7.21 (m, 2H), 7.17-7.12 (m, 1H), 6.97 (s, 1H), 6.84 (d, J=7.5 Hz, 1H), 6.51 (s, 1H), 6.38 (s, 1H), 4.36 (d, J=0.7 Hz, 2H), 3.79 (s, 2H). MS (ESI) m/z Found: 358.14 [M+H]$^+$, Calcd: 358.40.

834: White solid. Yield: 45%. $^1$H NMR (500 MHz, CDCl$_3$) δ 7.95 (br, 1H), 7.65-7.61 (m, 1H), 7.59-7.57 (m, 1H), 7.57-7.51 (m, 1H), 7.51-7.48 (m, 1H), 7.41-7.33 (m, 2H), 7.21-7.17 (m, 1H), 7.13-7.10 (m, 1H), 7.07-7.01 (m, 2H), 6.82-6.79 (m, 1H), 6.52-6.51 (m, 1H), 2.94-2.90 (m, 4H), 2.32-2.23 (m, 2H). HRMS (ESI) m/z Found: 387.1520 [M+H]$^+$, Calcd: 387.1503.

842: White solid. Yield: 53%. $^1$H NMR (500 MHz, CDCl$_3$) δ 8.16 (s, 1H), 7.81-7.72 (m, 1H), 7.48-7.47 (m, 1H), 7.39-7.34 (m, 2H), 7.33-7.28 (m, 2H), 7.23-7.18 (m, 2H), 7.17-7.14 (m, 1H), 6.90-6.87 (m, 1H), 6.79-6.78 (m, 1H), 6.49-6.48 (m, 1H), 4.34 (d, J=0.7 Hz, 2H), 3.81 (s, 3H).

840: Yellow syrup. Yield: 48%. $^1$H NMR (500 MHz, CDCl$_3$) δ 7.98 (br, 1H), 7.63 (d, J=7.9 Hz, 1H), 7.48-7.47 (m, 1H), 7.39-7.30 (m, 4H), 7.21-7.16 (m, 1H), 7.12-7.09 (m, 1H), 7.04-7.03 (m, 1H), 6.91-6.89 (m, 1H), 6.78-6.77 (m, 1H), 6.50-6.49 (m, 1H), 3.83 (s, 3H), 2.93-2.90 (m, 4H), 2.32-2.22 (m, 2H).

833: White solid. Yield: 62%. $^1$H NMR (500 MHz, CDCl$_3$) δ 9.08 (br, 1H), 8.11 (br, 1H), 7.79-7.72 (m, 1H), 7.41-7.36 (m, 2H), 7.34 (t, J=7.9 Hz, 1H), 7.32-7.30 (m, 1H), 7.26-7.21 (m, 2H), 7.19-7.16 (m, 1H), 6.91-6.89 (m, 1H), 6.85-6.84 (m, 1H), 6.65-6.63 (m, 1H), 6.29-6.22 (m, 1H), 4.33 (d, J=0.8 Hz, 2H), 3.83 (s, 3H).

830: White solid. Yield: 44%. $^1$H NMR (500 MHz, CDCl$_3$) δ 8.96 (br, 1H), 7.95 (br, 1H), 7.70-7.61 (m, 1H), 7.38-7.29 (m, 4H), 7.20-7.18 (m, 1H), 7.14-7.09 (m, 1H), 7.03 (d, J=2.3 Hz, 1H), 6.90-6.87 (m, 1H), 6.84-6.83 (m, 1H), 6.62-6.61 (m, 1H), 6.29-6.20 (m, 1H), 3.83 (s, 3H), 2.96-2.83 (m, 4H), 2.29-2.23 (m, 2H).

927: White solid, yield: 73%. $^1$H NMR (500 MHz, CDCl$_3$) δ 7.98 (br, 1H), 7.65-7.64 (m, 1H), 7.58-7.54 (m, 1H), 7.53-7.47 (m, 2H), 7.38-7.36 m, 2H), 7.24-7.18 (m, 1H), 7.15-7.13 (m, 1H), 7.08-7.01 (m, 2H), 6.82-6.81 (m, 1H), 6.53-6.52 (m, 1H), 3.35-3.32 (m, 2H), 3.27-3.22 (m, 2H).

Example 4—Preparation of Compounds of Class IIIa and Class IIIb

Schemes 8-12 below outline the chemical synthesis of compounds identified as "Class IIIa". These compounds are shown in Table 4 below.

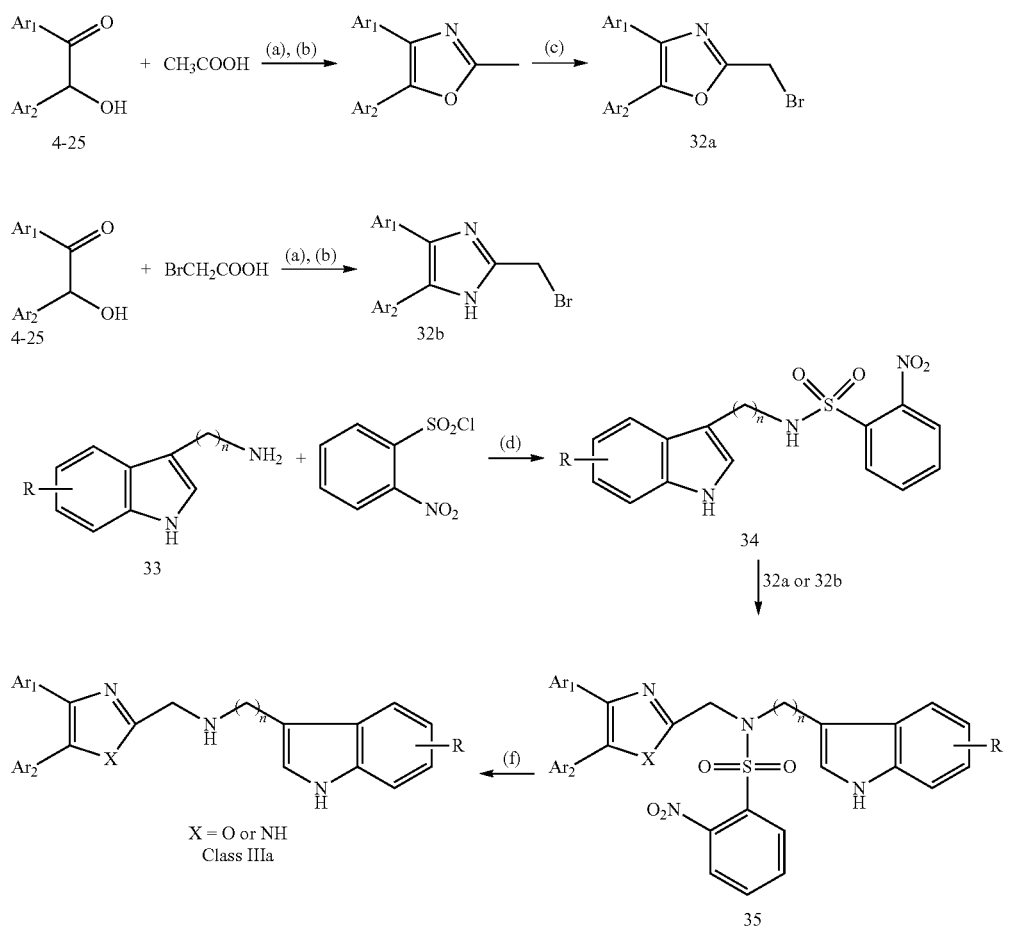

Scheme 8 - Preparation of compounds of Class IIIa.

X = O or NH
Class IIIa (a) DCC, DMAP, CH$_2$Cl$_2$;
(b) CH$_3$COONH$_4$, acetic acid, reflux, 2 h;
(c) (PhCO$_2$)$_2$, bromosuccinimide, CCl$_4$, 6 h, rt - reflux;
(d) Et$_3$N, CH$_2$Cl, rt, 0.5 h;
(e) K$_2$CO$_3$, THF, 60° C., 2 h;
(f) PhSH, KOH, CH$_3$CN, 40 min.

Secondary amines of Class IIIa may be prepared according to the procedure described in Scheme 8. Bromides 32a and 32b were synthesized according to methods known in the art.[70,71] Secondary amines of Class IIIa were obtained by firstly protection of amine 33 with 2-nitrobenzenesulfonyl chloride to give 34, which then reacted with 32a (or 32b), intermediate compound 35 was obtained. Lastly, deprotection of 35 gave the desired secondary amines, compounds of Class IIIa: 795, 874, 1041, 1042, 1096, 1369.

Scheme 9 - Preparation of compounds of Class IIIa.

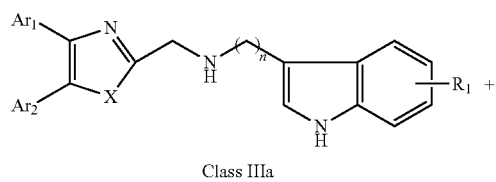

Class IIIa

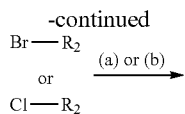

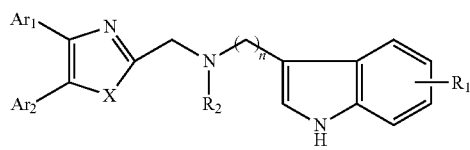

X = O, NH; n = 0, 1, 2, 3, etc
Class IIIa (a) K$_2$CO$_3$, THF, 60° C. 2 h;
(b) Et$_3$N, THF, reflux, 3 h.

Tertiary amines of Class IIIa were prepared by conventional methods as illustrated in Scheme 9. The Compounds of Class IIIa were reacted with bromide or acyl chloride in the presence of weak base such as K$_2$CO$_3$ or Et$_3$N to generate the desired tertiary amines, compounds of Class IIIa: 1186-1188.

Scheme 10 - Preparation of compounds of Class IIIa.

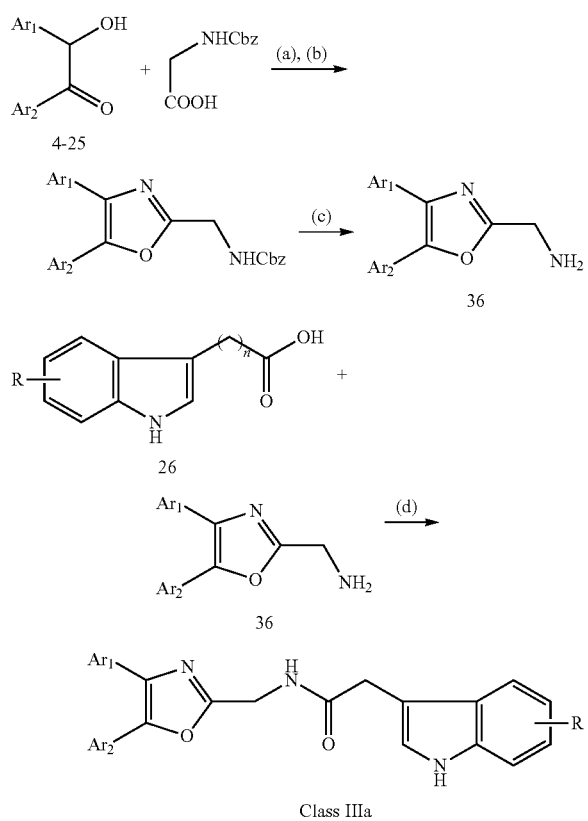

(a) DCC, DMAP, CH$_2$Cl$_2$;
(b) CH$_3$COONH, acetic acid, reflux, 2 h;
(c) Pd/C, H$_2$, 6 h, rt;
(d) Et$_3$N, HBTU, DMSO, rt, overnight.

Scheme 11 - Preparation of compounds of Class IIIa.

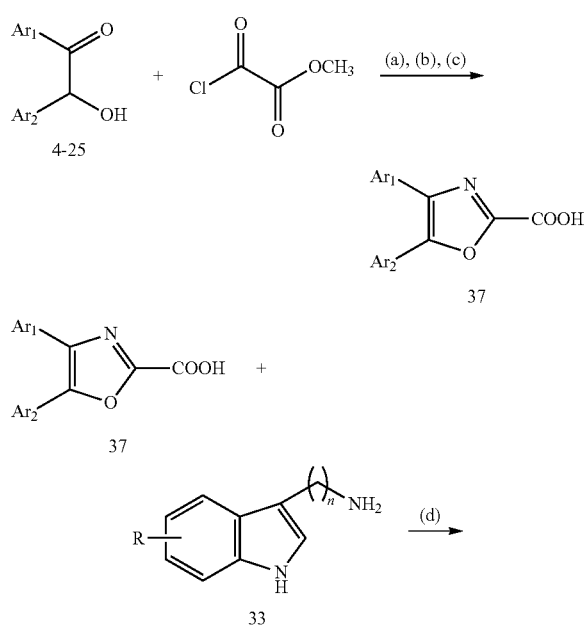

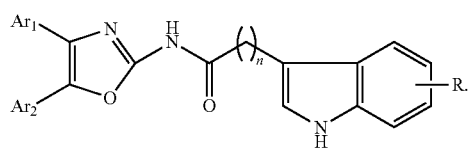

(a) n-Bu$_4$NH$_4$Br, DDQ, PPh$_3$, CH$_2$Cl$_2$; (b) Urea, acetonitrile, reflux, overnight;
(c) Et$_3$N, THF, reflux, 2 h

Scheme 12 - Preparation of compound of Class IIIa.

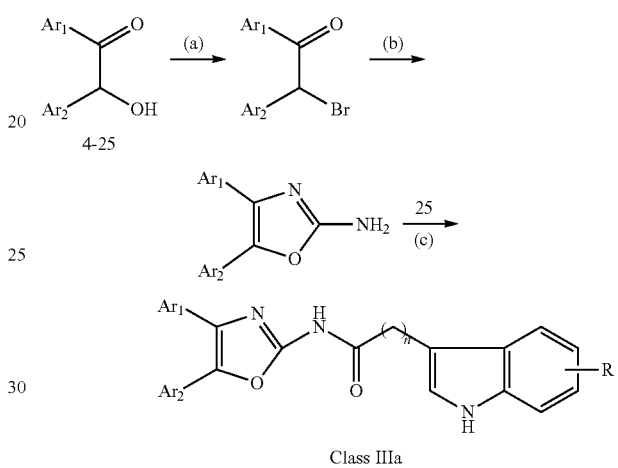

(a) n-Bu$_4$NH$_4$ Br, DDQ, PPH$_3$, CH$_2$Cl$_2$;
(b) Urea, acetonitrile, reflux, overnight;
(c) Et$_3$N, HBTU, DMSO, rt, overnight.

Intermediate compounds 36, 37 and 38 were synthesized according to methods known in the art.[70,71] By the condensation of 26 and 36 (Scheme 10), 33 and 37 (Scheme 11), 26 and 38 (Scheme 12), a series of amides, compounds of Class IIIa: 784, 853-856, 876, 1144, 1145 were obtained.

Scheme 13 and Scheme 14 below outline the chemical synthesis of compounds identified as "Class IIIb". These compounds are shown in Table 4 below.

Scheme 13 - Preparation of compounds of Class IIIb.

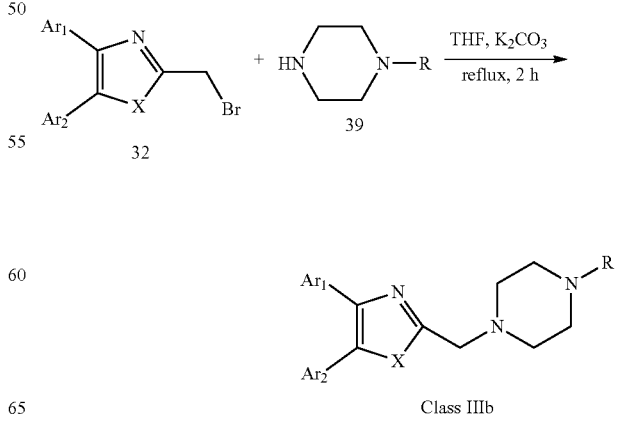

Scheme 14 - Preparation of compound of Class IIIb.

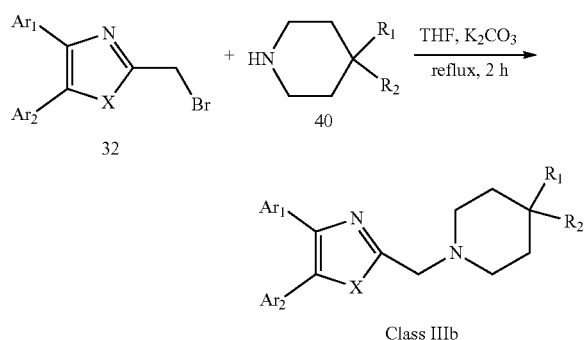

Alternatively, as illustrated in Scheme 13 and Scheme 14, by the reaction of 32 with substituted piperazines 39 or substituted piperidines 40 in the presence of $K_2CO_3$, a series of compounds of Class IIIb were obtained.

General Procedure for the Preparation of Compound 34 (Scheme 8).

To a mixture of 33 (2 mmol) and trimethylamine (0.278 mL, 49.6 mmol) in 10 mL of dichloromethane cooled in an ice-water bath, 0.44 g (2 mmol) of 2-nitrobenzenesulfonyl chloride was added portionwise over a period of 5 minutes under $N_2$. Then the ice bath is removed and the reaction mixture is allowed to warm to room temperature and stirred for 30 minutes. Water was added to quench the reaction and extracted with $CH_2Cl_2$. The combined organic phase was washed with saturated $NaHCO_3$ and dried with $Na_2SO_4$, filtered, concentrated in vacuum. The crude residue was subjected to chromatography on silica gel to give 34

General Procedure for the Preparation of Compound 35 (Scheme 8).

To a mixture of 35 (0.5 mmol), 0.21 g (1.5 mmol) of potassium carbonate, and 10 mL of anhydrous tetrahydrofuran, 32a (or 32b) (0.55 mmol) in 5 mL of anhydrous tetrahydrofuran was added dropwise under $N_2$. The resulting mixture was heated at 60° C. for 2 hours. The reaction mixture is allowed to cool to room temperature, diluted with 250 mL of water, and extracted with dichloromethane (3×15 mL). The combined organic extracts were washed with brine (10 mL), dried over $Na_2SO_4$, filtered, and concentrated in vacuum. The crude residue is purified by column chromatography on silica gel to give 35.

General Procedure for the Preparation of Compounds of Class IIIa as Illustrated in Scheme 8.

To a solution of 0.11 mL (1 mmol) of thiophenol in 10 mL of acetonitrile, 0.1 mL 10.9 M aqueous potassium hydroxide solution (1 mmol) is added dropwise at 0° C. Then the reaction mixture is allowed to warm to room temperature and 0.24 g (0.42 mmol) of 35 in 5 mL of acetonitrile was added dropwise. The reaction mixture is heated in a 50° C. oil bath for 40 minutes. After cooling to room temperature, 10 mL water was added, and extracted with dichloromethane (3×15 mL). The combined organic extracts were washed with brine, dried over $Na_2SO_4$, filtered, and concentrated under reduced pressure. The residue is purified by column chromatography to give the desired products, compounds of class IIIa as illustrated in Scheme 8: 795, 874, 1041, 1042, 1096.

General Procedure for the Preparation of Compounds of Class IIIa as Illustrated in Scheme 9.

Procedure (a): According to the same procedure outlined above for the preparation of 35. A series of compounds of class IIIa as illustrated in Scheme 9 were obtained: 1186-1188.

Procedure (b): To a mixture of Compounds of Class IIIa (1 mmol) and $NEt_3$ (0.83 mL, 6.0 mmol) in 10 mL of THF at 0° C. was added a solution of acyl chloride (1.1 mmol) in 4 mL of THF. The reaction mixture was heated under reflux for 2 hours. After cooling to room temperature, 10 mL water was added, and extracted with dichloromethane (3×15 mL). The combined organic extracts were washed with brine, dried over $Na_2SO_4$, filtered, and concentrated under reduced pressure. The residue is purified by column chromatography to give the desired products, compounds of Class IIIa as illustrated in Scheme 9.

General Procedure for the Preparation of Amides of Class IIIa as Illustrated in Scheme 10-12.

To a suspension of acid 26 (or 37) (0.12 mmol) and 36 (or 33 or 38) (0.1 mmol) and $Et_3N$ (0.4 mmol) in DMSO (3 mL), HBTU (0.4 mmol) was added. The mixture was stirred at room temperature overnight. 10 mL water was added and extracted with dichloromethane (3×15 mL). The combined organic phases were washed with brine, dried over $Na_2SO_4$, filtered, and concentrated under reduced pressure. The crude residue was purified by column chromatography to give products of Class IIIa: 784, 853-856, 876, 1144 and 1145.

General Procedure for the Preparation of Compounds of Class IIIb as Illustrated in Scheme 13 and Scheme 14.

A mixture of 32 (0.1 mmol), 39 or 40 (1 mmol) and 0.1 g (0.7 mmol) of potassium carbonate in 10 mL of anhydrous tetrahydrofuran was heated at 60° C. for 2 hours. The reaction mixture is allowed to cool to room temperature, diluted with 250 mL of water, and extracted with dichloromethane (3×15 mL). The combined organic extracts were washed with brine (10 mL), dried over $Na_2SO_4$, filtered, and concentrated in vacuum. The crude residue was purified by column chromatography on silica gel to give the desired products, compounds of Class IIIb.

TABLE 4

Structures of compounds of Class IIIa and Class IIIb.

| ID | Structure |
|---|---|
| 795 | 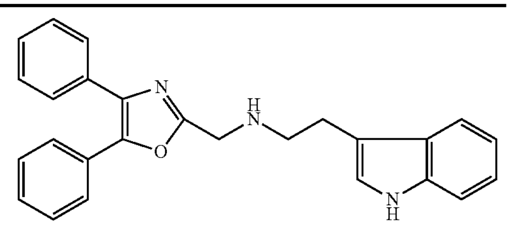 |
| 874 | 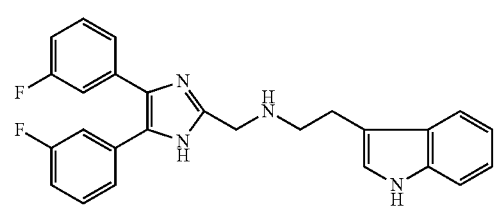 [SMILES: Fc1cccc(-c2nc(CNCCc3c[nH]c4ccccc34)[nH]c2-c2cccc(F)c2)c1] |

TABLE 4-continued
Structures of compounds of Class IIIa and Class IIIb.
| ID | Structure |
|---|---|
| 1041 | 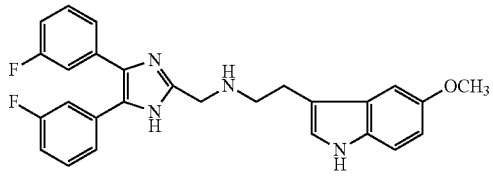 [SMILES: COc1ccc2[nH]cc(CCNCc3nc(-c4cccc(F)c4)c(-c4cccc(F)c4)[nH]3)c2c1] |
| 1042 | 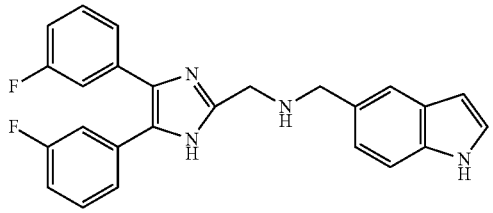 [SMILES: Fc1cccc(-c2nc(CNCc3ccc4[nH]ccc4c3)[nH]c2-c2cccc(F)c2)c1] |
| 1096 | 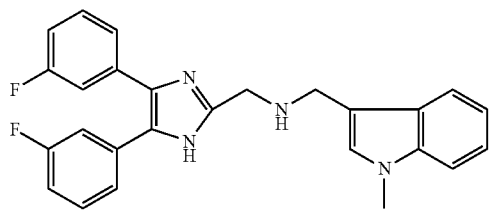 [SMILES: Cn1cc(CNCc2nc(-c3cccc(F)c3)c(-c3cccc(F)c3)[nH]2)c2ccccc21] |
| 1369 | 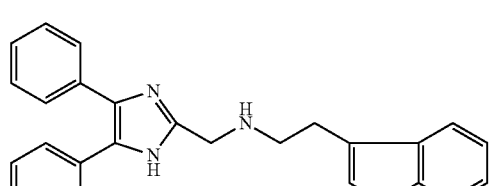 |
| 1186 | 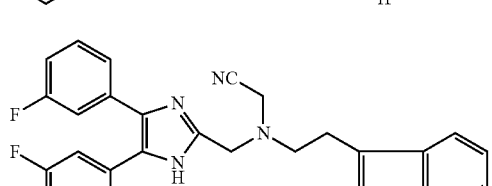 |
| 1187 | 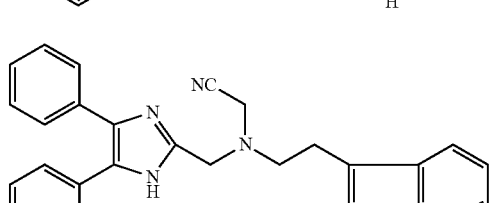 |
| 1188 | 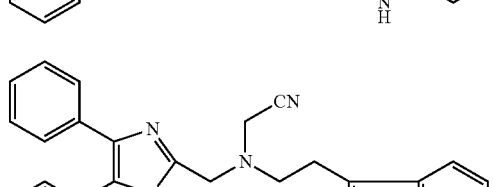 |
TABLE 4-continued
Structures of compounds of Class IIIa and Class IIIb.
| ID | Structure |
|---|---|
| 784 | 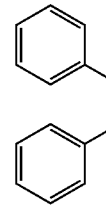 |
| 876 | 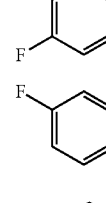 |
| 853 | 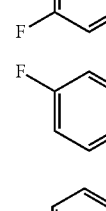 |
| 854 | 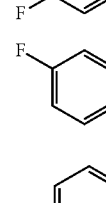 |
| 855 | 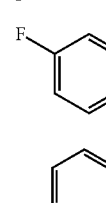 |
| 856 | 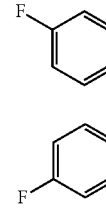 |
| 1144 | 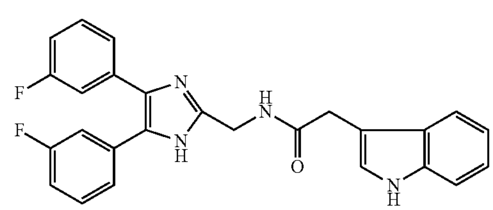 [SMILES: O=C(Cc1c[nH]c2ccccc12)NCc1nc(-c2cccc(F)c2)c(-c2cccc(F)c2)[nH]1] |

TABLE 4-continued

Structures of compounds of Class IIIa and Class IIIb.

| ID | Structure |
|---|---|
| 1145 | (structure) |
| 1076 | (structure) |
| 1077 | (structure) |
| 1078 | (structure) |
| 1079 | (structure) |
| 1080 | (structure) |
| 1089 | (structure) |
| 1090 | (structure) |
| 1091 | (structure) |
| 1092 | (structure) |
| 1093 | (structure) |
| 1094 | (structure) |

TABLE 4-continued
Structures of compounds of Class IIIa and Class IIIb.
| ID | Structure |
|---|---|
| 1097 | 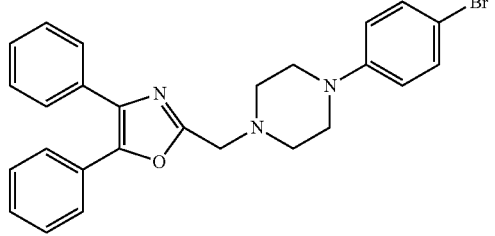 |
| 1098 | 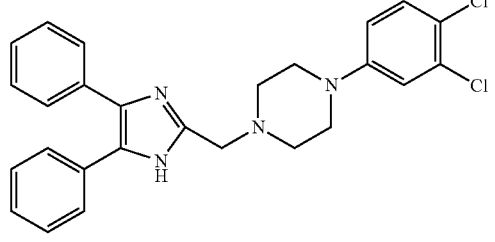 |
| 1099 | 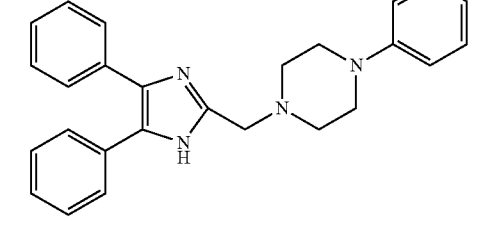 |
| 1100 | 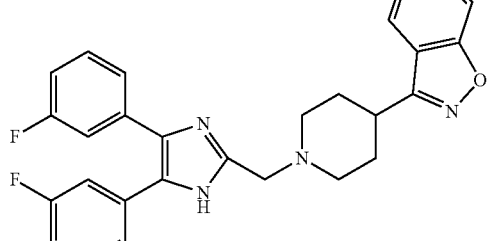 |
| 1101 | 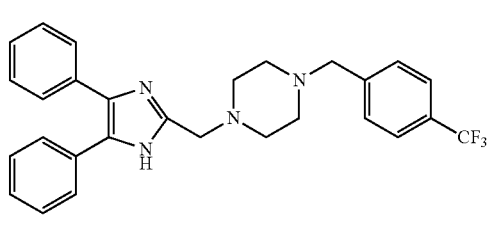 [SMILES: FC(F)(F)c1ccc(CN2CCN(Cc3nc(-c4ccccc4)c(-c4ccccc4)[nH]3)CC2)cc1] |
| 1102 | 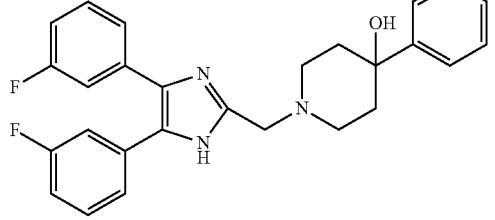 |
| 1103 | 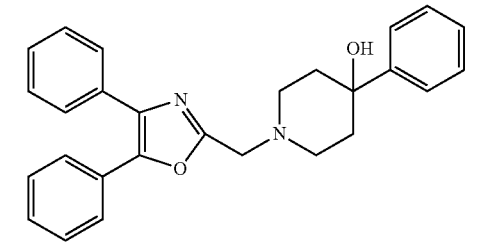 [SMILES: OC1(c2ccccc2)CCN(Cc2nc(-c3ccccc3)c(-c3ccccc3)o2)CC1] |
| 1104 | 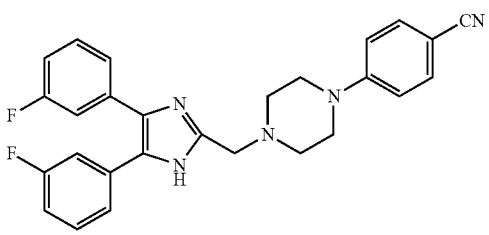 [SMILES: N#Cc1ccc(N2CCN(Cc3nc(-c4cccc(F)c4)c(-c4cccc(F)c4)[nH]3)CC2)cc1] |
| 1120 | 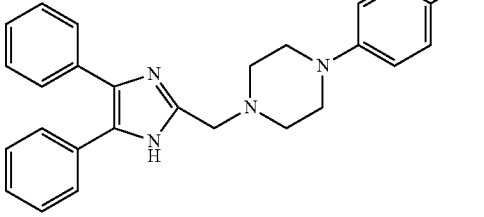 |
| 1121 | 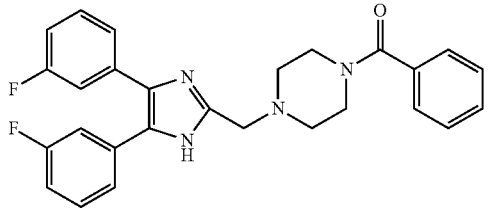 [SMILES: O=C(c1ccccc1)N1CCN(Cc2nc(-c3cccc(F)c3)c(-c3cccc(F)c3)[nH]2)CC1] |
| 1122 | 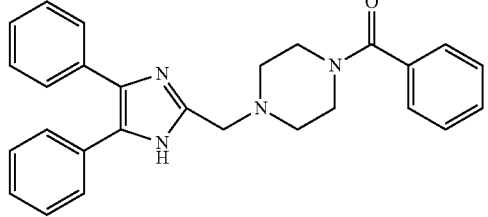 |
| 1123 | 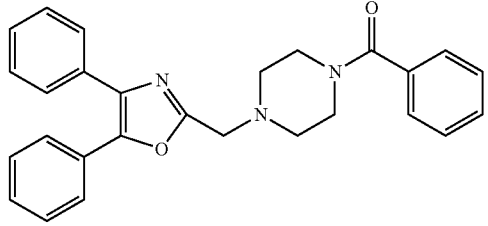 [SMILES: O=C(c1ccccc1)N1CCN(Cc2nc(-c3ccccc3)c(-c3ccccc3)o2)CC1] |

TABLE 4-continued

Structures of compounds of Class IIIa and Class IIIb.

| ID | Structure |
|---|---|
| 1124 | (structure) |
| 1125 | (structure) |
| 1126 | (structure) |
| 1127 | (structure) |
| 1129 | (structure) |
| 1137 | (structure) |
| 1139 | (structure) |
| 1140 | (structure) |
| 1141 | (structure) |
| 1142 | (structure) |
| 1143 | (structure) |
| 1173 | (structure) |

TABLE 4-continued

Structures of compounds of Class IIIa and Class IIIb.

| ID | Structure |
|----|-----------|
| 1174 | 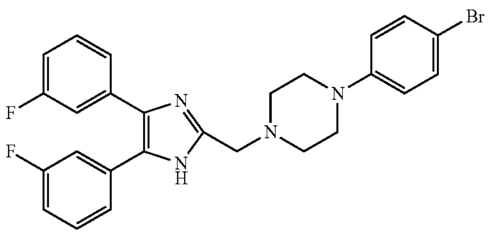 [SMILES: Fc1cccc(-c2nc(CN3CCN(c4ccc(Br)cc4)CC3)[nH]c2-c2cccc(F)c2)c1] |
| 1175 | 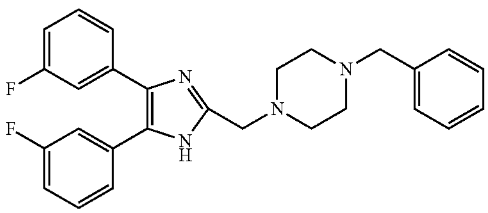 [SMILES: Fc1cccc(-c2nc(CN3CCN(Cc4ccccc4)CC3)[nH]c2-c2cccc(F)c2)c1] |
| 1176 | 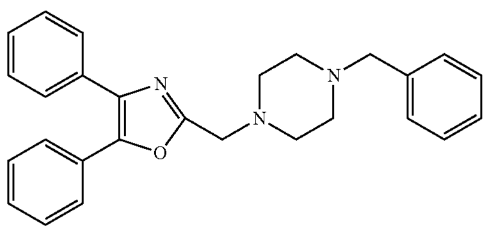 [SMILES: c1ccc(CN2CCN(Cc3nc(-c4ccccc4)c(-c4ccccc4)o3)CC2)cc1] |
| 1177 | 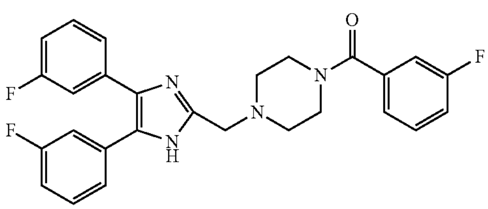 [SMILES: O=C(c1cccc(F)c1)N1CCN(Cc2nc(-c3cccc(F)c3)c(-c3cccc(F)c3)[nH]2)CC1] |
| 1178 | 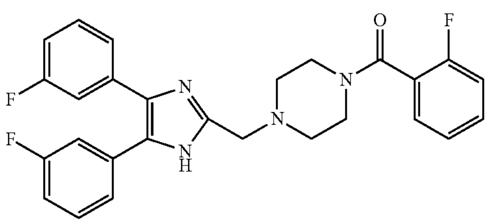 [SMILES: O=C(c1ccccc1F)N1CCN(Cc2nc(-c3cccc(F)c3)c(-c3cccc(F)c3)[nH]2)CC1] |
| 1179 | 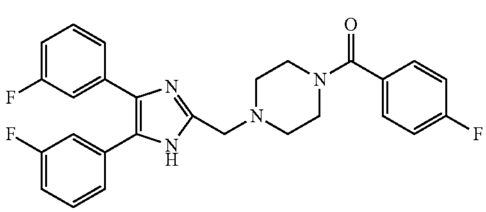 [SMILES: O=C(c1ccc(F)cc1)N1CCN(Cc2nc(-c3cccc(F)c3)c(-c3cccc(F)c3)[nH]2)CC1] |
| 1180 | 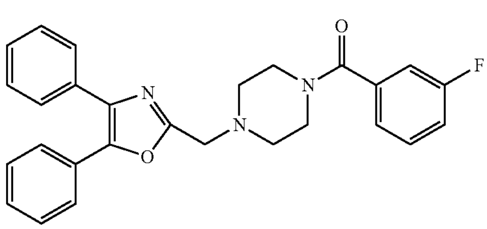 [SMILES: O=C(c1cccc(F)c1)N1CCN(Cc2nc(-c3ccccc3)c(-c3ccccc3)o2)CC1] |
| 1181 | |
| 1182 | |
| 1183 | |
| 1184 | |
| 1209 | |
| 1210 | |

TABLE 4-continued
Structures of compounds of Class IIIa and Class IIIb.
| ID | Structure |
|---|---|
| 1211 | 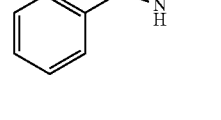 |
| 1212 | |
| 1213 | |
| 1214 | |
| 1227 | |
| 1229 | |
| 1284 | 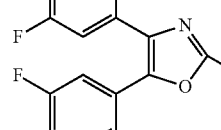 |
| 1285 | 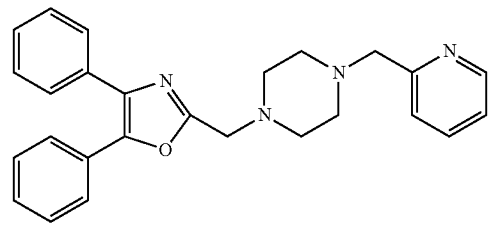 [SMILES: c1ccc(-c2nc(CN3CCN(Cc4ccccn4)CC3)oc2-c2ccccc2)cc1] |
| 1286 | 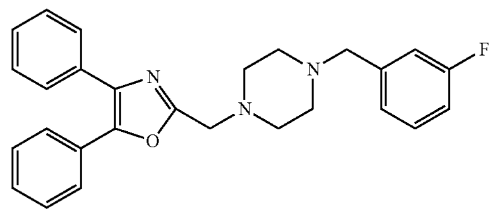 [SMILES: Fc1cccc(CN2CCN(Cc3nc(-c4ccccc4)c(-c4ccccc4)o3)CC2)c1] |
| 1287 | 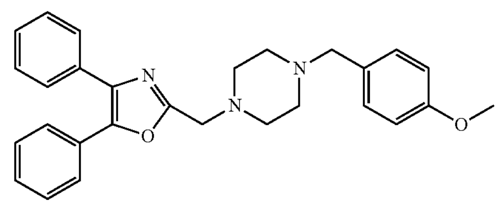 [SMILES: COc1ccc(CN2CCN(Cc3nc(-c4ccccc4)c(-c4ccccc4)o3)CC2)cc1] |
| 1288 | 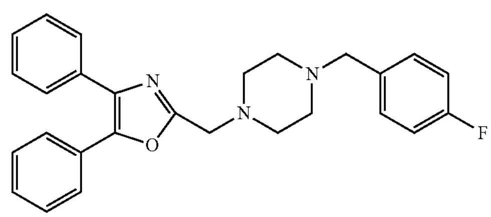 [SMILES: Fc1ccc(CN2CCN(Cc3nc(-c4ccccc4)c(-c4ccccc4)o3)CC2)cc1] |
| 1289 | 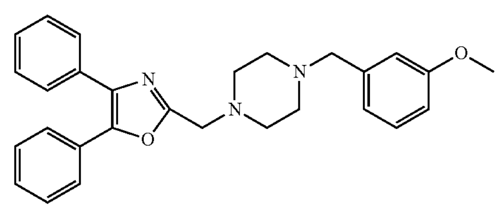 [SMILES: COc1cccc(CN2CCN(Cc3nc(-c4ccccc4)c(-c4ccccc4)o3)CC2)c1] |
| 1290 | 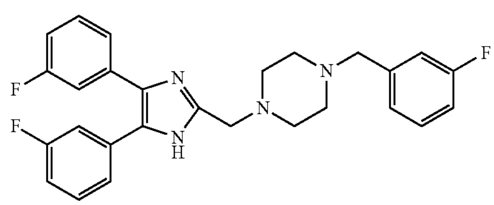 [SMILES: Fc1cccc(CN2CCN(Cc3nc(-c4cccc(F)c4)c(-c4cccc(F)c4)[nH]3)CC2)c1] |

TABLE 4-continued

Structures of compounds of Class IIIa and Class IIIb.

| ID | Structure |
|---|---|
| 1291 | |
| 1312 | C₂₆H₂₃F₃N₄ 448.49 |
| 1313 | |
| 1314 | |
| 1315 | |
| 1357 | |
| 1358 | 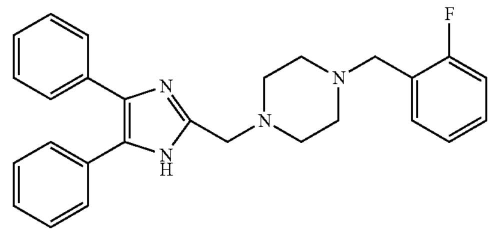 [SMILES: Fc1ccccc1CN1CCN(Cc2nc(-c3ccccc3)c(-c3ccccc3)[nH]2)CC1] |
| 1359 | 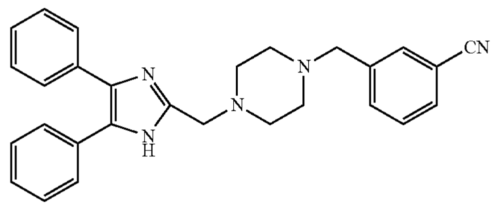 [SMILES: N#Cc1cccc(CN2CCN(Cc3nc(-c4ccccc4)c(-c4ccccc4)[nH]3)CC2)c1] |
| 1360 | 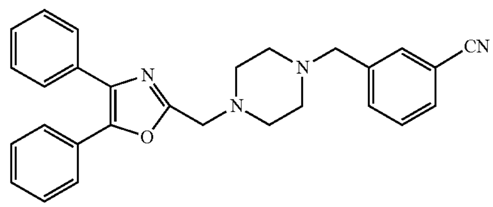 [SMILES: N#Cc1cccc(CN2CCN(Cc3nc(-c4ccccc4)c(-c4ccccc4)o3)CC2)c1] |
| 1361 | 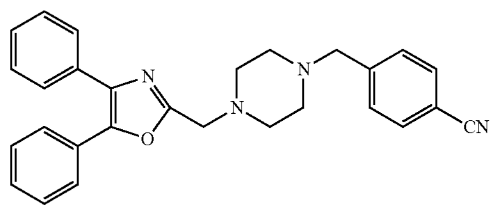 [SMILES: N#Cc1ccc(CN2CCN(Cc3nc(-c4ccccc4)c(-c4ccccc4)o3)CC2)cc1] |
| 1362 | 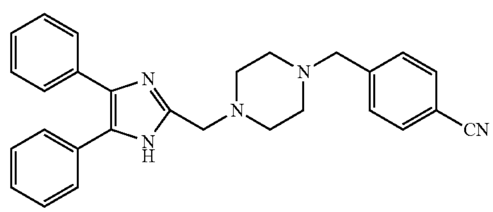 [SMILES: N#Cc1ccc(CN2CCN(Cc3nc(-c4ccccc4)c(-c4ccccc4)[nH]3)CC2)cc1] |
| 1363 | 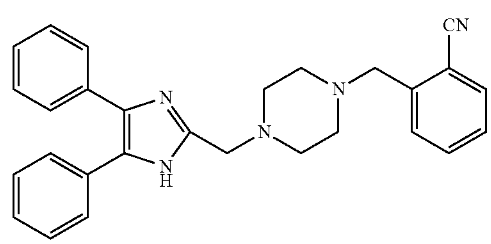 [SMILES: N#Cc1ccccc1CN1CCN(Cc2nc(-c3ccccc3)c(-c3ccccc3)[nH]2)CC1] |
| 1364 | 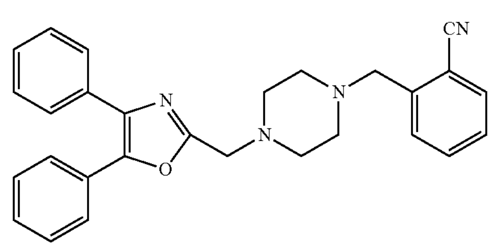 [SMILES: N#Cc1ccccc1CN1CCN(Cc2nc(-c3ccccc3)c(-c3ccccc3)o2)CC1] |

TABLE 4-continued
Structures of compounds of Class IIIa and Class IIIb.
| ID | Structure |
|---|---|
| 1366 | 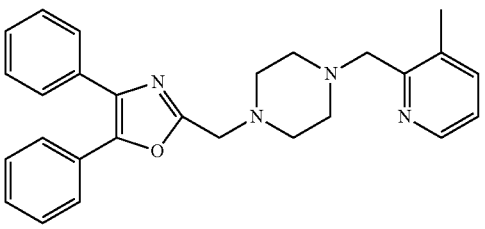 [SMILES: Cc1cccnc1CN1CCN(Cc2nc(-c3ccccc3)c(-c3ccccc3)o2)CC1] |
| 1367 | 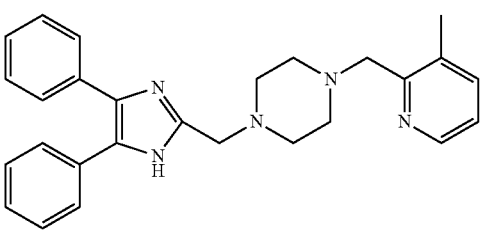 [SMILES: Cc1cccnc1CN1CCN(Cc2nc(-c3ccccc3)c(-c3ccccc3)[nH]2)CC1] |
| 1368 | 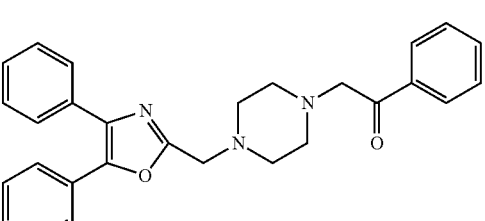 |
| 1369 | 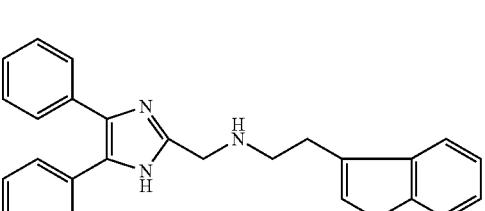 |
| 1370 | 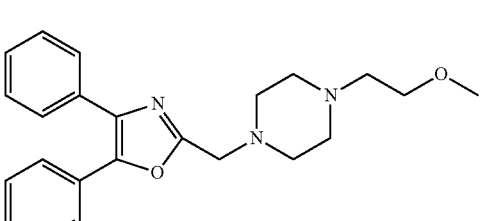 |
| 1371 | 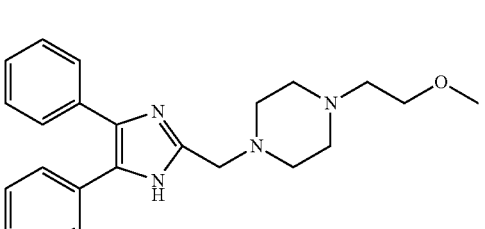 |
| 1372 | 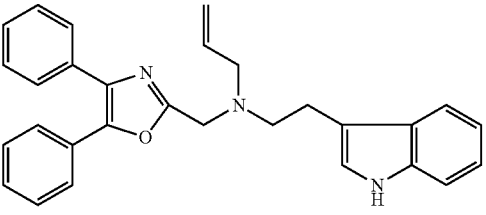 [SMILES: C=CCN(CCc1c[nH]c2ccccc12)Cc1nc(-c2ccccc2)c(-c2ccccc2)o1] |
| 1394 | 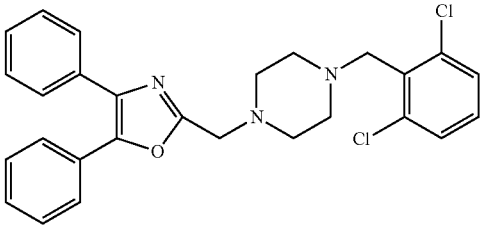 [SMILES: Clc1cccc(Cl)c1CN1CCN(Cc2nc(-c3ccccc3)c(-c3ccccc3)o2)CC1] |
| 1395 | 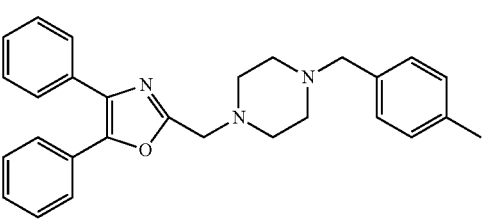 [SMILES: Cc1ccc(CN2CCN(Cc3nc(-c4ccccc4)c(-c4ccccc4)o3)CC2)cc1] |
| 1396 | 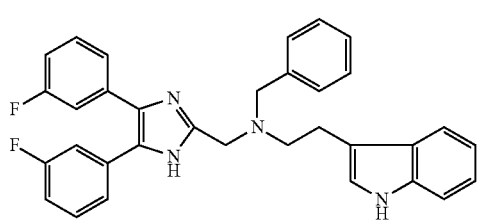 [SMILES: Fc1cccc(-c2nc(CN(CCc3c[nH]c4ccccc34)Cc3ccccc3)[nH]c2-c2cccc(F)c2)c1] |
| 1397 | 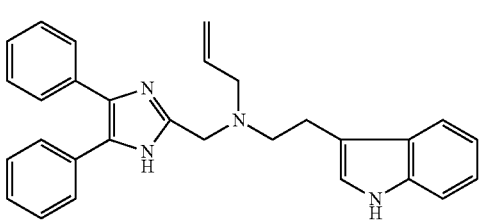 [SMILES: C=CCN(CCc1c[nH]c2ccccc12)Cc1nc(-c2ccccc2)c(-c2ccccc2)[nH]1] |
| 1400 | 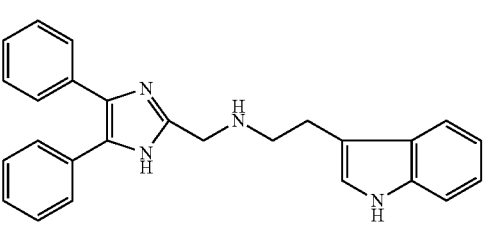 |
| 1401 | 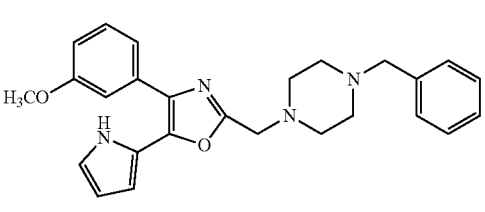 [SMILES: COc1cccc(-c2nc(CN3CCN(Cc4ccccc4)CC3)oc2-c2ccc[nH]2)c1] |

TABLE 4-continued

Structures of compounds of Class IIIa and Class IIIb.

| ID | Structure |
|---|---|
| 1402 | 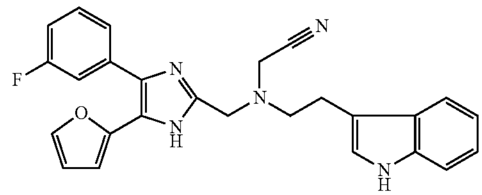 [SMILES: N#CCN(CCc1c[nH]c2ccccc12)Cc1nc(-c2cccc(F)c2)c(-c2ccco2)[nH]1] |
| 1403 | 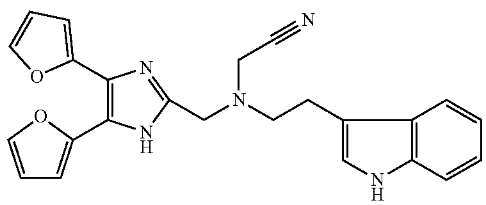 [SMILES: N#CCN(CCc1c[nH]c2ccccc12)Cc1nc(-c2ccco2)c(-c2ccco2)[nH]1] |
| 1404 | 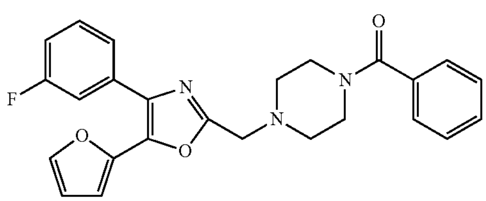 [SMILES: O=C(c1ccccc1)N1CCN(Cc2nc(-c3cccc(F)c3)c(-c3ccco3)o2)CC1] |
| 1405 | 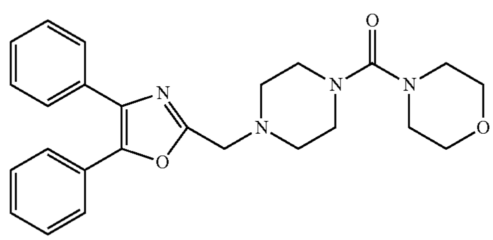 [SMILES: O=C(N1CCOCC1)N1CCN(Cc2nc(-c3ccccc3)c(-c3ccccc3)o2)CC1] |
| 1039 | 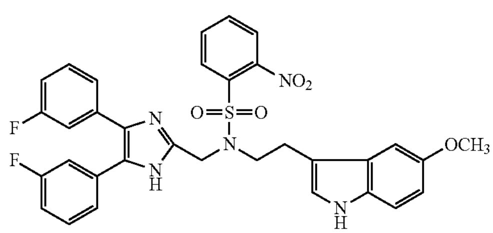 [SMILES: COc1ccc2[nH]cc(CCN(Cc3nc(-c4cccc(F)c4)c(-c4cccc(F)c4)[nH]3)S(=O)(=O)c3ccccc3[N+](=O)[O-])c2c1] |
| 1040 | 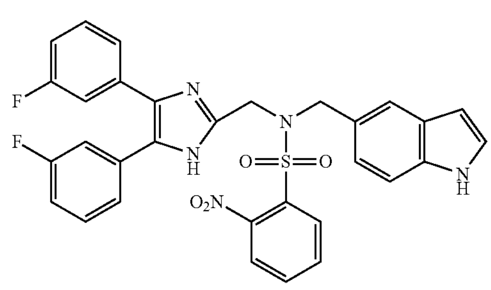 [SMILES: O=[N+]([O-])c1ccccc1S(=O)(=O)N(Cc1ccc2[nH]ccc2c1)Cc1nc(-c2cccc(F)c2)c(-c2cccc(F)c2)[nH]1] |

TABLE 4-continued

Structures of compounds of Class IIIa and Class IIIb.

| ID | Structure |
|---|---|
| 1373 | 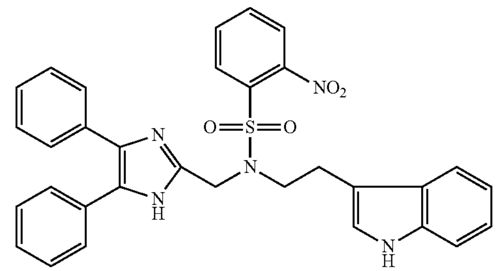 [SMILES: O=[N+]([O-])c1ccccc1S(=O)(=O)N(CCc1c[nH]c2ccccc12)Cc1nc(-c2ccccc2)c(-c2ccccc2)[nH]1] |

Characterization of Intermediate:

35a: White solid. Yield: 82%. $^1$H NMR (500 MHz, CDCl$_3$) δ 8.04-7.94 (m, 2H), 7.59-7.52 (m, 3H), 7.51-7.49 (m, 2H), 7.47-7.41 (m, 3H), 7.40-7.31 (m, 6H), 7.28 (d, J=8.1 Hz, 1H), 7.16-7.11 (m, 1H), 7.07 (s, 1H), 7.03-6.99 (m, 1H), 4.89 (s, 2H), 3.80-3.77 (m, 2H), 3.18-3.10 (m, 2H).

Characterization of Compounds of Class IIIa and Class IIIb:

784: White solid. Yield: 58%. $^1$H NMR (500 MHz, acetone-d$_6$) δ 10.15 (br, 1H), 7.65 (d, J=8.0 Hz, 1H), 7.61-7.57 (m, 3H), 7.51 (d, J=7.5 Hz, 2H), 7.45-7.32 (m, 7H), 7.11 (t, J=7.6 Hz, 1H), 6.99 (t, J=7.5 Hz, 1H), 4.58 (d, J=5.7 Hz, 2H), 3.75 (s, 2H). HRMS (ESI) m/z Found: 408.17033 [M+H]$^+$, Calcd: 408.17065 [M+H]$^+$.

795: Colorless syrup. Yield: 65%. $^1$H NMR (500 MHz, CDCl$_3$) δ 8.30 (s, 1H), 7.67-7.51 (m, 5H), 7.40-7.28 (m, 8H), 7.18-7.13 (m, 2H), 7.05-7.01 (m, 1H), 4.72 (d, J=17.4 Hz, 1H), 4.19 (s, 2H), 3.38-3.22 (m, 4H).

874: White solid. Yield: 49%. $^1$H NMR (500 MHz, CDCl$_3$) δ 8.00 (br, 1H), 7.61 (d, J=7.8 Hz, 1H), 7.34 (d, J=8.1 Hz, 1H), 7.29-7.22 (m, 3H), 7.20-7.08 (m, 5H), 7.03 (d, J=2.1 Hz, 1H), 6.98-6.94 (m, 2H), 3.97 (s, 2H), 3.03-3.06 (m, 2H), 3.02-2.99 (m, 2H). HRMS (ESI) m/z. Found: 429.18897 [M+H]$^+$, Calcd: 429.18886 [M+H]$^+$.

876: White solid. Yield: 64%. $^1$H NMR (500 MHz, CDCl$_3$) δ 11.35 (br, 1H), 8.12 (br, 1H), 7.41 (d, J=7.8 Hz, 1H), 7.37 (d, J=8.1 Hz, 1H), 7.33-7.24 (m, 4H), 7.24-7.17 (m, 3H), 7.15-7.08 (m, 2H), 7.02-6.98 (m, 1H), 6.97-6.91 (m, 1H), 4.61-4.42 (m, 4H).

1096: White solid. Yield: 86.4%. $^1$H NMR (500 MHz, CDCl$_3$) δ 7.61 (d, J=7.9 Hz, 1H), 7.29-7.20 (m, 5H), 7.19-7.08 (m, 6H), 7.03-6.92 (m, 2H), 4.06 (s, 2H), 4.01 (s, 2H) 3.70 (s, 3H).

1144: white solid. Yield: 83.2%. $^1$H NMR (500 MHz, Acetone-d$_6$) δ 11.26 (br, 1H), 10.14 (br, J=5.0 Hz, 1H), 7.65-7.59 (m, 1H), 7.56 (br, 1H), 7.45-7.17 (m, 8H), 7.11-6.98 (m, 4H), 4.48-4.39 (m, 2H), 3.72 (s, 2H). HRMS (ESI) m/z Found: 443.16855 [M+H]$^+$, Calcd: 443.16779 [M+H]$^+$.

1145: white solid. Yield: 77.3%. $^1$H NMR (500 MHz, Acetone-d$_6$) δ 10.14 (br, 1H), 7.63-7.62 (m, 1H), 7.56 (br, 1H), 7.46-7.45 (m, 4H), 7.40-7.38 (m, 1H), 7.32-7.29 (m, 5H), 7.26-7.23 (m, 2H), 7.12-7.09 (m, 1H), 7.01-6.98 (m, 1H), 4.44 (d, J=5.5 Hz, 2H), 3.72 (s, 2H).

1369: White solid. Yield: 80.1%. $^1$H NMR (500 MHz, Acetone-d$_6$) δ 7.60 (d, J=7.8 Hz, 1H), 7.51 (d, J=7.5 Hz, 5H), 7.36 (d, J=8.2 Hz, 1H), 7.31 (t, J=7.5 Hz, 4H), 7.24 (t, J=7.3 Hz, 2H), 7.18 (s, 1H), 7.09-7.06 (m, 1H), 6.98 (t, J=7.5 Hz, 1H), 4.00 (s, 2H), 3.10-3.04 (m, 2H), 3.03-2.98 (m, 2H).

1186: White solid. Yield: 89.5%. $^1$H NMR (500 MHz, Acetone-d$_6$) δ 11.48 (br, 1H), 9.99 (br, 1H), 7.57-7.55 (m, 1H), 7.48-7.43 (m, 1H), 7.41-7.27 (m, 5H), 7.23-7.18 (m, 2H), 7.15-7.12 (m, 1H), 7.08-7.04 (m, 1H), 7.01-6.92 (m, 2H), 3.99 (s, 2H), 3.96 (s, 2H), 3.07-2.99 (m, 4H). HRMS (ESI) m/z Found: 468.20018 [M+H]$^+$, Calcd: 468.19943 [M+H]$^+$.

1187: White solid. Yield: 92.1%. $^1$H NMR (500 MHz, Acetone-d$_6$) δ 11.32 (br, 1H), 9.98 (br, 1H), 7.69-7.14 (m, 13H), 7.10-7.03 (m, 1H), 6.96-6.93 (m, 1H), 3.99 (s, 2H), 3.94 (s, 2H), 3.06-2.99 (m, 4H). HRMS (ESI) m/z Found: 432.21891 [M+H]$^+$, Calcd: 432.21827 [M+H]$^+$.

1188: colorless syrup. Yield: 88.5%. $^1$H NMR (500 MHz, CDCl$_3$) δ 7.96 (br, 1H), 7.67-7.64 (m, 2H), 7.64-7.56 (m, 3H), 7.41-7.31 (m, 7H), 7.22-7.14 (m, 1H), 7.12-7.03 (m, 2H), 4.03 (s, 2H), 3.86 (s, 2H), 3.15-3.09 (m, 2H), 3.08-3.04 (m, 2H).

1076: White solid. Yield: 88.5%. $^1$H NMR (500 MHz, CDCl$_3$) δ 7.68-7.63 (m, 2H), 7.63-7.58 (m, 2H), 7.41-7.31 (m, 6H), 7.26 (d, J=9.0 Hz, 1H), 6.95 (d, J=2.9 Hz, 1H), 6.74 (dd, J=9.0, 2.9 Hz, 1H), 3.87 (s, 2H), 3.28-3.18 (m, 4H), 2.87-2.80 (m, 4H).

1077: White solid. Yield: 92.1%. $^1$H NMR (500 MHz, CDCl$_3$) δ 7.73-7.64 (m, 4H), 7.64-7.59 (m, 2H), 7.41-7.30 (m, 6H), 7.30-7.25 (m, 2H), 6.14 (br, 1H), 3.85 (s, 2H), 3.20-3.18 (m, 2H), 3.00 (d, J=4.9 Hz, 3H), 2.60-2.53 (m, 1H), 2.45-2.30 (m, 2H), 1.89-1.85 (m, 4H).

1078: White solid. Yield: 89.4%. $^1$H NMR (500 MHz, CDCl$_3$) δ 7.66-7.61 (m, 2H), 7.60-7.55 (m, 4H), 7.44 (d, J=8.0 Hz, 2H), 7.40-7.30 (m, 6H), 3.84 (s, 2H), 3.61 (s, 2H), 2.75 (br, 4H), 2.59 (br, 4H).

1079: White solid. Yield: 92.3%. $^1$H NMR (500 MHz, CDCl$_3$) δ 7.68-7.64 (m, 2H), 7.63-7.59 (m, 2H), 7.40-7.31 (m, 6H), 7.29-7.23 (m, 2H), 6.94-6.92 (m, 2H), 6.88-6.84 (m, 1H), 3.88 (s, 2H), 3.31-3.23 (m, 4H), 2.89-2.82 (m, 4H).

1080: White solid. Yield: 92.6%. $^1$H NMR (500 MHz, CDCl$_3$) δ 7.69-7.65 (m, 2H), 7.64-7.60 (m, 2H), 7.50-7.31 (m, 10H), 3.86 (s, 2H), 3.21-3.19 (m, 2H), 2.62-2.56 (m, 1H), 2.42-2.35 (m, 2H), 1.91-1.87 (m, 4H).

1089: White solid. Yield: 83.1%. $^1$H NMR (500 MHz, CDCl$_3$) δ 8.14-8.10 (m, 2H), 7.67-7.63 (m, 2H), 7.63-7.58 (m, 2H), 7.42-7.31 (m, 6H), 6.85-6.79 (m, 2H), 3.88 (s, 2H), 3.52-3.46 (m, 4H), 2.86-2.81 (m, 4H).

1090: White solid. Yield: 87.6%. $^1$H NMR (500 MHz, CDCl$_3$) δ 7.68-7.63 (m, 2H), 7.63-7.58 (m, 2H), 7.52-7.47 (m, 2H), 7.40-7.33 (m, 6H), 6.89-6.83 (m, 2H), 3.87 (s, 2H), 3.44-3.34 (m, 4H), 2.84-2.79 (m, 4H).

1091: White solid. Yield: 85.4%. $^1$H NMR (500 MHz, CDCl$_3$) δ 9.47 (br, 1H), 7.41-7.17 (m, 7H), 7.13-7.11 (m, 1H), 7.07-7.00 (m, 1H), 6.97-6.91 (m, 3H), 6.90-6.85 (m, 1H), 3.78 (s, 2H), 3.36-3.17 (m, 4H), 2.89-2.70 (m, 4H).

1092: White solid. Yield: 88.2%. $^1$H NMR (500 MHz, CDCl$_3$) δ 9.38 (br, 1H), 7.43-7.16 (m, 6H), 7.13-7.10 (m, 1H), 7.06-7.03 (m, 1H), 6.96-6.93 (m, 2H), 6.76-6.74 (m, 1H), 3.78 (s, 2H), 3.33-3.13 (m, 4H), 2.83-2.66 (m, 4H).

1093: White solid. Yield: 92.2%. $^1$H NMR (500 MHz, CDCl$_3$) δ 9.53 (br, 1H), 7.57 (d, J=8.0 Hz, 2H), 7.44 (d, J=8.0 Hz, 2H), 7.36-7.29 (m, 3H), 7.25-7.20 (m, 1H), 7.19-7.17 (m, 1H), 7.11-7.09 (m, 1H), 7.05-7.01 (m, 1H), 6.94-6.91 (m, 1H), 3.72 (s, 2H), 3.57 (s, 2H), 2.62 (br, 4H), 2.51 (br, 4H).

1094: White solid. Yield: 91.7%. $^1$H NMR (500 MHz, CDCl$_3$) δ 7.67-7.63 (m, 2H), 7.63-7.58 (m, 2H), 7.40-7.30 (m, 6H), 6.86-6.84 (m, 2H), 6.79-6.72 (m, 2H), 4.59 (br, 1H), 3.88 (s, 2H), 3.18-3.09 (m, 4H), 2.89-2.80 (m, 4H).

1097: White solid. Yield: 90.2%. $^1$H NMR (500 MHz, CDCl$_3$) δ 7.69-7.64 (m, 2H), 7.64-7.58 (m, 2H), 7.42-7.30 (m, 8H), 6.84-6.74 (m, 2H), 3.87 (s, 2H), 3.25-3.17 (m, 4H), 2.89-2.78 (m, 4H).

1098: White solid. Yield: 93.1%. $^1$H NMR (500 MHz, CDCl$_3$) δ 9.42 (br, 1H), 7.71-7.21 (m, 11H), 6.97-6.96 (m, 1H), 6.75-6.73 (m, 1H), 3.78 (s, 2H), 3.26-3.15 (m, 4H), 2.80-2.65 (m, 4H).

1099: White solid. Yield: 92.8%. $^1$H NMR (500 MHz, CDCl$_3$) δ 9.47 (br, 1H), 7.70-7.16 (m, 12H), 6.94--6.92 (m, 2H), 6.88-6.85 (m, 1H), 3.79 (s, 2H), 3.31-3.15 (m, 4H), 2.85-2.66 (m, 4H).

1100: White solid. Yield: 91.6%. $^1$H NMR (500 MHz, CDCl$_3$) δ 9.57 (br, 1H), 7.69-7.66 (m, 1H), 7.35-7.31 (m, 3H), 7.28-7.18 (m, 4H), 7.15-7.00 (m, 2H), 6.94 (s, 1H), 3.78 (s, 2H), 3.13-3.11 (m, 3H), 2.42-2.38 (m, 2H), 2.19-2.07 (m, 4H).

1101: White solid. Yield: 83.6%. $^1$H NMR (500 MHz, CDCl$_3$) δ 9.50 (br, 1H), 7.59-7.56 (m, 4H), 7.47-7.27 (m, 9H), 7.23-7.20 (m, 1H), 3.73 (s, 2H), 3.56 (s, 2H), 2.62 (s, 4H), 2.49 (s, 4H).

1102: White solid. Yield: 87.1%. $^1$H NMR (500 MHz, CDCl$_3$) δ 7.51-7.49 (m, 2H), 7.41-7.35 (m, 2H), 7.33-7.23 (m, 6H), 7.23-7.17 (m, 2H), 6.98-6.94 (m, 2H), 4.16 (s, 2H), 3.23-3.09 (m, 4H), 2.47-2.40 (m, 2H), 2.13 (s, 1H), 1.91-1.88 (m, 2H).

1103: White solid. Yield: 89.4%. $^1$H NMR (500 MHz, CDCl$_3$) δ 7.69-7.65 (m, 2H), 7.63-7.60 (m, 2H), 7.53-7.50 (m, 2H), 7.40-7.30 (m, 8H), 7.29-7.24 (m, 1H), 3.90 (s, 2H), 3.01-2.99 (m, 2H), 2.82-2.77 (m, 2H), 2.31-2.25 (m, 2H), 1.82-1.78 (m, 2H).

1104: White solid. Yield: 80.6%. $^1$H NMR (500 MHz, CDCl$_3$) δ 9.40 (br, 1H), 7.52-7.49 (m, 2H), 7.40-7.18 (m, 5H), 7.13-7.11 (m, 1H), 7.08-7.03 (m, 1H), 6.96-6.93 (m, 1H), 6.90-6.85 (m, 2H), 3.78 (s, 2H), 3.41-3.33 (m, 4H), 2.78-2.70 (m, 4H).

1120: White solid. Yield: 81.7%. $^1$H NMR (500 MHz, Acetone-d$_6$) δ 11.91 (br, 1H), 7.17-7.10 (m, 2H), 7.10-6.69 (m, 10H), 6.60-6.53 (m, 2H), 3.17 (s, 2H), 2.94-2.89 (m, 4H), 2.23-2.12 (m, 4H).

1121: White solid. Yield: 82.9%. $^1$H NMR (500 MHz, CDCl$_3$) δ 9.37 (br, 1H), 7.48-7.38 (m, 5H), 7.38-7.27 (m, 3H), 7.26-6.94 (m, 5H), 3.84 (br, 2H), 3.75 (s, 2H), 3.49 (br, 2H), 2.66-2.56 (m, 4H).

1122: White solid. Yield: 88.6%. $^1$H NMR (500 MHz, CDCl$_3$) δ 7.51-7.48 (m, 4H), 7.43-7.38 (m, 5H), 7.34-7.31 (m, 4H), 7.29-7.27 (m, 2H), 3.86 (br, 2H), 3.78 (s, 2H), 3.49 (br, 2H), 2.70-2.55 (m, 4H).

1123: Colorless syrup. Yield: 90.1%. $^1$H NMR (500 MHz, CDCl$_3$) δ 7.66-7.62 (m, 2H), 7.62-7.57 (m, 2H), 7.44-7.31 (m, 11H), 3.90-3.87 (m, 4H), 3.53 (br, 2H), 2.81 (br, 2H), 2.67 (br, 2H), 2.50 (br, 1H).

1124: Colorless syrup. Yield: 91.2%. $^1$H NMR (500 MHz, CDCl$_3$) δ 7.70-7.66 (m, 2H), 7.66-7.62 (m, 2H), 7.42-7.32 (m, 7H), 7.18-7.15 (m, 1H), 7.09-7.06 (m, 1H), 6.98-6.96 (m, 1H), 4.01 (br, 2H), 3.26 (br, 2H), 2.88-2.82 (m, 1H), 2.55 (br, 2H), 2.05 (s, 2H), 1.99 (br, 2H).

1125: White solid. Yield: 81.3%. $^1$H NMR (500 MHz, CDCl$_3$) δ 9.43 (br, 1H), 7.59-7.27 (m, 11H), 7.01-7.00 (m, 1H), 6.48-6.47 (m, 1H), 3.84 (br, 4H), 3.76 (s, 2H), 2.68-2.62 (m, 4H).

1126: Colorless syrup. Yield: 87.5%. $^1$H NMR (500 MHz, CDCl$_3$) δ 7.67-7.63 (m, 2H), 7.63-7.57 (m, 2H), 7.47-7.46 (m, 1H), 7.41-7.29 (m, 6H), 7.00-6.99 (m, 1H), 6.47-6.46 (m, 1H), 3.88 (br, 4H), 3.85 (s, 2H), 2.78-2.71 (m, 4H).

1127: Colorless syrup. Yield: 91.6%. $^1$H NMR (500 MHz, CDCl$_3$) δ 7.78 (s, 1H), 7.71-7.70 (m, 1H), 7.62-7.51 (m, 4H), 7.51-7.43 (m, 2H), 7.40-7.35 (m, 2H), 7.33-7.31 (m, 2H), 7.22-7.06 (m, 2H), 3.91 (s, 1H), 3.82 (s, 2H), 2.94-2.83 (m, 4H), 2.74-2.70 (m, 2H), 2.20-2.16 (m, 2H).

1128: White solid. Yield: 85.9%. ¹H NMR (500 MHz, CDCl₃) δ 8.24-8.09 (m, 2H), 7.81-7.63 (m, 3H), 7.34-7.20 (m, 1H), 7.15-6.98 (m, 1H), 3.89 (s, 2H), 3.18-3.09 (m, 3H), 2.47-2.42 (m, 2H), 2.23-2.02 (m, 5H).

1129: White solid. Yield: 83.3%. ¹H NMR (500 MHz, CDCl₃) δ 7.81 (s, 1H), 7.72-7.65 (m, 3H), 7.64-7.60 (m, 2H), 7.53-7.52 (m, 1H), 7.49-7.45 (m, 1H), 7.40-7.31 (m, 6H), 3.88 (s, 2H), 3.02-3.0 (m, 2H), 2.77-2.73 (m, 2H), 2.29-2.23 (m, 2H), 2.17 (s, 1H), 1.83-1.73 (m, 2H).

1137: White solid. Yield: 83.8%. ¹H NMR (500 MHz, Acetone-d₆) δ 10.11 (br, 1H), 7.75-7.73 (m, 1H), 7.43-7.34 (m, 10H), 7.10-7.07 (m, 3H), 7.02-6.98 (m, 1H), 4.62 (s, 2H), 3.75-3.63 (m, 2H), 3.45-3.40 (m, 2H), 2.48-2.29 (m, 5H).

1139: White solid. Yield: 88.1%. ¹H NMR (500 MHz, Acetone-d₆) δ 11.52 (br, 1H), 7.78 (br, 1H), 7.49-7.21 (m, 5H), 7.14-7.11 (m, 1H), 6.99-6.96 (m, 1H), 6.89-6.79 (m, 2H), 6.79-6.66 (m, 2H), 3.70 (s, 2H), 3.10-2.98 (m, 4H), 2.84 (br, 1H), 2.73-2.63 (m, 4H).

1140: White solid. Yield: 86.5%. ¹H NMR (500 MHz, CDCl₃) δ 12.99 (s, 1H), 7.63 (d, J=8.3 Hz, 2H), 7.47-7.44 (m, 1H), 7.24-7.19 (m, 3H), 7.17-7.09 (m, 5H), 6.85 (s, 2H), 3.88 (s, 2H), 3.35-3.33 (m, 2H), 3.04 (d, J=4.9 Hz, 3H), 2.55-2.51 (m, 1H), 2.45-2.40 (m, 2H), 1.84-1.81 (m, 2H), 1.35-1.21 (m, 2H).

1141: White solid. Yield: 87.6%. ¹H NMR (500 MHz, CDCl₃) δ 9.51 (br, 1H), 7.37-7.30 (m, 3H), 7.28-7.22 (m, 1H), 7.22-7.14 (m, 2H), 7.12-7.10 (m, 1H), 7.06-7.02 (m, 1H), 6.95-6.92 (m, 1H), 6.55-6.53 (m, 1H), 6.48-6.40 (m, 2H), 3.79 (s, 3H), 3.77 (s, 2H), 3.29-3.19 (m, 4H), 2.79-2.69 (m, 4H).

1142: White solid. Yield: 91.4%. ¹H NMR (500 MHz, CDCl₃) δ 7.69-7.63 (m, 2H), 7.63-7.58 (m, 2H), 7.40-7.30 (m, 6H), 7.20-7.14 (m, 1H), 6.56-6.52 (m, 1H), 6.47-6.46 (m, 1H), 6.44-6.39 (m, 1H), 3.87 (s, 2H), 3.78 (s, 3H), 3.29-3.21 (m, 4H), 2.87-2.79 (m, 4H).

1143: White solid. Yield: 82.6%. ¹H NMR (500 MHz, CDCl₃) δ 9.48 (br, 1H), 7.51 (br, 4H), 7.39-7.23 (m, 6H), 7.19-7.16 (m, 1H), 6.55-6.53 (m, 1H), 6.52-6.40 (m, 2H), 3.79 (s, 2H), 3.79 (s, 3H), 3.32-3.18 (m, 4H), 2.81-2.71 (m, 4H).

1173: White solid. Yield: 77.4%. ¹H NMR (500 MHz, Acetone-d₆) δ 11.51 (br, 1H), 7.47-7.43 (m, 1H), 7.41-7.28 (m, 6H), 7.26-7.23 (m, 1H), 7.15-7.11 (m, 1H), 7.00-6.96 (m, 1H), 6.92-6.88 (m, 2H), 3.71 (s, 2H), 3.22-3.16 (m, 4H), 2.82 (br, 1H), 2.73-2.67 (m, 4H).

1174: White solid. Yield: 88.2%. ¹H NMR (500 MHz, Acetone-d₆) δ 11.57 (br, 1H), 7.69-7.21 (m, 8H), 7.17-6.75 (m, 4H), 3.73 (s, 2H), 3.29-3.14 (m, 4H), 2.77-2.66 (m, 4H).

1175: White solid. Yield: 80.5%. ¹H NMR (500 MHz, Acetone-d₆) δ 11.46 (br, 1H), 7.46-7.42 (m, 1H), 7.40-7.27 (m, 8H), 7.26-7.20 (m, 2H), 7.14-7.10 (m, 1H), 6.98-6.95 (m, 1H), 3.64 (s, 2H), 3.48 (s, 2H), 2.56 (br, 4H), 2.44 (br, 4H).

1176: Colorless syrup. Yield: 92.5%. ¹H NMR (500 MHz, CDCl₃) δ 7.66-7.61 (m, 2H), 7.61-7.57 (m, 2H), 7.40-7.29 (m, 10H), 7.25-7.22 (m, 1H), 3.82 (s, 2H), 3.52 (s, 2H), 2.71 (br, 4H), 2.54 (br, 4H). HRMS (ESI) m/z Found: 410.22416 [M+H]⁺, Calcd: 410.22269 [M+H]⁺.

1177: White solid. Yield: 79.3%. ¹H NMR (500 MHz, Acetone-d₆) δ 11.47 (br, 1H), 7.57-7.19 (m, 10H), 7.12 (br, 1H), 6.96 (br, 1H), 3.64 (s, 2H), 3.48 (s, 2H), 2.56 (br, 4H), 2.44 (br, 4H).

1178: White solid. Yield: 82.4%. ¹H NMR (500 MHz, Acetone-d₆) δ 11.55 (br, 1H), 7.57-6.96 (m, 12H), 3.76 (br, 2H), 3.73 (s, 2H), 3.36-3.34 (m, 2H), 2.67-2.65 (m, 2H), 2.57 (br, 2H).

1179: White solid. Yield: 86.9%. ¹H NMR (500 MHz, Acetone-d₆) δ 11.52 (br, 1H), 7.56-6.92 (m, 12H), 3.71-3.62 (m, 4H), 3.45 (br, 2H), 2.60 (br, 4H).

1180: Colorless syrup. Yield: 91.3%. ¹H NMR (500 MHz, CDCl₃) δ 7.67-7.63 (m, 2H), 7.61-7.59 (m, 2H), 7.47-7.30 (m, 8H), 7.11-7.05 (m, 2H), 3.86-3.75 (m, 4H), 3.51 (br, 2H), 2.75-2.65 (m, 4H).

1181: White solid. Yield: 86.2%. ¹H NMR (500 MHz, Acetone-d₆) δ 11.51 (br, 1H), 8.04 (br, 1H), 7.51-7.21 (m, 6H), 7.18-7.10 (m, 1H), 7.06-6.94 (m, 2H), 6.46-6.38 (m, 2H), 6.29-6.27 (m, 1H), 3.70 (s, 2H), 3.17-3.12 (m, 4H), 2.71-2.65 (m, 4H).

1182: White solid. Yield: 88.1%. ¹H NMR (500 MHz, CDCl₃) δ 7.69-7.62 (m, 2H), 7.60-7.58 (m, 2H), 7.39-7.28 (m, 6H), 7.10-7.06 (m, 1H), 6.50-6.48 (m, 1H), 6.38 (s, 1H), 6.31-6.29 (m, 1H), 5.55 (br, 1H), 3.86 (s, 2H), 3.25-3.18 (m, 4H), 2.85-2.78 (m, 4H).

1183: White solid. Yield: 85.4%. ¹H NMR (500 MHz, Acetone-d₆) δ 11.51 (br, 1H), 7.53-7.22 (m, 7H), 7.18-7.09 (m, 2H), 6.99-6.95 (m, 2H), 6.87-6.75 (m, 2H), 3.73 (s, 2H), 2.94-2.93 (m, 4H), 2.76 (br, 4H).

1184: White solid. Yield: 87.9%. ¹H NMR (500 MHz, CDCl₃) δ 7.69-7.60 (m, 4H), 7.42-7.31 (m, 7H), 7.19-7.17 (m, 1H), 7.08-7.06 (m, 1H), 6.95-6.93 (m, 1H), 6.88-6.85 (m, 1H), 3.90 (s, 2H), 2.98-2.97 (m, 4H), 2.87 (Br, 4H).

1209: White solid. Yield: 85.4. ¹H NMR (500 MHz, Acetone-d₆) δ 11.48 (br, 1H), 7.88 (s, 1H), 7.81-7.79 (m, 1H), 7.57-7.56 (m, 2H), 7.44-6.97 (m, 8H), 4.19 (s, 1H), 3.74 (s, 2H), 2.87-2.85 (m, 2H), 2.75-2.70 (m, 2H), 2.17-2.11 (m, 2H), 1.75-1.72 (m, 2H).

1210: White solid. Yield: 87.9%. ¹H NMR (500 MHz, Acetone-d₆) δ 11.34 (br, 1H), 7.65-7.44 (m, 6H), 7.42-7.11 (m, 8H), 3.99 (br, 1H), 3.70 (s, 2H), 2.85-2.81 (m, 4H), 2.71-2.66 (m, 2H), 1.70-1.68 (m, 2H).

1211: White solid. Yield: 91.8%. ¹H NMR (500 MHz, Acetone-d₆) δ 12.16 (br, 1H), 7.52-7.47 (m, 8H), 7.45-7.44 (m, 3H), 7.18-7.15 (m, 2H), 7.11-7.08 (m, 1H), 3.93 (s, 2H), 3.01 (d, J=11.1 Hz, 2H), 2.74-2.69 (m, 2H), 1.84-1.78 (m, 2H), 1.71-1.60 (m, 2H).

1212: White solid. Yield: 88.7%. ¹H NMR (500 MHz, Acetone-d₆) δ 7.45-7.29 (m, 6H), 7.08-7.01 (m, 2H), 6.87-6.82 (m, 2H), 6.79-6.72 (m, 2H), 4.65 (s, 1H), 3.87 (s, 2H), 3.17-3.10 (m, 4H), 2.85-2.81 (m, 4H).

1213: White solid. Yield: 91.2%. ¹H NMR (500 MHz, CDCl₃) δ 7.45-7.22 (m, 8H), 7.10-7.01 (m, 2H), 6.94-6.93 (m, 2H), 6.88-6.85 (m, 1H), 3.87 (s, 2H), 3.32-3.21 (m, 4H), 2.91-2.80 (m, 4H).

1214 Colorless syrup. Yield: 77.4%. ¹H NMR (500 MHz, CDCl₃) δ ¹H NMR (500 MHz, CDCl₃) δ 7.98 (br, 1H), 7.67-7.65 (m, 1H), 7.47-7.33 (m, 7H), 7.21-7.18 (m, 1H), 7.13-7.04 (m, 3H), 7.00-6.98 (m, 1H), 3.89 (s, 2H), 3.21-3.18 (m, 2H), 2.91-2.82 (m, 1H), 2.48-2.44 (m, 2H), 2.12-2.10 (m, 2H), 1.97-1.92 (m, 2H).

1227: White solid. Yield: 86.4%. ¹H NMR (500 MHz, CDCl₃) δ 8.20-8.18 (m, 1H), 7.70-7.58 (m, 4H), 7.50-7.44 (m, 1H), 7.42-7.29 (m, 6H), 6.69-6.58 (m, 2H), 3.87 (s, 2H), 3.66-3.55 (m, 4H), 2.81-2.78 (m, 4H).

1228: Colorless syrup. Yield: 89.7%. ¹H NMR (500 MHz, CDCl₃) δ 8.00 (br, 1H), 7.68-7.64 (m, 1H), 7.62-7.59 (m, 2H), 7.45-7.39 (m, 1H), 7.38-7.33 (m, 1H), 7.31-7.28 (m, 1H), 7.24-7.17 (m, 1H), 7.15-7.10 (m, 2H), 4.08 (s, 2H), 3.88 (s, 2H), 3.20-2.94 (m, 4H).

1229: White solid. Yield: 89.1%. ¹H NMR (500 MHz, CDCl₃) δ 8.20 (d, J=5.2 Hz, 1H), 7.69-7.58 (m, 4H), 7.44-7.30 (m, 6H), 6.52 (d, J=5.2 Hz, 1H), 3.84 (s, 2H), 3.19-3.16 (m, 2H), 2.53-2.42 (m, 1H), 2.38-2.32 (m, 2H), 1.94-1.81 (m, 4H), 1.65 (br, 2H).

1284: White solid. Yield: 81.2%. $^1$H NMR (500 MHz, CDCl$_3$) δ 9.70 (br, 1H), 8.56-8.55 (m, 1H), 7.67-7.63 (m, 1H), 7.58-7.42 (br, 3H), 7.40 (d, J=7.8 Hz, 1H), 7.39-7.20 (m, 6H), 7.18-7.15 (m, 1H), 3.73 (s, 2H), 3.67 (s, 2H), 2.65 (s, 4H), 2.56 (s, 4H).

1285: Colorless syrup. Yield: 82.5%. $^1$H NMR (500 MHz, CDCl$_3$) δ 8.56 (d, J=4.2 Hz, 1H), 7.68-7.56 (m, 5H), 7.42-7.30 (m, 7H), 7.17-7.14 (m, 1H), 3.83 (s, 2H), 3.69 (s, 2H), 2.75 (br, 4H), 2.62 (br, 4H).

1286: Colorless syrup. Yield: 87.5%. $^1$H NMR (500 MHz, CDCl$_3$) δ 7.71-7.62 (m, 2H), 7.62-7.56 (m, 2H), 7.41-7.29 (m, 6H), 7.29-7.20 (m, 1H), 7.13-7.04 (m, 2H), 6.95-6.91 (m, 1H), 3.82 (s, 2H), 3.51 (s, 2H), 2.72 (br, 4H), 2.54 (br, 4H).

1287: Colorless syrup. Yield: 84.3%. $^1$H NMR (500 MHz, CDCl$_3$) δ 7.66-7.62 (m, 2H), 7.62-7.57 (m, 2H), 7.41-7.30 (m, 6H), 7.24-7.18 (m, 2H), 6.87-6.82 (m, 2H), 3.81 (s, 2H), 3.79 (s, 3H), 3.46 (s, 2H), 2.70 (br, 4H), 2.52 (br, 4H).

1288: Colorless syrup. Yield: 91.2%. $^1$H NMR (500 MHz, CDCl$_3$) δ 7.65-7.63 (m, 2H), 7.62-7.57 (m, 2H), 7.42-7.29 (m, 6H), 7.29-7.22 (m, 1H), 7.08-7.05 (m, 2H), 6.98-6.89 (m, 1H), 3.82 (s, 2H), 3.52 (s, 2H), 2.72 (br, 4H), 2.54 (br, 4H).

1289: White solid. Yield: 88.5%. $^1$H NMR (500 MHz, CDCl$_3$) δ 7.67-7.62 (m, 2H), 7.62-7.57 (m, 2H), 7.41-7.30 (m, 6H), 7.21 (t, J=7.9 Hz, 1H), 6.90-6.89 (m, 2H), 6.81-6.76 (m, 1H), 3.81 (s, 2H), 3.80 (s, 3H), 3.50 (s, 2H), 2.71 (br, 4H), 2.54 (br, 4H).

1290: White solid. Yield: 91.0%. $^1$H NMR (500 MHz, CDCl$_3$) δ 9.58 (br, 1H), 7.39-7.22 (m, 5H), 7.16 (d, J=7.6 Hz, 1H), 7.11-6.99 (m, 4H), 6.96-6.92 (m, 2H), 3.71 (s, 2H), 3.51 (s, 2H), 2.62 (br, 4H), 2.49 (br, 4H).

1291: White solid. Yield: 88.2%. $^1$H NMR (500 MHz, CDCl$_3$) δ 9.61 (br, 1H), 7.32 (br, 3H), 7.24-6.90 (m, 7H), 6.89-6.82 (m, 2H), 3.80 (s, 3H), 3.70 (s, 2H), 3.46 (s, 2H), 2.60 (br, 4H), 2.47 (br, 4H).

1312: White solid. Yield: 91.5%. $^1$H NMR (500 MHz, Acetone-d$_6$) δ 11.56 (br, 1H), 7.52-6.92 (m, 9H), 6.76-6.74 (m, 1H), 6.68-6.64 (m, 1H), 6.55-6.46 (m, 1H), 3.72 (s, 2H), 3.27-3.20 (m, 4H), 2.77-2.65 (m, 4H).

1313: Colorless syrup. Yield: 87.5%. $^1$H NMR (500 MHz, CDCl$_3$) δ 7.70-7.57 (m, 4H), 7.47-7.31 (m, 6H), 7.22-7.15 (m, 1H), 6.68-6.66 (m, 1H), 6.64-6.47 (m, 2H), 3.87 (s, 2H), 3.31-3.20 (m, 4H), 2.87-2.78 (m, 4H).

1314: White solid. Yield: 89.3%. $^1$H NMR (500 MHz, Acetone-d$_6$) δ 11.36 (br, 1H), 7.69-7.12 (m, 11H), 6.76-6.74 (m, 1H), 6.68-6.65 (m, 1H), 6.51-6.47 (m, 1H), 3.70 (s, 2H), 3.29-3.21 (m, 4H), 2.75-2.67 (m, 4H).

1315: White solid. Yield: 87.6%. $^1$H NMR (500 MHz, Acetone-d$_6$) δ 11.30 (br, 1H), 7.82-7.09 (m, 15H), 3.63 (s, 2H), 3.48 (s, 2H), 2.56 (br, 4H), 2.44 (br, 4H).

1357: White solid. Yield: 92.1%. $^1$H NMR (500 MHz, CDCl$_3$) δ 7.65-7.61 (m, 2H), 7.61-7.56 (m, 2H), 7.39-7.30 (m, 7H), 7.25-7.20 (m, 1H), 7.11-7.07 (m, 1H), 7.05-6.99 (m, 1H), 3.81 (s, 2H), 3.62 (s, 2H), 2.72 (br, 4H), 2.59 (br, 4H).

1358: White solid. Yield: 88.5%. $^1$H NMR (500 MHz, Acetone-d$_6$) δ 11.28 (br, 1H), 7.60-7.58 (m, 2H), 7.48-7.41 (m, 3H), 7.39-7.21 (m, 6H), 7.20-7.14 (m, 2H), 7.10-7.05 (m, 1H), 3.62 (s, 2H), 3.55 (s, 2H), 2.56 (br, 4H), 2.48 (br, 4H).

1359: Colorless syrup. Yield: 77.3%. $^1$H NMR (500 MHz, CDCl$_3$) δ 7.63 (s, 1H), 7.57-7.55 (m, 2H), 7.51-7.47 (m, 4H), 7.45-7.42 (m, 1H), 7.35-7.29 (m, 4H), 7.29-7.24 (m, 3H), 3.97 (s, 2H), 3.57 (s, 2H), 2.82 (br, J=4.9 Hz, 4H), 2.59 (br, 4H).

1360: Colorless syrup. Yield: 91.5%. $^1$H NMR (500 MHz, CDCl$_3$) δ 7.67-7.63 (m, 3H), 7.62-7.58 (m, 2H), 7.58-7.52 (m, 2H), 7.43-7.30 (m, 7H), 3.82 (s, 2H), 3.54 (s, 2H), 2.71 (br, 4H), 2.53 (br, 4H).

1361: Colorless syrup. Yield: 82.1%. $^1$H NMR (500 MHz, CDCl$_3$) δ 7.66-7.62 (m, 2H), 7.62-7.58 (m, 4H), 7.45-7.44 (m, 2H), 7.39-7.31 (m, 6H), 3.82 (s, 2H), 3.56 (s, 2H), 2.71 (br, 4H), 2.53 (br, 4H).

1362: Colorless syrup. Yield: 85.2%. $^1$H NMR (500 MHz, CDCl$_3$) δ 7.64-7.60 (m, 2H), 7.51-7.42 (m, 6H), 7.35-7.29 (m, 4H), 7.29-7.24 (m, 3H), 3.97 (s, 2H), 3.60 (s, 2H), 2.81 (br, 4H), 2.59 (br, 4H).

1363: Colorless syrup. Yield: 89.5%. $^1$H NMR (500 MHz, CDCl$_3$) δ 9.49 (br, 1H), 7.65-7.63 (m, 1H), 7.56-7.55 (m, 3H), 7.51-7.27 (m, 8H), 3.71 (s, 4H), 2.63 (br, 4H), 2.57 (br, 4H).

1364: Colorless syrup. Yield: 77.3%. $^1$H NMR (500 MHz, CDCl$_3$) δ 7.67-7.62 (m, 3H), 7.62-7.58 (m, 2H), 7.54-7.53 (m, 2H), 7.39-7.30 (m, 7H), 3.81 (s, 2H), 3.73 (s, 2H), 2.71 (s, 4H), 2.61 (s, 4H).

1366: Colorless syrup. Yield: 82.8%. $^1$H NMR (500 MHz, CDCl$_3$) δ 8.39-8.38 (m, 1H), 7.66-7.62 (m, 2H), 7.61-7.57 (m, 2H), 7.43-7.42 (m, 1H), 7.40-7.29 (m, 6H), 7.10-7.07 (m, 1H), 3.80 (s, 2H), 3.66 (s, 2H), 2.69 (br, 4H), 2.60 (br, 4H).

1367: White solid. Yield: 73.5%. $^1$H NMR (500 MHz, CDCl$_3$) δ 9.68 (br, 1H), 8.39-8.38 (m, 1H), 7.62-7.40 (m, 5H), 7.39-7.22 (m, 6H), 7.10 (dd, J=7.6, 4.8 Hz, 1H), 3.73 (s, 2H), 3.66 (s, 2H), 2.61 (br, 4H), 2.56 (br, 4H).

1368: Colorless syrup. Yield: 81.2%. $^1$H NMR (500 MHz, CDCl$_3$) δ 8.01-7.99 (m, 2H), 7.60-7.54 (m, 4H), 7.50-7.43 (m, 3H), 7.40-7.29 (m, 6H) 3.86 (s, 2H), 3.81 (s, 2H), 2.73 (br, 4H), 2.64 (br, 4H).

1369: White solid. Yield: 80.1%. $^1$H NMR (500 MHz, Acetone-d$_6$) δ 7.60 (d, J=7.8 Hz, 1H), 7.51 (d, J=7.5 Hz, 5H), 7.36 (d, J=8.2 Hz, 1H), 7.31 (t, J=7.5 Hz, 4H), 7.24 (t, J=7.3 Hz, 2H), 7.18 (s, 1H), 7.09-7.06 (m, 1H), 6.98 (t, J=7.5 Hz, 1H), 4.00 (s, 2H), 3.10-3.04 (m, 2H), 3.03-2.98 (m, 2H).

1370: Colorless syrup. Yield: 86.0%. $^1$H NMR (500 MHz, CDCl$_3$) δ 7.66-7.62 (m, 2H), 7.61-7.57 (m, 2H), 7.39-7.29 (m, 6H), 3.82 (s, 2H), 3.50 (t, J=5.6 Hz, 2H), 3.33 (s, 3H), 2.74 (s, 4H), 2.65-2.55 (m, 6H).

1371: Colorless syrup. Yield: 89.3%. $^1$H NMR (500 MHz, CDCl$_3$) δ 9.66 (br, 1H), 7.66-7.19 (m, 10H), 3.73 (s, 2H), 3.54-3.46 (m, 2H), 3.35 (t, J=3.3 Hz, 3H), 2.66 (s, 4H), 2.60-2.50 (m, 6H).

1372: White solid. Yield: 83.5%. $^1$H NMR (500 MHz, CDCl$_3$) δ 7.93 (br, 1H), 7.69-7.65 (m, 2H), 7.64-7.57 (m, 3H), 7.40-7.30 (m, 7H), 7.16-7.13 (m, 1H), 7.05-7.03 (m, 1H), 7.02-6.98 (m, 1H), 6.01-5.93 (m, 1H), 5.36-5.17 (m, 2H), 4.04 (s, 2H), 3.41 (d, J=6.5 Hz, 2H), 3.11-2.92 (m, 4H).

1394: White solid. Yield: 81.0%. $^1$H NMR (500 MHz, CDCl$_3$) δ 7.67-7.61 (m, 2H), 7.60-7.58 (m, 2H), 7.39-7.27 (m, 8H), 7.12 (t, J=8.0 Hz, 1H), 3.79 (s, 2H), 3.78 (s, 2H), 2.68 (br, 8H).

1395: White solid. Yield: 83.7%. $^1$H NMR (500 MHz, CDCl$_3$) δ 7.66-7.61 (m, 2H), 7.60-7.58 (m, 2H), 7.41-7.29 (m, 6H), 7.19 (d, J=7.9 Hz, 2H), 7.11 (d, J=7.9 Hz, 2H), 3.81 (s, 2H), 3.50 (s, 2H), 2.71 (br, 4H), 2.54 (br, 4H), 2.32 (s, 3H).

1396: Colorless syrup. Yield: 82.1%. $^1$H NMR (500 MHz, CDCl$_3$) δ 8.72 (br, 1H), 7.85 (br, 1H), 7.51-7.48 (m, 1H), 7.35-7.16 (m, 11H), 7.16-7.09 (m, 1H), 7.02-6.99 (m, 2H), 6.92-6.66 (m, 3H), 3.83 (s, 2H), 3.82 (s, 2H), 3.04-3.02 (m, 2H), 2.99-2.96 (m, 2H).

1397: Colorless syrup. Yield: 77.2%. $^1$H NMR (500 MHz, CDCl$_3$) δ 13.32 (br, 1H), 7.52-7.43 (m, 9H), 7.37-7.28 (m, 5H), 7.21-7.03 (m, 3H), 5.81-5.73 (m, 1H), 5.34-5.17 (m, 2H), 4.06 (s, 2H), 3.47 (d, J=7.0 Hz, 2H), 3.09-3.06 (m, 2H), 2.92-2.89 (m, 2H).

1039: Yellow syrup. Yield: 91.5%. $^1$H NMR (500 MHz, CDCl$_3$) δ 9.71 (br, 1H), 7.89-7.84 (m, 2H), 7.70-7.61 (m, 2H), 7.61-7.50 (m, 1H), 7.37-7.24 (m, 4H), 7.17 (d, J=8.8 Hz, 1H), 7.13-6.93 (m, 5H), 6.81 (dd, J=8.8, 2.4 Hz, 1H), 4.69 (s, 2H), 3.81-3.77 (m, 2H), 3.77 (s, 3H), 3.09-3.02 (m, 2H).

1040: Yellow syrup. Yield: 93.1%. $^1$H NMR (500 MHz, CDCl$_3$) δ 8.14 (s, 1H), 8.00 (d, J=7.7 Hz, 1H), 7.77-7.61 (m, 3H), 7.57 (s, 1H), 7.25-7.10 (m, 6H), 7.03-6.90 (m, 6H), 6.46 (s, 1H), 4.76 (s, 2H), 4.60 (s, 2H).

Example 5—Preparation of Compounds of Class IV

Scheme 15 outlines the chemical synthesis of compounds identified as "Class IV". These compounds are shown in Table 5 below.

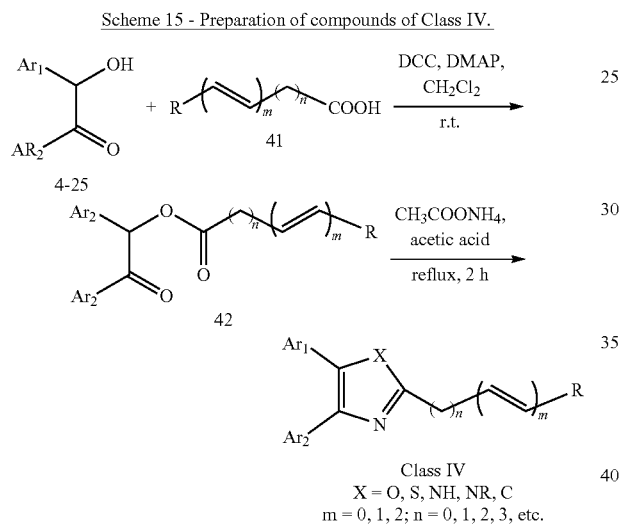

Scheme 15 - Preparation of compounds of Class IV.

Class IV
X = O, S, NH, NR, C
m = 0, 1, 2; n = 0, 1, 2, 3, etc.

General Procedure for the Preparation of Intermediate Compound 42.$^{56}$

To a vacuum flame-dried flask was added a benzoin 4 or its other derivatives (0.212 g, 1 mmol), acid 41 (1.1 mmol), dicyclohexylcarbodiimide (0.206 g, 1 mmol), 4-dimethylaminopyridine (12.2 mg, 0.1 mmol), dichloromethane (10 mL) under nitrogen atmosphere. The reaction mixture was stirred for 2 hours at room temperature. Then ethyl acetate was added and the reaction mixture was filtered. The filtrate was then washed with 5% HCl, saturated NaHCO$_3$, brine and dried with Na$_2$SO$_4$. After filtration, the solvent was concentrated in vacuum. This crude residue was then purified by flash chromatography to give Intermediates 42.

General Procedure for the Preparation of Compounds of Class IV

A mixture of 42 (0.5 mmol), ammonium acetate (2.5 mmol) in glacial acetic acid (5 mL) was refluxed for 2 hours. After cooling, water was added to the reaction mixture. After extracting with ethyl acetate, the combined organic phase was washed with saturated NaHCO$_3$, brine, dried with Na$_2$SO$_4$, filtered, and concentrated in vacuum. The crude residue was then purified by flash chromatography to give the desired product, compounds of Class IV: 684-689, 692, 693, 926, 1011-1033, 1033-1037.

TABLE 5

Structures of compounds of Class IV.

| ID | Structure |
|---|---|
| 684 | (4,5-diphenyloxazol-2-yl)-styryl-3-OCH$_3$ |
| 685 | (4,5-diphenyloxazol-2-yl)-vinyl-thiophene |
| 686 | (4,5-diphenyloxazol-2-yl)-vinyl-furan |
| 687 | (4,5-diphenyloxazol-2-yl)-CH$_2$-3-CF$_3$-phenyl |
| 688 | (4,5-diphenyloxazol-2-yl)-3-CF$_3$-phenyl |
| 689 | (4,5-diphenyloxazol-2-yl)-CH$_2$CH$_2$-3,5-bis-CF$_3$-phenyl |

TABLE 5-continued

Structures of compounds of Class IV.

| ID | Structure |
|---|---|
| 692 | 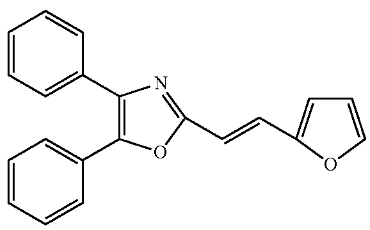 [SMILES: C(=C\c1nc(-c2ccccc2)c(-c2ccccc2)o1)/c1ccco1] |
| 693 | 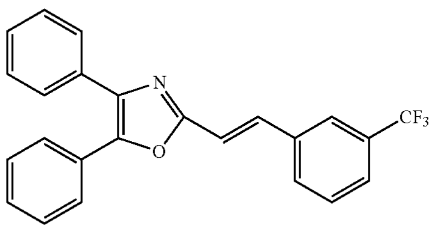 [SMILES: FC(F)(F)c1cccc(/C=C/c2nc(-c3ccccc3)c(-c3ccccc3)o2)c1] |
| 926 | 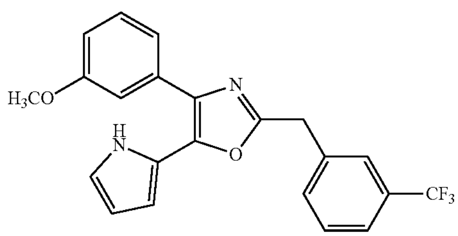 [SMILES: COc1cccc(-c2nc(Cc3cccc(C(F)(F)F)c3)oc2-c2ccc[nH]2)c1] |
| 1011 | 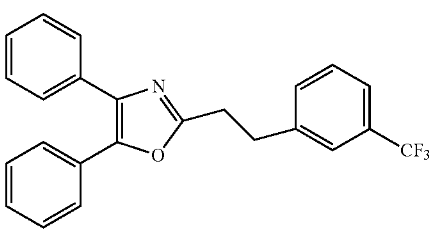 [SMILES: FC(F)(F)c1cccc(CCc2nc(-c3ccccc3)c(-c3ccccc3)o2)c1] |
| 1012 | 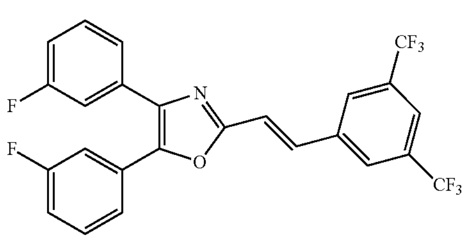 [SMILES: Fc1cccc(-c2nc(/C=C/c3cc(C(F)(F)F)cc(C(F)(F)F)c3)oc2-c2cccc(F)c2)c1] |
| 1013 | 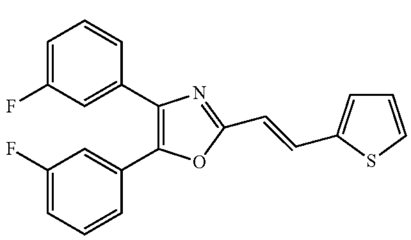 [SMILES: Fc1cccc(-c2nc(/C=C/c3cccs3)oc2-c2cccc(F)c2)c1] |
| 1033 | 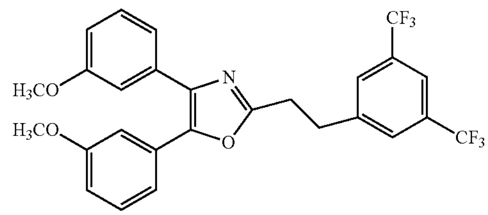 [SMILES: COc1cccc(-c2nc(CCc3cc(C(F)(F)F)cc(C(F)(F)F)c3)oc2-c2cccc(OC)c2)c1] |
| 1034 | 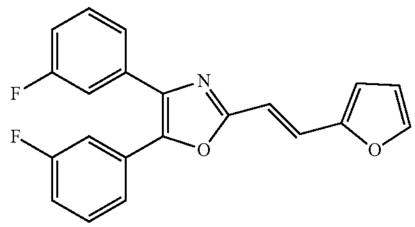 [SMILES: Fc1cccc(-c2nc(/C=C/c3ccco3)oc2-c2cccc(F)c2)c1] |
| 1035 | 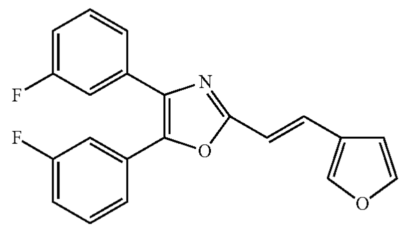 [SMILES: Fc1cccc(-c2nc(/C=C/c3ccoc3)oc2-c2cccc(F)c2)c1] |
| 1036 | 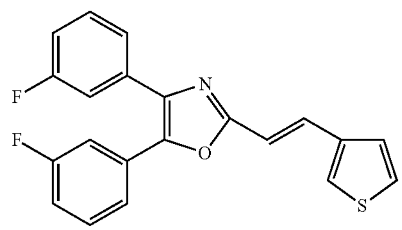 [SMILES: Fc1cccc(-c2nc(/C=C/c3ccsc3)oc2-c2cccc(F)c2)c1] |
| 1037 | 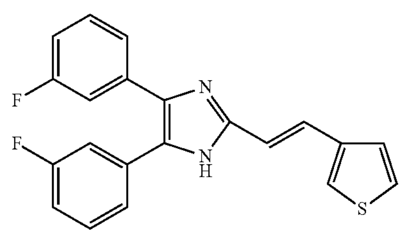 [SMILES: Fc1cccc(-c2nc(/C=C/c3ccsc3)[nH]c2-c2cccc(F)c2)c1] |

Characterization of Compounds of Class IV:

684: White solid, yield: 86%. $^1$H NMR (500 MHz, CDCl$_3$) δ 7.71-7.62 (m, 4H), 7.55 (d, J=16.3 Hz, 1H), 7.40-7.30 (m, 6H), 7.28 (d, J=8.0 Hz, 1H), 7.14 (d, J=7.7 Hz, 1H), 7.08-7.06 (m, 1H), 6.99 (d, J=16.3 Hz, 1H), 6.88 (dd, J=8.2, 2.4 Hz, 1H), 3.83 (s, 3H).

685: Yellow solid, yield: 83%. $^1$H NMR (500 MHz, CDCl$_3$) δ 7.72-7.60 (m, 5H), 7.38-7.28 (m, 7H), 7.19 (d, J=3.5 Hz, 1H), 7.04-7.01 (m, 1H), 6.81 (d, J=16.1 Hz, 1H).

686: Yellow solid, yield: 85%. $^1$H NMR (500 MHz, CDCl$_3$) δ 7.69-7.58 (m, 5H), 7.45 (d, J=16.2 Hz, 1H), 7.43-7.41 (m, 1H), 7.40-7.27 (m, 6H), 6.70 (d, J=16.1 Hz, 1H), 6.65-6.64 (m, 1H).

687: Yellow syrup, yield: 92%. $^1$H NMR (500 MHz, CDCl$_3$) δ 7.66 (s, 1H), 7.63-7.60 (m, 2H), 7.58 (d, J=7.6 Hz, 1H), 7.54-7.50 (m, 3H), 7.46-7.40 (m, 1H), 7.37-7.28 (m, 6H), 4.23 (s, 2H).

688: White solid, yield: 69%. $^1$H NMR (500 MHz, CDCl$_3$) δ 8.39 (s, 1H), 8.31 (d, J=7.9 Hz, 1H), 7.72-7.64 (m, 6H), 7.40-7.34 (m, 6H).

689: White solid, yield: 88%. $^1$H NMR (500 MHz, CDCl$_3$) δ 7.73-7.71 (m, 3H), 7.61-7.56 (m, 2H), 7.53-7.48 (m, 2H), 7.37-7.27 (m, 6H), 3.30 (t, J=7.6 Hz, 2H), 3.19 (t, J=7.5 Hz, 2H).

692: Yellow solid, yield: 89%. $^1$H NMR (500 MHz, CDCl$_3$) δ 7.66-7.61 (m, 4H), 7.45 (s, 1H), 7.40-7.27 (m, 7H), 6.87 (d, J=16.1 Hz, 1H), 6.55-6.42 (m, 2H).

693: White solid, yield: 91%. $^1$H NMR (500 MHz, CDCl$_3$) δ 7.77 (s, 1H), 7.71 (d, J=7.7 Hz, 1H), 7.67-7.63 (m, 4H), 7.59 (d, J=16.5 Hz, 1H), 7.56 (s, 1H), 7.50 (t, J=7.7 Hz, 1H), 7.41-7.30 (m, 6H), 7.06 (d, J=16.4 Hz, 1H).

926: White solid, yield: 73.0%. $^1$H NMR (500 MHz, CDCl$_3$) δ 9.46 (br, 1H), 7.59 (s, 1H), 7.54-7.48 (m, 2H), 7.45-7.41 (m, 1H), 7.08-7.04 (m, 1H), 7.02-6.99 (m, 1H), 6.99-6.95 (m, 1H), 6.93-6.91 (m, 1H), 6.88-6.86 (m, 1H), 6.56 (s, 1H), 6.22-6.20 (m, 1H), 3.90-3.81 (m, 2H), 3.77 (s, 3H).

1011: White solid, yield: 82.6%. $^1$H NMR (500 MHz, CDCl$_3$) δ 7.53-7.38 (m, 6H), 7.34-7.24 (m, 8H), 3.19 (t, J=7.6 Hz, 2H), 3.10-3.06 (m, 2H).

1012: White solid, yield: 85.7%. $^1$H NMR (500 MHz, CDCl$_3$) 57.76 (s, 1H), 7.74 (s, 2H), 7.40-7.28 (m, 5H), 7.24-7.22 (m, 1H), 7.09-7.02 (m, 2H), 3.33 (t, J=7.6 Hz, 2H), 3.24-3.19 (m, 2H).

1013: Yellow solid, yield: 81.6%. $^1$H NMR (500 MHz, CDCl$_3$) δ 7.97 (s, 2H), 7.83 (s, 1H), 7.71-7.61 (m, 4H), 7.43-7.34 (m, 5H), 7.16 (d, J=16.4 Hz, 1H).

1033: White solid, yield: 89.5%. $^1$H NMR (500 MHz, CDCl$_3$) δ 7.75-7.74 (m, 3H), 7.31-7.24 (m, 3H), 7.23-7.16 (m, 2H), 7.15-7.11 (m, 1H), 7.11-7.07 (m, 1H), 6.91-6.85 (m, 2H), 3.79 (s, 3H), 3.74 (s, 3H), 3.33 (t, J=7.6 Hz, 2H), 3.21 (t, J=7.6 Hz, 2H).

1034: White solid, yield: 84.2%. $^1$H NMR (500 MHz, CDCl$_3$) δ 7.42-7.41 (m, 1H), 7.34-7.26 (m, 4H), 7.24-7.19 (m, 3H), 7.00-6.97 (m, 2H), 6.82 (d, J=16.1 Hz, 1H), 6.46-6.38 (m, 2H).

1035: White solid, yield: 81.7%. $^1$H NMR (500 MHz, CDCl$_3$) δ 7.66 (s, 1H), 7.51 (d, J=16.2 Hz, 1H), 7.48-7.32 (m, 7H), 7.10-7.02 (m, 2H), 6.71 (d, J=16.2 Hz, 1H), 6.67-6.66 (m, 1H).

1036: White solid, yield: 43.2%. $^1$H NMR (500 MHz, CDCl$_3$) δ 7.68 (d, J=15.9 Hz, 1H), 7.62 (d, J=16.3 Hz, 1H), 7.50-7.49 (m, 1H), 7.47-7.28 (m, 7H), 7.11-7.03 (m, 1H), 6.83 (d, J=16.3 Hz, 1H), 6.27 (d, J=15.9 Hz, 1H).

1037: White solid, yield: 23.1%. $^1$H NMR (500 MHz, CDCl$_3$) δ 9.50 (br, 1H), 7.37 (d, J=16.4 Hz, 1H), 7.34-7.15 (m, 9H), 7.01-6.98 (t, J=7.4 Hz, 2H), 6.82 (d, J=16.4 Hz, 1H).

Example 6—Preparation of Compounds "V-131 Analogues" and "V-154 Analogues"

Scheme 16 below outlines the chemical synthesis of compounds identified as "V131 Analogues"; and Scheme 17 below outlines the chemical synthesis of compounds identified as "V154 Analogues". These compounds are shown in Table 6 below.

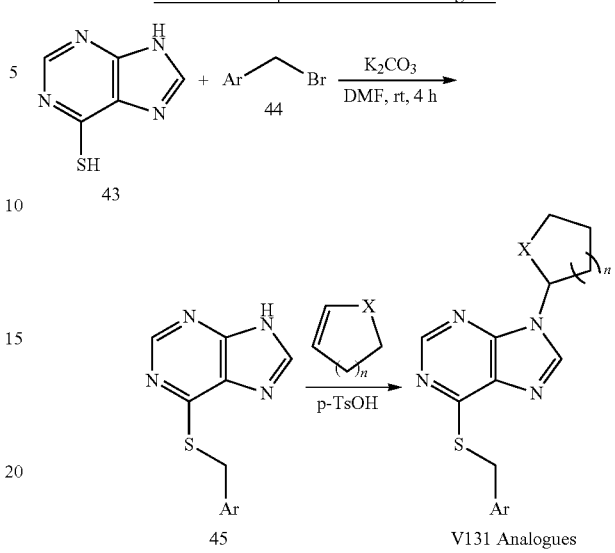

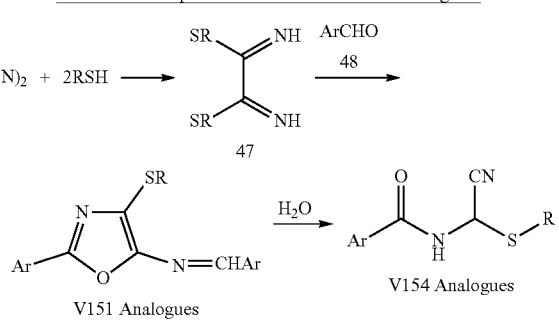

General Procedure for the Preparation of Intermediates 45

A mixture of 6-mercaptopurine 43 (10 mmol) and K$_2$CO$_3$ (10 mmol) in 25 mL of DMF was stirred for 5 minutes at room temperature. Then bromide 44 (10 mmol) was added dropwise. The reaction mixture was stirred at room temperature for 4 hours and 200 mL H$_2$O was added. The precipitate was collected by filtration, the solid was washed with EtOAc and CH$_2$Cl$_2$ and dried. Yielded 45 as white powder: 91%.

General Procedure for the Preparation of V131 Analogues.

To a solution of 45 (1.0 equiv) in 60 mL of anhydrous ethyl acetate at 50° C. was added and p-toluene-sulfonic acid (0.1 equiv). The mixture was vigorously stirred and 46 (3 equiv) was added dropwise. The reaction mixture was stirred for 1 hour and cooled to rt. Then concentrated aqueous ammonia was added and stirred for 5 minutes. The ethyl acetate phase was separated and washed twice with water. The ethyl acetate layer was dried with Na$_2$SO$_4$ and concentrated under reduced pressure. Recrystallization from petroleum ether to afford V131 Analogues.

General Procedure for the Preparation of V151 and V154 Analogues.

Preparation of V151: A mixture of 47 (2 mmol) and aldehyde 48 (5 mmol) was heated at 100° C. for 1.5 hour. Then 50 ml of anhydrous EtOH was added to the reaction mixture. On cooling, yellowish orange crystal was formed and collected by filtration, which was recrystallized from EtOH, V151 analogues were obtained.

Preparation of V154 Analogues: To V151 analogues (1 mmol) in 15 mL acetone, 10 mL 5% HCl was added, the mixture was stirred for 5 minutes at rt. Then Na₂CO₃ was added to adjust pH~7. The mixture was extracted with dichloromethane (3×15 mL). The combined organic extracts were washed with brine, dried over Na₂SO₄, filtered, and concentrated under reduced pressure. The residue is purified by column chromatography to give the desired products, compounds V154 Analogues as illustrated in Scheme 17.

TABLE 6

Structures of compounds V131 and V154 and analogues.

| ID | Structure |
|---|---|
| V131 (known in the art) | 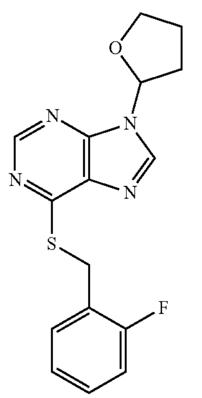 [SMILES: Fc1ccccc1CSc1ncnc2c1ncn2C1CCCO1] |
| V154 (known in the art) | 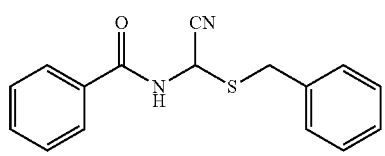 [SMILES: N#CC(NC(=O)c1ccccc1)SCc1ccccc1] |
| V151 (known in the art) | 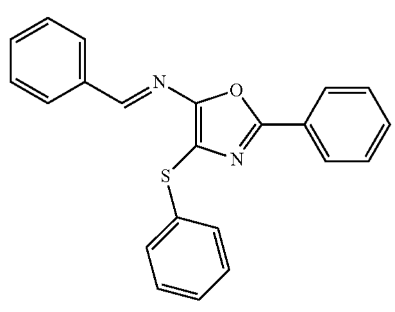 [SMILES: C(=N\c1oc(-c2ccccc2)nc1Sc1ccccc1)/c1ccccc1] |

Characterization of Compounds V131, V154, 151:

V131: White solid. $^1$H NMR (500 MHz, acetone-$d_6$) δ 8.76-8.70 (m, 1H), 8.35 (s, 1H), 7.66-7.59 (m, 1H), 7.38-7.28 (m, 1H), 7.17-7.10 (m, 2H), 6.40-6.38 (m, 1H), 4.73 (s, 2H), 4.31-4.26 (m, 1H), 4.07-3.97 (m, 1H), 2.64-2.62 (m, 1H), 2.58-2.48 (m, 1H), 2.35-2.25 (m, 1H), 2.20-2.09 (m, 1H).

V154: White solid. $^1$H NMR (500 MHz, acetone-$d_6$) δ 7.92-7.89 (m, 2H), 7.62-7.59 (m, 1H), 7.53-7.48 (m, 2H), 7.46-7.41 (m, 2H), 7.37-7.32 (m, 2H), 7.31-7.25 (m, 1H), 6.26-6.21 (m, 1H), 4.18 (dd, J=31.7, 13.0 Hz, 2H).

Example 7—Preparation of Compounds "V-248 Analogues"

Scheme 18, Scheme 19 and Scheme 20 below outlines the chemical synthesis of compounds identified as "V248 Analogues". These compounds are shown in Table 7 below.

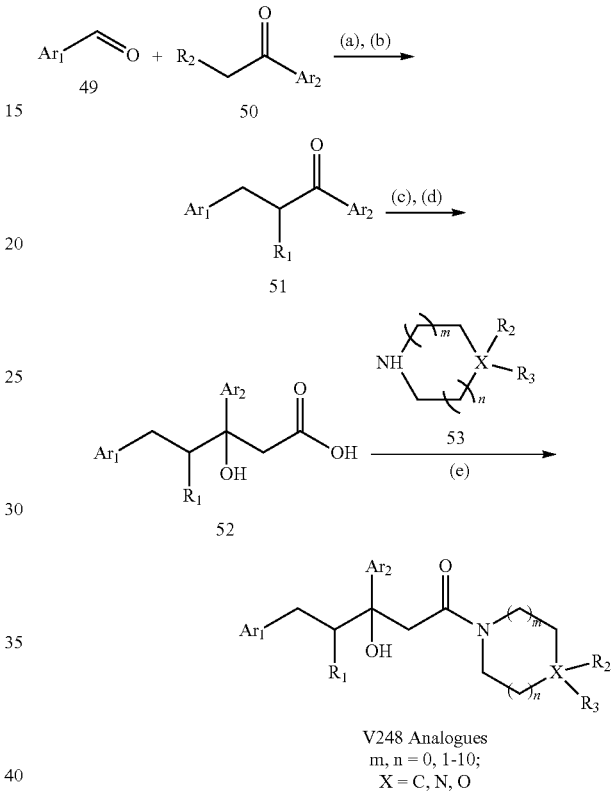

Scheme 18 - Preparation of V248 analogues.

V248 Analogues
m, n = 0, 1-10;
X = C, N, O (a) NaOH, MeOH;
(b) Pd/C, H2;
(c) Zn, BrCH₂COOEt;
(d) OH;
(e) HBTU, Et₃N, DMSO, rt, overnight.

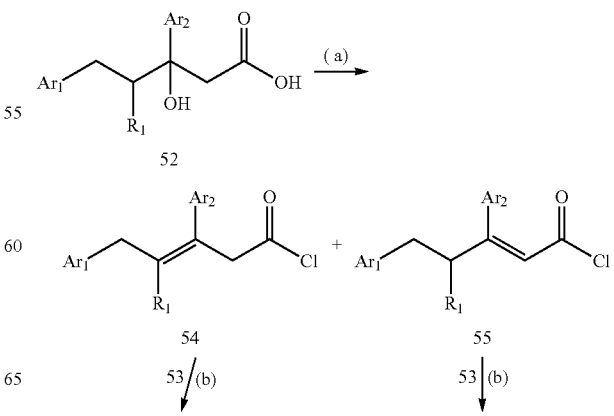

Scheme 19 - Preparation of V248 analogues.

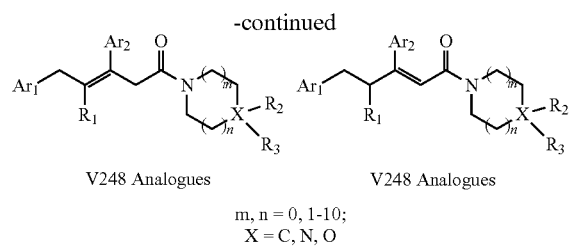

V248 Analogues     V248 Analogues m, n = 0, 1-10;
X = C, N, O (a) Oxalyl cloride, CH$_2$Cl$_2$, reflux;
(b) Et$_3$N, THF.

Scheme 20 - Preparation of V248 analogues.

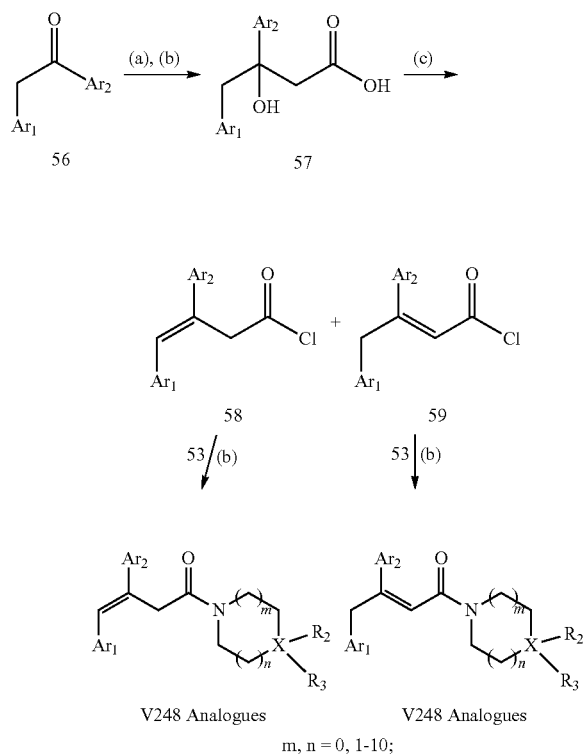

V248 Analogues     V248 Analogues m, n = 0, 1-10;
X = C, N, O (a) Zn, BrCH2COOEt;
(b) KOH;
(c) Oxalyl chloride, CH$_2$Cl$_2$, reflux;
(d) HBTU, Et$_3$N, DMSO, rt, overnight.

General Procedure for the Preparation of Intermediates.

Preparation of intermediates 51: Aldehyde 49 (1.0 equiv) was added to a solution of ketone 50 (1.0 equiv, 0.5 M in EtOH). Then a 10% aqueous solution of NaOH (0.5 equiv) was added dropwise at 0° C. The reaction was stirred at 0° C. for 4 hours. The mixture was diluted with water and extracted 3 times with CH$_2$Cl$_2$. The mixture was diluted with water (10 mL for each mmol of starting ketone 50) and extracted 3 times with CH$_2$Cl$_2$ (10 mL for each mmol of starting ketone 6). The organic layers were combined and dried over Na$_2$SO$_4$. Solvents were removed under reduced pressure to afford the crude products, which were purified through flash chromatography on silica gel (Hexane/EtOAc 50:1 to 20:1 as the eluent). The obtained product (1.0 equiv) was then dissolved in MeOH. 10% Pd/C was added and the flask was aerated with H$_2$. After stirring for 2 hours at room temperature, the mixture was filtered. Solvents were removed under reduced pressure to afford the crude product, which were purified through flash chromatography on silica gel (Hexane/EtOAc 50:1 to 15:1 as the eluent) to give 51.

Preparation of intermediates 52 and 57: Freshly activated zinc (2.5 equiv) in powder was kept in a flame-dried flask under N$_2$ atmosphere. Traces of iodine and 4 mL of dry THF were added. Then, ethyl bromoacetate (2.0 equiv) was added and the mixture was heated to make sure the reaction was initiated. A solution of compound 51 (1.0 equiv) in THF was added dropwise at room temperature. The reaction was stirred overnight at room temperature (when needed, warming up the reaction to 50° C. Monitored by TLC.) The reaction mixture was filtered through celite, diluted with EtOAc and washed with 0.5 M HCl aqueous. The organic layer was dried over Na$_2$SO$_4$. Solvents were removed under reduced pressure, the crude residue was then purified through flash chromatography on silica gel (Hexane/EtOAc 50:1 to 15:1 as the eluent) to give the ester, which (1.0 equiv) was dissolved in MeOH. KOH (2.0 equiv) was added to the solution. The mixture was stirred at 50° C. for 4 hours until full conversion of compound 9. Then the mixture was diluted with CH$_2$Cl$_2$ and extracted with water. The pH of aqueous phase was then adjusted to 2 by slowly adding a 1 M HCl solution. The aqueous phase was extracted with CH$_2$Cl$_2$ for 5 times. The organic layers were combined and dried over Na$_2$SO$_4$. Solvents were removed under reduced pressure, the crude products was purified through recrystallization (solvents: Hexane/DCM=1:1) to give 52.

Intermediates 57 were obtained according to the same procedure for the preparation of intermediates 52 as described above.

General Procedure for the Preparation of V248 Analogues.

Procedure A: To a mixture of acid 52 (0.12 mmol), 53 (0.1 mmol) and Et$_3$N (0.4 mmol) in DMSO (3 mL), HBTU (0.4 mmol) was added. The mixture was stirred at room temperature overnight. 10 mL water was added and extracted with dichloromethane (3×15 mL). The combined organic phases were washed with brine, dried over Na$_2$SO$_4$, filtered, and concentrated under reduced pressure. The crude residue was purified by column chromatography to give the desired products, compounds V248 analogues (Scheme 18).

Procedure B: To a solution of compound 52 (or 57) (1.0 equiv) in dry CH$_2$Cl$_2$, oxalyl (1.2 equiv) and catalytic amount of DMF were added in turn. The mixture was refluxed for 30 minutes and the solvent was removed through distillation to give a mixture of 54 and 55 (or 58 and 59), which was then dissolved in dry THF and used without further purification. To a solution of compound 53 (1.2 equiv) and Et$_3$N (1.5 equiv). The above solution was added dropwise at 0° C. The mixture was stirred at 0° C. for 30 minutes. Then the reaction was quenched with water and extracted with EtOAc. The organic layer was dried over Na$_2$SO$_4$. Solvents were removed under reduced pressure, the crude residue was then purified through flash chromatography on silica gel (Hexane/EtOAc 5:1 to 2:1 as the eluent) to give compounds V248 analogues (Schemes 19 and 20).

TABLE 7

Structure of compound V248 and its analogues.

| ID | Structure |
| --- | --- |
| V248 | 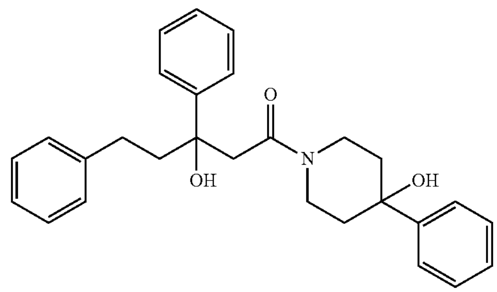 [SMILES: O=C(CC(O)(CCc1ccccc1)c1ccccc1)N1CCC(O)(c2ccccc2)CC1] |
| 859 | 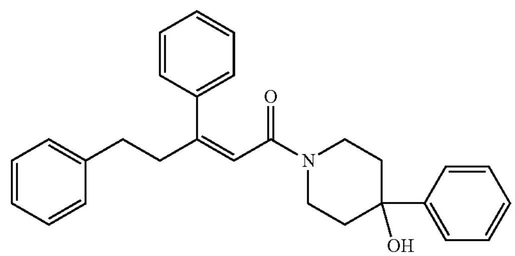 [SMILES: O=C(/C=C(/CCc1ccccc1)c1ccccc1)N1CCC(O)(c2ccccc2)CC1] |
| 858 | 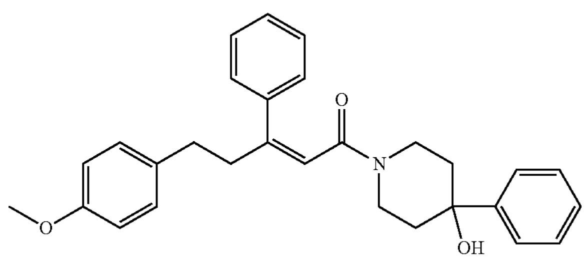 [SMILES: COc1ccc(CC/C(=C/C(=O)N2CCC(O)(c3ccccc3)CC2)c2ccccc2)cc1] |
| 860 | 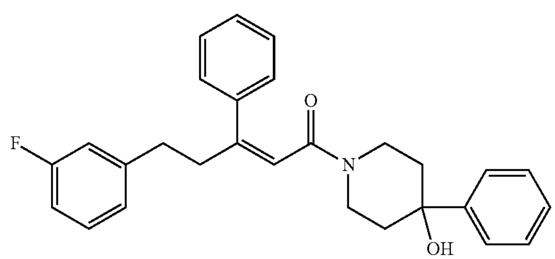 [SMILES: O=C(/C=C(/CCc1cccc(F)c1)c1ccccc1)N1CCC(O)(c2ccccc2)CC1] |
| 868 | 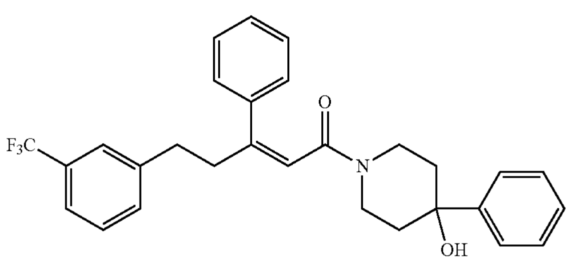 [SMILES: O=C(/C=C(/CCc1cccc(C(F)(F)F)c1)c1ccccc1)N1CCC(O)(c2ccccc2)CC1] |

TABLE 7-continued

Structure of compound V248 and its analogues.

| ID | Structure |
|---|---|
| 869 | 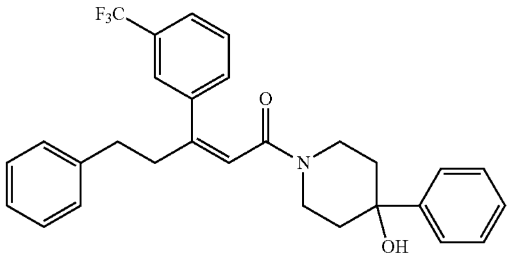 [SMILES: O=C(/C=C(/CCc1ccccc1)c1cccc(C(F)(F)F)c1)N1CCC(O)(c2ccccc2)CC1] |
| 870 | 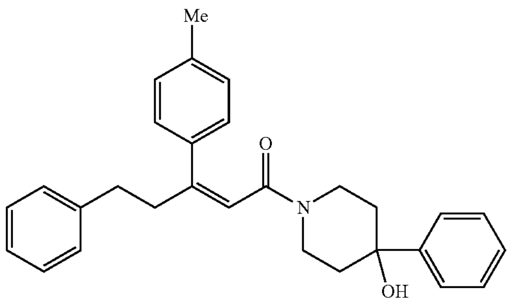 [SMILES: Cc1ccc(/C(=C\C(=O)N2CCC(O)(c3ccccc3)CC2)CCc2ccccc2)cc1] |
| 871 | 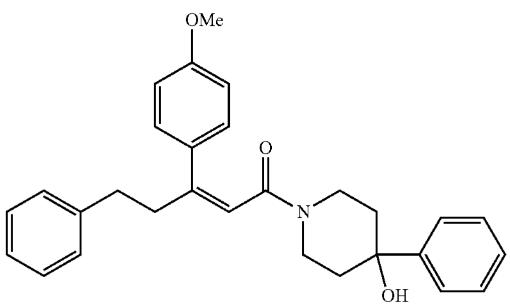 [SMILES: COc1ccc(/C(=C\C(=O)N2CCC(O)(c3ccccc3)CC2)CCc2ccccc2)cc1] |
| 872 | 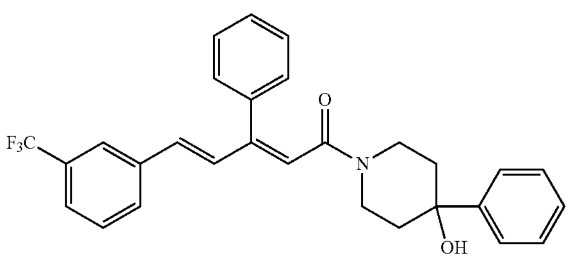 [SMILES: O=C(/C=C(/C=C/c1cccc(C(F)(F)F)c1)c1ccccc1)N1CCC(O)(c2ccccc2)CC1] |
| 880 | 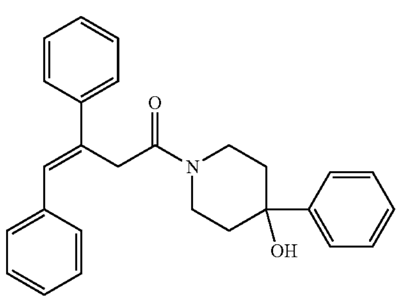 [SMILES: O=C(C/C(=C\c1ccccc1)c1ccccc1)N1CCC(O)(c2ccccc2)CC1] |

TABLE 7-continued

Structure of compound V248 and its analogues.

| ID | Structure |
|---|---|
| 881 | 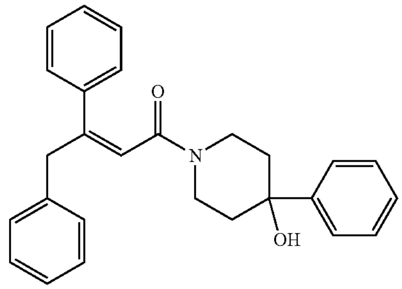 [SMILES: O=C(/C=C(/Cc1ccccc1)c1ccccc1)N1CCC(O)(c2ccccc2)CC1] |
| 882 | 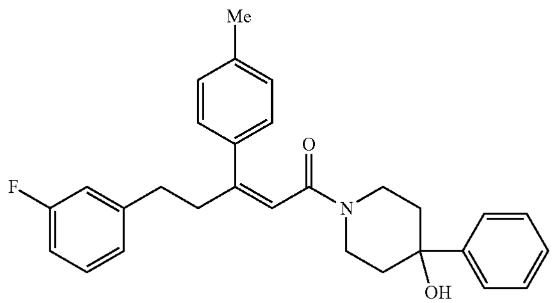 [SMILES: Cc1ccc(/C(=C\C(=O)N2CCC(O)(c3ccccc3)CC2)CCc2cccc(F)c2)cc1] |
| 883 | 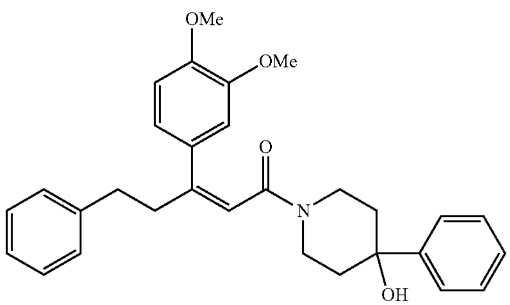 [SMILES: COc1ccc(/C(=C\C(=O)N2CCC(O)(c3ccccc3)CC2)CCc2ccccc2)cc1OC] |
| 889 | 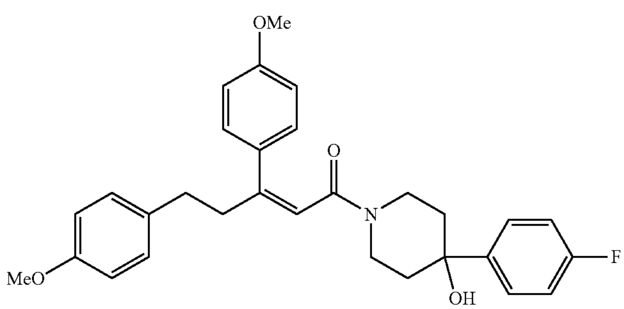 [SMILES: COc1ccc(CC/C(=C/C(=O)N2CCC(O)(c3ccc(F)cc3)CC2)c2ccc(OC)cc2)cc1] |
| 895 | 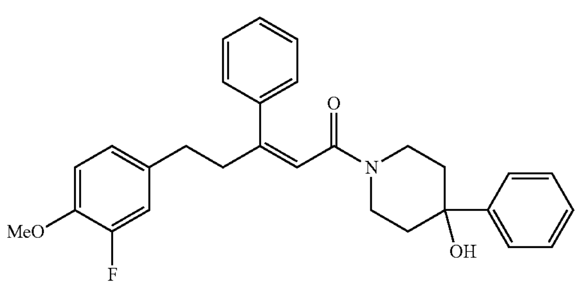 [SMILES: COc1ccc(CC/C(=C/C(=O)N2CCC(O)(c3ccccc3)CC2)c2ccccc2)cc1F] |

TABLE 7-continued

Structure of compound V248 and its analogues.

| ID | Structure |
|---|---|
| 1200 | 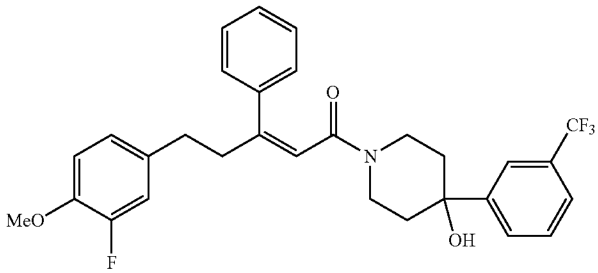 [SMILES: COc1ccc(CC/C(=C/C(=O)N2CCC(O)(c3cccc(C(F)(F)F)c3)CC2)c2ccccc2)cc1F] |
| 1201 | 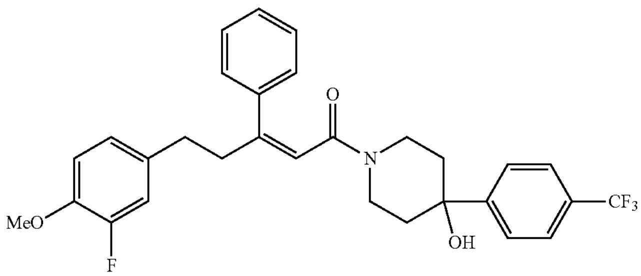 [SMILES: COc1ccc(CC/C(=C/C(=O)N2CCC(O)(c3ccc(C(F)(F)F)cc3)CC2)c2ccccc2)cc1F] |
| 1225 | 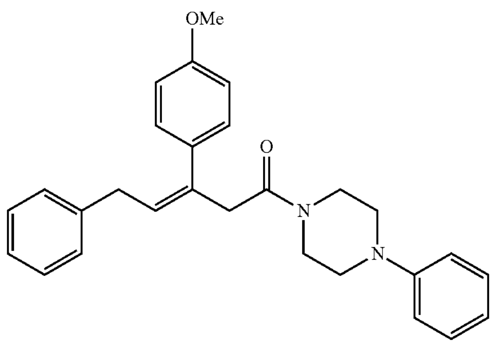 [SMILES: COc1ccc(/C(=C\Cc2ccccc2)CC(=O)N2CCN(c3ccccc3)CC2)cc1] |
| 1235 | 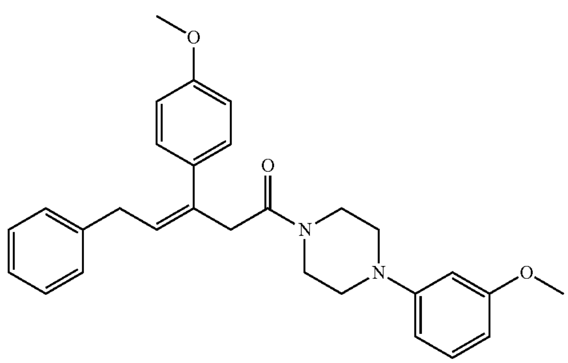 [SMILES: COc1ccc(/C(=C\Cc2ccccc2)CC(=O)N2CCN(c3cccc(OC)c3)CC2)cc1] |
| 1236 | 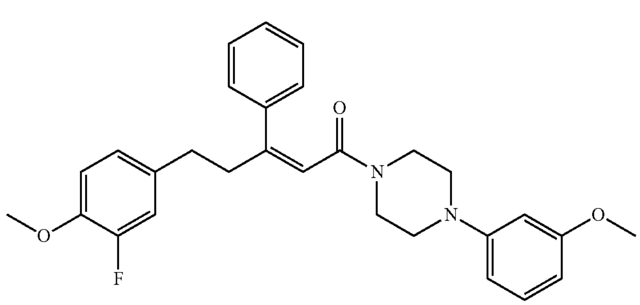 |

TABLE 7-continued
Structure of compound V248 and its analogues.
| ID | Structure |
|---|---|
| 1237 | 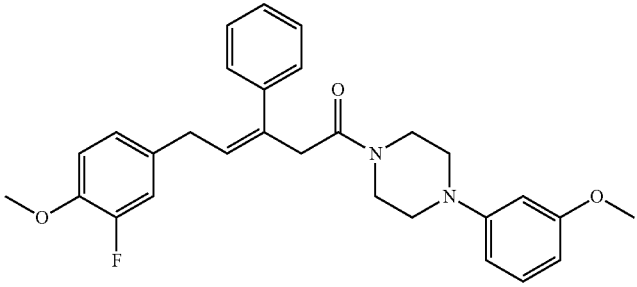 |
| 1238 | 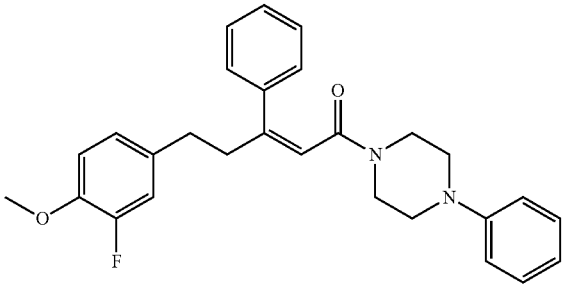 |
| 1239 | 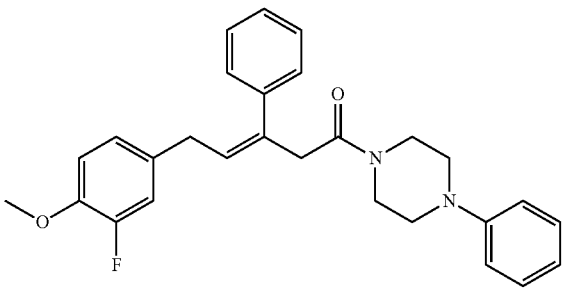 |
| 1240 | 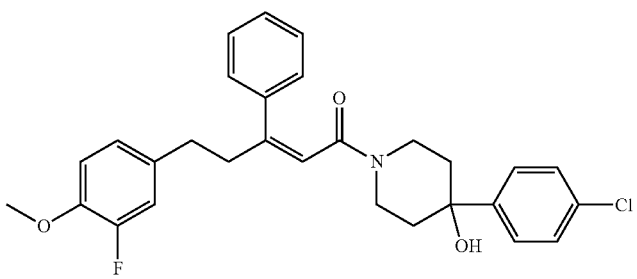 [SMILES: COc1ccc(CC/C(=C/C(=O)N2CCC(O)(c3ccc(Cl)cc3)CC2)c2ccccc2)cc1F] |
| 1241 | 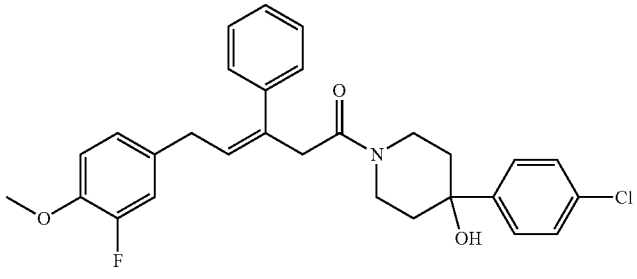 [SMILES: COc1ccc(C/C=C(/CC(=O)N2CCC(O)(c3ccc(Cl)cc3)CC2)c2ccccc2)cc1F] |

TABLE 7-continued

Structure of compound V248 and its analogues.

| ID | Structure |
|---|---|
| 1244 | 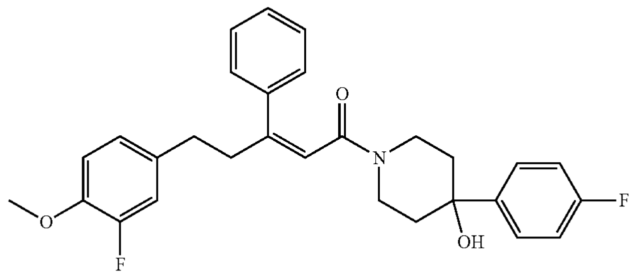 [SMILES: COc1ccc(CC/C(=C/C(=O)N2CCC(O)(c3ccc(F)cc3)CC2)c2ccccc2)cc1F] |
| 1245 | 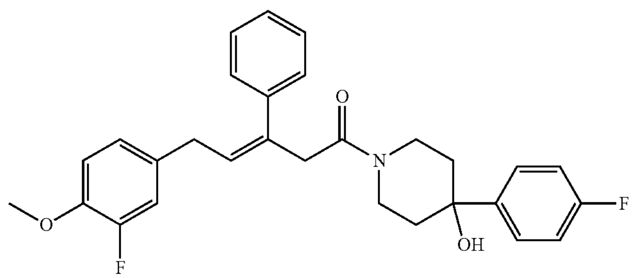 [SMILES: COc1ccc(C/C=C(/CC(=O)N2CCC(O)(c3ccc(F)cc3)CC2)c2ccccc2)cc1F] |
| 1246 | 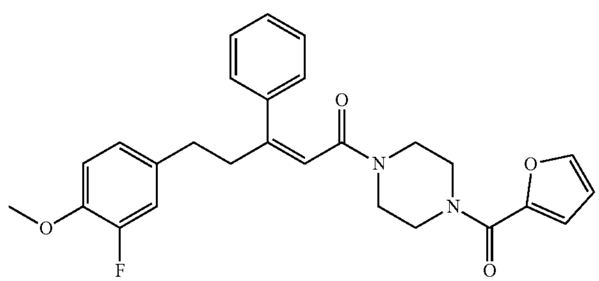 [SMILES: COc1ccc(CC/C(=C/C(=O)N2CCN(C(=O)c3ccco3)CC2)c2ccccc2)cc1F] |
| 1247 | 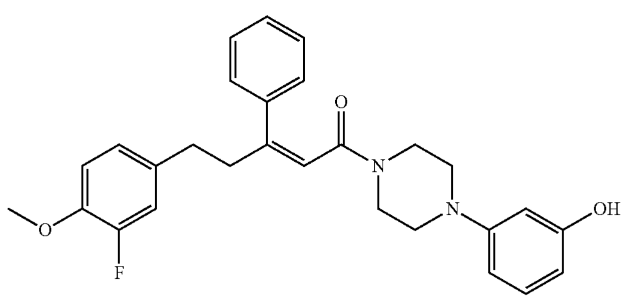 [SMILES: COc1ccc(CC/C(=C/C(=O)N2CCN(c3cccc(O)c3)CC2)c2ccccc2)cc1F] |
| 1248 | 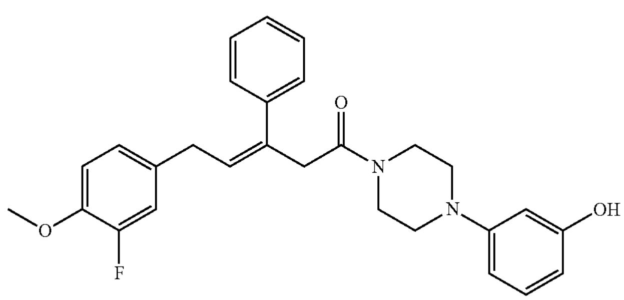 [SMILES: COc1ccc(C/C=C(/CC(=O)N2CCN(c3cccc(O)c3)CC2)c2ccccc2)cc1F] |

TABLE 7-continued

Structure of compound V248 and its analogues.

| ID | Structure |
|---|---|
| 1249 | 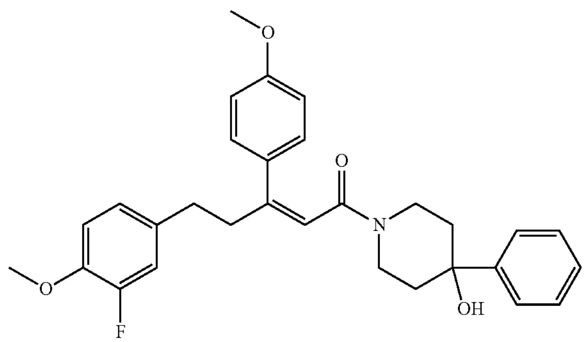 [SMILES: COc1ccc(/C(=C\C(=O)N2CCC(O)(c3ccccc3)CC2)CCc2ccc(OC)c(F)c2)cc1] |
| 1250 | 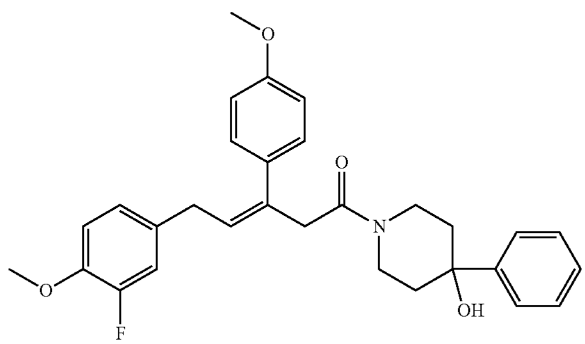 [SMILES: COc1ccc(/C(=C\Cc2ccc(OC)c(F)c2)CC(=O)N2CCC(O)(c3ccccc3)CC2)cc1] |
| 1257 | 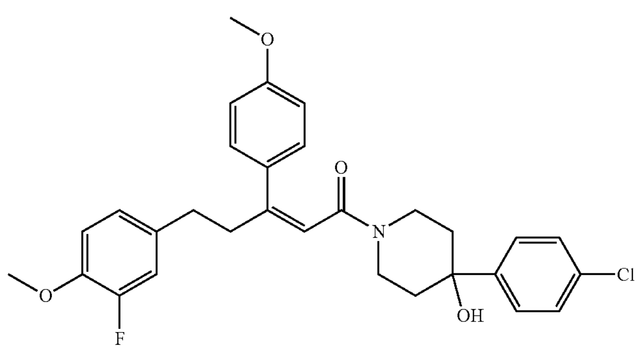 [SMILES: COc1ccc(/C(=C\C(=O)N2CCC(O)(c3ccc(Cl)cc3)CC2)CCc2ccc(OC)c(F)c2)cc1] |
| 1258 | 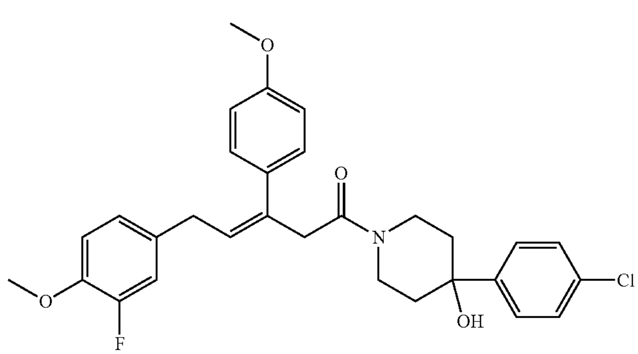 [SMILES: COc1ccc(/C(=C\Cc2ccc(OC)c(F)c2)CC(=O)N2CCC(O)(c3ccc(Cl)cc3)CC2)cc1] |

TABLE 7-continued

Structure of compound V248 and its analogues.

| ID | Structure |
|---|---|
| 1259 | 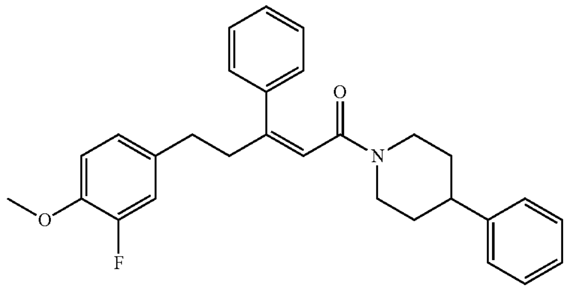 [SMILES: COc1ccc(CC/C(=C/C(=O)N2CCC(c3ccccc3)CC2)c2ccccc2)cc1F] |
| 1260 | 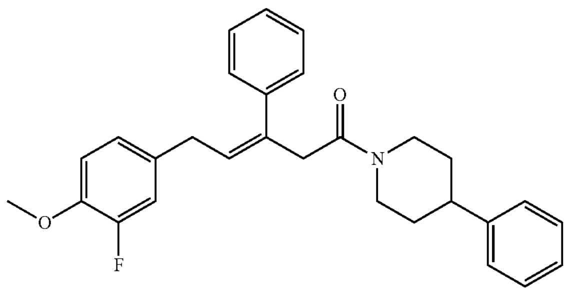 [SMILES: COc1ccc(C/C=C(/CC(=O)N2CCC(c3ccccc3)CC2)c2ccccc2)cc1F] |
| 1261 | 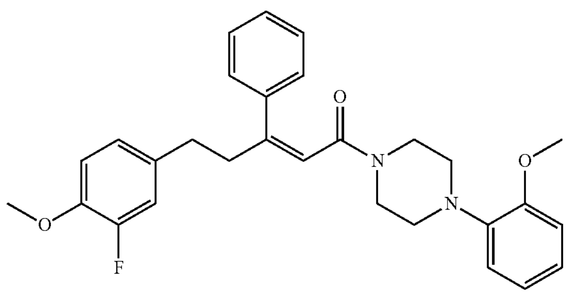 |
| 1262 | 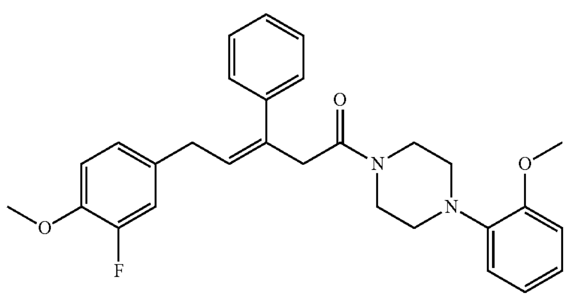 |
| 1273 | 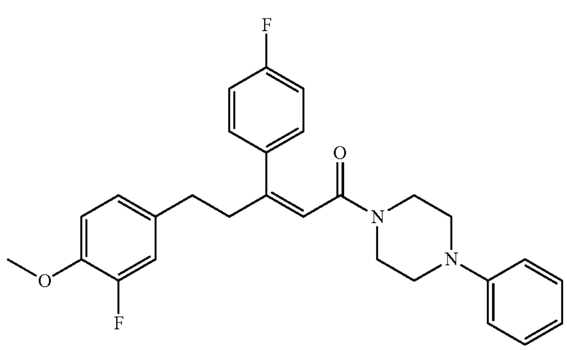 [SMILES: COc1ccc(CC/C(=C/C(=O)N2CCN(c3ccccc3)CC2)c2ccc(F)cc2)cc1F] |

TABLE 7-continued

Structure of compound V248 and its analogues.

| ID | Structure |
|---|---|
| 1274 | 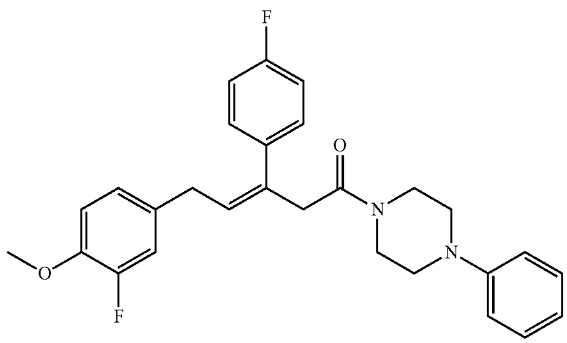 [SMILES: COc1ccc(C/C=C(/CC(=O)N2CCN(c3ccccc3)CC2)c2ccc(F)cc2)cc1F] |
| 1275 | 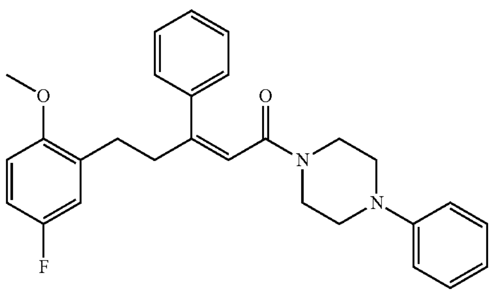 [SMILES: COc1ccc(F)cc1CC/C(=C/C(=O)N1CCN(c2ccccc2)CC1)c1ccccc1] |
| 1276 | 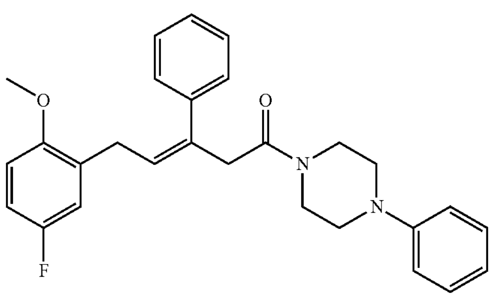 [SMILES: COc1ccc(F)cc1C/C=C(/CC(=O)N1CCN(c2ccccc2)CC1)c1ccccc1] |
| 1298 | 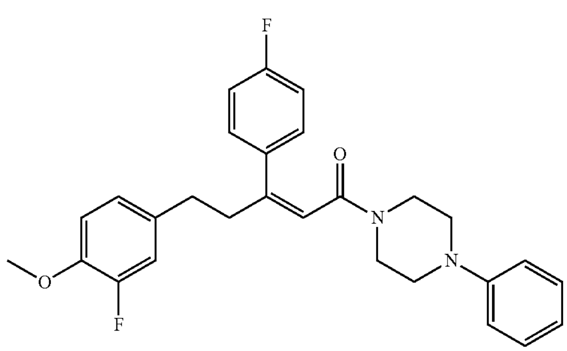 [SMILES: COc1ccc(CC/C(=C/C(=O)N2CCN(c3ccccc3)CC2)c2ccc(F)cc2)cc1F] |

TABLE 7-continued

Structure of compound V248 and its analogues.

| ID | Structure |
|---|---|
| 1299 | 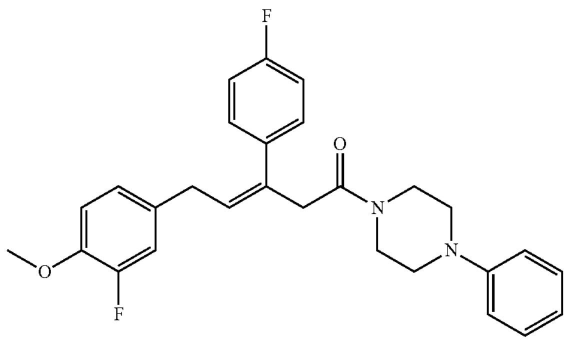 [SMILES: COc1ccc(C/C=C(/CC(=O)N2CCN(c3ccccc3)CC2)c2ccc(F)cc2)cc1F] |
| 1300 | 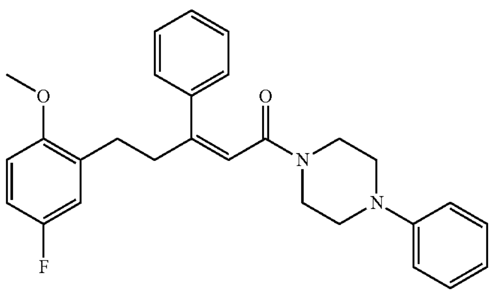 [SMILES: COc1ccc(F)cc1CC/C(=C/C(=O)N1CCN(c2ccccc2)CC1)c1ccccc1] |
| 1301 | 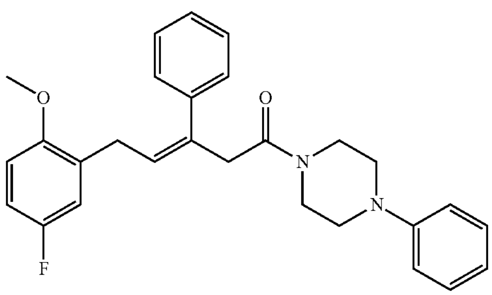 [SMILES: COc1ccc(F)cc1C/C=C(/CC(=O)N1CCN(c2ccccc2)CC1)c1ccccc1] |
| 1302 | 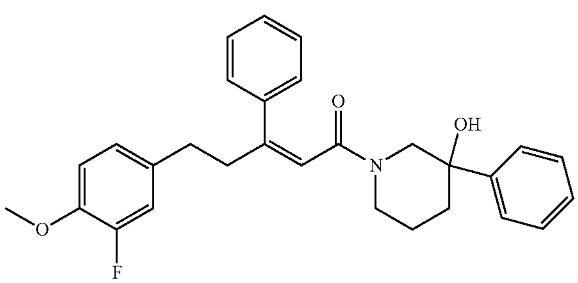 [SMILES: COc1ccc(CC/C(=C/C(=O)N2CCCC(O)(c3ccccc3)C2)c2ccccc2)cc1F] |
| 1303 | 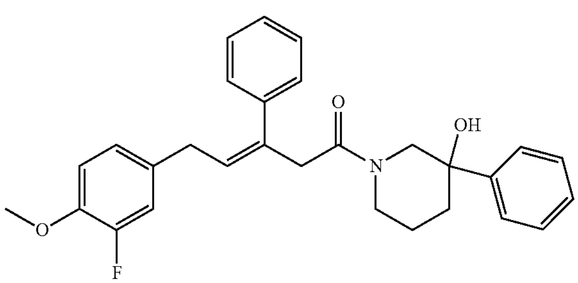 [SMILES: COc1ccc(C/C=C(/CC(=O)N2CCCC(O)(c3ccccc3)C2)c2ccccc2)cc1F] |

125 126
TABLE 7-continued
Structure of compound V248 and its analogues.
| ID | Structure |
|---|---|
| 1306 | 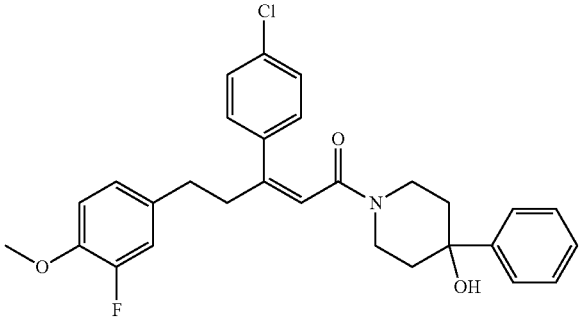 [SMILES: COc1ccc(CC/C(=C/C(=O)N2CCC(O)(c3ccccc3)CC2)c2ccc(Cl)cc2)cc1F] |
| 1307 | 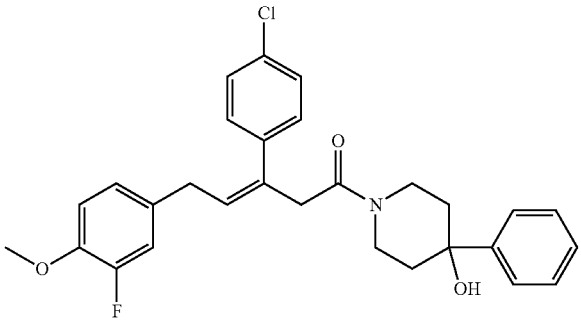 [SMILES: COc1ccc(C/C=C(/CC(=O)N2CCC(O)(c3ccccc3)CC2)c2ccc(Cl)cc2)cc1F] |
| 1308 | 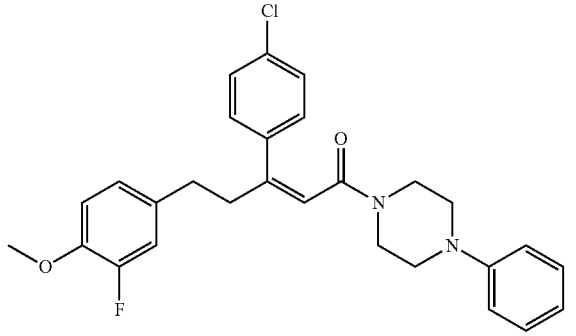 |
| 1309 | 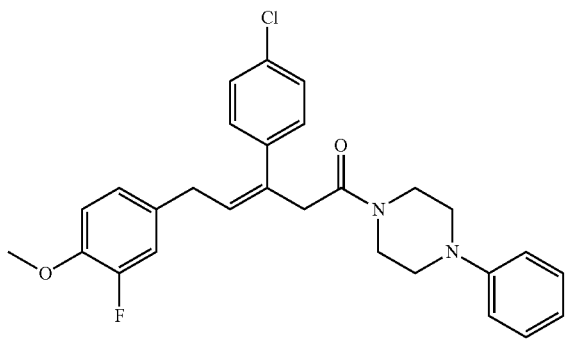 |

TABLE 7-continued

Structure of compound V248 and its analogues.

| ID | Structure |
|---|---|
| 1310 | 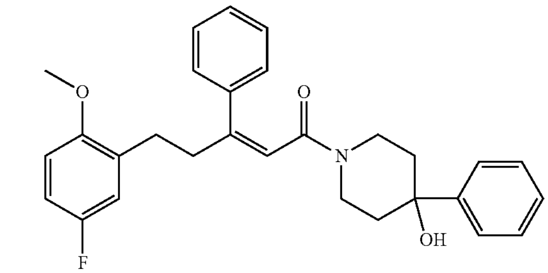 [SMILES: COc1ccc(F)cc1CC/C(=C/C(=O)N1CCC(O)(c2ccccc2)CC1)c1ccccc1] |
| 1303 | 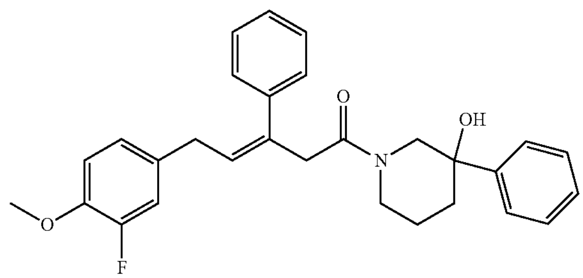 [SMILES: COc1ccc(C/C=C(/CC(=O)N2CCCC(O)(c3ccccc3)C2)c2ccccc2)cc1F] |
| 1306 | 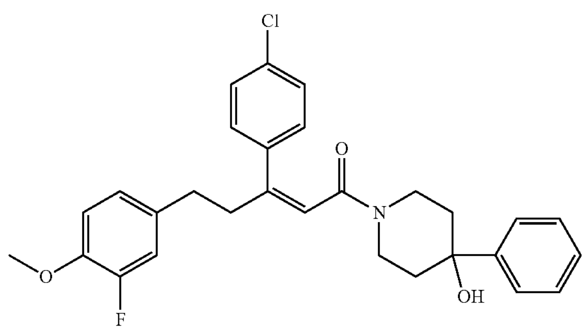 [SMILES: COc1ccc(CC/C(=C/C(=O)N2CCC(O)(c3ccccc3)CC2)c2ccc(Cl)cc2)cc1F] |
| 1307 | 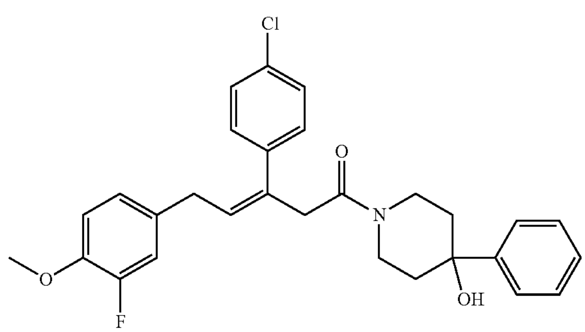 [SMILES: COc1ccc(C/C=C(/CC(=O)N2CCC(O)(c3ccccc3)CC2)c2ccc(Cl)cc2)cc1F] |
| 1308 | 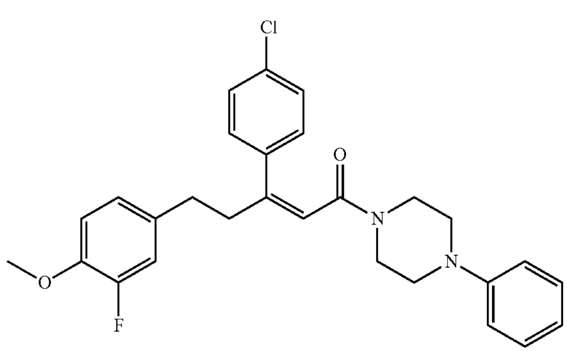 |

TABLE 7-continued

Structure of compound V248 and its analogues.

| ID | Structure |
|---|---|
| 1309 | 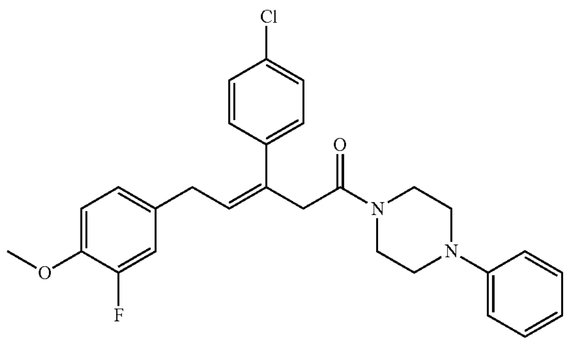 |
| 1310 | 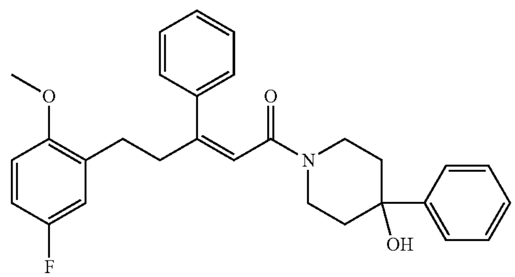 [SMILES: COc1ccc(F)cc1CC/C(=C/C(=O)N1CCC(O)(c2ccccc2)CC1)c1ccccc1] |
| 1311 | 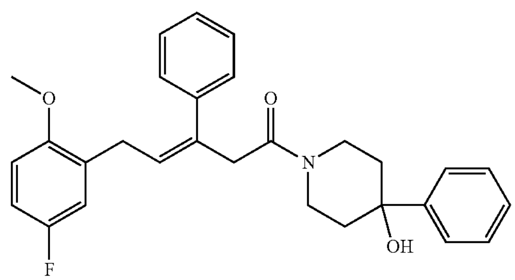 [SMILES: COc1ccc(F)cc1C/C=C(/CC(=O)N1CCC(O)(c2ccccc2)CC1)c1ccccc1] |
| 1320 | 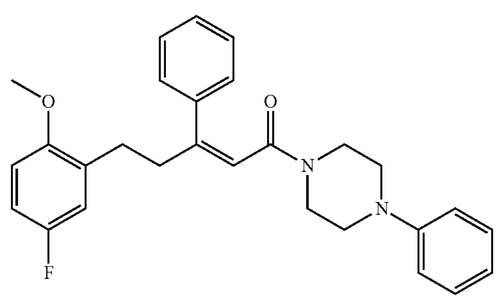 [SMILES: COc1ccc(F)cc1CC/C(=C/C(=O)N1CCN(c2ccccc2)CC1)c1ccccc1] |
| 1321 | 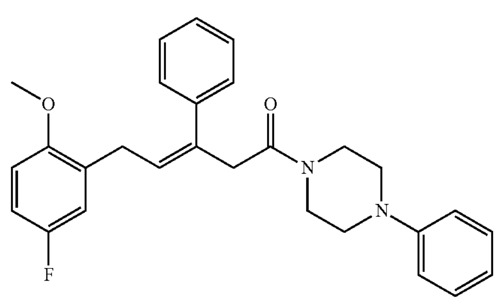 [SMILES: COc1ccc(F)cc1C/C=C(/CC(=O)N1CCN(c2ccccc2)CC1)c1ccccc1] |

TABLE 7-continued

Structure of compound V248 and its analogues.

| ID | Structure |
|---|---|
| 1322 | 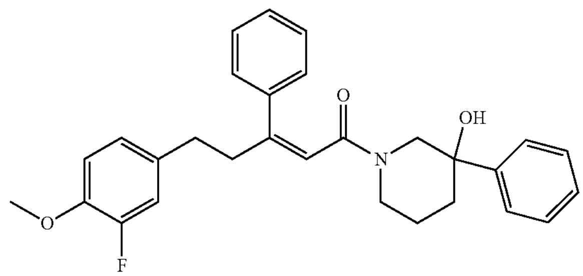 [SMILES: COc1ccc(CC/C(=C/C(=O)N2CCCC(O)(c3ccccc3)C2)c2ccccc2)cc1F] |
| 1323 | 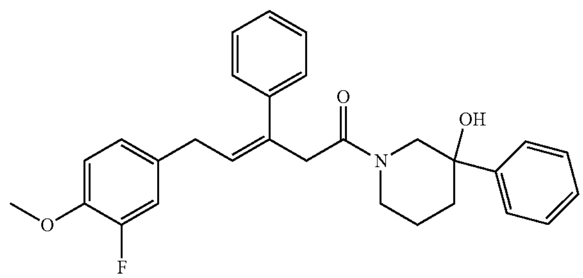 [SMILES: COc1ccc(C/C=C(/CC(=O)N2CCCC(O)(c3ccccc3)C2)c2ccccc2)cc1F] |
| 1345 | 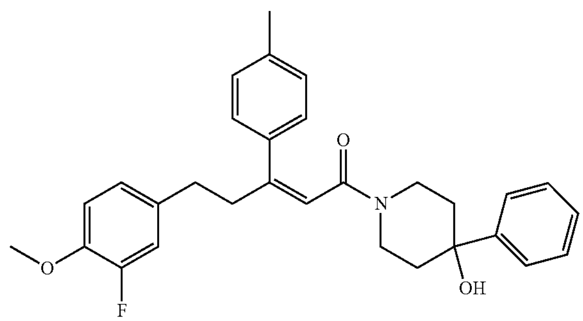 [SMILES: COc1ccc(CC/C(=C/C(=O)N2CCC(O)(c3ccccc3)CC2)c2ccc(C)cc2)cc1F] |
| 1348 | 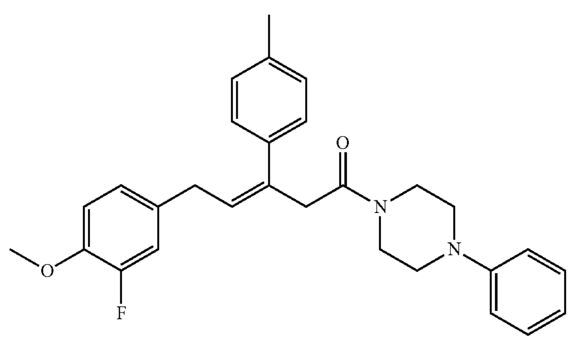 [SMILES: COc1ccc(C/C=C(/CC(=O)N2CCN(c3ccccc3)CC2)c2ccc(C)cc2)cc1F] |
| 1406 | 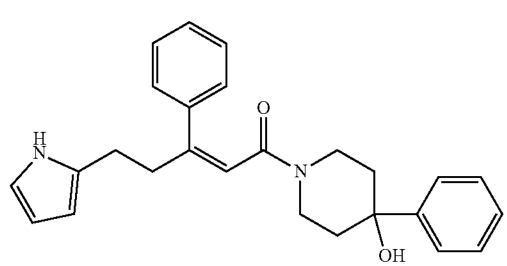 [SMILES: O=C(/C=C(/CCc1ccc[nH]1)c1ccccc1)N1CCC(O)(c2ccccc2)CC1] |

TABLE 7-continued

Structure of compound V248 and its analogues.

| ID | Structure |
|---|---|
| 1407 | 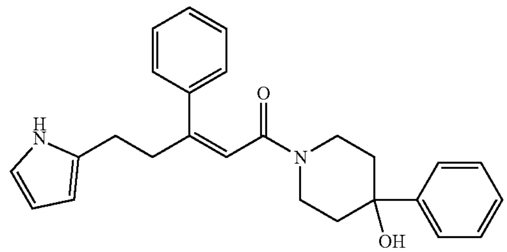 [SMILES: O=C(/C=C(/CCc1ccc[nH]1)c1ccccc1)N1CCC(O)(c2ccccc2)CC1] |

Characterization of Compound V248 and its Analogues

V248: Light yellow solid. $^1$H NMR (500 MHz, CDCl$_3$) δ 7.54-7.45 (m, 2H), 7.44-7.33 (m, 5H), 7.31-7.20 (m, 5H), 7.13 (q, J=7.4 Hz, 3H), 6.44 (s, 1H), 6.14 (s, 1H), 4.47 (t, J=14.5 Hz, 1H), 3.68 (dd, J=29.3, 13.6 Hz, 1H), 3.56-3.31 (m, 1H), 3.06 (t, J=15.3 Hz, 1H), 3.01-2.91 (m, 1H), 2.86-2.76 (m, 1H), 2.70-2.67 (m, 1H), 2.41-2.04 (m, 3H), 2.03-1.86 (m, 1H), 1.83-1.69 (m, 1H), 1.62-1.58 (m, 1H), 1.30-1.21 (m, 1H).

858: Light yellow solid, 71.2% in yield. $^1$H NMR (500 MHz, CDCl$_3$) δ 7.47-7.42 (m, 4H), 7.41-7.32 (m, 5H), 7.29 (dt, J=3.9, 1.6 Hz, 1H), 7.08 (d, J=8.6 Hz, 2H), 6.79 (d, J=8.6 Hz, 2H), 6.22 (s, 1H), 5.30 (s, 1H), 4.62 (d, J=13.1 Hz, 1H), 3.83-3.75 (m, 1H), 3.75 (s, 3H), 3.46 (td, J=12.9, 2.7 Hz, 1H), 3.18 (td, J=12.7, 2.7 Hz, 1H), 3.13-3.01 (m, 2H), 2.66 (t, J=8.1 Hz, 2H), 2.04 (s, 1H), 1.93-1.80 (m, 2H), 1.78-1.72 (m, 2H). TOF MS (ESI), m/z: 442.24 [M+H]$^+$.

859: light yellow solid, 57.5% in yield. $^1$H NMR (500 MHz, CDCl$_3$) δ 7.47-7.42 (m, 4H), 7.42-7.33 (m, 5H), 7.31-7.21 (m, 3H), 7.19-7.12 (m, 3H), 6.22 (s, 1H), 4.60 (ddd, J=29.7, 16.0, 13.7 Hz, 1H), 3.75 (ddd, J=31.7, 17.0, 6.7 Hz, 1H), 3.56-3.37 (m, 1H), 3.17 (td, J=13.0, 3.0 Hz, 1H), 3.10 (q, J=7.9 Hz, 2H), 2.72 (t, J=8.0 Hz, 2H), 2.10-2.00 (m, 1H), 1.93-1.71 (m, 3H), 1.67 (s, 1H). TOF MS (ESI), m/z: 412.23 [M+H]$^+$.

860: Light yellow syrup, 50.0% in yield. $^1$H NMR (500 MHz, CDCl$_3$) δ 7.49-7.33 (m, 9H), 7.32-7.27 (m, 1H), 7.19 (td, J=7.9, 6.1 Hz, 1H), 6.93 (d, J=7.6 Hz, 1H), 6.89-6.81 (m, 2H), 6.23 (s, 1H), 4.72-4.56 (m, 1H), 3.82-3.73 (m, 1H), 3.48 (td, J=13.1, 2.9 Hz, 1H), 3.18 (td, J=12.9, 3.0 Hz, 1H), 3.14-3.03 (m, 2H), 2.72 (t, J=8.0 Hz, 2H), 2.06 (td, J=13.3, 4.8 Hz, 1H), 1.93-1.72 (m, 3H), 1.64 (s, 1H). TOF MS (ESI), m/z: 430.22 [M+H]$^+$.

868: Colorless syrup, 67.5% in yield. $^1$H NMR (500 MHz, CDCl$_3$) δ 7.47-7.31 (m, 13H), 7.31-7.26 (m, 1H), 6.23 (s, 1H), 4.60 (d, J=11.0 Hz, 1H), 3.74 (d, J=13.4 Hz, 1H), 3.45 (t, J=11.4 Hz, 1H), 3.23-3.04 (m, 3H), 2.79 (t, J=7.5 Hz, 2H), 2.04 (td, J=13.3, 4.8 Hz, 1H), 1.91-1.79 (m, 2H), 1.79-1.71 (m, 2H).

869: Light yellow syrup, 52.3% in yield. $^1$H NMR (500 MHz, CDCl$_3$) δ 7.64 (s, 1H), 7.60 (d, J=8.0 Hz, 2H), 7.51 (t, J=7.8 Hz, 1H), 7.47-7.42 (m, 2H), 7.37 (t, J=7.6 Hz, 2H), 7.29 (t, J=7.3 Hz, 1H), 7.24 (t, J=7.4 Hz, 2H), 7.18-7.10 (m, 3H), 6.24 (s, 1H), 4.62 (d, J=13.2 Hz, 1H), 3.74 (d, J=15.5 Hz, 1H), 3.48 (td, J=13.0, 2.9 Hz, 1H), 3.19 (td, J=12.9, 3.0 Hz, 1H), 3.16-3.03 (m, 2H), 2.71 (t, J=8.0 Hz, 2H), 2.11-2.00 (m, 1H), 1.94-1.73 (m, 3H), 1.62 (s, 1H).

870: Light yellow syrup, 49.1% in yield. $^1$H NMR (500 MHz, CDCl$_3$) δ 7.47-7.42 (m, 2H), 7.39-7.33 (m, 4H), 7.29 (t, J=7.3 Hz, 1H), 7.24 (d, J=7.4 Hz, 2H), 7.20 (d, J=7.9 Hz, 2H), 7.19-7.12 (m, 3H), 6.20 (s, 1H), 4.61 (d, J=15.2 Hz, 1H), 3.77 (d, J=13.3 Hz, 1H), 3.44 (td, J=13.0, 2.8 Hz, 1H), 3.16 (td, J=12.8, 2.7 Hz, 1H), 3.12-3.02 (m, 2H), 2.72 (t, J=8.1 Hz, 2H), 2.39 (s, 3H), 2.12-1.99 (m, 1H), 1.94-1.70 (m, 3H), 1.58 (s, 1H).

871: White solid, 64.5% in yield. $^1$H NMR (500 MHz, CDCl$_3$) δ 7.44 (d, J=7.2 Hz, 2H), 7.42-7.34 (m, 4H), 7.31-7.26 (m, 1H), 7.24 (d, J=7.4 Hz, 2H), 7.19-7.13 (m, 3H), 6.93 (d, J=8.8 Hz, 2H), 6.18 (s, 1H), 4.61 (d, J=13.2 Hz, 1H), 3.84 (s, 3H), 3.78 (d, J=13.3 Hz, 1H), 3.45 (td, J=13.0, 2.3 Hz, 1H), 3.16 (td, J=12.9, 2.7 Hz, 1H), 3.11-3.04 (m, 2H), 2.72 (t, J=8.0 Hz, 2H), 2.09-2.01 (m, 1H), 1.93-1.69 (m, 3H), 1.63 (s, 1H).

872: Light yellow solid, 59.0% in yield. $^1$H NMR (500 MHz, CDCl$_3$) δ 7.84 (d, J=16.2 Hz, 1H), 7.66 (d, J=7.8 Hz, 1H), 7.59 (s, 1H), 7.50 (d, J=7.8 Hz, 1H), 7.46-7.37 (m, 8H), 7.34 (t, J=7.5 Hz, 2H), 7.30-7.26 (m, 1H), 6.55 (d, J=16.3 Hz, 1H), 6.16 (s, 1H), 4.71 (d, J=13.2 Hz, 1H), 3.95 (d, J=13.5 Hz, 1H), 3.65 (td, J=13.1, 2.7 Hz, 1H), 3.27 (td, J=12.9, 2.9 Hz, 1H), 2.12 (td, J=13.3, 4.8 Hz, 1H), 1.99 (td, J=13.2, 4.7 Hz, 1H), 1.88 (dd, J=14.0, 2.5 Hz, 1H), 1.82 (dd, J=13.7, 2.4 Hz, 1H), 1.64 (s, 1H).

880: Colorless syrup, 30.0% in yield. $^1$H NMR (500 MHz, CDCl$_3$) δ 7.54 (dt, J=8.3, 1.8 Hz, 2H), 7.42-7.34 (m, 10H), 7.33-7.27 (m, 3H), 6.99 (s, 1H), 4.51 (d, J=13.2 Hz, 1H), 3.78 (q, J=16.0 Hz, 2H), 3.65 (d, J=13.5 Hz, 1H), 3.46 (td, J=13.2, 2.8 Hz, 1H), 3.04 (td, J=13.0, 2.7 Hz, 1H), 1.93-1.82 (m, 1H), 1.78 (td, J=13.1, 4.6 Hz, 1H), 1.73-1.66 (m, 2H), 1.52 (s, 1H).

881: Colorless syrup, 33.7% in yield. $^1$H NMR (500 MHz, CDCl$_3$) δ 7.46-7.38 (m, 7H), 7.36-7.29 (m, 3H), 7.27-7.19 (m, 4H), 7.13 (t, J=7.2 Hz, 1H), 6.47 (s, 1H), 4.70-4.61 (m, 1H), 4.23 (d, J=15.0 Hz, 1H), 4.13 (d, J=15.0 Hz, 1H), 3.98-3.87 (m, 1H), 3.58 (td, J=12.9, 3.3 Hz, 1H), 3.25-3.13 (m, 2H), 2.03 (td, J=13.3, 4.9 Hz, 1H), 1.88-1.74 (m, 3H), 1.62 (s, 1H).

882: Colorless syrup, 57.8% in yield. $^1$H NMR (500 MHz, CDCl$_3$) δ 7.48-7.42 (m, 2H), 7.40-7.26 (m, 5H), 7.23-7.16 (m, 3H), 6.94 (d, J=7.7 Hz, 1H), 6.89-6.78 (m, 2H), 6.21 (s, 1H), 4.61 (d, J=13.1 Hz, 1H), 3.77 (d, J=11.3 Hz, 1H), 3.47 (td, J=13.0, 2.8 Hz, 1H), 3.17 (td, J=13.0, 2.9 Hz, 1H), 3.12-3.02 (m, 2H), 2.72 (t, J=8.0 Hz, 2H), 2.38 (s, 3H), 2.05 (td, J=13.3, 4.8 Hz, 1H), 1.92-1.71 (m, 3H), 1.66 (s, 1H).

883: Light yellow syrup, 57.5% in yield. $^1$H NMR (500 MHz, CDCl$_3$) δ 7.47-7.42 (m, 2H), 7.36 (t, J=7.7 Hz, 2H), 7.31-7.22 (m, 3H), 7.19-7.11 (m, 3H), 7.02 (dd, J=8.3, 2.1 Hz, 1H), 6.94 (d, J=2.1 Hz, 1H), 6.88 (d, J=8.4 Hz, 1H), 6.18 (s, 1H), 4.62 (d, J=13.0 Hz, 1H), 3.91 (s, 3H), 3.90 (s, 3H), 3.83-3.76 (m, 1H), 3.54-3.42 (m, 1H), 3.18 (td, J=12.9, 2.7

Hz, 1H), 3.10-2.98 (m, 2H), 2.74 (t, J=8.1 Hz, 2H), 2.06 (td, J=13.5, 4.6 Hz, 1H), 1.90-1.68 (m, 3H), 1.63 (s, 1H).

884: Light yellow syrup, 60.0% in yield. $^1$H NMR (500 MHz, CDCl$_3$) δ 7.51-7.44 (m, 2H), 7.43-7.35 (m, 3H), 7.34-7.29 (m, 1H), 7.26-7.21 (m, 1H), 7.19-7.12 (m, 1H), 7.12-7.04 (m, 3H), 6.85-6.79 (m, 2H), 6.24 (s, 1H), 4.63 (d, J=12.3 Hz, 1H), 3.82-3.71 (m, 4H), 3.48 (t, J=12.0 Hz, 1H), 3.20 (td, J=12.7, 0.9 Hz, 1H), 3.13-2.99 (m, 2H), 2.68 (t, J=7.6 Hz, 2H), 2.07 (td, J=12.9, 4.3 Hz, 1H), 1.96-1.75 (m, 3H), 1.71 (s, 1H).

888: Colorless syrup, 63.2% in yield. $^1$H NMR (500 MHz, CDCl$_3$) δ 7.43-7.37 (m, 2H), 7.31 (t, J=7.9 Hz, 1H), 7.10-6.99 (m, 5H), 6.97-6.94 (m, 1H), 6.89 (dd, J=7.9, 2.2 Hz, 1H), 6.83-6.75 (m, 2H), 6.20 (s, 1H), 4.60 (d, J=13.5 Hz, 1H), 3.84 (s, 3H), 3.79-3.76 (m, 1H), 3.75 (s, 3H), 3.42 (td, J=13.2, 2.8 Hz, 1H), 3.14 (td, J=12.9, 2.8 Hz, 1H), 3.09-2.97 (m, 2H), 2.66 (t, J=8.0 Hz, 2H), 2.00 (td, J=13.4, 4.9 Hz, 1H), 1.89-1.76 (m, 2H), 1.76-1.68 (m, 1H), 1.66 (s, 1H).

889: Light yellow solid, 68.9% in yield. $^1$H NMR (500 MHz, CDCl$_3$) δ 7.43-7.36 (m, 4H), 7.09-7.01 (m, 4H), 6.94-6.89 (m, 2H), 6.81-6.77 (m, 2H), 6.15 (s, 1H), 4.60 (d, J=13.4 Hz, 1H), 3.84 (s, 3H), 3.79-3.77 (m, 1H), 3.75 (s, 3H), 3.42 (td, J=13.1, 2.6 Hz, 1H), 3.14 (td, J=12.7, 2.4 Hz, 1H), 3.09-3.00 (m, 2H), 2.66 (t, J=8.0 Hz, 2H), 2.00 (td, J=13.3, 4.7 Hz, 1H), 1.89-1.76 (m, 2H), 1.76-1.66 (m, 2H).

895: Light yellow syrup, 39.5% in yield. $^1$H NMR (500 MHz, CDCl$_3$) δ 7.49-7.32 (m, 6H), 7.31-7.26 (m, 1H), 7.12-6.99 (m, 2H), 6.95-6.87 (m, 2H), 6.82-6.75 (m, 2H), 6.17 (s, 1H), 4.61 (d, J=13.5 Hz, 1H), 3.84 (s, 3H), 3.78 (d, J=4.3 Hz, 1H), 3.49-3.42 (m, 1H), 3.16 (td, J=13.2, 2.8 Hz, 1H), 3.09-2.99 (m, 2H), 2.67 (t, J=6.5 Hz, 2H), 2.05 (td, J=13.1, 3.8 Hz, 1H), 1.91-1.72 (m, 3H), 1.60 (s, 1H). HRMS-ESI (m/z): [M+H]$^+$ calcd for C$_{29}$H$_{31}$FNO$_3$, 460.2283; found 460.2296.

1200: Colorless syrup, 80.0% in yield. $^1$H NMR (500 MHz, cdcl$_3$) δ 7.77 (s, 1H), 7.63 (d, J=7.9 Hz, 1H), 7.57 (d, J=7.8 Hz, 1H), 7.50 (t, J=7.8 Hz, 1H), 7.45-7.33 (m, 5H), 6.90 (d, J=12.6 Hz, 1H), 6.87-6.80 (m, 2H), 6.23 (s, 1H), 4.68 (d, J=13.4 Hz, 1H), 3.86-3.78 (m, 4H), 3.48 (t, J=12.2 Hz, 1H), 3.22-3.02 (m, 3H), 2.67 (td, J=7.9, 2.4 Hz, 2H), 2.08 (dt, J=13.3, 5.1 Hz, 1H), 1.95-1.80 (m, 2H), 1.77 (d, J=13.6 Hz, 1H), 1.72 (s, 1H).

1201: Colorless syrup, 78.6% in yield. $^1$H NMR (500 MHz, cdcl$_3$) δ 7.64 (d, J=8.4 Hz, 2H), 7.59 (d, J=8.4 Hz, 2H), 7.47-7.34 (m, 5H), 6.91 (d, J=12.7 Hz, 1H), 6.88-6.81 (m, 2H), 6.23 (s, 1H), 4.67 (d, J=13.4 Hz, 1H), 3.94-3.74 (m, 4H), 3.47 (t, J=12.6 Hz, 1H), 3.26-3.00 (m, 3H), 2.67 (t, J=7.9 Hz, 2H), 2.07 (td, J=13.2, 5.9 Hz, 1H), 1.93-1.78 (m, 2H), 1.75 (d, J=13.1 Hz, 1H), 1.66 (s, 1H).

1225: Colorless syrup, 27.5% in yield. $^1$H NMR (400 MHz, cdcl$_3$) δ 7.35-7.13 (m, 9H), 6.92-6.84 (m, 3H), 6.81 (dd, J=8.7, 1.0 Hz, 2H), 5.82 (s, 1H), 3.77 (s, 3H), 3.68-3.59 (m, 2H), 3.20-3.09 (m, 2H), 3.03-2.93 (m, 2H), 2.86-2.68 (m, 4H), 2.63-2.51 (m, 2H).

1235: Colorless syrup, 29.0% in yield. $^1$H NMR (400 MHz, cdcl$_3$) δ 7.36-7.10 (m, 8H), 6.92-6.81 (m, 2H), 6.49-6.39 (m, 2H), 6.34 (t, J=2.3 Hz, 1H), 5.82 (s, 1H), 3.78 (s, 3H), 3.77 (s, 3H), 3.67-3.57 (m, 2H), 3.18-3.09 (m, 2H), 3.02-2.92 (m, 2H), 2.83-2.75 (m, 2H), 2.75-2.68 (m, 2H), 2.61-2.52 (m, 2H).

1236: Colorless syrup, 52.5% in yield. $^1$H NMR (500 MHz, cdcl$_3$) δ 7.49-7.35 (m, 5H), 7.20 (t, J=8.4 Hz, 1H), 6.93-6.75 (m, 3H), 6.60-6.50 (m, 1H), 6.50-6.41 (m, 2H), 6.22 (s, 1H), 3.82 (s, 3H), 3.81 (s, 3H), 3.64-3.52 (m, 2H), 3.25-3.14 (m, 2H), 3.14-3.05 (m, 2H), 2.72-2.59 (m, 2H).

1237: Colorless syrup, 23.7% in yield. $^1$H NMR (500 MHz, cdcl$_3$) δ 7.39-7.28 (m, 5H), 7.15 (t, J=8.2 Hz, 1H), 6.94-6.80 (m, 3H), 6.47-6.38 (m, 2H), 6.33 (t, J=2.3 Hz, 1H), 5.90 (s, 1H), 3.88 (s, 3H), 3.78 (s, 3H), 3.65-3.58 (m, 2H), 3.24-3.16 (m, 2H), 2.99-2.91 (m, 2H), 2.83-2.76 (m, 2H), 2.71-2.64 (m, 2H), 2.55-2.46 (m, 2H).

1238: Colorless syrup, 55.5% in yield. $^1$H NMR (500 MHz, cdcl$_3$) δ 7.47-7.35 (m, 5H), 7.33-7.28 (m, 2H), 6.98-6.78 (m, 6H), 6.22 (s, 1H), 3.88-3.83 (m, 2H), 3.81 (s, 3H), 3.64-3.56 (m, 2H), 3.23-3.16 (m, 2H), 3.13-3.06 (m, 4H), 2.70-2.62 (m, 2H).

1239: Colorless syrup, 21.0% in yield. $^1$H NMR (500 MHz, cdcl$_3$) δ 7.41-7.21 (m, 7H), 6.96-6.76 (m, 6H), 5.90 (s, 1H), 3.88 (s, 3H), 3.67-3.58 (m, 2H), 3.26-3.17 (m, 2H), 2.99-2.91 (m, 2H), 2.85-2.75 (m, 2H), 2.72-2.64 (m, 2H), 2.57-2.47 (m, 2H).

1240: Colorless syrup, 50.5% in yield. $^1$H NMR (500 MHz, cdcl$_3$) δ 7.49-7.31 (m, 9H), 6.99-6.76 (m, 3H), 6.22 (s, 1H), 4.63 (s, 1H), 3.84 (s, 3H), 3.79 (s, 1H), 3.45 (s, 1H), 3.08 (d, J=6.7 Hz, 2H), 2.66 (t, J=7.9 Hz, 2H), 2.01 (s, 1H), 1.78 (s, 3H), 1.63 (s, 2H). HRMS-ESI (m/z): [M+H]$^+$ calcd for C$_{29}$H$_{30}$ClFNO$_3$, 494.1893; found 494.1909.

1241: Colorless syrup, 22.1% in yield. $^1$H NMR (500 MHz, cdcl$_3$) δ 7.40-7.32 (m, 5H), 7.31-7.27 (m, 2H), 7.16-7.12 (m, 2H), 6.95-6.78 (m, 3H), 5.92 (s, 1H), 4.54-4.45 (m, 1H), 3.86 (s, 3H), 3.63-3.54 (m, 1H), 3.10 (td, J=13.0, 2.8 Hz, 1H), 2.97-2.86 (m, 1H), 2.86-2.71 (m, 2H), 2.71-2.63 (m, 2H), 1.67-1.52 (m, 3H), 1.48 (s, 1H), 1.27 (s, 1H). HRMS-ESI (m/z): [M+H]$^+$ calcd for C$_{29}$H$_{30}$ClFNO$_3$, 494.1893; found 494.1965.

1244: Colorless syrup, 48.5% in yield. $^1$H NMR (500 MHz, cdcl$_3$) δ 7.49-7.31 (m, 7H), 7.10-7.01 (m, 2H), 6.95-6.79 (m, 3H), 6.22 (s, 1H), 4.63 (d, J=10.6 Hz, 1H), 3.83 (s, 3H), 3.78 (t, J=11.7 Hz, 1H), 3.45 (dd, J=25.9, 12.3 Hz, 1H), 3.25-2.99 (m, 3H), 2.66 (t, J=8.0 Hz, 2H), 1.92-1.72 (m, 3H), 1.63 (s, 2H).

1245: Colorless syrup, 21.5% in yield. $^1$H NMR (500 MHz, cdcl$_3$) δ 7.42-7.30 (m, 5H), 7.22-7.15 (m, 2H), 7.00 (t, J=8.7 Hz, 2H), 6.92-6.81 (m, 3H), 5.92 (s, 1H), 4.55-4.45 (m, 1H), 3.86 (s, 3H), 3.64-3.54 (m, 1H), 3.10 (td, J=13.0, 2.8 Hz, 1H), 2.98-2.87 (m, 1H), 2.85-2.72 (m, 2H), 2.68 (d, J=8.1 Hz, 2H), 1.67-1.59 (m, 2H), 1.40 (s, 1H), 1.33-1.25 (m, 3H).

1246: Colorless syrup, 55.8% in yield. $^1$H NMR (500 MHz, cdcl$_3$) δ 7.52 (s, 1H), 7.46-7.38 (m, 5H), 7.07 (dd, J=3.5, 0.8 Hz, 1H), 6.93-6.79 (m, 3H), 6.52 (dd, J=3.5, 1.8 Hz, 1H), 6.19 (s, 1H), 3.87-3.82 (m, 5H), 3.81-3.68 (m, 4H), 3.60-3.46 (m, 2H), 3.19-3.06 (m, 2H), 2.72-2.58 (m, 2H).

1247: Colorless syrup, 50.6% in yield. $^1$H NMR (500 MHz, cdcl$_3$) δ 7.44-7.37 (m, 5H), 7.14 (t, J=8.1 Hz, 1H), 6.92-6.79 (m, 3H), 6.51 (dd, J=8.3, 1.7 Hz, 1H), 6.44-6.36 (m, 2H), 6.21 (s, 1H), 3.82 (s, 5H), 3.58 (s, 2H), 3.23-3.14 (m, 2H), 3.14-3.03 (m, 4H), 2.71-2.61 (m, 2H).

1248: Colorless oil, 25.0% in yield. $^1$H NMR (500 MHz, cdcl$_3$) δ 7.39-7.28 (m, 5H), 7.10 (t, J=8.1 Hz, 1H), 6.93-6.79 (m, 3H), 6.39 (s, 2H), 5.90 (s, 1H), 3.88 (s, 4H), 3.64 (s, 2H), 3.23 (s, 2H), 2.95 (s, 2H), 2.86-2.74 (m, 2H), 2.71-2.61 (m, 3H), 2.57-2.43 (m, 2H).

1249: Colorless syrup, 45.8% in yield. $^1$H NMR (500 MHz, cdcl$_3$) δ 7.49-7.44 (m, 2H), 7.42-7.33 (m, 4H), 7.30 (d, J=7.3 Hz, 1H), 6.96-6.80 (m, 5H), 6.19 (s, 1H), 4.63 (d, J=13.2 Hz, 1H), 3.85 (s, 3H), 3.83 (s, 3H), 3.80-3.77 (m, 1H), 3.56-3.43 (m, 1H), 3.24-3.13 (m, 1H), 3.13-2.99 (m, 2H), 2.72-2.61 (m, 2H), 2.12-2.06 (m, 1H), 1.94-1.72 (m, 3H), 1.64 (s, 1H).

1250: Colorless syrup, 18.5% in yield. $^1$H NMR (500 MHz, cdcl$_3$) δ 7.37-7.27 (m, 5H), 7.23-7.19 (m, 2H), 6.94-6.82 (m, 5H), 5.87 (s, 1H), 4.59-4.48 (m, 1H), 3.86 (s, 3H), 3.81 (s, 3H), 3.64-3.57 (m, 1H), 3.15 (td, J=13.0, 2.8 Hz, 1H), 2.96 (td, J=12.8, 3.3 Hz, 1H), 2.83-2.64 (m, 4H), 1.73-1.54 (m, 4H), 1.46 (s, 1H).

1257: Colorless syrup, 47.0% in yield. $^1$H NMR (500 MHz, cdcl$_3$) δ 7.42-7.32 (m, 6H), 6.96-6.81 (m, 5H), 6.18 (s, 1H), 4.63 (d, J=12.9 Hz, 1H), 3.85 (d, J=2.0 Hz, 3H), 3.84 (s, 3H), 3.82-3.76 (m, 1H), 3.50-3.40 (m, 1H), 3.19-3.11 (m, 1H), 3.11-3.00 (m, 2H), 2.67 (t, J=8.0 Hz, 2H), 2.04-1.97 (m, 1H), 1.88-1.70 (m, 3H), 1.27 (t, J=7.2 Hz, 1H).

1258: Colorless syrup, 16.5% in yield. $^1$H NMR (500 MHz, cdcl$_3$) δ 7.35-7.27 (m, 4H), 7.18-7.09 (m, 2H), 6.95-6.78 (m, 5H), 5.86 (s, 1H), 4.60-4.48 (m, 1H), 3.86 (s, 3H), 3.81 (s, 3H), 3.65-3.56 (m, 1H), 3.13 (td, J=13.0, 2.7 Hz, 1H), 2.93 (td, J=12.6, 3.7 Hz, 1H), 2.84-2.62 (m, 4H), 1.30-1.23 (m, 3H), 0.90-0.80 (m, 1H), 0.72 (td, J=13.2, 4.8 Hz, 1H).

1259: Colorless syrup, 49.6% in yield. $^1$H NMR (500 MHz, cdcl$_3$) δ 7.46-7.30 (m, 7H), 7.25-7.18 (m, 3H), 6.96-6.78 (m, 3H), 6.23 (s, 1H), 4.84 (d, J=13.2 Hz, 1H), 4.00 (t, J=10.2 Hz, 1H), 3.84 (s, 3H), 3.15-2.99 (m, 3H), 2.81-2.62 (m, 4H), 1.95 (d, J=13.2 Hz, 1H), 1.86 (d, J=12.9 Hz, 1H), 1.73-1.62 (m, 1H), 1.58-1.51 (m, 1H).

1260: Colorless syrup, 18.9% in yield. $^1$H NMR (500 MHz, cdcl$_3$) δ 7.42-7.34 (m, 5H), 7.30-7.24 (m, 2H), 7.20 (t, J=7.3 Hz, 1H), 6.99 (d, J=7.2 Hz, 2H), 6.93-6.80 (m, 3H), 5.93 (s, 1H), 4.69 (d, J=11.3 Hz, 1H), 3.86 (s, 3H), 3.78 (dd, J=11.3, 2.0 Hz, 1H), 2.85-2.72 (m, 2H), 2.72-2.61 (m, 2H), 2.55-2.41 (m, 2H), 1.73 (d, J=13.3 Hz, 1H), 1.46 (d, J=13.0 Hz, 1H), 1.36-1.24 (m, 2H), 0.62 (qd, J=12.8, 4.3 Hz, 1H).

1261: Colorless syrup, 51.5% in yield. $^1$H NMR (500 MHz, cdcl$_3$) δ 7.45-7.35 (m, 5H), 7.08-7.02 (m, 1H), 6.97-6.81 (m, 6H), 6.23 (s, 1H), 3.89 (s, 3H), 3.89-3.85 (m, 2H), 3.83 (s, 3H), 3.66 (dd, J=9.9, 5.0 Hz, 2H), 3.12-3.04 (m, 4H), 3.01-2.95 (m, 2H), 2.67 (dd, J=9.1, 6.8 Hz, 2H).

1262: Colorless syrup, 22.3% in yield. $^1$H NMR (500 MHz, cdcl$_3$) δ 7.39-7.29 (m, 5H), 7.06-6.97 (m, 1H), 6.92-6.83 (m, 5H), 6.71 (dd, J=7.8, 1.4 Hz, 1H), 5.91 (s, 1H), 3.87 (s, 3H), 3.84 (s, 3H), 3.70-3.62 (m, 2H), 3.31-3.23 (m, 2H), 2.84-2.74 (m, 4H), 2.72-2.64 (m, 2H), 2.45-2.35 (m, 2H).

1273: Colorless syrup, 50.8% in yield. $^1$H NMR (500 MHz, cdcl$_3$) δ 7.49-7.43 (m, 2H), 7.43-7.35 (m, 4H), 7.33-7.28 (m, 1H), 7.15-7.05 (m, 2H), 6.93-6.78 (m, 3H), 6.19 (s, 1H), 3.85 (d, J=18.8 Hz, 3H), 3.35 (s, 1H), 3.09-3.00 (m, 2H), 2.70-2.59 (m, 2H), 2.18 (s, 1H), 1.98 (s, 2H), 1.82 (d, J=13.1 Hz, 2H), 1.68 (s, 2H), 1.33-1.24 (m, 1H).

1274: Colorless syrup, 19.6% in yield. $^1$H NMR (500 MHz, cdcl$_3$) δ 7.39-7.31 (m, 4H), 7.30-7.23 (m, 4H), 7.13-7.03 (m, 2H), 6.93-6.77 (m, 3H), 5.94 (s, 1H), 4.56-4.44 (m, 1H), 3.86 (s, 3H), 3.61-3.52 (m, 1H), 3.15 (td, J=13.0, 2.9 Hz, 1H), 3.01-2.92 (m, 1H), 2.80-2.73 (m, 2H), 2.70-2.64 (m, 2H), 1.76-1.67 (m, 1H), 1.67-1.63 (m, 1H), 1.46 (s, 1H), 1.41 (dd, J=13.8, 2.4 Hz, 1H), 1.02 (td, J=13.2, 4.8 Hz, 1H).

1275: Colorless syrup, 49.5% in yield. $^1$H NMR (500 MHz, cdcl$_3$) δ 7.45-7.36 (m, 2H), 7.37-7.29 (m, 2H), 7.26-7.15 (m, 3H), 7.13-7.03 (m, 2H), 6.94-6.79 (m, 3H), 6.19 (s, 1H), 4.84 (d, J=13.3 Hz, 1H), 4.03-3.93 (m, 1H), 3.84 (s, 3H), 3.16-2.97 (m, 3H), 2.82-2.59 (m, 5H), 1.95 (d, J=13.4 Hz, 1H), 1.87 (d, J=12.7 Hz, 1H), 1.73-1.61 (m, 1H), 1.58-1.49 (m, 1H).

1276: Colorless syrup, 18.9% in yield. $^1$H NMR (500 MHz, cdcl$_3$) δ 7.36-7.28 (m, 4H), 7.23-7.18 (m, 1H), 7.15-7.05 (m, 2H), 7.04-6.98 (m, 2H), 6.94-6.76 (m, 3H), 5.93 (s, 1H), 4.78-4.62 (m, 1H), 3.86 (s, 3H), 3.81-3.71 (m, 1H), 2.85-2.72 (m, 2H), 2.70-2.64 (m, 3H), 2.58-2.43 (m, 2H), 1.76 (d, J=13.3 Hz, 1H), 1.52 (d, J=13.2 Hz, 1H), 1.41-1.29 (m, 2H), 0.74 (qd, J=12.7, 4.3 Hz, 1H).

1298: Colorless syrup, 53.0% in yield. $^1$H NMR (500 MHz, cdcl$_3$) δ 7.45-7.35 (m, 2H), 7.34-7.27 (m, 2H), 7.14-7.05 (m, 2H), 6.97-6.78 (m, 6H), 6.18 (s, 1H), 3.88-3.82 (m, 2H), 3.81 (s, 3H), 3.63-3.56 (m, 2H), 3.23-3.16 (m, 2H), 3.13-3.04 (m, 4H), 2.65 (dd, J=8.8, 6.9 Hz, 2H).

1299: Colorless syrup, 17.5% in yield. $^1$H NMR (500 MHz, cdcl$_3$) δ 7.32-7.21 (m, 4H), 7.10-7.00 (m, 2H), 6.96-6.76 (m, 6H), 5.90 (s, 1H), 3.88 (s, 3H), 3.68-3.57 (m, 2H), 3.26-3.17 (m, 2H), 3.03-2.95 (m, 2H), 2.84-2.73 (m, 2H), 2.72-2.63 (m, 4H).

1300: Colorless syrup, 55.1% in yield. $^1$H NMR (500 MHz, cdcl$_3$) δ 7.59 (d, J=8.0 Hz, 2H), 7.46 (d, J=8.0 Hz, 2H), 7.42-7.34 (m, 5H), 6.92-6.86 (m, 1H), 6.86-6.81 (m, 2H), 6.16 (s, 1H), 3.86 (s, 3H), 3.75-3.66 (m, 2H), 3.57 (s, 2H), 3.49-3.41 (m, 2H), 3.06 (dd, J=9.0, 6.9 Hz, 2H), 2.64 (dd, J=8.9, 6.9 Hz, 2H), 2.51-2.43 (m, 2H), 2.39-2.31 (m, 2H).

1301: Colorless syrup, 22.4% in yield. $^1$H NMR (500 MHz, cdcl$_3$) δ 7.56 (d, J=8.1 Hz, 2H), 7.40-7.31 (m, 4H), 7.30-7.25 (m, 3H), 6.93-6.78 (m, 3H), 5.85 (s, 1H), 3.83 (s, 3H), 3.54-3.45 (m, 2H), 3.38 (s, 2H), 3.10-3.03 (m, 2H), 2.79-2.72 (m, 2H), 2.65 (dd, J=9.3, 6.2 Hz, 2H), 2.21 (t, J=5.0 Hz, 2H), 1.84-1.76 (m, 2H).

1302: Colorless syrup, 48.9% in yield. $^1$H NMR (500 MHz, cdcl$_3$) δ 7.47-7.34 (m, 5H), 6.95-6.80 (m, 7H), 6.22 (s, 1H), 3.87-3.83 (m, 2H), 3.82 (s, 3H), 3.79 (s, 3H), 3.64-3.57 (m, 2H), 3.13-3.03 (m, 4H), 3.01-2.94 (m, 2H), 2.70-2.62 (m, 2H).

1303: Colorless syrup, 18.5% in yield. $^1$H NMR (500 MHz, cdcl$_3$) δ 7.39-7.28 (m, 5H), 6.92-6.74 (m, 7H), 5.90 (s, 1H), 3.87 (s, 3H), 3.77 (s, 3H), 3.67-3.58 (m, 2H), 3.25-3.18 (m, 2H), 2.86-2.76 (m, 4H), 2.68 (dd, J=9.3, 6.3 Hz, 2H), 2.43-2.35 (m, 2H).

1306: Colorless syrup, 44.5% in yield. $^1$H NMR (500 MHz, cdcl$_3$) δ 7.48-7.43 (m, 2H), 7.42-7.33 (m, 7H), 6.91-6.81 (m, 3H), 6.21 (s, 1H), 4.62 (dd, J=10.9, 2.3 Hz, 1H), 3.83 (s, 3H), 3.75 (d, J=13.2 Hz, 1H), 3.53-3.44 (m, 1H), 3.20 (td, J=12.9, 2.9 Hz, 1H), 3.12-2.97 (m, 2H), 2.68-2.61 (m, 2H), 2.11-2.02 (m, 1H), 1.94-1.76 (m, 4H).

1307: Colorless syrup, 16.8% in yield. $^1$H NMR (500 MHz, cdcl$_3$) δ 7.40-7.35 (m, 4H), 7.33-7.29 (m, 2H), 7.25-7.21 (m, 2H), 6.95-6.77 (m, 3H), 5.95 (s, 1H), 4.59-4.42 (m, 1H), 3.86 (s, 3H), 3.64-3.50 (m, 1H), 3.19 (td, J=13.0, 2.8 Hz, 1H), 2.97 (td, J=12.7, 3.4 Hz, 1H), 2.82-2.70 (m, 2H), 2.70-2.62 (m, 2H), 1.73-1.62 (m, 4H), 1.38 (dd, J=13.8, 2.4 Hz, 1H), 1.27 (s, 1H).

1308: Colorless syrup, 48.5% in yield. $^1$H NMR (500 MHz, cdcl$_3$) δ 7.42-7.27 (m, 6H), 6.98-6.78 (m, 6H), 6.20 (s, 1H), 3.86-3.82 (m, 2H), 3.81 (s, 3H), 3.65-3.53 (m, 2H), 3.24-3.14 (m, 2H), 3.13-3.00 (m, 4H), 2.72-2.56 (m, 2H).

1309: Colorless syrup, 20.7% in yield. $^1$H NMR (500 MHz, cdcl$_3$) δ 7.39 (s, 2H), 7.34 (d, J=8.4 Hz, 2H), 7.23 (d, J=8.4 Hz, 2H), 6.99-6.79 (m, 6H), 5.92 (s, 1H), 3.88 (s, 3H), 3.67-3.61 (m, 2H), 3.25-3.19 (m, 2H), 3.03-2.97 (m, 2H), 2.77 (t, J=7.6 Hz, 2H), 2.72-2.63 (m, 4H).

1310: Colorless syrup, 45.0% in yield. $^1$H NMR (500 MHz, cdcl$_3$) δ 7.51-7.44 (m, 4H), 7.42-7.31 (m, 6H), 6.87-6.79 (m, 2H), 6.70 (dd, J=8.7, 4.5 Hz, 1H), 6.25 (s, 1H), 4.56 (s, 1H), 3.77 (s, 3H), 3.34-3.16 (m, 1H), 3.12-2.96 (m, 2H), 2.75-2.67 (m, 2H), 2.14-1.86 (m, 3H), 1.88-1.77 (m, 3H), 1.38-1.18 (m, 1H).

1311: Colorless syrup, 15.6% in yield. $^1$H NMR (500 MHz, cdcl$_3$) δ 7.44-7.29 (m, 7H), 7.29-7.25 (m, 1H), 7.24-7.20 (m, 2H), 6.90-6.70 (m, 3H), 5.94 (s, 1H), 4.62-4.44 (m, 1H), 3.79 (s, 3H), 3.66-3.55 (m, 1H), 3.12 (td, J=13.0, 2.9 Hz, 1H), 3.02-2.90 (m, 1H), 2.84-2.68 (m, 4H), 1.75-1.59 (m, 3H), 1.33 (ddd, J=13.7, 4.8, 2.4 Hz, 1H), 0.90 (td, J=13.2, 4.8 Hz, 1H).

1320: Colorless syrup, 47.7% in yield. $^1$H NMR (500 MHz, cdcl$_3$) δ 7.51-7.28 (m, 7H), 6.98-6.73 (m, 6H), 6.24 (s, 1H), 3.87-3.82 (m, 2H), 3.75 (s, 3H), 3.66-3.60 (m, 2H), 3.23-3.18 (m, 2H), 3.15-3.10 (m, 2H), 3.09-3.03 (m, 2H), 2.74-2.69 (m, 2H).

1321: Colorless syrup, 23.0% in yield. $^1$H NMR (500 MHz, cdcl$_3$) δ 7.36-7.32 (m, 4H), 7.31-7.28 (m, 1H), 7.27-7.23 (m, 2H), 6.93-6.83 (m, 2H), 6.83-6.73 (m, 4H), 5.91 (s, 1H), 3.80 (s, 3H), 3.64 (dd, J=10.1, 4.9 Hz, 2H), 3.25-3.18 (m, 2H), 2.99-2.91 (m, 2H), 2.83-2.70 (m, 4H), 2.55-2.48 (m, 2H).

1322: Colorless syrup, 46.9% in yield. $^1$H NMR (500 MHz, cdcl$_3$) δ 7.69-7.32 (m, 9H), 6.98-6.73 (m, 3H), 6.29 (s, 1H), 4.59 (d, J=13.7 Hz, 1H), 3.95 (d, J=12.9 Hz, 1H), 3.86 (s, 3H), 3.75 (d, J=12.7 Hz, 1H), 3.24-2.94 (m, 4H), 2.80-2.62 (m, 2H), 1.99 (s, 3H), 1.27 (s, 1H).

1323: Colorless syrup, 15.6% in yield. $^1$H NMR (500 MHz, cdcl$_3$) δ 7.52-7.28 (m, 9H), 6.97-6.80 (m, 3H), 5.93 (s, 1H), 4.40 (d, J=13.6 Hz, 1H), 3.88 (s, 3H), 3.63 (dd, J=22.9, 13.1 Hz, 1H), 2.89-2.75 (m, 2H), 2.75-2.59 (m, 4H), 1.90-1.75 (m, 3H), 1.44-1.32 (m, 2H).

Biological Results According to Aspects of the Invention

Embodiments of the invention relate to compounds 648, V131 and a series of other novel compounds as potent inhibitor of ERG (FIG. 1.1-1.1d). According to embodiments of the invention, the compounds also inhibit other member of ETS family, including ETV1 (FIG. 1.4a-1.4d) and ESE-1 and ETS-2 (FIG. 1.2a and FIG. 1.3a). Direct binding of 648 with ERG was confirmed by SPR analysis (FIG. 1.5a and FIG. 1.5b). Compound 648 potently inhibits invasion of VCaP and C4-2B cells, but not the DU145 cells (FIG. 1.7). VCaP and C4-2B cells endogenously express ERG and ETV-1, respectively. In contract, DU145 is ERG-negative and ETV1-negative. In embodiments of the invention, compounds 827 and 832 are cytotoxic in the ETV1-postive LNCaP cells (FIG. 1.8a).

In embodiments of the invention, the androgen-bound AR is regressing GATA2 expression and inhibition of AR via castration or use of antiandrogen releases such expression. This suggest a feedback loop between AR and GATA2, in which inhibition of AR rapidly leads to elevated expression of GATA2, which subsequently results in resistance to castration and antiandrogen by activating the AR. Our findings are consistent with the recent work done by He et al. which found that activated AR binds with promoter region of GATA2 and regulates GATA2 expression.[61] Embodiments of the inventions relate to a series of novel compounds that potently inhibit GATA2-dependent reporter assay in IHH cells (FIG. 2.1a, FIG. 2.1b and FIG. 2.2a-2.2g). Further embodiments of the invention demonstrate that 673 and its analogues selectively inhibit GATA2 among GATA family members (FIG. 2.3a-2.3c and FIG. 2.4). Direct binding of 670, 673, 817 and V248 with GATA2 was confirmed by SPR analysis, using recombinant protein of human GATA2 (FIG. 2.5a and FIG. 2.5b). Other embodiments showed that 673 potently inhibits the AR signaling in C4-2B CRPC prostate cancer cells (FIG. 2.6) and are cytotoxic to A549 and H23 KRAS mutant NSCLC cells (FIG. 2.7). Overexpression of GATA2 confers resistance to antiandrogen bicalutamide (Bic) (FIG. 2.9). Compound 673 is effective against the LNCaP stably transfected with GATA2-expressing plasmid (referred to as LNCaP-GATA2 cells) (FIG. 2.8). By breaking AR-GATA2 feedback loop, 673 suppresses the AR signalling in CRPC cells (FIG. 11). Further, we demonstrated the synergistic effect of 673 with bicalutamide (Bic) in PSA-luc reporter assay and BrdU cell proliferation assay in LNCaP-GATA2 cells (FIG. 12). The embodiment in FIG. 10 indicated that 673 is targeting the N-terminal domain of GATA2.

Further embodiments of the invention relate to a series of novel compounds that activate human Sting (hSting) and/or mouse Sting (mSting)-dependent reporter assay (FIG. 3.1a-3.1e, FIG. 3.2, and FIG. 3.4a-3.4j). Direct binding of 817 with hSting was confirmed by SPR analysis (FIG. 3.3). Embodiments of the invention demonstrated that 834, 874, 761, 840 and 1176 activate interferon signaling pathway in THP-1 cells, which endogenously express hSting (FIG. 3.5).

Direct binding of compounds 784 and 895 with KRAS G12D mutant was confirmed by Surface Plasmon Resonance (SPR) analysis, using recombinant human KRAS 12D mutant protein (TP700052, ORIGENE) (FIG. 4.1). The SPR analysis revealed that 895 is a tighter binder of the G12D mutant than 784 (Kd of 784 and 895 are 190 and 45 µM, respectively). Since activation of KRAS leads to activation of NF-kB,[69] we performed in vitro screening of our compounds by KRAS mutant-dependent NF-kB-luc reporter assay in HEK293 cells. We demonstrated that 784, 895 and a series of other compounds potently inhibited KRAS G12D, G12V and G12C mutants (FIGS. 4.2a)-4.2c)). Next, we demonstrated that our compounds are active in PANC 10.05 pancreatic cancer cells, which endogenously express KRAS G12D mutant. Specifically, compounds of the invention inhibit NF-kB-luc reporter activity in PANC 10.05 cells (FIGS. 4.3a)-4.3i)). Compounds of the invention inhibit ERK phosphorylation in Panc 10.05 and HCT-116 cells, which express endogenous KRAS G12D and G13D mutants, respectively (FIGS. 4.4a)-4.4c)). Also, compounds of the invention are cytotoxic to PANC 10.05 pancreatic cancer cells, H23 NSCLC cells and HCT-116 colorectal cancer cells (FIG. 4.5).

Although the present invention has been described hereinabove by way of specific embodiments thereof, it may be modified, without departing from the spirit and nature of the subject invention as defined in the appended claims.

The present description refers to a number of documents, the content of which is herein incorporated by reference in their entirety.

REFERENCES

1. Riely, G. J.; Marks, J.; Pao, W. KRAS mutations in non-small cell lung cancer. *Proc. Am. Thorac. Soc.* 2009, 6, 201-205.
2. Whyte, D. B.; Kirschmeier, P.; Hockenberry, T. N.; Nunez-Oliva, I.; James, L.; Catino, J. J.; Bishop, W. R.; Pai, J. K. K- and N-Ras are geranylgeranylated in cells treated with farnesyl protein transferase inhibitors. *J. Biol. Chem.* 1997, 272, 14459-14464.
3. Gysin, S.; Salt, M.; Young, A.; McCormick, F. Therapeutic strategies for targeting ras proteins. *Genes Cancer* 2011, 2, 359-372.
4. Mallucci, L.; Wells, V. The end of KRAS, and other, cancers? A new way forward. *Drug Discov. Today* 2014, 19, 383-387.
5. Scholl, C.; Frohling, S.; Dunn, I. F.; Schinzel, A. C.; Barbie, D. A.; Kim, S. Y.; Silver, S. J.; Tamayo, P.; Wadlow, R. C.; Ramaswamy, S.; Dohner, K.; Bullinger, L.; Sandy, P.; Boehm, J. S.; Root, D. E.; Jacks, T.; Hahn, W. C.; Gilliland, D. G. Synthetic Lethal Interaction between Oncogenic KRAS Dependency and STK33 Suppression in Human Cancer Cells. *Cell* 2009, 137, 821-834.
6. Singh, A.; Greninger, P.; Rhodes, D.; Koopman, L.; Violette, S.; Bardeesy, N.; Settleman, J. A Gene Expression Signature Associated with "K-Ras Addiction" Reveals Regulators of EMT and Tumor Cell Survival. *Cancer Cell* 2009, 15, 489-500.
7. Kumar, M. S.; Hancock, D. C.; Molina-Arcas, M.; Steckel, M.; East, P.; Diefenbacher, M.; Armenteros-Monterroso, E.; Lassailly, F.; Matthews, N.; Nye, E.; Stamp, G.; Behrens, A.; Downward, J. The GATA2 transcriptional network is requisite for RAS oncogene-driven non-small cell lung cancer. *Cell* 2012, 149, 642-655.
8. Steckel, M.; Molina-Arcas, M.; Weigelt, B.; Marani, M.; Warne, P. H.; Kuznetsov, H.; Kelly, G.; Saunders, B.; Howell, M.; Downward, J.; Hancock, D. C. Determination of synthetic lethal interactions in KRAS oncogene-dependent cancer cells reveals novel therapeutic targeting strategies. *Cell Res.* 2012, 22, 1227-1245.
9. Shen, S.; Mao, C. Q.; Yang, X. Z.; Du, X. J.; Liu, Y.; Zhu, Y. H.; Wang, J. Cationic lipid-assisted polymeric nanoparticle mediated GATA2 siRNA delivery for synthetic lethal therapy of KRAS mutant non-small-cell lung carcinoma. *Mol. Pharm.* 2014, 11, 2612-2622.
10. Katsumura, K. R.; Yang, C. X.; Boyer, M. E.; Li, L. J.; Bresnick, E. H. Molecular basis of crosstalk between oncogenic Ras and the master regulator of hematopoiesis GATA-2. *EMBO Rep.* 2014, 15, 938-947.
11. Munugalavadla, V.; Dore, L. C.; Tan, B. L.; Hong, L.; Vishnu, M.; Weiss, M. J.; Kapur, R. Repression of c-kit and its downstream substrates by GATA-1 inhibits cell proliferation during erythroid maturation. *Mol. Cell Biol.* 2005, 25, 6747-6759.
12. Rylski, M.; Welch, J. J.; Chen, Y. Y.; Letting, D. L.; Diehl, J. A.; Chodosh, L. A.; Blobel, G. A.; Weiss, M. J. GATA-1-mediated proliferation arrest during erythroid maturation. *Mol. Cell Biol.* 2003, 23, 5031-5042.
13. Zheng, R.; Blobel, G. A. GATA Transcription Factors and Cancer. *Genes Cancer* 2010, 1, 1178-1188.
14. Bresnick, E. H.; Katsumura, K. R.; Lee, H. Y.; Johnson, K. D.; Perkins, A. S. Master regulatory GATA transcription factors: mechanistic principles and emerging links to hematologic malignancies. *Nucleic Acids Res.* 2012, 40, 5819-5831.
15. Masuda, A.; Hashimoto, K.; Yokoi, T.; Doi, T.; Kodama, T.; Kume, H.; Ohno, K.; Matsuguchi, T. Essential role of GATA transcriptional factors in the activation of mast cells. *J. Immunol.* 2007, 178, 360-368.
16. Culig Z., Klocker H., Bartsch G., Hobisch A. Androgen receptors in prostate cancer. *Endocr. Relat Cancer* 2002, 9(3), 155-170.
17. Balk S. P. Androgen receptor as a target in androgen-independent prostate cancer. *Urology* 2002, 60(3A), 132-138.
18. Taplin M. E., Ho S. M. The endocrinology of prostate cancer. *J. Clin. Endocrinol. Metab.* 2001, 86(8), 3467-3477.
19. Tannock I. F., de Wit R., Berry W. R. et al. Docetaxel plus prednisone or mitoxantrone plus prednisone for advanced prostate cancer. *N. Engl. J. Med.* 2004, 351(15), 1502-1512.
20. Petrylak D. P., Tangen C. M., Hussain M. H. et al. Docetaxel and estramustine compared with mitoxantrone and prednisone for advanced refractory prostate cancer. *N. Engl. J. Med.* 2004, 351(15), 1513-1520.
21. Ang J. E., Olmos D., de Bono J. S. CYP17 blockade by abiraterone: Further evidence for frequent continued hormone-dependence in castration-resistant prostate cancer. *Br. J. Cancer* 2009, 100(5), 671-675.
22. Scher H. I., Beer T. M., Higano C S et al. Phase I/II study of MDV3100 in patients (pts) with progressive castration-resistant prostate cancer (CRPC). *J. Clin. Oncol.* (Meeting Abstracts) 2008, 26(15_suppl), 5006.
23. Tran C., Ouk S., Clegg N. J. et al. Development of a Second-Generation Antiandrogen for Treatment of Advanced Prostate Cancer. *Science* 2009, 324(5928), 787-790.
24. Scher H. I., Beer T. M., Higano C. S. et al. Antitumour activity of MDV3100 in castration-resistant prostate cancer: a phase 1-2 study. *Lancet* 2010, 375(9724), 1437-1446.
25 Attard G., Cooper C. S., de Bono J. S. Steroid hormone receptors in prostate cancer: a hard habit to break? *Cancer Cell* 2009, 16(6), 458-462.
26. Attard G., Reid A. H. M., Olmos D., de Bono J. S. Antitumor activity with CYP17 blockade indicates that castration-resistant prostate cancer frequently remains hormone driven. *Cancer Res.* 2009, 69(12), 4937-4940.
27. Shen H. C., Balk S. P. Development of Androgen Receptor Antagonists with Promising Activity in Castration-Resistant Prostate Cancer. *Cancer Cell* 2009, 15(6), 461-463.
28. Tomlins S. A., Rhodes D. R., Perner S. et al. Recurrent Fusion of TMPRSS2 and ETS Transcription Factor Genes in Prostate Cancer. *Science* 2005, 310(5748), 644-648.
29. Tomlins S. A., Bjartell A., Chinnaiyan A. M. et al. ETS Gene Fusions in Prostate Cancer: From Discovery to Daily Clinical Practice. *Eur. Urol.* 2009, 56(2), 275-286.
30. Mehra R., Tomlins S. A., Yu J. J. et al. Characterization of TMPRSS2-ETS gene aberrations in androgen-independent metastatic prostate cancer. *Cancer Res.* 2008, 68(10), 3584-3590.
31. Oikawa T. ETS transcription factors: possible targets for cancer therapy. *Cancer Sci.* 2004, 95(8), 626-633.
32. Tomlins S. A., Laxman B., Varambally S. et al. Role of the TMPRSS2-ERG gene fusion in prostate cancer. *Neoplasia* 2008, 10(2), 177-188.
33. St. John J., Powell K., Katie Conley-LaComb M., Chinni S. R. TMPRSS2-ERG fusion gene expression in prostate tumor cells and its clinical and biological significance in prostate cancer progression. *Journal of Cancer Science and Therapy* 2012, 4(4), 94-101.
34. Demichelis F., Fall K., Perner S. et al. TMPRSS2:ERG gene fusion associated with lethal prostate cancer in a watchful waiting cohort. *Oncogene* 2007, 26(31), 4596-4599.
35. Attard G., Clark J., Ambroisine L. et al. Duplication of the fusion of TMPRSS2 to ERG sequences identifies fatal human prostate cancer. *Oncogene* 2008, 27(3), 253-263.
36. FitzGerald L. M., Agalliu I., Johnson K. et al. Association of TMPRSS2-ERG gene fusion with clinical characteristics and outcomes: results from a population-based study of prostate cancer. *BMC Cancer* 2008, 8, 230.
37. Mehra R., Tomlins S. A., Shen R. et al. Comprehensive assessment of TMPRSS2 and ETS family gene aberrations in clinically localized prostate cancer. *Mod. Pathol.* 2007, 20(5), 538-544.
38. Perner S., Svensson M. A., Hossain R. R. et al. ERG rearrangement metastasis patterns in locally advanced prostate cancer. *Urology* 2010, 75(4), 762-767.
39. Furusato B., Tan S. H., Young D. et al. ERG oncoprotein expression in prostate cancer: clonal progression of ERG-positive tumor cells and potential for ERG-based stratification. *Prostate Cancer Prostatic Dis.* 2010, 13(3), 228-237.
40. Gao X., Li L. Y., Zhou F. J. et al. ERG rearrangement for predicting subsequent cancer diagnosis in high-grade prostatic intraepithelial neoplasia and lymph node metastasis. *Clin. Cancer Res.* 2012, 18(15), 4163-4172.
41. Wang J., Cai Y., Yu W., Ren C., Spencer D. M., Ittmann M. Pleiotropic biological activities of alternatively spliced TMPRSS2/ERG fusion gene transcripts. *Cancer Res.* 2008, 68(20), 8516-8524.
42. Sun C., Dobi A., Mohamed A. et al. TMPRSS2-ERG fusion, a common genomic alteration in prostate cancer activates C-MYC and abrogates prostate epithelial differentiation. *Oncogene* 2008, 27(40), 5348-5353.
43. Rosen P., Sesterhenn I. A., Brassell S. A., McLeod D. G., Srivastava S., Dobi A. Clinical potential of the ERG oncoprotein in prostate cancer. *Nature Reviews Urology* 2012, 9(3), 131-137.
44. Braun M., Goltz D., Shaikhibrahim Z. et al. ERG protein expression and genomic rearrangement status in primary and metastatic prostate cancer—A comparative study of two monoclonal antibodies. *Prostate Cancer and Prostatic Diseases* 2012, 15(2), 165-169.
45. Rubin M. A., Maher C. A., Chinnaiyan A. M. Common gene rearrangements in prostate cancer. *J. Clin. Oncol.* 2011, 29(27), 3659-3668.
46. Sreenath T. L., Dobi A., Petrovics G., Srivastava S. Oncogenic activation of ERG: A predominant mechanism in prostate cancer. *J. Carcinog.* 2011, 10, 37.
47. Leshem O., Madar S., Kogan-Sakin I. et al. TMPRSS2/ERG promotes epithelial to mesenchymal transition through the ZEB1/ZEB2 axis in a prostate cancer model. *PLoS ONE* 2011, 6(7).
48. Yu J., Yu J., Mani R. S. et al. An Integrated Network of Androgen Receptor, Polycomb, and TMPRSS2-ERG Gene Fusions in Prostate Cancer Progression. *Cancer Cell* 2010, 17(5), 443-454.
49. Flajollet S., Tian T. V., Flourens A. et al. Abnormal expression of the ERG transcription factor in prostate cancer cells activates osteopontin. *Molecular Cancer Research* 2011, 9(7), 914-924.
50. Kunderfranco P., Mello-Grand M., Cangemi R. et al. ETS transcription factors control transcription of EZH2 and epigenetic silencing of the tumor suppressor gene Nkx3.1 in prostate cancer. *PLoS ONE* 2010, 5(5).
51. Mohamed A. A., Tan S. H., Sun C. et al. ERG oncogene modulates prostaglandin signaling in prostate cancer cells. *Cancer Biology & Therapy* 2011, 11(4), 410-417.
52. Wang J., Cai Y., Shao L. J. et al. Activation of NF-{kappa}B by TMPRSS2/ERG Fusion Isoforms through Toll-Like Receptor-4. *Cancer Res.* 2011, 71(4), 1325-1333.
53. Nelson W. G., De Marzo A. M., Yegnasubramanian S. Epigenetic alterations in human prostate cancers. *Endocrinol.* 2009, 150(9), 3991-4002.
54. Sebastian de Bono J., Sandhu S., Attard G. Beyond Hormone Therapy for Prostate Cancer with PARP inhibitors. *Cancer Cell* 2011, 19(5), 573-574.
55. Rahim S., Beauchamp E. M., Kong Y., Brown M. L., Toretsky J. A., Äoeren A. YK-4-279 inhibits ERG and ETV1 mediated prostate cancer cell invasion. *PLoS ONE* 2011, 6(4).
56. Baena E., Shao Z., Linn D. E. et al. ETV1 directs androgen metabolism and confers aggressive prostate cancer in targeted mice and patients. *Genes Dev.* 2013, 27(6), 683-698.
57. Ran L., Sirota I., Cao Z. et al. Combined inhibition of MAP kinase and KIT signaling synergistically destabilizes ETV1 and suppresses GIST tumor growth. *Cancer Discov.* 2015, 5(3), 304-315.
58. Xie L., Gazin C., Park S. M. et al. A synthetic interaction screen identifies factors selectively required for proliferation and TERT transcription in p53-deficient human cancer cells. *PLoS Genet.* 2012, 8(12), e1003151.
59. Woo S. R., Fuertes M. B., Corrales L. et al. STING-dependent cytosolic DNA sensing mediates innate immune recognition of immunogenic tumors. *Immunity* 2014, 41(5), 830-842.
60. Iwamoto, K.-I., Kimura, H., Oike, M., Sato. M. *Org. Biomol. Chem.* 2008, 6, 912-915.
61. He B., Lanz R. B., Fiskus W. et al. GATA2 facilitates steroid receptor coactivator recruitment to the androgen receptor complex. *Proc. Natl. Acad. Sci. USA* 2014, 111(51), 18261-18266.
62. Ryan D P, Hong T S, Bardeesy N. Pancreatic adenocarcinoma. *N. Engl. J. Med.* 2014, 371(22), 2140-2141.
63. Garrido-Laguna I, Hidalgo M. Pancreatic cancer: from state-of-the-art treatments to promising novel therapies. *Nat. Rev. Clin. Oncol.* 2015, 12(6), 319-334.
64. Collins M A, Bednar F, Zhang Y et al. Oncogenic Kras is required for both the initiation and maintenance of pancreatic cancer in mice. *J. Clin. Invest.* 2012, 122(2), 639-653.
65. Pylayeva-Gupta Y, Grabocka E, Bar-Sagi D. RAS oncogenes: weaving a tumorigenic web. *Nat. Rev. Cancer* 2011, 11(11), 761-774.
66. Ostrem J M, Peters U, Sos M L, Wells J A, Shokat K M. K-Ras(G12C) inhibitors allosterically control GTP affinity and effector interactions. *Nature* 2013, 503(7477), 548-551.
67. Lito P, Solomon M, Li L S, Hansen R, Rosen N. Allele-specific inhibitors inactivate mutant KRAS G12C by a trapping mechanism. *Science* 2016, 351(6273), 604-608.
68. Lim S M, Westover K D, Ficarro S B et al. Therapeutic targeting of oncogenic K-Ras by a covalent catalytic site inhibitor. *Angew Chem. Int. Ed. Engl.* 2014, 53(1), 199-204.
69. Mizumoto Y, Kyo S, Kiyono T et al. Activation of NF-kappaB is a novel target of KRAS-induced endometrial carcinogenesis. *Clin. Cancer Res.* 2011, 17(6), 1341-1350.
70. Meanwell, N. A. et al. *J. Med. Chem.* 1993, 36, 3884-3903.
71. Meanwell, N. A.; Rosenfeld, M. J.; Trehan, A. K. Wright, J. J. K.; Brassard, C. L.; Buchanan, J.; Federici, M. E.; Fleming, J. S.; Gamberdella, M.; Zavoico, G. B.; Seiler, S. M. *J. Med. Chem.* 1992, 35, 3483-3497.

The invention claimed is:
1. A compound of formula IVA:

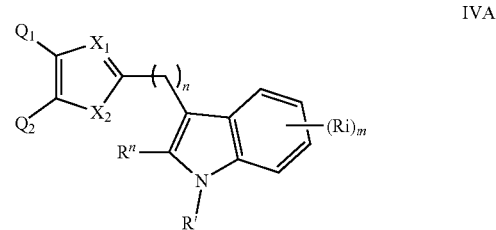

or a pharmaceutically acceptable salt thereof,
wherein:
 $X_1$ is N;
 $X_2$ is O;

Q¹ is phenyl, optionally substituted with a substituent selected from the group consisting of halogen, CN, NO₂, alkyl, halogeno alkyl, alkyl(aryloxy), NH₂, OH, alkoxy, halogeno alkoxy, aryloxy, SH, thioalkoxy, halogeno thioalkoxy, thioalkyl(aryloxy), thioaryloxy, cycloalkyl, and aryl;

Q² is phenyl, optionally substituted with a substituent selected from the group consisting of halogen, CN, NO₂, alkyl, halogeno alkyl, alkyl(aryloxy), NH₂, OH, alkoxy, halogeno alkoxy, aryloxy, SH, thioalkoxy, halogeno thioalkoxy, thioalkyl(aryloxy), thioaryloxy, cycloalkyl, and aryl;

R' is H, CN, NO₂, alkyl, (CH₂)CN, alkoxy, halogeno thioalkoxy, S(O)₂R¹, or cycloalkyl;

R" is H, CN, NO₂, alkyl, (CH₂)CN, alkoxy, halogeno thioalkoxy, S(O)₂R¹, or cycloalkyl;

each Ri is independently H, CN, NO₂, alkyl, (CH₂)$_n$CN, alkoxy, halogeno thioalkoxy, S(O)₂R¹, or cycloalkyl;

each R¹ is independently alkyl, cycloalkyl, or aryl;

m is 0, 1, 2, 3, or 4; and n is 1, 2, 3, 4, 5, or 6.

2. The compound according to claim 1, wherein the compound is selected from the group consisting of:

630

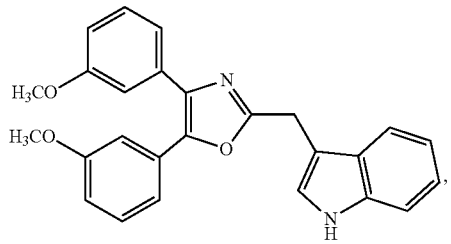

631

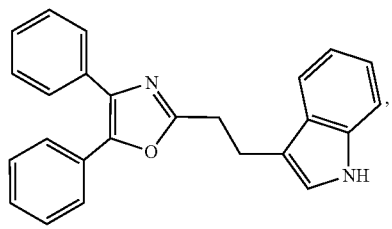

632

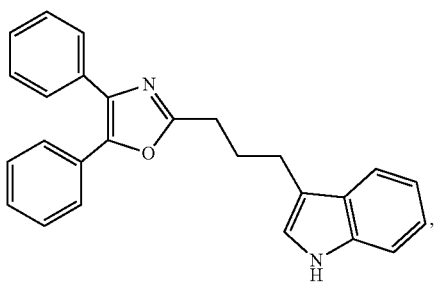

637

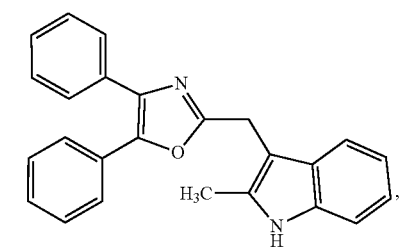

-continued

638

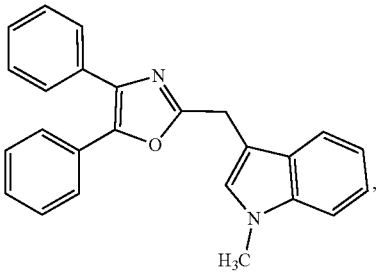

639

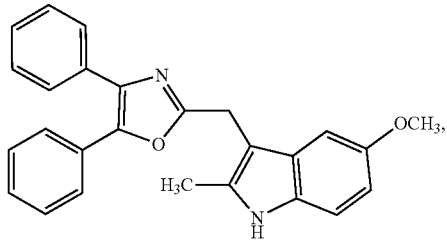

640

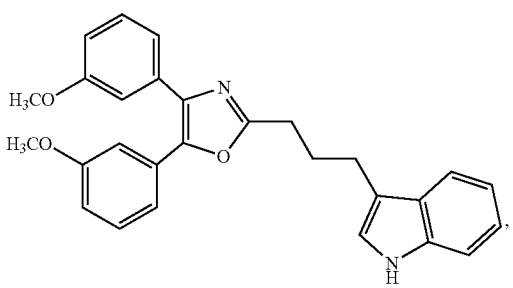

641

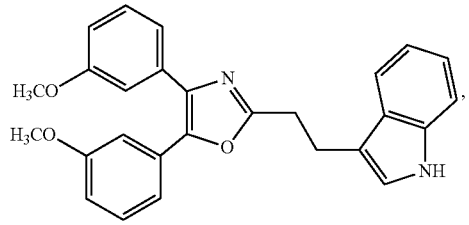

648

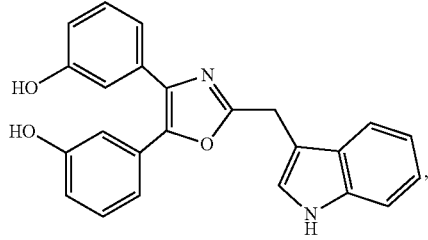

650

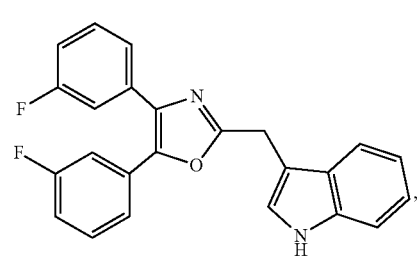

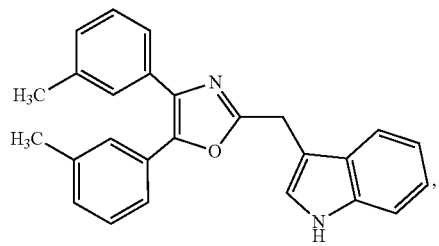
651
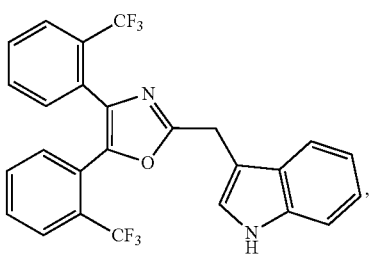
659
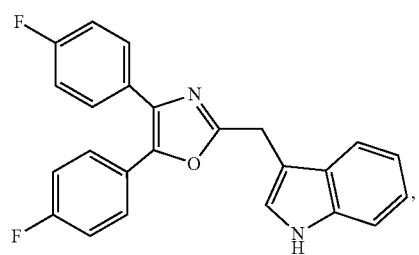
652
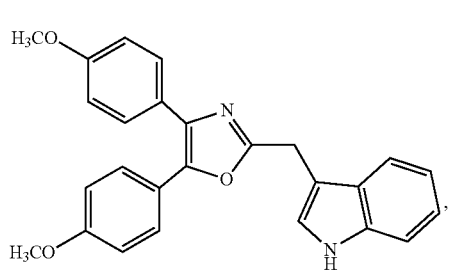
660
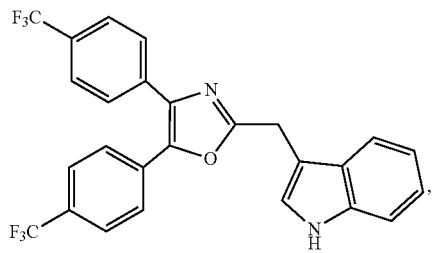
653
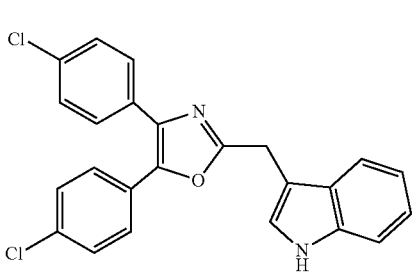
661
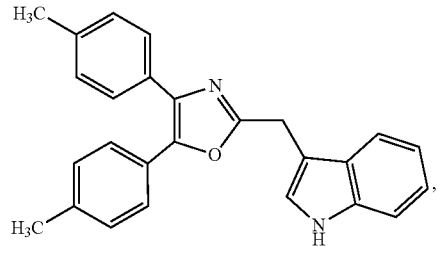
654
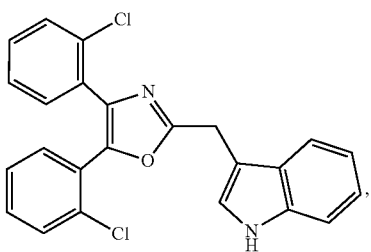
662
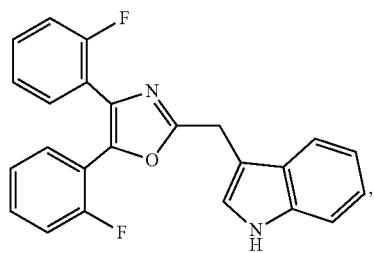
655
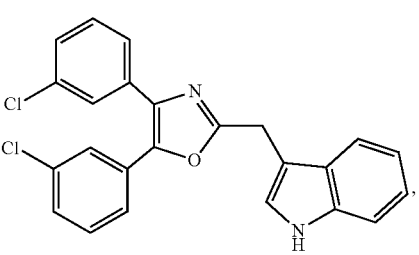
663
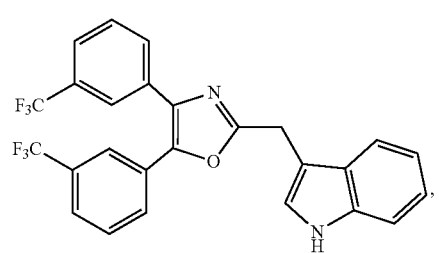
656
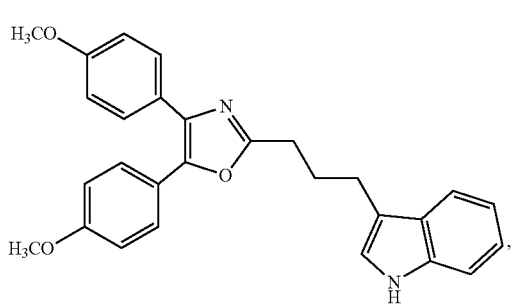
670

671
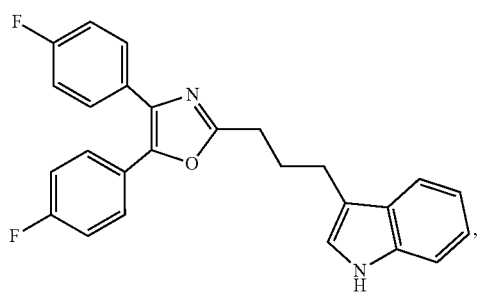
672
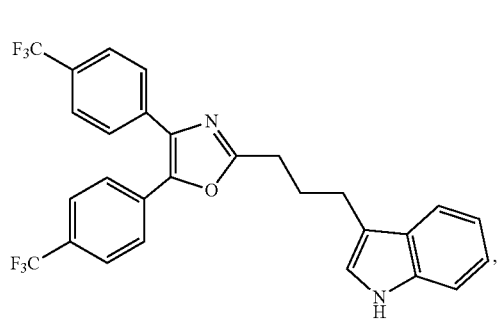
673
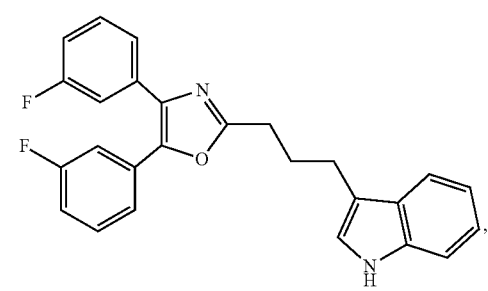
675
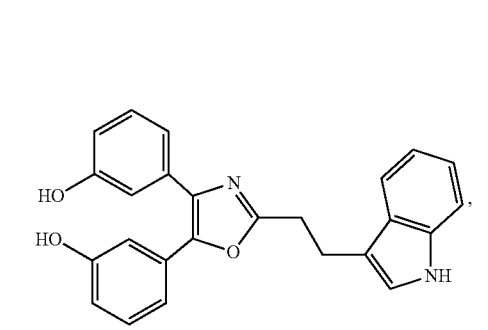
676
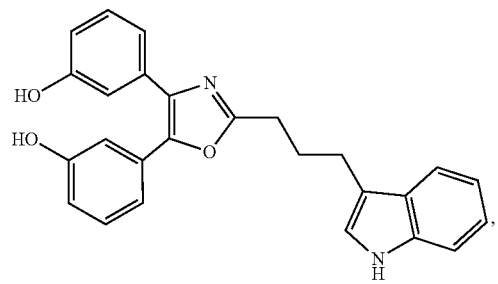
677
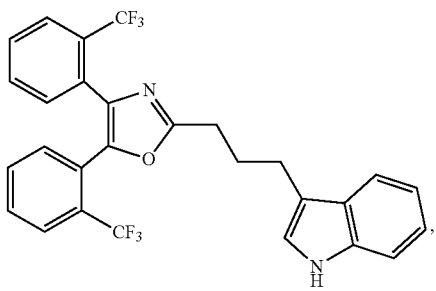
678
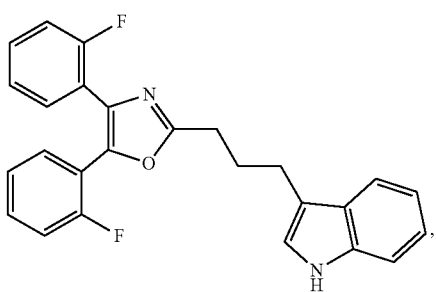
681
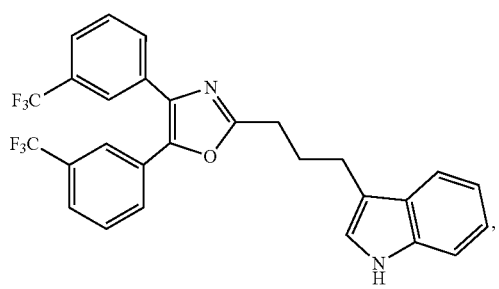
696
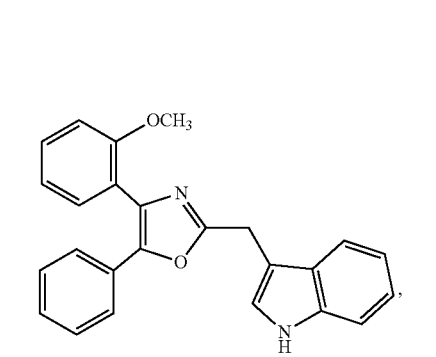
697
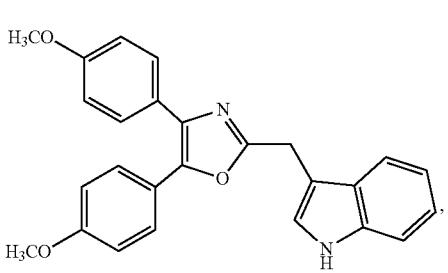

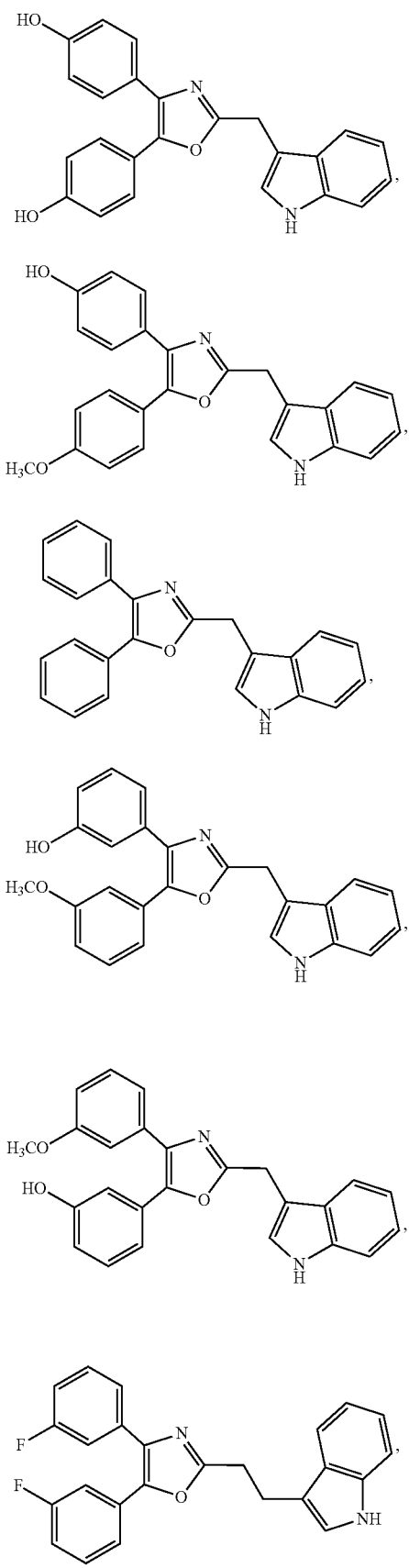
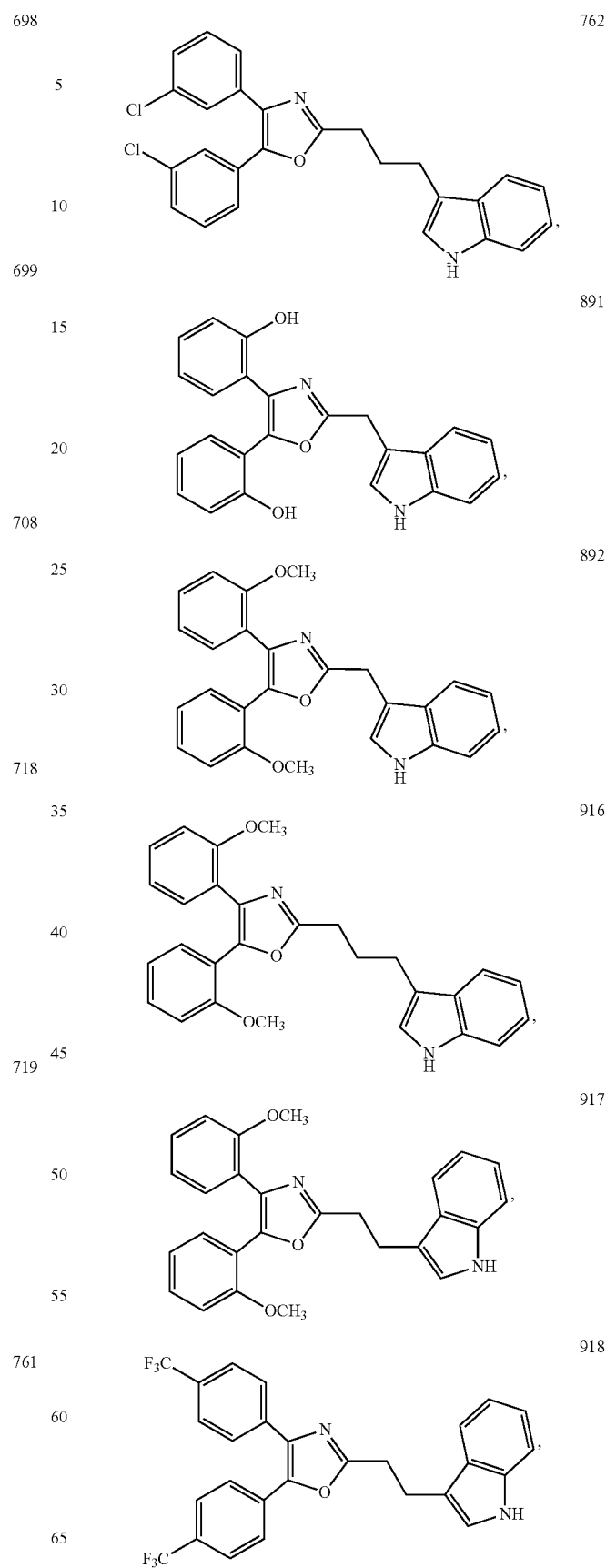

920

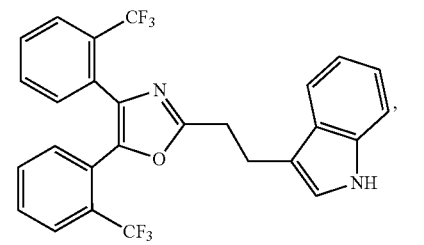

924

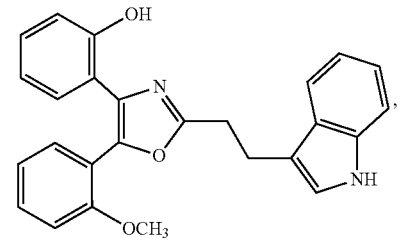

925

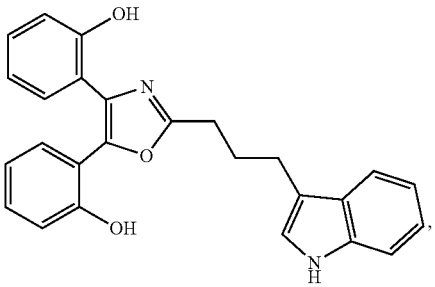

931

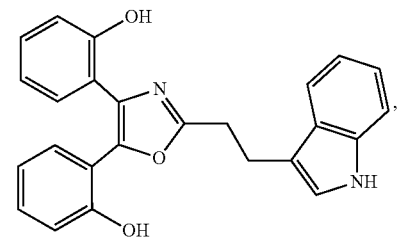

932

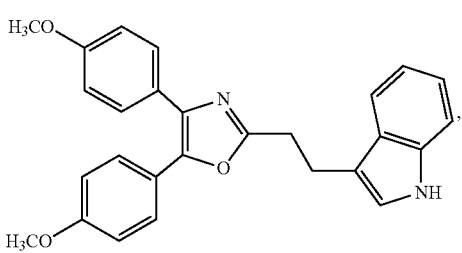

933

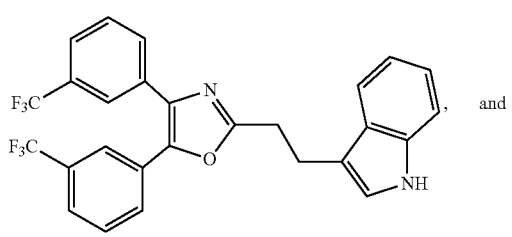

and

936

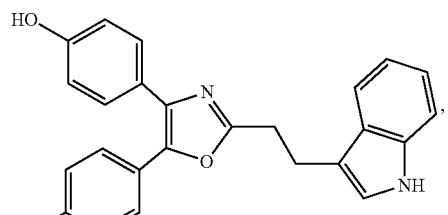

or a pharmaceutically acceptable salt thereof.

3. A pharmaceutical composition comprising a compound according to claim 1, or a pharmaceutically acceptable salt thereof, and a pharmaceutically acceptable carrier.

4. A method for inhibiting a KRAS mutant in a subject, comprising administering to a subject in need thereof a therapeutically effective amount of a compound according to claim 1, or a pharmaceutically acceptable salt thereof.

5. The method according to claim 4, wherein the KRAS mutant is G12C, G12D, G12V, or G13D.

6. A method for stimulating an interferon gene in a subject, comprising administering to a subject in need thereof a therapeutically effective amount of a compound according to claim 1, or a pharmaceutically acceptable salt thereof.

7. The method according to claim 6, wherein the interferon gene is a human interferon gene or a mouse interferon gene.

8. A method for targeting an ETS transcription factor in a subject, comprising administering to a subject in need thereof a therapeutically effective amount of a compound according to claim 1, or a pharmaceutically acceptable salt thereof.

9. The method according to claim 8, wherein the ETS transcription factor is ERG or ETV.

10. A method for targeting a GATA transcription factor in a subject, comprising administering to a subject in need thereof a therapeutically effective amount of a compound according to claim 1, or a pharmaceutically acceptable salt thereof.

11. The method according to claim 10, wherein the GATA transcription factor is GATA2.

12. A compound selected from the group consisting of:

636

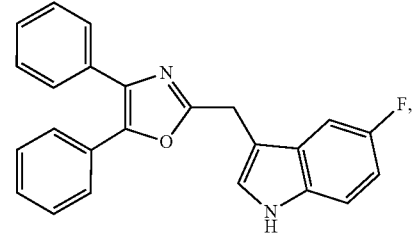

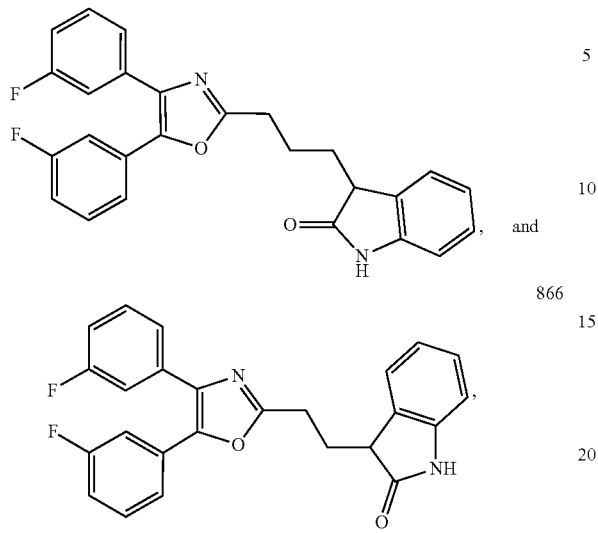
or a pharmaceutically acceptable salt thereof.

UNITED STATES PATENT AND TRADEMARK OFFICE
CERTIFICATE OF CORRECTION

| | | |
|---|---|---|
| PATENT NO. | : 10,844,051 B2 | Page 1 of 1 |
| APPLICATION NO. | : 15/746230 | |
| DATED | : November 24, 2020 | |
| INVENTOR(S) | : Jian Hui Wu, Xiaohong Tian and Qianhui Yi | |

It is certified that error appears in the above-identified patent and that said Letters Patent is hereby corrected as shown below:

On the Title Page

Item (71) Applicant: "THE ROYAL INSTITUTION FOR THE ADCANCEMENT OF LEARNING/McGILL UNIVERSITY, Montreal (CA)" should read --THE ROYAL INSTITUTION FOR THE ADVANCEMENT OF LEARNING/McGILL UNIVERSITY, Montreal (CA)--

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*